(12) United States Patent
Gori

(10) Patent No.: US 11,352,591 B2
(45) Date of Patent: Jun. 7, 2022

(54) CLEANING COMPOSITIONS AND USES THEREOF

(71) Applicant: Novozymes A/S, Bagsvaerd (DK)

(72) Inventor: Klaus Gori, Dyssegaard (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 16/500,423

(22) PCT Filed: Mar. 16, 2018

(86) PCT No.: PCT/EP2018/056735
§ 371 (c)(1),
(2) Date: Oct. 3, 2019

(87) PCT Pub. No.: WO2018/184817
PCT Pub. Date: Oct. 11, 2018

(65) Prior Publication Data
US 2020/0190436 A1 Jun. 18, 2020

(30) Foreign Application Priority Data

Apr. 6, 2017 (EP) ..................................... 17165320

(51) Int. Cl.
*C11D 3/386* (2006.01)
*C11D 11/00* (2006.01)

(52) U.S. Cl.
CPC ...... *C11D 3/38618* (2013.01); *C11D 3/38636* (2013.01); *C11D 11/0017* (2013.01)

(58) Field of Classification Search
None
See application file for complete search history.

(56) References Cited

U.S. PATENT DOCUMENTS 10,041,055 B2    8/2018   Krogh

FOREIGN PATENT DOCUMENTS

| WO | 2014/087011 | A1 | 6/2014 |
|---|---|---|---|
| WO | 2015/155350 | A1 | 10/2015 |
| WO | 2016/066756 | A2 | 5/2016 |
| WO | 2016/066757 | A2 | 5/2016 |
| WO | 2016/087619 | A1 | 6/2016 |
| WO | 2017/001471 | A1 | 1/2017 |
| WO | 2017/059802 | A1 | 4/2017 |
| WO | 2017/060475 | A2 | 4/2017 |
| WO | 2017/060493 | A1 | 4/2017 |
| WO | 2017/060518 | A1 | 4/2017 |

OTHER PUBLICATIONS

Anonymous, 2016, NCBI Reference sequence WP_062748019.1.
Anonymous, 2017, NCBI Reference sequence WP_029565313.1.

*Primary Examiner* — Kagnew H Gebreyesus
(74) *Attorney, Agent, or Firm* — Yoshimi Barron

(57) ABSTRACT

The present invention relates to compositions such as cleaning compositions comprising a mix of enzymes. The invention further relates, use of compositions comprising such enzymes in cleaning processes.

10 Claims, No Drawings
Specification includes a Sequence Listing.

CLEANING COMPOSITIONS AND USES THEREOF

CROSS-REFERENCE TO RELATED APPLICATIONS

This application is a 35 U.S.C. 371 national application of international application no. PCT/EP2018/056735 filed Mar. 16, 2018 which claims priority or the benefit under 35 U.S.C. 119 of European application nos. EP 17165320.7 filed Apr. 6, 2017, the contents of which are fully incorporated herein by reference.

REFERENCE TO A SEQUENCE LISTING

This application contains a Sequence Listing in computer readable form, which is incorporated herein by reference.

BACKGROUND OF THE INVENTION

The present invention relates to compositions such as cleaning compositions comprising a mix of enzymes. The invention further relates, use of compositions comprising such enzymes in cleaning processes and/or for deep cleaning of organic stains, methods for removal or reduction of components of organic matter.

DESCRIPTION OF THE RELATED ART

Enzymes have been used in detergents for decades. Usually a cocktail of various enzymes is added to detergent compositions. The enzyme cocktail often comprises various enzymes, wherein each enzyme targets it specific substrate e.g. amylases are active towards starch stains, proteases on protein stains and so forth. Textiles surface and hard surfaces, such as dishes or the inner space of a laundry machine enduring a number of wash cycles, become soiled with many different types of soiling which may compose of proteins, grease, starch etc. One type of stains may be associated with organic matter such as biofilm, EPS, etc. Organic matter may compose of different molecules such as polysaccharides, extracellular DNA (eDNA), and proteins. Some organic matter composes an extracellular polymeric matrix, which may be sticky or gluing, which when present on textile, attracts soils and may course redeposition or backstaining of soil resulting in a greying of the textile. Additionally, organic matters such as biofilms often cause malodor issue as various malodor molecules can be adhered by the polysaccharides, extracellular DNA (eDNA), and proteins in the complex extracellular matrix and be slowly released to cause consumer noticeable malodor issue. There is still a need for cleaning compositions, which effectively prevent, reduce or remove stains e.g. associated with biofilm, such as protein and DNA. The present invention provides new compositions fulfilling such need.

SUMMARY OF THE INVENTION

A first aspect of the present invention relates to a cleaning composition comprising a DNase, a protease and at least one cleaning component.

Another aspect of the present invention relates to a cleaning composition comprising at least 0.001 ppm DNase, at least 0.001 ppm protease and a cleaning component, wherein the cleaning component is selected from
  a. 0.1 to 15 wt % of at least one a surfactant;
  b. 0.5 to 20 wt % of at least one builder; and
  c. 0.01 to 10 wt % of at least one bleach component.

The invention further relates to the use of a composition for deep cleaning of an item, wherein the item is a textile or a surface. The invention further relates to Use of a cleaning composition comprising a DNase, a protease and at least one cleaning component for deep cleaning of an item, wherein the item is a textile or a surface.

The invention further relates to a method of formulating a cleaning composition comprising adding a DNase, a protease and at least one cleaning component. The invention further relates to a kit intended for deep cleaning, wherein the kit comprises a solution of an enzyme mixture comprising a DNase and a protease. The invention further relates to a method of deep cleaning on an item, comprising the steps of: a) contacting the item with a solution comprising an enzyme mixture comprising a DNase, a protease and a cleaning component, wherein the cleaning component is selected from 0.1 to 15 wt % of at least one a surfactant; 0.5 to 20 wt % of at least one builder; and 0.01 to 10 wt % of at least one bleach component; and b) optionally rinsing the item, wherein the item is preferably a textile. The invention further relates to a method of deep cleaning of an item, comprising the steps of:
  a) contacting the item with a cleaning composition comprising a DNase, a protease and at least one cleaning component; and
  b) and optionally rinsing the item, wherein the item is preferably a textile.

DETAILED DESCRIPTION OF THE INVENTION

Various enzymes are applied in cleaning processes each targeting specific types of stains such as protein, starch and grease stains. Enzymes are now standard ingredients in detergents for laundry and dish wash. The effectiveness of these commercial enzymes provides detergents which removes much of the soiling. However, components of organic matters such as biofilm and EPS (extracellular polymeric substance) constitute a challenging type of staining due to the complex nature of such organic matters. None of the commercially available cleaning compositions effectively remove or reduce EPS and/or biofilm related stains. Biofilm may be produced when a group of microorganisms' cells stick to each other or stick to a surface, such as a textile, dishware or hard surface or another kind of surface. These adherent cells are frequently embedded within a self-produced matrix of extracellular polymeric substance (EPS), which constitute 50% to 90% of the biofilm's total organic matter. EPS is mostly composed of polysaccharides (exopolysaccharides) and proteins, but include other macro-molecules such as eDNA, lipids and other organic substances. These proteins and macromolecules such as DNA are difficult to remove with the traditional cleaning compositions. Organic matter like EPS or biofilm may be sticky or gluing, which when present on textile, may give rise to redeposition or backstaining of soil resulting in a greying of the textile. When dirty laundry items are washed together with less dirty laundry items the dirt present in the wash liquor tend to stick to organic matter e.g. biofilm or biofilm components as a result, hereof the laundry item is more "soiled" after wash than before wash. This is effect may also be termed re-deposition. Another drawback of the presence organic matter e.g. biofilm is the malodor.

The compositions of the invention comprise a blend of DNase and protease and effectively reduce or remove organic components, such as protein and DNA from surfaces such as textiles and hard surfaces e.g. dishes.

The compositions of the invention comprise a blend of DNase and protease and effectively reduce or limit redeposition when applied in e.g. laundry process.

The compositions of the invention comprise a blend of DNase and protease and effectively reduce or limit malodor of e.g. textiles or hard surfaces such as dishes.

The compositions of the invention comprise a blend of DNase and protease and improve whiteness of textile.

A composition of the invention is preferably a cleaning composition, the composition of the invention comprises at least one DNase and at least one protease. Examples of useful DNases and proteases are mentioned below in the sections "Polypeptides having DNase activity" and "Polypeptides having protease activity" respectively.

Polypeptides Having DNase Activity

The term "DNase" means a polypeptide with DNase (deoxyribonuclease) activity that catalyzes the hydrolytic cleavage of phosphodiester linkages in a DNA backbone, thus degrading DNA. Exodeoxyribonuclease cut or cleaves residues at the end of the DNA back bone where endodeoxyribonucleases cleaves or cut within the DNA backbone. A DNase may cleave only double-stranded DNA or may cleave double stranded and single stranded DNA. The term "DNases" and the expression "a polypeptide with DNase activity" are used interchangeably throughout the application. For purposes of the present invention, DNase activity is determined according to the procedure described in the Assay I or Assay III.

Preferably the DNase is selected from any of the enzyme classes E.C.3.1, preferably E.C.3.1.21, e.g. such as E.C.3.1.21.X, where X=1, 2, 3, 4, 5, 6, 7, 8 or 9, or e.g. Deoxyribonuclease I, Deoxyribonuclease IV, Type I site-specific deoxyribonuclease, Type II site-specific deoxyribonuclease, Type III site-specific deoxyribonuclease, CC-preferring endo-deoxyribonuclease, Deoxyribonuclease V, T(4) deoxyribonuclease II, T(4) deoxyribonuclease IV or E.C. 3.1.22.Y where Y=1, 2, 4 or 5, e.g. Deoxyribonuclease II, *Aspergillus* deoxyribonuclease K(1), Crossover junction endo-deoxyribonuclease, Deoxyribonuclease X.

Preferably, the polypeptide having DNase activity is obtained from a microorganism and the DNase is a microbial enzyme. The DNase is preferably of fungal or bacterial origin.

The DNase may be obtainable from *Bacillus* e.g. such as a *Bacillus licheniformis, Bacillus subtilis, Bacillus* sp-62451, *Bacillus horikoshii, Bacillus* sp-62451, *Bacillus* sp-16840, *Bacillus* sp-62668, *Bacillus* sp-13395, *Bacillus horneckiae, Bacillus* sp-11238, *Bacillus cibi, Bacillus idriensis, Bacillus* sp-62520, *Bacillus* sp-16840, *Bacillus* sp-62668, *Bacillus algicola, Bacillus vietnamensis, Bacillus hwajinpoensis, Bacillus indicus, Bacillus marisflavi, Bacillus luciferensis, Bacillus* sp. SA2-6.

The DNase may also be obtained from any of the following *Pyrenochaetopsis* sp; *Vibrissea flavovirens, Setosphaeria rostrate, Endophragmiella valdina, Corynespora cassiicola, Paraphoma* sp. XZ1965, *Monilinia fructicola, Curvularia lunata, Penicillium reticulisporum, Penicillium quercetorum, Setophaeosphaeria* sp., *Alternaria, Alternaria* sp. XZ2545, *Trichoderma reesei, Chaetomium thermophilum, Scytalidium thermophilum, Metapochonia suchlasporia, Daldinia fissa, Acremonium* sp. XZ2007, *Acremonium* sp. XZ2414, *Acremonium dichromosporum, Sarocladium* sp. XZ2014, *Metarhizium* sp. HNA15-2, *Isaria tenuipes Scytalidium circinaturn, Metarhizium lepidiotae, Thermobispora bispora, Sporormia fimetaria, Pycnidiophora* cf. *dispera*, Enviromental sample D, Enviromental sample O, Clavicipitaceae sp-70249, *Westerdykella* sp. AS85-2, *Humicolopsis cephalosporioides, Neosartorya massa, Roussoella intermedia, Pleosporales, Phaeosphaeria* or *Didymosphaeria futilis*.

The DNases to be used in a composition of the invention preferable belong to the NUC1 group of DNases. The NUC1 group of DNases comprises polypeptides which in addition to having DNase activity, may comprise one or more of the motifs [T/D/S][G/N]PQL (SEQ ID NO 69), [F/LN/I]A[N/R]D[L/I/P/V] (SEQ ID NO: 70), or C[D/N]T[A/R] (SEQ ID NO: 71). One embodiment of the invention relates to a composition comprising a protease and polypeptides having DNase activity, wherein the polypeptides comprises one or more of the motifs [T/D/S][G/N]PQL (SEQ ID NO 69), [F/LN/I]A[N/R]D[L/I/P/V] (SEQ ID NO: 70) or C[D/N]T [A/R] (SEQ ID NO: 71). The DNases preferably comprises a NUC1_A domain [D/Q][IN]DH (SEQ ID NO 72). In addition to comprising any of the domain motifs [T/D/S] [G/N]PQL, [F/LN/I]A[N/R]D[L/I/P/V] or C[D/N]T[A/R] the polypeptides having DNase activity, to be used in a composition of the invention, may comprise the NUC1_A domain and may share the common motif [D/Q][I/V]DH (SEQ ID NO 72). One embodiment the invention relates to compositions comprising a protease and polypeptides, which comprises one or more motifs selected from the motifs [T/D/S][G/N]PQL, [F/LN/I]A[N/R]D[L/I/PN], C[D/N]T[A/R] and [D/Q][I/V]DH, wherein the polypeptides have DNase activity.

The DNases to be added to a composition of the invention preferably belong to the group of DNases comprised in the GYS-clade, which are group of DNases on the same branch of a phylogenetic tree having both structural and functional similarities. These NUC1 and/or NUC1_A DNases comprise the conservative motifs [D/M/L][S/T]GYSR[D/N] (SEQ ID NO: 73) or ASXNRSKG (SEQ ID NO: 74) and share similar structural and functional properties. The DNases of the GYS-clade are preferably obtained from *Bacillus* genus.

One embodiment of the invention relates to a composition comprising a protease and a polypeptide of the GYS Glade having DNase activity, optionally wherein the polypeptide comprise one or both of the motifs [D/M/L][S/T]GYSR[D/N] (SEQ ID NO: 73), ASXNRSKG (SEQ ID NO: 74) and wherein the polypeptide is selected from the group of polypeptides:

a) a polypeptide having at least 60%, at least 65%, at least 70%, at least 75% at least 80%, at least 85%, at least 90%, at least 95%, at least 98% or 100% sequence identity to the polypeptide shown in SEQ ID NO: 1, b) a polypeptide having at least 60%, at least 65%, at least 70%, at least 75% at least 80%, at least 85%, at least 90%, at least 95%, at least 98% or 100% sequence identity to the polypeptide shown in SEQ ID NO: 2, c) a polypeptide having at least 60%, at least 65%, at least 70%, at least 75% at least 80%, at least 85%, at least 90%, at least 95%, at least 98% or 100% sequence identity to the polypeptide shown in SEQ ID NO: 3, d) a polypeptide having at least 60%, at least 65%, at least 70%, at least 75% at least 80%, at least 85%, at least 90%, at least 95%, at least 98% or 100% sequence identity to the polypeptide shown in SEQ ID NO: 4, e) a polypeptide having at least 60%, at least 65%, at least 70%, at least 75% at least 80%, at least 85%, at least 90%, at least 95%, at least 98% or 100% sequence identity to the polypeptide shown in SEQ ID NO: 5, f) a polypeptide having at least 60%, at least 65%, at least 70%, at least 75% at least 80%, at least 85%, at least 90%, at least 95%, at least 98% or 100% sequence identity to the polypeptide shown in SEQ ID NO: 6, g) a polypeptide having at least 60%, at least 65%, at least 70%, at least 75% at least 80%, at least 85%, at least 90%, at least 95%, at least 98% or 100% sequence identity to the polypeptide shown in SEQ ID NO: 7, h) a polypeptide having at least 60%, at least 65%, at least 70%, at least 75% at least 80%, at least 85%, at least 90%, at least 95%, at least 98% or 100% sequence identity to the polypeptide shown in SEQ ID NO: 8, i) a polypeptide having at least 60%, at least 65%, at least 70%, at least 75% at least 80%, at least 85%, at least 90%, at least 95%, at least 98% or 100% sequence identity to the polypeptide shown in SEQ ID NO: 9, j) a polypeptide having at least 60%, at least 65%, at least 70%, at least 75% at least 80%, at least 85%, at least 90%, at least 95%, at least 98% or 100% sequence identity to the polypeptide shown in SEQ ID NO: 10, k) a polypeptide having at least 60%, at least 65%, at least 70%, at least 75% at least 80%, at least 85%, at least 90%, at least 95%, at least 98% or 100% sequence identity to the polypeptide shown in SEQ ID NO: 11, l) a polypeptide having at least 60%, at least 65%, at least 70%, at least 75% at least 80%, at least 85%, at least 90%, at least 95%, at least 98% or 100% sequence identity to the polypeptide shown in SEQ ID NO: 12, m) a polypeptide having at least 60%, at least 65%, at least 70%, at least 75% at least 80%, at least 85%, at least 90%, at least 95%, at least 98% or 100% sequence identity to the polypeptide shown in SEQ ID NO: 13, n) a polypeptide having at least 60%, at least 65%, at least 70%, at least 75% at least 80%, at least 85%, at least 90%, at least 95%, at least 98% or 100% sequence identity to the polypeptide shown in SEQ ID NO: 14, o) a polypeptide having at least 60%, at least 65%, at least 70%, at least 75% at least 80%, at least 85%, at least 90%, at least 95%, at least 98% or 100% sequence identity to the polypeptide shown in SEQ ID NO: 15, p) a polypeptide having at least 60%, at least 65%, at least 70%, at least 75% at least 80%, at least 85%, at least 90%, at least 95%, at least 98% or 100% sequence identity to the polypeptide shown in SEQ ID NO: 16, q) a polypeptide having at least 60%, at least 65%, at least 70%, at least 75% at least 80%, at least 85%, at least 90%, at least 95%, at least 98% or 100% sequence identity to the polypeptide shown in SEQ ID NO: 17, r) a polypeptide having at least 60%, at least 65%, at least 70%, at least 75% at least 80%, at least 85%, at least 90%, at least 95%, at least 98% or 100% sequence identity to the polypeptide shown in SEQ ID NO: 18, s) a polypeptide having at least 60%, at least 65%, at least 70%, at least 75% at least 80%, at least 85%, at least 90%, at least 95%, at least 98% or 100% sequence identity to the polypeptide shown in SEQ ID NO: 19, t) a polypeptide having at least 60%, at least 65%, at least 70%, at least 75% at least 80%, at least 85%, at least 90%, at least 95%, at least 98% or 100% sequence identity to the polypeptide shown in SEQ ID NO: 20, u) a polypeptide having at least 60%, at least 65%, at least 70%, at least 75% at least 80%, at least 85%, at least 90%, at least 95%, at least 98% or 100% sequence identity to the polypeptide shown in SEQ ID NO: 21, v) a polypeptide having at least 60%, at least 65%, at least 70%, at least 75% at least 80%, at least 85%, at least 90%, at least 95%, at least 98% or 100% sequence identity to the polypeptide shown in SEQ ID NO: 22, w) a polypeptide having at least 60%, at least 65%, at least 70%, at least 75% at least 80%, at least 85%, at least 90%, at least 95%, at least 98% or 100% sequence identity to the polypeptide shown in SEQ ID NO: 23, x) a polypeptide having at least 60%, at least 65%, at least 70%, at least 75% at least 80%, at least 85%, at least 90%, at least 95%, at least 98% or 100% sequence identity to the polypeptide shown in SEQ ID NO: 24, and y) a polypeptide having at least 60%, at least 65%, at least 70%, at least 75% at least 80%, at least 85%, at least 90%, at least 95%, at least 98% or 100% sequence identity to the polypeptide shown in SEQ ID NO: 25.

Polypeptides having DNase activity and which comprise the GYS-clade motifs have shown particularly good deep cleaning properties e.g. the DNases are particularly effective in removing or reducing components of organic matter, such as DNA, from an item such as a textile or a hard surface. In addition, these DNases are particularly effective in removing or reducing malodor, from an item such as a textile or a hard surface. Further, the GYS-clade DNases are particularly effective in preventing redeposition when laundering an item such as textile.

In one embodiment the DNases to be added in a composition of the invention preferably belong to the group of DNases comprised in the NAWK-clade, which are NUC1 and NUC1_A DNases, which may further comprise the conservative motifs [V/I]PL[S/A]NAWK (SEQ ID NO: 75) or NPQL (SEQ ID NO: 76).

One embodiment of the invention relates to a composition comprising a protease and a polypeptide of the NAWK-clade having DNase activity, optionally wherein the polypeptide comprise one or both of the motifs [V/I]PL[S/A]NAWK (SEQ ID NO: 75) or NPQL (SEQ ID NO: 76) and wherein the polypeptide is selected from the group of polypeptides:

a) a polypeptide having at least 60%, at least 65%, at least 70%, at least 75% at least 80%, at least 85%, at least 90%, at least 95%, at least 98% or 100% sequence identity to the polypeptide shown in SEQ ID NO: 26, b) a polypeptide having at least 60%, at least 65%, at least 70%, at least 75% at least 80%, at least 85%, at least 90%, at least 95%, at least 98% or 100% sequence identity to the polypeptide shown in SEQ ID NO: 27, c) a polypeptide having at least 60%, at least 65%, at least 70%, at least 75% at least 80%, at least 85%, at least 90%, at least 95%, at least 98% or 100% sequence identity to the polypeptide shown in SEQ ID NO: 28, d) a polypeptide having at least 60%, at least 65%, at least 70%, at least 75% at least 80%, at least 85%, at least 90%, at least 95%, at least 98% or 100% sequence identity to the polypeptide shown in SEQ ID NO: 29, e) a polypeptide having at least 60%, at least 65%, at least 70%, at least 75% at least 80%, at least 85%, at least 90%, at least 95%, at least 98% or 100% sequence identity to the polypeptide shown in SEQ ID NO: 30, f) a polypeptide having at least 60%, at least 65%, at least 70%, at least 75% at least 80%, at least 85%, at least 90%, at least 95%, at least 98% or 100% sequence identity to the polypeptide shown in SEQ ID NO: 31, g) a polypeptide having at least 60%, at least 65%, at least 70%, at least 75% at least 80%, at least 85%, at least 90%, at least 95%, at least 98% or 100% sequence identity to the polypeptide shown in SEQ ID NO: 32, h) a polypeptide having at least 60%, at least 65%, at least 70%, at least 75% at least 80%, at least 85%, at least 90%, at least 95%, at least 98% or 100% sequence identity to the polypeptide shown in SEQ ID NO: 33,
i) a polypeptide having at least 60%, at least 65%, at least 70%, at least 75% at least 80%, at least 85%, at least 90%, at least 95%, at least 98% or 100% sequence identity to the polypeptide shown in SEQ ID NO: 34,
j) a polypeptide having at least 60%, at least 65%, at least 70%, at least 75% at least 80%, at least 85%, at least 90%, at least 95%, at least 98% or 100% sequence identity to the polypeptide shown in SEQ ID NO: 35,
k) a polypeptide having at least 60%, at least 65%, at least 70%, at least 75% at least 80%, at least 85%, at least 90%, at least 95%, at least 98% or 100% sequence identity to the polypeptide shown in SEQ ID NO: 36,
l) a polypeptide having at least 60%, at least 65%, at least 70%, at least 75% at least 80%, at least 85%, at least 90%, at least 95%, at least 98% or 100% sequence identity to the polypeptide shown in SEQ ID NO: 37, and
m) a polypeptide having at least 60%, at least 65%, at least 70%, at least 75% at least 80%, at least 85%, at least 90%, at least 95%, at least 98% or 100% sequence identity to the polypeptide shown in SEQ ID NO: 38.

Polypeptides having DNase activity and which comprise the NAWK-clade motifs have shown particularly good deep cleaning properties e.g. the DNases are particularly effective in removing or reducing components of organic matter, such as DNA, from an item such as a textile or a hard surface. In addition, these DNases are particularly effective in removing or reducing malodor, from an item such as a textile or a hard surface. Further, the NAWK-clade DNases are particularly effective in preventing redeposition when laundering an item such as textile.

The DNases to be added in a composition of the invention preferably belong to the group of DNases comprised in the KNAW-clade, which are NUC1 and NUC1_A DNases which may further comprise the conservative motifs P[Q/E]L[W/Y] (SEQ ID NO: 77) or [K/H/E]NAW (SEQ ID NO: 78).

One embodiment of the invention relates to a composition comprising a protease and a polypeptide of the KNAW Glade having DNase activity, optionally wherein the polypeptide comprise one or both of the motifs P[Q/E]L[W/Y] (SEQ ID NO: 77) or [K/H/E]NAW (SEQ ID NO: 78), and wherein the polypeptide is selected from the group of polypeptides:
a) a polypeptide having at least 60%, at least 65%, at least 70%, at least 75% at least 80%, at least 85%, at least 90%, at least 95%, at least 98% or 100% sequence identity to the polypeptide shown in SEQ ID NO: 39,
b) a polypeptide having at least 60%, at least 65%, at least 70%, at least 75% at least 80%, at least 85%, at least 90%, at least 95%, at least 98% or 100% sequence identity to the polypeptide shown in SEQ ID NO: 40,
c) a polypeptide having at least 60%, at least 65%, at least 70%, at least 75% at least 80%, at least 85%, at least 90%, at least 95%, at least 98% or 100% sequence identity to the polypeptide shown in SEQ ID NO: 41,
d) a polypeptide having at least 60%, at least 65%, at least 70%, at least 75% at least 80%, at least 85%, at least 90%, at least 95%, at least 98% or 100% sequence identity to the polypeptide shown in SEQ ID NO: 42,
e) a polypeptide having at least 60%, at least 65%, at least 70%, at least 75% at least 80%, at least 85%, at least 90%, at least 95%, at least 98% or 100% sequence identity to the polypeptide shown in SEQ ID NO: 43
f) a polypeptide having at least 60%, at least 65%, at least 70%, at least 75% at least 80%, at least 85%, at least 90%, at least 95%, at least 98% or 100% sequence identity to the polypeptide shown in SEQ ID NO: 44,
g) a polypeptide having at least 60%, at least 65%, at least 70%, at least 75% at least 80%, at least 85%, at least 90%, at least 95%, at least 98% or 100% sequence identity to the polypeptide shown in SEQ ID NO: 45,
h) a polypeptide having at least 60%, at least 65%, at least 70%, at least 75% at least 80%, at least 85%, at least 90%, at least 95%, at least 98% or 100% sequence identity to the polypeptide shown in SEQ ID NO: 46,
i) a polypeptide having at least 60%, at least 65%, at least 70%, at least 75% at least 80%, at least 85%, at least 90%, at least 95%, at least 98% or 100% sequence identity to the polypeptide shown in SEQ ID NO: 47,
j) a polypeptide having at least 60%, at least 65%, at least 70%, at least 75% at least 80%, at least 85%, at least 90%, at least 95%, at least 98% or 100% sequence identity to the polypeptide shown in SEQ ID NO: 48,
k) a polypeptide having at least 60%, at least 65%, at least 70%, at least 75% at least 80%, at least 85%, at least 90%, at least 95%, at least 98% or 100% sequence identity to the polypeptide shown in SEQ ID NO: 49,
l) a polypeptide having at least 60%, at least 65%, at least 70%, at least 75% at least 80%, at least 85%, at least 90%, at least 95%, at least 98% or 100% sequence identity to the polypeptide shown in SEQ ID NO: 50, and
m) a polypeptide having at least 60%, at least 65%, at least 70%, at least 75% at least 80%, at least 85%, at least 90%, at least 95%, at least 98% or 100% sequence identity to the polypeptide shown in SEQ ID NO: 51.

Polypeptides having DNase activity and which comprise the KNAW-clade motifs have shown particularly good deep cleaning properties e.g. the DNases are particularly effective in removing or reducing components of organic matter, such as DNA, from an item such as a textile or a hard surface. In addition, these DNases are particularly effective in removing or reducing malodor, from an item such as a textile or a hard surface. Further, the KNAW-clade DNases are particularly effective in preventing redeposition when laundering an item such as textile.

In some embodiments, the present invention relates compositions comprising a protease and a polypeptide obtainable from *Bacillus* e.g. obtainable from *Bacillus* sp-62451 and having a sequence identity to the polypeptide shown in SEQ ID NO: 1 of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 1.

In some embodiments, the present invention relates to compositions comprising a protease and a polypeptide obtainable from *Bacillus* e.g. obtainable from *Bacillus horikoshii* and having a sequence identity to the polypeptide shown in SEQ ID NO: 2 of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 2.

In some embodiments, the present invention relates to compositions comprising a protease and a polypeptide obtainable from *Bacillus* e.g. obtainable from *Bacillus* sp-62520 and having a sequence identity to the polypeptide shown in SEQ ID NO: 3 of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 3.

In some embodiments, the present invention relates to compositions comprising a protease and a polypeptide obtainable from *Bacillus* e.g. obtainable from *Bacillus* sp-62520 and having a sequence identity to the polypeptide shown in SEQ ID NO: 4 of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 4.

In some embodiments, the present invention relates to compositions comprising a protease and a polypeptide obtainable from *Bacillus* e.g. obtainable from *Bacillus horikoshii* and having a sequence identity to the polypeptide shown in SEQ ID NO: 5 of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 5.

In some embodiments, the present invention relates to compositions comprising a protease and a polypeptide obtainable from *Bacillus* e.g. obtainable from *Bacillus horikoshii* and having a sequence identity to the polypeptide shown in SEQ ID NO: 6 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 6.

In some embodiments, the present invention relates to compositions comprising a protease and a polypeptide obtainable from *Bacillus* e.g. obtainable from *Bacillus* sp-16840 and having a sequence identity to the polypeptide shown in SEQ ID NO: 7 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 7.

In some embodiments, the present invention relates to compositions comprising a protease and a polypeptide obtainable from *Bacillus* e.g. obtainable from *Bacillus* sp-16840 and having a sequence identity to the polypeptide shown in SEQ ID NO: 8 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 8.

In some embodiments, the present invention relates to compositions comprising a protease and a polypeptide obtainable from *Bacillus* e.g. obtainable from *Bacillus* sp-62668 and having a sequence identity to the polypeptide shown in SEQ ID NO: 9 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 9.

In some embodiments, the present invention relates to compositions comprising a protease and a polypeptide obtainable from *Bacillus* e.g. obtainable from *Bacillus* sp-13395 and having a sequence identity to the polypeptide shown in SEQ ID NO: 10 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 10.

In some embodiments, the present invention relates to compositions comprising a protease and a polypeptide obtainable from *Bacillus* e.g. obtainable from *Bacillus* horneckiae and having a sequence identity to the polypeptide shown in SEQ ID NO: 11 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 11.

In some embodiments, the present invention relates to compositions comprising a protease and a polypeptide obtainable from *Bacillus* e.g. obtainable from *Bacillus* sp-11238 and having a sequence identity to the polypeptide shown in SEQ ID NO: 12 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 12.

In some embodiments, the present invention relates to compositions comprising a protease and a polypeptide obtainable from *Bacillus* e.g. obtainable from *Bacillus* cibi and having a sequence identity to the polypeptide shown in SEQ ID NO: 13 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 13.

In some embodiments, the present invention relates to compositions comprising a protease and a polypeptide obtainable from *Bacillus* e.g. obtainable from *Bacillus* sp-18318 and having a sequence identity to the polypeptide shown in SEQ ID NO: 14 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 14.

In some embodiments, the present invention relates to compositions comprising a protease and a polypeptide obtainable from *Bacillus* e.g. obtainable from *Bacillus idriensis* and having a sequence identity to the polypeptide shown in SEQ ID NO: 15 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 15.

In some embodiments, the present invention relates to compositions comprising a protease and a polypeptide obtainable from *Bacillus* e.g. obtainable from *Bacillus algicola* having a sequence identity to the polypeptide shown in SEQ ID NO: 16 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 16.

In some embodiments, the present invention relates to compositions comprising a protease and a polypeptide obtainable from Enviromental sample J and having a sequence identity to the polypeptide shown in SEQ ID NO: 17 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 17.

In some embodiments, the present invention relates to compositions comprising a protease and a polypeptide obtainable from *Bacillus* e.g. obtainable from *Bacillus vietnamensis* and having a sequence identity to the polypeptide shown in SEQ ID NO: 18 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 18.

In some embodiments, the present invention relates to compositions comprising a protease and a polypeptide obtainable from *Bacillus* e.g. obtainable from *Bacillus hwajinpoensis* and having a sequence identity to the polypeptide shown in SEQ ID NO: 19 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 19.

In some embodiments, the present invention relates to compositions comprising a protease and a polypeptide obtainable from *Paenibacillus mucilaginosus* and having a sequence identity to the polypeptide shown in SEQ ID NO: 20 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 20.

In some embodiments, the present invention relates to compositions comprising a protease and a polypeptide obtainable from *Bacillus* e.g. obtainable from *Bacillus indicus* and having a sequence identity to the polypeptide shown in SEQ ID NO: 21 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 21.

In some embodiments, the present invention relates to compositions comprising a protease and a polypeptide obtainable from *Bacillus* e.g. obtainable from *Bacillus marisflavi* and having a sequence identity to the polypeptide shown in SEQ ID NO: 22 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 22.

In some embodiments, the present invention relates to compositions comprising a protease and a polypeptide obtainable from *Bacillus* e.g. obtainable from *Bacillus luciferensis* and having a sequence identity to the polypeptide shown in SEQ ID NO: 23 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 23.

In some embodiments, the present invention relates to compositions comprising a protease and a polypeptide obtainable from *Bacillus* e.g. obtainable from *Bacillus marisflavi* and having a sequence identity to the polypeptide shown in SEQ ID NO: 24 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 24.

In some embodiments, the present invention relates to compositions comprising a protease and a polypeptide obtainable from *Bacillus* e.g. obtainable from *Bacillus* sp. SA2-6 and having a sequence identity to the polypeptide shown in SEQ ID NO: 25 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 25.

In some embodiments, the present invention relates to compositions comprising a protease and a polypeptide obtainable from *Pyrenochaetopsis* sp. and having a sequence identity to the polypeptide shown in SEQ ID NO: 26 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 26.

In some embodiments, the present invention relates to compositions comprising a protease and a polypeptide obtainable from *Vibrissea flavovirens* and having a sequence identity to the polypeptide shown in SEQ ID NO: 27 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 27.

In some embodiments, the present invention relates to compositions comprising a protease and a polypeptide obtainable from *Setosphaeria rostrate* and having a sequence identity to the polypeptide shown in SEQ ID NO: 28 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 28.

In some embodiments, the present invention relates to compositions comprising a protease and a polypeptide obtainable from *Endophragmiella valdina* and having a sequence identity to the polypeptide shown in SEQ ID NO: 29 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 29.

In some embodiments, the present invention relates to compositions comprising a protease and a polypeptide obtainable from *Corynespora cassiicola* and having a sequence identity to the polypeptide shown in SEQ ID NO: 30 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 30.

In some embodiments, the present invention relates to compositions comprising a protease and a polypeptide obtainable from *Paraphoma* sp. XZ1965 and having a sequence identity to the polypeptide shown in SEQ ID NO: 31 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 31.

In some embodiments, the present invention relates to compositions comprising a protease and a polypeptide obtainable from *Monilinia fructicola* and having a sequence identity to the polypeptide shown in SEQ ID NO: 32 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 32.

In some embodiments, the present invention relates to compositions comprising a protease and a polypeptide obtainable from *Curvularia lunata* and having a sequence identity to the polypeptide shown in SEQ ID NO: 33 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 33.

In some embodiments, the present invention relates to compositions comprising a protease and a polypeptide obtainable from *Penicillium reticulisporum* and having a sequence identity to the polypeptide shown in SEQ ID NO: 34 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 34.

In some embodiments, the present invention relates to compositions comprising a protease and a polypeptide obtainable from *Penicillium quercetorum* and having a sequence identity to the polypeptide shown in SEQ ID NO: 35 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 35.

In some embodiments, the present invention relates to compositions comprising a protease and a polypeptide obtainable from *Setophaeosphaeria* sp. and having a sequence identity to the polypeptide shown in SEQ ID NO: 36 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 36.

In some embodiments, the present invention relates to compositions comprising a protease and a polypeptide obtainable from *Alternaria* sp. XZ2545 and having a sequence identity to the polypeptide shown in SEQ ID NO: 37 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 37.

In some embodiments, the present invention relates to compositions comprising a protease and a polypeptide obtainable from *Alternaria* and having a sequence identity to the polypeptide shown in SEQ ID NO: 38 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 38.

In some embodiments, the present invention relates to compositions comprising a protease and a polypeptide obtainable from *Trichoderma reesei* and having a sequence identity to the polypeptide shown in SEQ ID NO: 39 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 39.

In some embodiments, the present invention relates to compositions comprising a protease and a polypeptide obtainable from *Chaetomium thermophilum* and having a sequence identity to the polypeptide shown in SEQ ID NO: 40 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 40.

In some embodiments, the present invention relates to compositions comprising a protease and a polypeptide obtainable from *Scytalidium thermophilum* and having a sequence identity to the polypeptide shown in SEQ ID NO: 41 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 41.

In some embodiments, the present invention relates to compositions comprising a protease and a polypeptide obtainable from *Metapochonia suchlasporia* and having a sequence identity to the polypeptide shown in SEQ ID NO: 42 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 42.

In some embodiments, the present invention relates to compositions comprising a protease and a polypeptide obtainable from *Daldinia fissa* and having a sequence identity to the polypeptide shown in SEQ ID NO: 43 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 43.

In some embodiments, the present invention relates to compositions comprising a protease and a polypeptide obtainable from *Acremonium* sp. XZ2007 and having a sequence identity to the polypeptide shown in SEQ ID NO: 44 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 44.

In some embodiments, the present invention relates to compositions comprising a protease and a polypeptide obtainable from *Acremonium dichromosporum* and having a sequence identity to the polypeptide shown in SEQ ID NO: 45 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 45.

In some embodiments, the present invention relates to compositions comprising a protease and a polypeptide obtainable from *Sarocladium* sp. XZ2014 and having a sequence identity to the polypeptide shown in SEQ ID NO: 46 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 46.

In some embodiments, the present invention relates to compositions comprising a protease and a polypeptide obtainable from *Metarhizium* sp. HNA15-2 and having a sequence identity to the polypeptide shown in SEQ ID NO: 47 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 47.

In some embodiments, the present invention relates to compositions comprising a protease and a polypeptide obtainable from *Acremonium* sp. XZ2414 and having a sequence identity to the polypeptide shown in SEQ ID NO: 48 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 48.

In some embodiments, the present invention relates to compositions comprising a protease and a polypeptide obtainable from *Isaria tenuipes* and having a sequence identity to the polypeptide shown in SEQ ID NO: 49 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 49.

In some embodiments, the present invention relates to compositions comprising a protease and a polypeptide obtainable from *Scytalidium circinatum* and having a sequence identity to the polypeptide shown in SEQ ID NO: 50 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 50.

In some embodiments, the present invention relates to compositions comprising a protease and a polypeptide obtainable from *Metarhizium lepidiotae* and having a sequence identity to the polypeptide shown in SEQ ID NO: 51 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 51.

In some embodiments, the present invention relates to compositions comprising a protease and a polypeptide obtainable from *Thermobispora bispora* and having a sequence identity to the polypeptide shown in SEQ ID NO: 52 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 52.

In some embodiments, the present invention relates to compositions comprising a protease and a polypeptide obtainable from *Sporormia fimetaria* and having a sequence identity to the polypeptide shown in SEQ ID NO: 53 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 53.

In some embodiments, the present invention relates to compositions comprising a protease and a polypeptide obtainable from *Pycnidiophora* cf. *dispera* and having a sequence identity to the polypeptide shown in SEQ ID NO: 54 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 54.

In some embodiments, the present invention relates to compositions comprising a protease and a polypeptide obtainable from Enviromental sample D and having a sequence identity to the polypeptide shown in SEQ ID NO: 55 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 55.

In some embodiments, the present invention relates to compositions comprising a protease and a polypeptide obtainable from Enviromental sample 0 and having a sequence identity to the polypeptide shown in SEQ ID NO: 56 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 56.

In some embodiments, the present invention relates to compositions comprising a protease and a polypeptide obtainable from Clavicipitaceae sp-70249 and having a sequence identity to the polypeptide shown in SEQ ID NO: 57 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 57.

In some embodiments, the present invention relates to compositions comprising a protease and a polypeptide obtainable from *Westerdykella* sp. AS85-2 and having a sequence identity to the polypeptide shown in SEQ ID NO: 58 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 58.

In some embodiments, the present invention relates to compositions comprising a protease and a polypeptide obtainable from *Humicolopsis cephalosporioides* and having a sequence identity to the polypeptide shown in SEQ ID NO: 59 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 59.

In some embodiments, the present invention relates to compositions comprising a protease and a polypeptide obtainable from *Neosartorya massa* and having a sequence identity to the polypeptide shown in SEQ ID NO: 60 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 60.

In some embodiments, the present invention relates to compositions comprising a protease and a polypeptide obtainable from *Roussoella intermedia* and having a sequence identity to the polypeptide shown in SEQ ID NO: 61 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 61.

In some embodiments, the present invention relates to compositions comprising a protease and a polypeptide obtainable from *Pleosporales* and having a sequence identity to the polypeptide shown in SEQ ID NO: 62 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 62.

In some embodiments, the present invention relates to compositions comprising a protease and a polypeptide obtainable from *Phaeosphaeria* and having a sequence identity to the polypeptide shown in SEQ ID NO: 63 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 63.

In some embodiments, the present invention relates to compositions comprising a protease and a polypeptide obtainable from *Didymosphaeria futilis* and having a sequence identity to the polypeptide shown in SEQ ID NO: 64 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 64.

In some embodiments, the present invention relates to compositions comprising a protease and a polypeptide obtainable from *Bacillus* e.g. obtainable from *Bacillus licheniformis* having a sequence identity to the polypeptide shown in SEQ ID NO: 65 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 65.

In some embodiments, the present invention relates to compositions comprising a protease and a polypeptide obtainable from *Bacillus* e.g. obtainable from *Bacillus subtilis* having a sequence identity to the polypeptide shown in SEQ ID NO: 66 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 66.

In some embodiments, the present invention relates to compositions comprising a protease and a polypeptide obtainable from *Aspergillus* e.g. obtainable from *Aspergillus oryzae* having a sequence identity to the polypeptide shown in SEQ ID NO: 67 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 67.

In some embodiments, the present invention relates to compositions comprising a protease and a polypeptide obtainable from *Trichoderma* e.g. obtainable from *Trichoderma harzianum* having a sequence identity to the polypeptide shown in SEQ ID NO: 68 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 68.

Polypeptides Having Protease Activity

Suitable proteases include those of bacterial, fungal, plant, viral or animal origin e.g. vegetable or microbial origin. Microbial origin is preferred. Chemically modified or protein engineered mutants are included. It may be an alkaline protease, such as a serine protease or a metalloprotease. A serine protease may for example be of the S1 family, such as trypsin, or the S8 family such as subtilisin. A metalloproteases protease may for example be a thermolysin from e.g. family M4 or other metalloproteases such as those from M5, M7 or M8 families. Serine proteases are a subgroup of proteases characterized by having a serine in the active site, which forms a covalent adduct with the substrate. The subtilases may be divided into 6 sub-divisions, i.e. the Subtilisin family, the Thermitase family, the Proteinase K family, the Lantibiotic peptidase family, the Kexin family and the Pyrolysin family. The term "subtilases" refers to a sub-group of serine protease according to Siezen et al., Protein Engng. 4 (1991) 719-737 and Siezen et al. Protein Science 6 (1997) 501-523. Examples of subtilases are those derived from *Bacillus* such as *Bacillus lentus, B. alkalophilus, B. subtilis, B. amyloliquefaciens, B. pumilus* and B. *gibsonii* described in; U.S. Pat. No. 7,262,042 and WO09/021867, and subtilisin *lentus*, subtilisin *Novo*, subtilisin Carlsberg, *Bacillus licheniformis*, subtilisin BPN', subtilisin 309, subtilisin 147 and subtilisin 168 described in WO89/06279 and protease PD138 described in (WO93/18140). Other useful proteases may be those described in WO92/175177, WO01/016285, WO02/026024 and WO02/016547. Examples of trypsin-like proteases are trypsin (e.g. of porcine or bovine origin) and the *Fusarium* protease described in WO89/06270, WO94/25583 and WO05/040372, and the chymotrypsin proteases derived from *Cellumonas* described in WO05/052161 and WO05/052146. A further preferred protease is the alkaline protease from *Bacillus lentus* DSM 5483, as described for example in WO95/23221, and variants thereof, which are described in WO92/21760, WO95/23221, EP1921147 and EP1921148. Examples of metalloproteases are the neutral metalloprotease as described in WO07/044993 (Genencor Int.) such as those derived from *Bacillus amyloliquefaciens*. Suitable commercially available protease enzymes include those sold under the trade names Alcalase®, Duralase$^T$m, Durazym$^T$m, Relase®, Relase® Ultra, Savinase®, Savinase® Ultra, Primase®, Polarzyme®, Kannase®, Liquanase®, Liquanase® Ultra, Ovozyme®, Coronase®, Coronase® Ultra, Blaze®, Blaze Evity® 100T, Blaze Evity® 125T, Blaze Evity® 150T, Neutrase®, Everlase® and Esperase® (Novozymes NS), those sold under the tradename Maxatase®, Maxacal®, Maxapem®, Purafect Ox®, Purafect OxP®, Puramax®, FN2®, FN3®, FN4®, Excellase®, Excellenz P1000™, Excellenz P1250™, Eraser®, Preferenz P100™, Purafect Prime®, Preferenz P110™, Effectenz P1000™, Purafect®™, Effectenz P1050™, Purafect Ox®™, Effectenz P2000™, Purafast®, Properase®, Opticlean® and Optimase® (Danisco/DuPont), Axapem™ (Gist-Brocases N.V.), BLAP (sequence shown in FIG. 29 of U.S. Pat. No. 5,352,604) and variants hereof (Henkel AG) and KAP (*Bacillus alkalophilus subtilisin*) from Kao.

In one aspect, the protease useful in the present invention is selected from a group consisting of:

i) a protease variant of a protease parent, wherein the protease variant comprises one or more alteration(s) compared to a protease shown in SEQ ID NO 79 or SEQ ID NO 80 in one or more of the following positions: 3, 4, 9, 15, 24, 27, 42, 55, 59, 60, 66, 74, 85, 96, 97, 98, 99, 100, 101, 102, 104, 116, 118, 121, 126, 127, 128, 154, 156, 157, 158, 161, 164, 176, 179, 182, 185, 188, 189, 193, 198, 199, 200, 203, 206, 211, 212, 216, 218, 226, 229, 230, 239, 246, 255, 256, 268 and 269, wherein the positions correspond to the positions of the protease shown in SEQ ID NO 79 and wherein the protease variant has at least 60%, at least 65%, at least 70%, at least 75% at least 80%, at least 85%, at least 90%, at least 95%, at least 98% but less than 100% sequence identity to SEQ ID NO 79 or SEQ ID NO 80;

ii) a protease variant of a protease parent, wherein the protease variant comprises one or more mutation selected from the group consisting of: X3T, X4I, X9R, X9E, X15T, X24G, X24R, X27R, X42R, X55P, X59E, X59D, X60D, X60E, X66A, X74D, X85R, X96S, X97G, X97D, X97A, X97XD, X99E, X99D, X99G, X99M, X99N, X99R, X99H, X101A, X102I, X102Y, X102N, X104A, X116V, X116R, X118D, X118N, X120S, X126L, X127Q, X128A, X154D, X156E, X157D, X157P, X158E, X161A, X164S, X176E, X179E, X182E, X185N, X188P, X189E, X193M, X198D, X199I, X203W, X206G, X211Q, X211D, X212D, X212S, X216S, X226V, X229L, X230H, X239R, X246K, X255W, X255D, X255E, X256E, X256D X268A and X269H, wherein the positions correspond to the positions of the protease shown in SEQ ID NO 79, wherein the protease variant has at least 60%, at least 65%, at least 70%, at least 75% at least 80%, at least 85%, at least 90%, at least 95%, at least 98% but less than 100% sequence identity to SEQ ID NO 79 or SEQ ID NO 80;

iii) a protease comprising a substitution at one or more positions corresponding to positions 171, 173, 175, 179, or 180 of SEQ ID NO: 81, compared to the protease shown in SEQ ID NO 81, wherein the protease variant has a sequence identity of at least 60%, at least 65%, at least 70%, at least 75% at least 80%, at least 85%, at least 90%, at least 95%, at least 98% but less than 100% sequence identity to the amino acid sequence 1 to 311 of SEQ ID NO 81, iv) a protease comprising the amino acid sequence shown in SEQ ID NO 79, 80, 81 or a protease having at least 60%, at least 65%, at least 70%, at least 75% at least 80%, at least 85%, at least 90%, at least 95%, at least 98% or 100% sequence identity to; the polypeptide comprising amino acids 1-269 of SEQ ID NO 79, the polypeptide comprising amino acids 1-311 of SEQ ID NO 81 the polypeptide comprising amino acids 1-275 of SEQ ID NO 80;

v) a protease comprising the amino acid sequence shown in SEQ ID NO 82, SEQ ID NO 83, SEQ ID NO 84, SEQ ID NO 85, SEQ ID NO 86 or a protease having at least 60%, at least 65%, at least 70%, at least 75% at least 80%, at least 85%, at least 90%, at least 95%, at least 98% or preferably 100% sequence identity hereto;

vi) One or more of the following protease variants selected from the group:

SEQ ID NO 79+T22R+S99G+S101A+V102I+A226V+Q239R,

SEQ ID NO 80+S24G+S53G+S78N+S101N+G128A+Y217Q,

SEQ ID NO 80+S24G+S53G+S78N+S101N+G128S+Y217Q,

SEQ ID NO 79+S9E+N42R+N74D+V199I+Q200L+Y203W+S253D+N255W+L256E,

SEQ ID NO 79+S9E+N42R+N74D+H118V+Q176E+A188P+V199I+Q200L Y203W+S250D+S253D+N255W+L256E

SEQ ID NO 79+S9E+N42R+N74D+Q176E+A188P+V199I+Q200L+Y203W 5250D+5253D+N255W+L256E

SEQ ID NO 79+S3V+N74D+H118V+Q176E+N179E+S182E+V199I+Q200L Y203W+5210V+5250D+5253D+N255W+L256E

SEQ ID NO 79+T22A+N60D+S99G+S101A+V102I+N114L+G157D+S182 D+T207A+A226V+Q239R+N242 D+E265F,

SEQ ID NO 79+S9E+N42R+N74D+H118V+Q176E+A188P+V199I+Q200L+Y203W+S250D+S253D+N255W+L256E,

SEQ ID NO 79+S9E+N42R+N74D+Q176E+A188P+V199I+Q200L+Y203W+S250D+S253D+N255W+L256E,

SEQ ID NO 79+S9E+N42R+N74D+H118V+Q176E+A188P+V199I+Q200L+Y203W+S250D+N255W+L256E+*269aH+*269bH,

SEQ ID NO 79+S3V+N74D+H118V+Q176E+N179E+S182E+V199I+Q200L+Y203W+S210V+S250D+N255W+L256E,

SEQ ID NO 79+S9E+N74D+G113W+G157P+Q176E+V199I+Q200L+Y203W+S250D+T254E+N255W+L256E,

SEQ ID NO 79+S3V+S9R+N74D+H118V+Q176E+N179E+S182E+V199I+Q200L+Y203W+S212V+S250D+N255W+L256E,

SEQ ID NO 79+S99E, and

SEQ ID NO 80+L217D.

The nomenclature in section ii) e.g. X3T means that any of the 20 natural amino acids may be replaced by Threonine (T). Thus, X represent any of the 20 natural amino acids and reflect the different starting proteases (parent proteases) may have different amino acids in the position corresponding to position 3 of SEQ ID NO 79. If the protease already comprises Threonine in position 3 it's clear to the skilled person that there is no replacement.

The term "corresponding to" reflects the numbering system used and that various starting proteases (parent proteases) may have different length. Thus, a given starting protease is aligned with e.g. SEQ ID NO 79 and the position corresponding to e.g. pos 3 is determined.

SEQ ID NO XX+mutation(s) is to be understood as variants of a protease parent comprising specified mutations compared to the specific parent sequence e.g. SEQ ID NO 80+L217D is a variant of a protease shown in SEQ ID NO 80, which compared to SEQ ID NO 80 comprise the mutation L217D (substitution of Leucine in position 217 of SEQ ID NO 80 with Aspartic acid).

The protease suitable for combining with the DNase in a composition of the invention are preferably any of the above, such proteases are very useful in detergents and are suitable for combining with DNases.

Compositions

The invention relates to cleaning compositions comprising a DNase and a protease in combination with one or more additional cleaning composition components.

One embodiment of the invention relates to a cleaning composition comprising a DNase, a protease and at least one cleaning component. The protease may be any of the proteases mentioned under the heading "Polypeptides having protease activity". Preferably the protease is a subtilase and even more preferably the protease belongs to the subtilisin sub group of subtilases. One embodiment relates to a cleaning composition comprising a DNase, a protease and at least one cleaning component, wherein the protease is a subtilase, preferably a subtilisin. The most relevant cleaning proteases are those obtainable from Bacillus, such proteases have shown to be active at high pH and to effectively remove protease stains. Further, as shown in the examples of the present invention the subtilisin proteases of the genus Bacillus act synergistically with the DNase in reduction, and removal of biofilm or components hereof. Biofilm is a complex structure comprising e.g. protein and DNA, the target substrate e.g. the DNA may be embedded in the biofilm structure and It's believed that when the DNases and proteases are acting together, the DNA and protein components are more effectively removed. It is thus advantageous to formulate DNases with proteases in cleaning compositions e.g. for deep cleaning. One aspect of the invention relates to a method of formulating a cleaning composition comprising adding a DNase, a protease and at least one cleaning component. The invention further relates to a kit intended for deep cleaning, wherein the kit comprises a solution of an enzyme mixture comprising a DNase and a protease.

As mentioned above the most relevant proteases used in the cleaning industry today are obtained from Bacillus e.g. Bacillus lentus and Bacillus amyloliquefaciens. One embodiment of the invention relates to a cleaning composition comprising a DNase, a protease and at least one cleaning component, wherein the protease is obtained from Bacillus preferably from Bacillus lentus, Bacillus amyloliquefaciens, Bacillus licheniformis, Bacillus pumilus, Bacillus halodurans or Bacillus subtilis.

Proteases suitable for combining with the DNases in the cleaning composition of the invention are preferably proteases suitable for cleaning and which has high stain removal capacity under cleaning conditions e.g. in the presence of surfactants, builders or other cleaning components.

One embodiment relates to a cleaning composition comprising a DNase, a protease and at least one cleaning component, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 79, SEQ ID NO 80 or SEQ ID NO 81.

One embodiment relates to a cleaning composition comprising a DNase, a protease and at least one cleaning component, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 79.

One embodiment relates to a cleaning composition comprising a DNase, a protease and at least one cleaning component, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 80.

One embodiment relates to a cleaning composition comprising a DNase, a protease and at least one cleaning component, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 81.

One embodiment relates to a cleaning composition comprising a DNase, a protease and at least one cleaning component, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 82.

One embodiment relates to a cleaning composition comprising a DNase, a protease and at least one cleaning component, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 83.

One embodiment relates to a cleaning composition comprising a DNase, a protease and at least one cleaning component, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 84.

One embodiment relates to a cleaning composition comprising a DNase, a protease and at least one cleaning component, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 85.

One embodiment relates to a cleaning composition comprising a DNase, a protease and at least one cleaning component, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 86.

One embodiment relates to a cleaning composition comprising a DNase, a protease and at least one cleaning component, wherein the protease is obtained from Bacillus preferably from Bacillus lentus, Bacillus amyloliquefaciens, Bacillus licheniformis, Bacillus pumilus, Bacillus halodurans or Bacillus subtilis and wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 79, SEQ ID NO 80 or SEQ ID NO 81.

One embodiment relates to a cleaning composition comprising a DNase, a protease and at least one cleaning component, wherein the protease is obtained from Bacillus preferably from Bacillus lentus and wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 79.

One embodiment relates to a cleaning composition comprising a DNase, a protease and at least one cleaning component, wherein the protease is obtained from Bacillus preferably from Bacillus amyloliquefaciens and wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 80.

One embodiment relates to a cleaning composition comprising a DNase, a protease and at least one cleaning component, wherein the protease is obtained from *Bacillus* preferably from *Bacillus* sp and wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 81.

Thus, as mentioned the protease should be compatible with cleaning components and likewise, the DNases to be formulated together with the protease or to be used together with the protease should also be compatible with cleaning components. DNases are at present not standard ingredients in cleaning compositions. However, the applicant has identified DNases suitable for use in cleaning compositions e.g. in WO2017/060475, WO2014/087011, WO2015/155350 and WO2015/155351. Enzymes, such as DNases should not only be compatible with the cleaning components the DNases should also be compatible with other enzymes which may be present in a typical cleaning composition. It's well known that proteases may negatively influence the performance of other enzymes as the protease may degrade these enzymes (being themselves proteins). Surprisingly, it was found that proteases and DNases not only are compatible but even act synergistically in respect of biofilm stain reduction and removal e.g. in deep cleaning.

Particularly useful DNases may be those of microbial origin. One embodiment of the invention relates to a cleaning composition comprising a DNase, a protease and at least one cleaning component, wherein the DNase is microbial, preferably obtained from bacteria or fungi. In one embodiment, the cleaning composition comprise a DNase from bacteria. One embodiment of the invention relates to a cleaning composition comprising a DNase, a protease and at least one cleaning component, wherein the DNase is obtained from *Bacillus*, preferably *Bacillus* cibi, *Bacillus horikoshii*, *Bacillus licheniformis*, *Bacillus subtilis*, *Bacillus horneckiae*, *Bacillus idriensis*, *Bacillus algicola*, *Bacillus vietnamensis*, *Bacillus hwajinpoensis*, *Bacillus indicus*, *Bacillus marisflavi* or *Bacillus luciferensis*.

As mentioned above the DNases to be used in a composition of the invention preferable belong to the NUC1 group of DNases. The NUC1 group of DNases may comprise one or more of the motifs [T/D/S][G/N]PQL (SEQ ID NO 69), [F/LN/I]A[N/R]D[L/I/P/V] (SEQ ID NO: 70), or C[D/N]T[A/R] (SEQ ID NO: 71). One embodiment of the invention relates to a cleaning composition comprising a DNase, a protease and at least one cleaning component, wherein the DNase comprises one or more of the motifs [T/D/S][G/N]PQL, [F/LN/I]A[N/R]D[L/I/P/V] or C[D/N]T[A/R]. The DNases preferably additionally comprises a NUC1_A domain [D/Q][I/V]DH (SEQ ID NO 72).

One embodiment of the invention relates to a cleaning composition comprising a DNase, a protease and at least one cleaning component, wherein the DNase comprises one or more motifs selected from the motifs [T/D/S][G/N]PQL, [F/LN/I]A[N/R]D[L/I/P/V], C[D/N]T[A/R] and [D/Q][IN]DH.

One preferred embodiment of the invention relates to a cleaning composition comprising a DNase, a protease and at least one cleaning component, wherein the DNase comprises two or more motifs selected from the motifs [T/D/S][G/N]PQL, [F/LN/I]A[N/R]D[L/I/P/V], C[D/N]T[A/R] and [D/Q][I/V]DH.

One preferred embodiment of the invention relates to a cleaning composition comprising a DNase, a protease and at least one cleaning component, wherein the DNase comprises three or more motifs selected from the motifs [T/D/S][G/N]PQL, [F/LN/I]A[N/R]D[L/I/P/V], C[D/N]T[A/R] and [D/Q][I/V]DH.

One preferred embodiment of the invention relates to a cleaning composition comprising a DNase, a protease and at least one cleaning component, wherein the DNase comprises four or more motifs selected from the motifs [T/D/S][G/N]PQL, [F/LN/I]A[N/R]D[L/I/P/V], C[D/N]T[A/R] and [D/Q][I/V]DH.

One preferred embodiment of the invention relates to a cleaning composition comprising a DNase, a protease and at least one cleaning component, wherein the DNase comprises all five motifs [T/D/S][G/N]PQL, [F/LN/I]A[N/R]D[L/I/P/V], C[D/N]T[A/R] and [D/Q][I/V]DH.

The DNases to be added to a composition of the invention preferably belong to the group of DNases comprised in the GYS-clade, which are NUC1 and NUC1_A DNases further comprising the conservative motifs [D/M/L][S/T]GYSR[D/N] (SEQ ID NO: 73) or ASXNRSKG (SEQ ID NO: 74) and which share similar structural and functional properties. The DNases of the GYS-clade are preferably obtained from *Bacillus* genus.

One embodiment of the invention relates to a cleaning composition comprising a DNase, a protease and at least one cleaning component, wherein the DNase comprises one or both of the motif(s) [D/M/L][S/T]GYSR[D/N] (SEQ ID NO: 73) or ASXNRSKG (SEQ ID NO: 74).

In a particularly preferred embodiment the *Bacillus* DNase comprises one or both of the motif(s) [D/M/L][S/T]GYSR[D/N] (SEQ ID NO: 73) or ASXNRSKG (SEQ ID NO: 74). In another particularly preferred embodiment the DNase comprises one or both of the motif(s) [D/M/L][S/T]GYSR[D/N] (SEQ ID NO: 73) or ASXNRSKG (SEQ ID NO: 74) and is obtained from *Bacillus* cibi. In yet another preferred embodiment the DNase comprises the amino acid sequence shown in SEQ ID NO 13 or DNases closely related hereto.

One embodiment of the invention relates to a cleaning composition comprising a DNase, a protease and at least one cleaning component, wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO 13. Other preferred DNases include those comprising the amino acid sequence shown in SEQ ID NO 65 and 66.

One embodiment of the invention relates to a cleaning composition comprising a DNase, a protease and at least one cleaning component, wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO 65.

One embodiment of the invention relates to a cleaning composition comprising a DNase, a protease and at least one cleaning component, wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO 66.

The DNase may also preferably be fungal. Particularly preferred are DNases obtained from *Aspergillus* in particular, *Aspergillus oryzae*.

One embodiment of the invention relates to a cleaning composition comprising a DNase, a protease and at least one cleaning component, wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO 67.

Other particularly preferred are DNases obtained from *Trichoderma* in particular, *Trichoderma harzianum*.

One embodiment of the invention relates to a cleaning composition comprising a DNase, a protease and at least one cleaning component, wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO 68.

One embodiment relates to a cleaning composition comprising a *Bacillus* DNase, a protease and at least one cleaning component, wherein the protease is obtained from *Bacillus* preferably from *Bacillus lentus* and wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 79.

One embodiment relates to a cleaning composition comprising a *Bacillus* DNase, a protease and at least one cleaning component, wherein the protease is obtained from *Bacillus* preferably from *Bacillus amyloliquefaciens* and wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 80.

One embodiment relates to a cleaning composition comprising a *Bacillus* DNase, a protease and at least one cleaning component, wherein the protease is obtained from *Bacillus* preferably from *Bacillus* sp and wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 81.

One embodiment relates to a cleaning composition comprising a *Bacillus* DNase, a protease and at least one cleaning component, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 82.

One embodiment relates to a cleaning composition comprising a *Bacillus* DNase, a protease and at least one cleaning component, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 83.

One embodiment relates to a cleaning composition comprising a *Bacillus* DNase, a protease and at least one cleaning component, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 84.

One embodiment relates to a cleaning composition comprising a *Bacillus* DNase, a protease and at least one cleaning component, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 85.

One embodiment relates to a cleaning composition comprising a *Bacillus* DNase, a protease and at least one cleaning component, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 86.

One embodiment relates to a cleaning composition comprising a DNase, a protease and at least one cleaning component, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 79 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO 13. One embodiment relates to a cleaning composition comprising a DNase, a protease and at least one cleaning component, wherein the DNase comprises or consists of the polypeptide comprising the amino acid sequence shown in SEQ ID NO 13 and wherein the protease comprises or consists of the polypeptide comprising the amino acid sequence shown in SEQ ID NO 79.

One embodiment relates to a cleaning composition comprising a DNase, a protease and at least one cleaning component, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 80 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO 13. One embodiment relates to a cleaning composition comprising a DNase, a protease and at least one cleaning component, wherein the DNase comprises or consists of the polypeptide comprising the amino acid sequence shown in SEQ ID NO 13 and wherein the protease comprises or consists of the polypeptide comprising the amino acid sequence shown in SEQ ID NO 80.

One embodiment relates to a cleaning composition comprising a DNase, a protease and at least one cleaning component, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 81 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO 13. One embodiment relates to a cleaning composition comprising a DNase, a protease and at least one cleaning component, wherein the DNase comprises or consists of the polypeptide comprising the amino acid sequence shown in SEQ ID NO 13 and wherein the protease comprises or consists of the polypeptide comprising the amino acid sequence shown in SEQ ID NO 81.

One embodiment relates to a cleaning composition comprising a DNase, a protease and at least one cleaning component, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 82 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO 13. One embodiment relates to a cleaning composition comprising a DNase, a protease and at least one cleaning component, wherein the DNase comprises or consists of the polypeptide comprising the amino acid sequence shown in SEQ ID NO 13 and wherein the protease comprises or consists of the polypeptide comprising the amino acid sequence shown in SEQ ID NO 82.

One embodiment relates to a cleaning composition comprising a DNase, a protease and at least one cleaning component, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 83 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO 13. One embodiment relates to a cleaning composition comprising a DNase, a protease and at least one cleaning component, wherein the DNase comprises or consists of the polypeptide comprising the amino acid sequence shown in SEQ ID NO 13 and wherein the protease comprises or consists of the polypeptide comprising the amino acid sequence shown in SEQ ID NO 83.

One embodiment relates to a cleaning composition comprising a DNase, a protease and at least one cleaning component, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 84 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO 13. One embodiment relates to a cleaning composition comprising a DNase, a protease and at least one cleaning component, wherein the DNase comprises or consists of the polypeptide comprising the amino acid sequence shown in SEQ ID NO 13 and wherein the protease comprises or consists of the polypeptide comprising the amino acid sequence shown in SEQ ID NO 84.

One embodiment relates to a cleaning composition comprising a DNase, a protease and at least one cleaning component, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 85 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO 13. One embodiment relates to a cleaning composition comprising a DNase, a protease and at least one cleaning component, wherein the DNase comprises or consists of the polypeptide comprising the amino acid sequence shown in SEQ ID NO 13 and wherein the protease comprises or consists of the polypeptide comprising the amino acid sequence shown in SEQ ID NO 85.

One embodiment relates to a cleaning composition comprising a DNase, a protease and at least one cleaning component, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 86 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO 13. One embodiment relates to a cleaning composition comprising a DNase, a protease and at least one cleaning component, wherein the DNase comprises or consists of the polypeptide comprising the amino acid sequence shown in SEQ ID NO 13 and wherein the protease comprises or consists of the polypeptide comprising the amino acid sequence shown in SEQ ID NO 86.

One embodiment relates to a cleaning composition comprising a DNase, a protease and at least one cleaning component, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 79 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO 65. One embodiment relates to a cleaning composition comprising a DNase, a protease and at least one cleaning component, wherein the DNase comprises or consists of the polypeptide comprising the amino acid sequence shown in SEQ ID NO 65 and wherein the protease comprises or consists of the polypeptide comprising the amino acid sequence shown in SEQ ID NO 79.

One embodiment relates to a cleaning composition comprising a DNase, a protease and at least one cleaning component, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 80 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO 65. One embodiment relates to a cleaning composition comprising a DNase, a protease and at least one cleaning component, wherein the DNase comprises or consists of the polypeptide comprising the amino acid sequence shown in SEQ ID NO 65 and wherein the protease comprises or consists of the polypeptide comprising the amino acid sequence shown in SEQ ID NO 80.

One embodiment relates to a cleaning composition comprising a DNase, a protease and at least one cleaning component, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 81 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO 65. One embodiment relates to a cleaning composition comprising a DNase, a protease and at least one cleaning component, wherein the DNase comprises or consists of the polypeptide comprising the amino acid sequence shown in SEQ ID NO 65 and wherein the protease comprises or consists of the polypeptide comprising the amino acid sequence shown in SEQ ID NO 81.

One embodiment relates to a cleaning composition comprising a DNase, a protease and at least one cleaning component, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 82 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO 65. One embodiment relates to a cleaning composition comprising a DNase, a protease and at least one cleaning component, wherein the DNase comprises or consists of the polypeptide comprising the amino acid sequence shown in SEQ ID NO 65 and wherein the protease comprises or consists of the polypeptide comprising the amino acid sequence shown in SEQ ID NO 82.

One embodiment relates to a cleaning composition comprising a DNase, a protease and at least one cleaning component, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 83 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO 65. One embodiment relates to a cleaning composition comprising a DNase, a protease and at least one cleaning component, wherein the DNase comprises or consists of the polypeptide comprising the amino acid sequence shown in SEQ ID NO 65 and wherein the protease comprises or consists of the polypeptide comprising the amino acid sequence shown in SEQ ID NO 83.

One embodiment relates to a cleaning composition comprising a DNase, a protease and at least one cleaning component, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 84 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO 65. One embodiment relates to a cleaning composition comprising a DNase, a protease and at least one cleaning component, wherein the DNase comprises or consists of the polypeptide comprising the amino acid sequence shown in SEQ ID NO 65 and wherein the protease comprises or consists of the polypeptide comprising the amino acid sequence shown in SEQ ID NO 84.

One embodiment relates to a cleaning composition comprising a DNase, a protease and at least one cleaning component, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 85 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO 65. One embodiment relates to a cleaning composition comprising a DNase, a protease and at least one cleaning component, wherein the DNase comprises or consists of the polypeptide comprising the amino acid sequence shown in SEQ ID NO 65 and wherein the protease comprises or consists of the polypeptide comprising the amino acid sequence shown in SEQ ID NO 85.

One embodiment relates to a cleaning composition comprising a DNase, a protease and at least one cleaning component, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 86 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO 65. One embodiment relates to a cleaning composition comprising a DNase, a protease and at least one cleaning component, wherein the DNase comprises or consists of the polypeptide comprising the amino acid sequence shown in SEQ ID NO 65 and wherein the protease comprises or consists of the polypeptide comprising the amino acid sequence shown in SEQ ID NO 86.

One embodiment relates to a cleaning composition comprising a DNase, a protease and at least one cleaning component, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 79 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO 66. One embodiment relates to a cleaning composition comprising a DNase, a protease and at least one cleaning component, wherein the DNase comprises or consists of the polypeptide comprising the amino acid sequence shown in SEQ ID NO 66 and wherein the protease comprises or consists of the polypeptide comprising the amino acid sequence shown in SEQ ID NO 79.

One embodiment relates to a cleaning composition comprising a DNase, a protease and at least one cleaning component, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 80 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO 66. One embodiment relates to a cleaning composition comprising a DNase, a protease and at least one cleaning component, wherein the DNase comprises or consists of the polypeptide comprising the amino acid sequence shown in SEQ ID NO 66 and wherein the protease comprises or consists of the polypeptide comprising the amino acid sequence shown in SEQ ID NO 80.

One embodiment relates to a cleaning composition comprising a DNase, a protease and at least one cleaning component, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 81 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO 66. One embodiment relates to a cleaning composition comprising a DNase, a protease and at least one cleaning component, wherein the DNase comprises or consists of the polypeptide comprising the amino acid sequence shown in SEQ ID NO 66 and wherein the protease comprises or consists of the polypeptide comprising the amino acid sequence shown in SEQ ID NO 81.

One embodiment relates to a cleaning composition comprising a DNase, a protease and at least one cleaning component, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 82 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO 66. One embodiment relates to a cleaning composition comprising a DNase, a protease and at least one cleaning component, wherein the DNase comprises or consists of the polypeptide comprising the amino acid sequence shown in SEQ ID NO 66 and wherein the protease comprises or consists of the polypeptide comprising the amino acid sequence shown in SEQ ID NO 82.

One embodiment relates to a cleaning composition comprising a DNase, a protease and at least one cleaning component, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 83 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO 66. One embodiment relates to a cleaning composition comprising a DNase, a protease and at least one cleaning component, wherein the DNase comprises or consists of the polypeptide comprising the amino acid sequence shown in SEQ ID NO 66 and wherein the protease comprises or consists of the polypeptide comprising the amino acid sequence shown in SEQ ID NO 83.

One embodiment relates to a cleaning composition comprising a DNase, a protease and at least one cleaning component, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 84 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO 66. One embodiment relates to a cleaning composition comprising a DNase, a protease and at least one cleaning component, wherein the DNase comprises or consists of the polypeptide comprising the amino acid sequence shown in SEQ ID NO 66 and wherein the protease comprises or consists of the polypeptide comprising the amino acid sequence shown in SEQ ID NO 84.

One embodiment relates to a cleaning composition comprising a DNase, a protease and at least one cleaning component, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 85 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO 66. One embodiment relates to a cleaning composition comprising a DNase, a protease and at least one cleaning component, wherein the DNase comprises or consists of the polypeptide comprising the amino acid sequence shown in SEQ ID NO 66 and wherein the protease comprises or consists of the polypeptide comprising the amino acid sequence shown in SEQ ID NO 85.

One embodiment relates to a cleaning composition comprising a DNase, a protease and at least one cleaning component, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 86 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO 66. One embodiment relates to a cleaning composition comprising a DNase, a protease and at least one cleaning component, wherein the DNase comprises or consists of the polypeptide comprising the amino acid sequence shown in SEQ ID NO 66 and wherein the protease comprises or consists of the polypeptide comprising the amino acid sequence shown in SEQ ID NO 86.

One embodiment relates to a cleaning composition comprising a DNase, a protease and at least one cleaning component, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 79 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO 67. One embodiment relates to a cleaning composition comprising a DNase, a protease and at least one cleaning component, wherein the DNase comprises or consists of the polypeptide comprising the amino acid sequence shown in SEQ ID NO 67 and wherein the protease comprises or consists of the polypeptide comprising the amino acid sequence shown in SEQ ID NO 79.

One embodiment relates to a cleaning composition comprising a DNase, a protease and at least one cleaning component, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 80 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO 67. One embodiment relates to a cleaning composition comprising a DNase, a protease and at least one cleaning component, wherein the DNase comprises or consists of the polypeptide comprising the amino acid sequence shown in SEQ ID NO 67 and wherein the protease comprises or consists of the polypeptide comprising the amino acid sequence shown in SEQ ID NO 80.

One embodiment relates to a cleaning composition comprising a DNase, a protease and at least one cleaning component, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 81 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO 67. One embodiment relates to a cleaning composition comprising a DNase, a protease and at least one cleaning component, wherein the DNase comprises or consists of the polypeptide comprising the amino acid sequence shown in SEQ ID NO 67 and wherein the protease comprises or consists of the polypeptide comprising the amino acid sequence shown in SEQ ID NO 81.

One embodiment relates to a cleaning composition comprising a DNase, a protease and at least one cleaning component, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 82 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO 67. One embodiment relates to a cleaning composition comprising a DNase, a protease and at least one cleaning component, wherein the DNase comprises or consists of the polypeptide comprising the amino acid sequence shown in SEQ ID NO 67 and wherein the protease comprises or consists of the polypeptide comprising the amino acid sequence shown in SEQ ID NO 82.

One embodiment relates to a cleaning composition comprising a DNase, a protease and at least one cleaning component, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 83 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO 67. One embodiment relates to a cleaning composition comprising a DNase, a protease and at least one cleaning component, wherein the DNase comprises or consists of the polypeptide comprising the amino acid sequence shown in SEQ ID NO 67 and wherein the protease comprises or consists of the polypeptide comprising the amino acid sequence shown in SEQ ID NO 83.

One embodiment relates to a cleaning composition comprising a DNase, a protease and at least one cleaning component, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 84 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO 67. One embodiment relates to a cleaning composition comprising a DNase, a protease and at least one cleaning component, wherein the DNase comprises or consists of the polypeptide comprising the amino acid sequence shown in SEQ ID NO 67 and wherein the protease comprises or consists of the polypeptide comprising the amino acid sequence shown in SEQ ID NO 84.

One embodiment relates to a cleaning composition comprising a DNase, a protease and at least one cleaning component, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 85 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO 67. One embodiment relates to a cleaning composition comprising a DNase, a protease and at least one cleaning component, wherein the DNase comprises or consists of the polypeptide comprising the amino acid sequence shown in SEQ ID NO 67 and wherein the protease comprises or consists of the polypeptide comprising the amino acid sequence shown in SEQ ID NO 85.

One embodiment relates to a cleaning composition comprising a DNase, a protease and at least one cleaning component, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 86 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO 67. One embodiment relates to a cleaning composition comprising a DNase, a protease and at least one cleaning component, wherein the DNase comprises or consists of the polypeptide comprising the amino acid sequence shown in SEQ ID NO 67 and wherein the protease comprises or consists of the polypeptide comprising the amino acid sequence shown in SEQ ID NO 86.

One embodiment relates to a cleaning composition comprising a DNase, a protease and at least one cleaning component, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 79 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO 68. One embodiment relates to a cleaning composition comprising a DNase, a protease and at least one cleaning component, wherein the DNase comprises or consists of the polypeptide comprising the amino acid sequence shown in SEQ ID NO 68 and wherein the protease comprises or consists of the polypeptide comprising the amino acid sequence shown in SEQ ID NO 79.

One embodiment relates to a cleaning composition comprising a DNase, a protease and at least one cleaning component, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 80 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO 68. One embodiment relates to a cleaning composition comprising a DNase, a protease and at least one cleaning component, wherein the DNase comprises or consists of the polypeptide comprising the amino acid sequence shown in SEQ ID NO 68 and wherein the protease comprises or consists of the polypeptide comprising the amino acid sequence shown in SEQ ID NO 80.

One embodiment relates to a cleaning composition comprising a DNase, a protease and at least one cleaning component, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 81 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO 68. One embodiment relates to a cleaning composition comprising a DNase, a protease and at least one cleaning component, wherein the DNase comprises or consists of the polypeptide comprising the amino acid sequence shown in SEQ ID NO 68 and wherein the protease comprises or consists of the polypeptide comprising the amino acid sequence shown in SEQ ID NO 81.

One embodiment relates to a cleaning composition comprising a DNase, a protease and at least one cleaning component, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 82 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO 68. One embodiment relates to a cleaning composition comprising a DNase, a protease and at least one cleaning component, wherein the DNase comprises or consists of the polypeptide comprising the amino acid sequence shown in SEQ ID NO 68 and wherein the protease comprises or consists of the polypeptide comprising the amino acid sequence shown in SEQ ID NO 82.

One embodiment relates to a cleaning composition comprising a DNase, a protease and at least one cleaning component, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 83 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO 68. One embodiment relates to a cleaning composition comprising a DNase, a protease and at least one cleaning component, wherein the DNase comprises or consists of the polypeptide comprising the amino acid sequence shown in SEQ ID NO 68 and wherein the protease comprises or consists of the polypeptide comprising the amino acid sequence shown in SEQ ID NO 83.

One embodiment relates to a cleaning composition comprising a DNase, a protease and at least one cleaning component, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 84 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO 68. One embodiment relates to a cleaning composition comprising a DNase, a protease and at least one cleaning component, wherein the DNase comprises or consists of the polypeptide comprising the amino acid sequence shown in SEQ ID NO 68 and wherein the protease comprises or consists of the polypeptide comprising the amino acid sequence shown in SEQ ID NO 84.

One embodiment relates to a cleaning composition comprising a DNase, a protease and at least one cleaning component, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 85 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO 68. One embodiment relates to a cleaning composition comprising a DNase, a protease and at least one cleaning component, wherein the DNase comprises or consists of the polypeptide comprising the amino acid sequence shown in SEQ ID NO 68 and wherein the protease comprises or consists of the polypeptide comprising the amino acid sequence shown in SEQ ID NO 85.

One embodiment relates to a cleaning composition comprising a DNase, a protease and at least one cleaning component, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 86 and wherein the DNase has at least 60%, at least 65%, at least 70%, at least 75%, at least 80%, at least 85%, at least 90%, at least 95%, at least 98% or 100% sequence identity to the amino acid sequence shown in SEQ ID NO 68. One embodiment relates to a cleaning composition comprising a DNase, a protease and at least one cleaning component, wherein the DNase comprises or consists of the polypeptide comprising the amino acid sequence shown in SEQ ID NO 68 and wherein the protease comprises or consists of the polypeptide comprising the amino acid sequence shown in SEQ ID NO 86.

One embodiment of the invention relates to a composition, preferably a cleaning composition, comprising a protease, a polypeptide having DNase activity, optionally wherein the polypeptide comprise one or both of the motifs [D/M/L][S/T]GYSR[D/N] (SEQ ID NO: 73), ASXNRSKG (SEQ ID NO: 74), wherein the polypeptide is selected from the group of polypeptides:

a) a polypeptide having at least 60%, at least 65%, at least 70%, at least 75% at least 80%, at least 85%, at least 90%, at least 95%, at least 98% or 100% sequence identity to the polypeptide shown in SEQ ID NO: 1,
  b) a polypeptide having at least 60%, at least 65%, at least 70%, at least 75%, at least 80%, at least 85%, at least 90%, at least 95%, at least 98% or 100% sequence identity to the polypeptide shown in SEQ ID NO: 2,
  c) a polypeptide having at least 60%, at least 65%, at least 70%, at least 75%, at least 80%, at least 85%, at least 90%, at least 95%, at least 98% or 100% sequence identity to the polypeptide shown in SEQ ID NO: 3,
  d) a polypeptide having at least 60%, at least 65%, at least 70%, at least 75% at least 80%, at least 85%, at least 90%, at least 95%, at least 98% or 100% sequence identity to the polypeptide shown in SEQ ID NO: 4,
  e) a polypeptide having at least 60%, at least 65%, at least 70%, at least 75%, at least 80%, at least 85%, at least 90%, at least 95%, at least 98% or 100% sequence identity to the polypeptide shown in SEQ ID NO: 5,
  f) a polypeptide having at least 60%, at least 65%, at least 70%, at least 75%, at least 80%, at least 85%, at least 90%, at least 95%, at least 98% or 100% sequence identity to the polypeptide shown in SEQ ID NO: 6,
  g) a polypeptide having at least 60%, at least 65%, at least 70%, at least 75%, at least 80%, at least 85%, at least 90%, at least 95%, at least 98% or 100% sequence identity to the polypeptide shown in SEQ ID NO: 7,
  h) a polypeptide having at least 60%, at least 65%, at least 70%, at least 75%, at least 80%, at least 85%, at least 90%, at least 95%, at least 98% or 100% sequence identity to the polypeptide shown in SEQ ID NO: 8,
  i) a polypeptide having at least 60%, at least 65%, at least 70%, at least 75%, at least 80%, at least 85%, at least 90%, at least 95%, at least 98% or 100% sequence identity to the polypeptide shown in SEQ ID NO: 9, j) a polypeptide having at least 60%, at least 65%, at least 70%, at least 75% at least 80%, at least 85%, at least 90%, at least 95%, at least 98% or 100% sequence identity to the polypeptide shown in SEQ ID NO: 10, k) a polypeptide having at least 60%, at least 65%, at least 70%, at least 75% at least 80%, at least 85%, at least 90%, at least 95%, at least 98% or 100% sequence identity to the polypeptide shown in SEQ ID NO: 11, l) a polypeptide having at least 60%, at least 65%, at least 70%, at least 75% at least 80%, at least 85%, at least 90%, at least 95%, at least 98% or 100% sequence identity to the polypeptide shown in SEQ ID NO: 12, m) a polypeptide having at least 60%, at least 65%, at least 70%, at least 75% at least 80%, at least 85%, at least 90%, at least 95%, at least 98% or 100% sequence identity to the polypeptide shown in SEQ ID NO: 13, n) a polypeptide having at least 60%, at least 65%, at least 70%, at least 75% at least 80%, at least 85%, at least 90%, at least 95%, at least 98% or 100% sequence identity to the polypeptide shown in SEQ ID NO: 14, o) a polypeptide having at least 60%, at least 65%, at least 70%, at least 75% at least 80%, at least 85%, at least 90%, at least 95%, at least 98% or 100% sequence identity to the polypeptide shown in SEQ ID NO: 15, p) a polypeptide having at least 60%, at least 65%, at least 70%, at least 75% at least 80%, at least 85%, at least 90%, at least 95%, at least 98% or 100% sequence identity to the polypeptide shown in SEQ ID NO: 16, q) a polypeptide having at least 60%, at least 65%, at least 70%, at least 75% at least 80%, at least 85%, at least 90%, at least 95%, at least 98% or 100% sequence identity to the polypeptide shown in SEQ ID NO: 17, r) a polypeptide having at least 60%, at least 65%, at least 70%, at least 75% at least 80%, at least 85%, at least 90%, at least 95%, at least 98% or 100% sequence identity to the polypeptide shown in SEQ ID NO: 18, s) a polypeptide having at least 60%, at least 65%, at least 70%, at least 75% at least 80%, at least 85%, at least 90%, at least 95%, at least 98% or 100% sequence identity to the polypeptide shown in SEQ ID NO: 19, t) a polypeptide having at least 60%, at least 65%, at least 70%, at least 75% at least 80%, at least 85%, at least 90%, at least 95%, at least 98% or 100% sequence identity to the polypeptide shown in SEQ ID NO: 20, u) a polypeptide having at least 60%, at least 65%, at least 70%, at least 75% at least 80%, at least 85%, at least 90%, at least 95%, at least 98% or 100% sequence identity to the polypeptide shown in SEQ ID NO: 21, v) a polypeptide having at least 60%, at least 65%, at least 70%, at least 75% at least 80%, at least 85%, at least 90%, at least 95%, at least 98% or 100% sequence identity to the polypeptide shown in SEQ ID NO: 22, w) a polypeptide having at least 60%, at least 65%, at least 70%, at least 75% at least 80%, at least 85%, at least 90%, at least 95%, at least 98% or 100% sequence identity to the polypeptide shown in SEQ ID NO: 23, x) a polypeptide having at least 60%, at least 65%, at least 70%, at least 75% at least 80%, at least 85%, at least 90%, at least 95%, at least 98% or 100% sequence identity to the polypeptide shown in SEQ ID NO: 24, y) a polypeptide having at least 60%, at least 65%, at least 70%, at least 75% at least 80%, at least 85%, at least 90%, at least 95%, at least 98% or 100% sequence identity to the polypeptide shown in SEQ ID NO: 25, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 79, and wherein the composition preferably comprises at least one cleaning component. One embodiment relates to a cleaning composition comprising a DNase, a protease and at least one cleaning component, wherein the DNase comprises or consists of a polypeptide selected from the group of polypeptides comprising the amino acid sequence shown in; SEQ ID NO 1, SEQ ID NO 2, SEQ ID NO 3, SEQ ID NO 4, SEQ ID NO 5, SEQ ID NO 6, SEQ ID NO 7, SEQ ID NO 8, SEQ ID NO 9, SEQ ID NO 10, SEQ ID NO 11, SEQ ID NO 12, SEQ ID NO 13, SEQ ID NO 14, SEQ ID NO 15, SEQ ID NO 16, SEQ ID NO 17, SEQ ID NO 18, SEQ ID NO 19, SEQ ID NO 20, SEQ ID NO 21, SEQ ID NO 22, SEQ ID NO 23, SEQ ID NO 24 and SEQ ID NO 25 and wherein the protease comprises or consists of the polypeptide comprising the amino acid sequence shown in SEQ ID NO 79.

One embodiment of the invention relates to a composition, preferably a cleaning composition, comprising a protease, a polypeptide having DNase activity, optionally wherein the polypeptide comprise one or both of the motifs [D/M/L][S/T]GYSR[D/N] (SEQ ID NO: 73), ASXNRSKG (SEQ ID NO: 74), wherein the polypeptide is selected from the group of polypeptides:

a) a polypeptide having at least 60%, at least 65%, at least 70%, at least 75% at least 80%, at least 85%, at least 90%, at least 95%, at least 98% or 100% sequence identity to the polypeptide shown in SEQ ID NO: 1, b) a polypeptide having at least 60%, at least 65%, at least 70%, at least 75% at least 80%, at least 85%, at least 90%, at least 95%, at least 98% or 100% sequence identity to the polypeptide shown in SEQ ID NO: 2, c) a polypeptide having at least 60%, at least 65%, at least 70%, at least 75% at least 80%, at least 85%, at least 90%, at least 95%, at least 98% or 100% sequence identity to the polypeptide shown in SEQ ID NO: 3, d) a polypeptide having at least 60%, at least 65%, at least 70%, at least 75% at least 80%, at least 85%, at least 90%, at least 95%, at least 98% or 100% sequence identity to the polypeptide shown in SEQ ID NO: 4, e) a polypeptide having at least 60%, at least 65%, at least 70%, at least 75% at least 80%, at least 85%, at least 90%, at least 95%, at least 98% or 100% sequence identity to the polypeptide shown in SEQ ID NO: 5, f) a polypeptide having at least 60%, at least 65%, at least 70%, at least 75% at least 80%, at least 85%, at least 90%, at least 95%, at least 98% or 100% sequence identity to the polypeptide shown in SEQ ID NO: 6, g) a polypeptide having at least 60%, at least 65%, at least 70%, at least 75% at least 80%, at least 85%, at least 90%, at least 95%, at least 98% or 100% sequence identity to the polypeptide shown in SEQ ID NO: 7, h) a polypeptide having at least 60%, at least 65%, at least 70%, at least 75% at least 80%, at least 85%, at least 90%, at least 95%, at least 98% or 100% sequence identity to the polypeptide shown in SEQ ID NO: 8, i) a polypeptide having at least 60%, at least 65%, at least 70%, at least 75% at least 80%, at least 85%, at least 90%, at least 95%, at least 98% or 100% sequence identity to the polypeptide shown in SEQ ID NO: 9, j) a polypeptide having at least 60%, at least 65%, at least 70%, at least 75% at least 80%, at least 85%, at least 90%, at least 95%, at least 98% or 100% sequence identity to the polypeptide shown in SEQ ID NO: 10, k) a polypeptide having at least 60%, at least 65%, at least 70%, at least 75% at least 80%, at least 85%, at least 90%, at least 95%, at least 98% or 100% sequence identity to the polypeptide shown in SEQ ID NO: 11, l) a polypeptide having at least 60%, at least 65%, at least 70%, at least 75% at least 80%, at least 85%, at least 90%, at least 95%, at least 98% or 100% sequence identity to the polypeptide shown in SEQ ID NO: 12, m) a polypeptide having at least 60%, at least 65%, at least 70%, at least 75% at least 80%, at least 85%, at least 90%, at least 95%, at least 98% or 100% sequence identity to the polypeptide shown in SEQ ID NO: 13, n) a polypeptide having at least 60%, at least 65%, at least 70%, at least 75% at least 80%, at least 85%, at least 90%, at least 95%, at least 98% or 100% sequence identity to the polypeptide shown in SEQ ID NO: 14, o) a polypeptide having at least 60%, at least 65%, at least 70%, at least 75% at least 80%, at least 85%, at least 90%, at least 95%, at least 98% or 100% sequence identity to the polypeptide shown in SEQ ID NO: 15, p) a polypeptide having at least 60%, at least 65%, at least 70%, at least 75% at least 80%, at least 85%, at least 90%, at least 95%, at least 98% or 100% sequence identity to the polypeptide shown in SEQ ID NO: 16, q) a polypeptide having at least 60%, at least 65%, at least 70%, at least 75% at least 80%, at least 85%, at least 90%, at least 95%, at least 98% or 100% sequence identity to the polypeptide shown in SEQ ID NO: 17, r) a polypeptide having at least 60%, at least 65%, at least 70%, at least 75% at least 80%, at least 85%, at least 90%, at least 95%, at least 98% or 100% sequence identity to the polypeptide shown in SEQ ID NO: 18, s) a polypeptide having at least 60%, at least 65%, at least 70%, at least 75% at least 80%, at least 85%, at least 90%, at least 95%, at least 98% or 100% sequence identity to the polypeptide shown in SEQ ID NO: 19, t) a polypeptide having at least 60%, at least 65%, at least 70%, at least 75% at least 80%, at least 85%, at least 90%, at least 95%, at least 98% or 100% sequence identity to the polypeptide shown in SEQ ID NO: 20, u) a polypeptide having at least 60%, at least 65%, at least 70%, at least 75% at least 80%, at least 85%, at least 90%, at least 95%, at least 98% or 100% sequence identity to the polypeptide shown in SEQ ID NO: 21, v) a polypeptide having at least 60%, at least 65%, at least 70%, at least 75% at least 80%, at least 85%, at least 90%, at least 95%, at least 98% or 100% sequence identity to the polypeptide shown in SEQ ID NO: 22, w) a polypeptide having at least 60%, at least 65%, at least 70%, at least 75% at least 80%, at least 85%, at least 90%, at least 95%, at least 98% or 100% sequence identity to the polypeptide shown in SEQ ID NO: 23, x) a polypeptide having at least 60%, at least 65%, at least 70%, at least 75% at least 80%, at least 85%, at least 90%, at least 95%, at least 98% or 100% sequence identity to the polypeptide shown in SEQ ID NO: 24, and y) a polypeptide having at least 60%, at least 65%, at least 70%, at least 75% at least 80%, at least 85%, at least 90%, at least 95%, at least 98% or 100% sequence identity to the polypeptide shown in SEQ ID NO: 25, and wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 80, and wherein the composition preferably comprises at least one cleaning component. One embodiment relates to a cleaning composition comprising a DNase, a protease and at least one cleaning component, wherein the DNase comprises or consists of a polypeptide selected from the group of polypeptides comprising the amino acid sequence shown in; SEQ ID NO 1, SEQ ID NO 2, SEQ ID NO 3, SEQ ID NO 4, SEQ ID NO 5, SEQ ID NO 6, SEQ ID NO 7, SEQ ID NO 8, SEQ ID NO 9, SEQ ID NO 10, SEQ ID NO 11, SEQ ID NO 12, SEQ ID NO 13, SEQ ID NO 14, SEQ ID NO 15, SEQ ID NO 16, SEQ ID NO 17, SEQ ID NO 18, SEQ ID NO 19, SEQ ID NO 20, SEQ ID NO 21, SEQ ID NO 22, SEQ ID NO 23, SEQ ID NO 24 and SEQ ID NO 25 and wherein the protease comprises or consists of the polypeptide comprising the amino acid sequence shown in SEQ ID NO 80.

One embodiment of the invention relates to a composition, preferably a cleaning composition, comprising a protease, a polypeptide having DNase activity, optionally wherein the polypeptide comprise one or both of the motifs [D/M/L][S/T]GYSR[D/N] (SEQ ID NO: 73), ASXNRSKG (SEQ ID NO: 74), wherein the polypeptide is selected from the group of polypeptides:

a) a polypeptide having at least 60%, at least 65%, at least 70%, at least 75% at least 80%, at least 85%, at least 90%, at least 95%, at least 98% or 100% sequence identity to the polypeptide shown in SEQ ID NO: 1, b) a polypeptide having at least 60%, at least 65%, at least 70%, at least 75% at least 80%, at least 85%, at least 90%, at least 95%, at least 98% or 100% sequence identity to the polypeptide shown in SEQ ID NO: 2, c) a polypeptide having at least 60%, at least 65%, at least 70%, at least 75% at least 80%, at least 85%, at least 90%, at least 95%, at least 98% or 100% sequence identity to the polypeptide shown in SEQ ID NO: 3, d) a polypeptide having at least 60%, at least 65%, at least 70%, at least 75% at least 80%, at least 85%, at least 90%, at least 95%, at least 98% or 100% sequence identity to the polypeptide shown in SEQ ID NO: 4, e) a polypeptide having at least 60%, at least 65%, at least 70%, at least 75% at least 80%, at least 85%, at least 90%, at least 95%, at least 98% or 100% sequence identity to the polypeptide shown in SEQ ID NO: 5, f) a polypeptide having at least 60%, at least 65%, at least 70%, at least 75% at least 80%, at least 85%, at least 90%, at least 95%, at least 98% or 100% sequence identity to the polypeptide shown in SEQ ID NO: 6, g) a polypeptide having at least 60%, at least 65%, at least 70%, at least 75% at least 80%, at least 85%, at least 90%, at least 95%, at least 98% or 100% sequence identity to the polypeptide shown in SEQ ID NO: 7, h) a polypeptide having at least 60%, at least 65%, at least 70%, at least 75% at least 80%, at least 85%, at least 90%, at least 95%, at least 98% or 100% sequence identity to the polypeptide shown in SEQ ID NO: 8, i) a polypeptide having at least 60%, at least 65%, at least 70%, at least 75% at least 80%, at least 85%, at least 90%, at least 95%, at least 98% or 100% sequence identity to the polypeptide shown in SEQ ID NO: 9, j) a polypeptide having at least 60%, at least 65%, at least 70%, at least 75% at least 80%, at least 85%, at least 90%, at least 95%, at least 98% or 100% sequence identity to the polypeptide shown in SEQ ID NO: 10, k) a polypeptide having at least 60%, at least 65%, at least 70%, at least 75% at least 80%, at least 85%, at least 90%, at least 95%, at least 98% or 100% sequence identity to the polypeptide shown in SEQ ID NO: 11, l) a polypeptide having at least 60%, at least 65%, at least 70%, at least 75% at least 80%, at least 85%, at least 90%, at least 95%, at least 98% or 100% sequence identity to the polypeptide shown in SEQ ID NO: 12, m) a polypeptide having at least 60%, at least 65%, at least 70%, at least 75% at least 80%, at least 85%, at least 90%, at least 95%, at least 98% or 100% sequence identity to the polypeptide shown in SEQ ID NO: 13,
n) a polypeptide having at least 60%, at least 65%, at least 70%, at least 75%, at least 80%, at least 85%, at least 90%, at least 95%, at least 98% or 100% sequence identity to the polypeptide shown in SEQ ID NO: 14,
o) a polypeptide having at least 60%, at least 65%, at least 70%, at least 75% at least 80%, at least 85%, at least 90%, at least 95%, at least 98% or 100% sequence identity to the polypeptide shown in SEQ ID NO: 15,
p) a polypeptide having at least 60%, at least 65%, at least 70%, at least 75% at least 80%, at least 85%, at least 90%, at least 95%, at least 98% or 100% sequence identity to the polypeptide shown in SEQ ID NO: 16,
q) a polypeptide having at least 60%, at least 65%, at least 70%, at least 75% at least 80%, at least 85%, at least 90%, at least 95%, at least 98% or 100% sequence identity to the polypeptide shown in SEQ ID NO: 17,
r) a polypeptide having at least 60%, at least 65%, at least 70%, at least 75% at least 80%, at least 85%, at least 90%, at least 95%, at least 98% or 100% sequence identity to the polypeptide shown in SEQ ID NO: 18,
s) a polypeptide having at least 60%, at least 65%, at least 70%, at least 75% at least 80%, at least 85%, at least 90%, at least 95%, at least 98% or 100% sequence identity to the polypeptide shown in SEQ ID NO: 19,
t) a polypeptide having at least 60%, at least 65%, at least 70%, at least 75%, at least 80%, at least 85%, at least 90%, at least 95%, at least 98% or 100% sequence identity to the polypeptide shown in SEQ ID NO: 20,
u) a polypeptide having at least 60%, at least 65%, at least 70%, at least 75%, at least 80%, at least 85%, at least 90%, at least 95%, at least 98% or 100% sequence identity to the polypeptide shown in SEQ ID NO: 21,
v) a polypeptide having at least 60%, at least 65%, at least 70%, at least 75%, at least 80%, at least 85%, at least 90%, at least 95%, at least 98% or 100% sequence identity to the polypeptide shown in SEQ ID NO: 22,
w) a polypeptide having at least 60%, at least 65%, at least 70%, at least 75%, at least 80%, at least 85%, at least 90%, at least 95%, at least 98% or 100% sequence identity to the polypeptide shown in SEQ ID NO: 23,
x) a polypeptide having at least 60%, at least 65%, at least 70%, at least 75%, at least 80%, at least 85%, at least 90%, at least 95%, at least 98% or 100% sequence identity to the polypeptide shown in SEQ ID NO: 24, and
y) a polypeptide having at least 60%, at least 65%, at least 70%, at least 75%, at least 80%, at least 85%, at least 90%, at least 95%, at least 98% or 100% sequence identity to the polypeptide shown in SEQ ID NO: 25, and
wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 81, and wherein the composition preferably comprises at least one cleaning component. One embodiment relates to a cleaning composition comprising a DNase, a protease and at least one cleaning component, wherein the DNase comprises or consists of a polypeptide selected from the group of polypeptides comprising the amino acid sequence shown in; SEQ ID NO 1, SEQ ID NO 2, SEQ ID NO 3, SEQ ID NO 4, SEQ ID NO 5, SEQ ID NO 6, SEQ ID NO 7, SEQ ID NO 8, SEQ ID NO 9, SEQ ID NO 10, SEQ ID NO 11, SEQ ID NO 12, SEQ ID NO 13, SEQ ID NO 14, SEQ ID NO 15, SEQ ID NO 16, SEQ ID NO 17, SEQ ID NO 18, SEQ ID NO 19, SEQ ID NO 20, SEQ ID NO 21, SEQ ID NO 22, SEQ ID NO 23, SEQ ID NO 24 and SEQ ID NO 25 and wherein the protease comprises or consists of the polypeptide comprising the amino acid sequence shown in SEQ ID NO 81.

One embodiment of the invention relates to a composition, preferably a cleaning composition, comprising a protease, a polypeptide having DNase activity, optionally wherein the polypeptide comprise one or both of the motifs [D/M/L][S/T]GYSR[D/N] (SEQ ID NO: 73), ASXNRSKG (SEQ ID NO: 74), wherein the polypeptide is selected from the group of polypeptides:
a) a polypeptide having at least 60%, at least 65%, at least 70%, at least 75% at least 80%, at least 85%, at least 90%, at least 95%, at least 98% or 100% sequence identity to the polypeptide shown in SEQ ID NO: 1,
b) a polypeptide having at least 60%, at least 65%, at least 70%, at least 75% at least 80%, at least 85%, at least 90%, at least 95%, at least 98% or 100% sequence identity to the polypeptide shown in SEQ ID NO: 2,
c) a polypeptide having at least 60%, at least 65%, at least 70%, at least 75% at least 80%, at least 85%, at least 90%, at least 95%, at least 98% or 100% sequence identity to the polypeptide shown in SEQ ID NO: 3,
d) a polypeptide having at least 60%, at least 65%, at least 70%, at least 75% at least 80%, at least 85%, at least 90%, at least 95%, at least 98% or 100% sequence identity to the polypeptide shown in SEQ ID NO: 4,
e) a polypeptide having at least 60%, at least 65%, at least 70%, at least 75% at least 80%, at least 85%, at least 90%, at least 95%, at least 98% or 100% sequence identity to the polypeptide shown in SEQ ID NO: 5,
f) a polypeptide having at least 60%, at least 65%, at least 70%, at least 75% at least 80%, at least 85%, at least 90%, at least 95%, at least 98% or 100% sequence identity to the polypeptide shown in SEQ ID NO: 6,
g) a polypeptide having at least 60%, at least 65%, at least 70%, at least 75% at least 80%, at least 85%, at least 90%, at least 95%, at least 98% or 100% sequence identity to the polypeptide shown in SEQ ID NO: 7,
h) a polypeptide having at least 60%, at least 65%, at least 70%, at least 75% at least 80%, at least 85%, at least 90%, at least 95%, at least 98% or 100% sequence identity to the polypeptide shown in SEQ ID NO: 8,
i) a polypeptide having at least 60%, at least 65%, at least 70%, at least 75% at least 80%, at least 85%, at least 90%, at least 95%, at least 98% or 100% sequence identity to the polypeptide shown in SEQ ID NO: 9,
j) a polypeptide having at least 60%, at least 65%, at least 70%, at least 75% at least 80%, at least 85%, at least 90%, at least 95%, at least 98% or 100% sequence identity to the polypeptide shown in SEQ ID NO: 10,
k) a polypeptide having at least 60%, at least 65%, at least 70%, at least 75% at least 80%, at least 85%, at least 90%, at least 95%, at least 98% or 100% sequence identity to the polypeptide shown in SEQ ID NO: 11,
l) a polypeptide having at least 60%, at least 65%, at least 70%, at least 75% at least 80%, at least 85%, at least 90%, at least 95%, at least 98% or 100% sequence identity to the polypeptide shown in SEQ ID NO: 12,
m) a polypeptide having at least 60%, at least 65%, at least 70%, at least 75% at least 80%, at least 85%, at least 90%, at least 95%, at least 98% or 100% sequence identity to the polypeptide shown in SEQ ID NO: 13,
n) a polypeptide having at least 60%, at least 65%, at least 70%, at least 75% at least 80%, at least 85%, at least 90%, at least 95%, at least 98% or 100% sequence identity to the polypeptide shown in SEQ ID NO: 14, o) a polypeptide having at least 60%, at least 65%, at least 70%, at least 75% at least 80%, at least 85%, at least 90%, at least 95%, at least 98% or 100% sequence identity to the polypeptide shown in SEQ ID NO: 15,
p) a polypeptide having at least 60%, at least 65%, at least 70%, at least 75% at least 80%, at least 85%, at least 90%, at least 95%, at least 98% or 100% sequence identity to the polypeptide shown in SEQ ID NO: 16,
q) a polypeptide having at least 60%, at least 65%, at least 70%, at least 75% at least 80%, at least 85%, at least 90%, at least 95%, at least 98% or 100% sequence identity to the polypeptide shown in SEQ ID NO: 17,
r) a polypeptide having at least 60%, at least 65%, at least 70%, at least 75% at least 80%, at least 85%, at least 90%, at least 95%, at least 98% or 100% sequence identity to the polypeptide shown in SEQ ID NO: 18,
s) a polypeptide having at least 60%, at least 65%, at least 70%, at least 75% at least 80%, at least 85%, at least 90%, at least 95%, at least 98% or 100% sequence identity to the polypeptide shown in SEQ ID NO: 19,
t) a polypeptide having at least 60%, at least 65%, at least 70%, at least 75% at least 80%, at least 85%, at least 90%, at least 95%, at least 98% or 100% sequence identity to the polypeptide shown in SEQ ID NO: 20,
u) a polypeptide having at least 60%, at least 65%, at least 70%, at least 75% at least 80%, at least 85%, at least 90%, at least 95%, at least 98% or 100% sequence identity to the polypeptide shown in SEQ ID NO: 21,
v) a polypeptide having at least 60%, at least 65%, at least 70%, at least 75% at least 80%, at least 85%, at least 90%, at least 95%, at least 98% or 100% sequence identity to the polypeptide shown in SEQ ID NO: 22,
w) a polypeptide having at least 60%, at least 65%, at least 70%, at least 75% at least 80%, at least 85%, at least 90%, at least 95%, at least 98% or 100% sequence identity to the polypeptide shown in SEQ ID NO: 23,
x) a polypeptide having at least 60%, at least 65%, at least 70%, at least 75% at least 80%, at least 85%, at least 90%, at least 95%, at least 98% or 100% sequence identity to the polypeptide shown in SEQ ID NO: 24, and
y) a polypeptide having at least 60%, at least 65%, at least 70%, at least 75% at least 80%, at least 85%, at least 90%, at least 95%, at least 98% or 100% sequence identity to the polypeptide shown in SEQ ID NO: 25, and wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 82, and wherein the composition preferably comprises at least one cleaning component. One embodiment relates to a cleaning composition comprising a DNase, a protease and at least one cleaning component, wherein the DNase comprises or consists of a polypeptide selected from the group of polypeptides comprising the amino acid sequence shown in; SEQ ID NO 1, SEQ ID NO 2, SEQ ID NO 3, SEQ ID NO 4, SEQ ID NO 5, SEQ ID NO 6, SEQ ID NO 7, SEQ ID NO 8, SEQ ID NO 9, SEQ ID NO 10, SEQ ID NO 11, SEQ ID NO 12, SEQ ID NO 13, SEQ ID NO 14, SEQ ID NO 15, SEQ ID NO 16, SEQ ID NO 17, SEQ ID NO 18, SEQ ID NO 19, SEQ ID NO 20, SEQ ID NO 21, SEQ ID NO 22, SEQ ID NO 23, SEQ ID NO 24 and SEQ ID NO 25 and wherein the protease comprises or consists of the polypeptide comprising the amino acid sequence shown in SEQ ID NO 82.

One embodiment of the invention relates to a composition, preferably a cleaning composition, comprising a protease, a polypeptide having DNase activity, optionally wherein the polypeptide comprise one or both of the motifs [D/M/L][S/T]GYSR[D/N] (SEQ ID NO: 73), ASXNRSKG (SEQ ID NO: 74), wherein the polypeptide is selected from the group of polypeptides:
a) a polypeptide having at least 60%, at least 65%, at least 70%, at least 75% at least 80%, at least 85%, at least 90%, at least 95%, at least 98% or 100% sequence identity to the polypeptide shown in SEQ ID NO: 1,
b) a polypeptide having at least 60%, at least 65%, at least 70%, at least 75% at least 80%, at least 85%, at least 90%, at least 95%, at least 98% or 100% sequence identity to the polypeptide shown in SEQ ID NO: 2,
c) a polypeptide having at least 60%, at least 65%, at least 70%, at least 75% at least 80%, at least 85%, at least 90%, at least 95%, at least 98% or 100% sequence identity to the polypeptide shown in SEQ ID NO: 3,
d) a polypeptide having at least 60%, at least 65%, at least 70%, at least 75% at least 80%, at least 85%, at least 90%, at least 95%, at least 98% or 100% sequence identity to the polypeptide shown in SEQ ID NO: 4,
e) a polypeptide having at least 60%, at least 65%, at least 70%, at least 75% at least 80%, at least 85%, at least 90%, at least 95%, at least 98% or 100% sequence identity to the polypeptide shown in SEQ ID NO: 5,
f) a polypeptide having at least 60%, at least 65%, at least 70%, at least 75% at least 80%, at least 85%, at least 90%, at least 95%, at least 98% or 100% sequence identity to the polypeptide shown in SEQ ID NO: 6,
g) a polypeptide having at least 60%, at least 65%, at least 70%, at least 75% at least 80%, at least 85%, at least 90%, at least 95%, at least 98% or 100% sequence identity to the polypeptide shown in SEQ ID NO: 7,
h) a polypeptide having at least 60%, at least 65%, at least 70%, at least 75% at least 80%, at least 85%, at least 90%, at least 95%, at least 98% or 100% sequence identity to the polypeptide shown in SEQ ID NO: 8,
i) a polypeptide having at least 60%, at least 65%, at least 70%, at least 75% at least 80%, at least 85%, at least 90%, at least 95%, at least 98% or 100% sequence identity to the polypeptide shown in SEQ ID NO: 9,
j) a polypeptide having at least 60%, at least 65%, at least 70%, at least 75% at least 80%, at least 85%, at least 90%, at least 95%, at least 98% or 100% sequence identity to the polypeptide shown in SEQ ID NO: 10,
k) a polypeptide having at least 60%, at least 65%, at least 70%, at least 75% at least 80%, at least 85%, at least 90%, at least 95%, at least 98% or 100% sequence identity to the polypeptide shown in SEQ ID NO: 11,
l) a polypeptide having at least 60%, at least 65%, at least 70%, at least 75% at least 80%, at least 85%, at least 90%, at least 95%, at least 98% or 100% sequence identity to the polypeptide shown in SEQ ID NO: 12,
m) a polypeptide having at least 60%, at least 65%, at least 70%, at least 75% at least 80%, at least 85%, at least 90%, at least 95%, at least 98% or 100% sequence identity to the polypeptide shown in SEQ ID NO: 13,
n) a polypeptide having at least 60%, at least 65%, at least 70%, at least 75% at least 80%, at least 85%, at least 90%, at least 95%, at least 98% or 100% sequence identity to the polypeptide shown in SEQ ID NO: 14,
o) a polypeptide having at least 60%, at least 65%, at least 70%, at least 75% at least 80%, at least 85%, at least 90%, at least 95%, at least 98% or 100% sequence identity to the polypeptide shown in SEQ ID NO: 15,
p) a polypeptide having at least 60%, at least 65%, at least 70%, at least 75% at least 80%, at least 85%, at least 90%, at least 95%, at least 98% or 100% sequence identity to the polypeptide shown in SEQ ID NO: 16,
q) a polypeptide having at least 60%, at least 65%, at least 70%, at least 75% at least 80%, at least 85%, at least 90%, at least 95%, at least 98% or 100% sequence identity to the polypeptide shown in SEQ ID NO: 17,
r) a polypeptide having at least 60%, at least 65%, at least 70%, at least 75% at least 80%, at least 85%, at least 90%, at least 95%, at least 98% or 100% sequence identity to the polypeptide shown in SEQ ID NO: 18,
s) a polypeptide having at least 60%, at least 65%, at least 70%, at least 75% at least 80%, at least 85%, at least 90%, at least 95%, at least 98% or 100% sequence identity to the polypeptide shown in SEQ ID NO: 19,
t) a polypeptide having at least 60%, at least 65%, at least 70%, at least 75% at least 80%, at least 85%, at least 90%, at least 95%, at least 98% or 100% sequence identity to the polypeptide shown in SEQ ID NO: 20,
u) a polypeptide having at least 60%, at least 65%, at least 70%, at least 75% at least 80%, at least 85%, at least 90%, at least 95%, at least 98% or 100% sequence identity to the polypeptide shown in SEQ ID NO: 21,
v) a polypeptide having at least 60%, at least 65%, at least 70%, at least 75% at least 80%, at least 85%, at least 90%, at least 95%, at least 98% or 100% sequence identity to the polypeptide shown in SEQ ID NO: 22,
w) a polypeptide having at least 60%, at least 65%, at least 70%, at least 75% at least 80%, at least 85%, at least 90%, at least 95%, at least 98% or 100% sequence identity to the polypeptide shown in SEQ ID NO: 23,
x) a polypeptide having at least 60%, at least 65%, at least 70%, at least 75% at least 80%, at least 85%, at least 90%, at least 95%, at least 98% or 100% sequence identity to the polypeptide shown in SEQ ID NO: 24, and
y) a polypeptide having at least 60%, at least 65%, at least 70%, at least 75% at least 80%, at least 85%, at least 90%, at least 95%, at least 98% or 100% sequence identity to the polypeptide shown in SEQ ID NO: 25, and wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 83, and wherein the composition preferably comprises at least one cleaning component. One embodiment relates to a cleaning composition comprising a DNase, a protease and at least one cleaning component, wherein the DNase comprises or consists of a polypeptide selected from the group of polypeptides comprising the amino acid sequence shown in; SEQ ID NO 1, SEQ ID NO 2, SEQ ID NO 3, SEQ ID NO 4, SEQ ID NO 5, SEQ ID NO 6, SEQ ID NO 7, SEQ ID NO 8, SEQ ID NO 9, SEQ ID NO 10, SEQ ID NO 11, SEQ ID NO 12, SEQ ID NO 13, SEQ ID NO 14, SEQ ID NO 15, SEQ ID NO 16, SEQ ID NO 17, SEQ ID NO 18, SEQ ID NO 19, SEQ ID NO 20, SEQ ID NO 21, SEQ ID NO 22, SEQ ID NO 23, SEQ ID NO 24 and SEQ ID NO 25 and wherein the protease comprises or consists of the polypeptide comprising the amino acid sequence shown in SEQ ID NO 83.

One embodiment of the invention relates to a composition, preferably a cleaning composition, comprising a protease, a polypeptide having DNase activity, optionally wherein the polypeptide comprise one or both of the motifs [D/M/L][S/T]GYSR[D/N] (SEQ ID NO: 73), ASXNRSKG (SEQ ID NO: 74), wherein the polypeptide is selected from the group of polypeptides:

a) a polypeptide having at least 60%, at least 65%, at least 70%, at least 75% at least 80%, at least 85%, at least 90%, at least 95%, at least 98% or 100% sequence identity to the polypeptide shown in SEQ ID NO: 1,
b) a polypeptide having at least 60%, at least 65%, at least 70%, at least 75% at least 80%, at least 85%, at least 90%, at least 95%, at least 98% or 100% sequence identity to the polypeptide shown in SEQ ID NO: 2,
c) a polypeptide having at least 60%, at least 65%, at least 70%, at least 75% at least 80%, at least 85%, at least 90%, at least 95%, at least 98% or 100% sequence identity to the polypeptide shown in SEQ ID NO: 3,
d) a polypeptide having at least 60%, at least 65%, at least 70%, at least 75% at least 80%, at least 85%, at least 90%, at least 95%, at least 98% or 100% sequence identity to the polypeptide shown in SEQ ID NO: 4,
e) a polypeptide having at least 60%, at least 65%, at least 70%, at least 75% at least 80%, at least 85%, at least 90%, at least 95%, at least 98% or 100% sequence identity to the polypeptide shown in SEQ ID NO: 5,
f) a polypeptide having at least 60%, at least 65%, at least 70%, at least 75% at least 80%, at least 85%, at least 90%, at least 95%, at least 98% or 100% sequence identity to the polypeptide shown in SEQ ID NO: 6,
g) a polypeptide having at least 60%, at least 65%, at least 70%, at least 75% at least 80%, at least 85%, at least 90%, at least 95%, at least 98% or 100% sequence identity to the polypeptide shown in SEQ ID NO: 7,
h) a polypeptide having at least 60%, at least 65%, at least 70%, at least 75% at least 80%, at least 85%, at least 90%, at least 95%, at least 98% or 100% sequence identity to the polypeptide shown in SEQ ID NO: 8,
i) a polypeptide having at least 60%, at least 65%, at least 70%, at least 75% at least 80%, at least 85%, at least 90%, at least 95%, at least 98% or 100% sequence identity to the polypeptide shown in SEQ ID NO: 9,
j) a polypeptide having at least 60%, at least 65%, at least 70%, at least 75% at least 80%, at least 85%, at least 90%, at least 95%, at least 98% or 100% sequence identity to the polypeptide shown in SEQ ID NO: 10,
k) a polypeptide having at least 60%, at least 65%, at least 70%, at least 75% at least 80%, at least 85%, at least 90%, at least 95%, at least 98% or 100% sequence identity to the polypeptide shown in SEQ ID NO: 11,
l) a polypeptide having at least 60%, at least 65%, at least 70%, at least 75% at least 80%, at least 85%, at least 90%, at least 95%, at least 98% or 100% sequence identity to the polypeptide shown in SEQ ID NO: 12,
m) a polypeptide having at least 60%, at least 65%, at least 70%, at least 75% at least 80%, at least 85%, at least 90%, at least 95%, at least 98% or 100% sequence identity to the polypeptide shown in SEQ ID NO: 13,
n) a polypeptide having at least 60%, at least 65%, at least 70%, at least 75% at least 80%, at least 85%, at least 90%, at least 95%, at least 98% or 100% sequence identity to the polypeptide shown in SEQ ID NO: 14,
o) a polypeptide having at least 60%, at least 65%, at least 70%, at least 75% at least 80%, at least 85%, at least 90%, at least 95%, at least 98% or 100% sequence identity to the polypeptide shown in SEQ ID NO: 15,
p) a polypeptide having at least 60%, at least 65%, at least 70%, at least 75% at least 80%, at least 85%, at least 90%, at least 95%, at least 98% or 100% sequence identity to the polypeptide shown in SEQ ID NO: 16,
q) a polypeptide having at least 60%, at least 65%, at least 70%, at least 75% at least 80%, at least 90%, at least 95%, at least 98% or 100% sequence identity to the polypeptide shown in SEQ ID NO: 17,
r) a polypeptide having at least 60%, at least 65%, at least 70%, at least 75% at least 80%, at least 85%, at least 90%, at least 95%, at least 98% or 100% sequence identity to the polypeptide shown in SEQ ID NO: 18,
s) a polypeptide having at least 60%, at least 65%, at least 70%, at least 75% at least 80%, at least 85%, at least 90%, at least 95%, at least 98% or 100% sequence identity to the polypeptide shown in SEQ ID NO: 19,
t) a polypeptide having at least 60%, at least 65%, at least 70%, at least 75% at least 80%, at least 85%, at least 90%, at least 95%, at least 98% or 100% sequence identity to the polypeptide shown in SEQ ID NO: 20,
u) a polypeptide having at least 60%, at least 65%, at least 70%, at least 75% at least 80%, at least 85%, at least 90%, at least 95%, at least 98% or 100% sequence identity to the polypeptide shown in SEQ ID NO: 21,
v) a polypeptide having at least 60%, at least 65%, at least 70%, at least 75% at least 80%, at least 85%, at least 90%, at least 95%, at least 98% or 100% sequence identity to the polypeptide shown in SEQ ID NO: 22,
w) a polypeptide having at least 60%, at least 65%, at least 70%, at least 75% at least 80%, at least 85%, at least 90%, at least 95%, at least 98% or 100% sequence identity to the polypeptide shown in SEQ ID NO: 23,
x) a polypeptide having at least 60%, at least 65%, at least 70%, at least 75% at least 80%, at least 85%, at least 90%, at least 95%, at least 98% or 100% sequence identity to the polypeptide shown in SEQ ID NO: 24, and
y) a polypeptide having at least 60%, at least 65%, at least 70%, at least 75% at least 80%, at least 85%, at least 90%, at least 95%, at least 98% or 100% sequence identity to the polypeptide shown in SEQ ID NO: 25, and
wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 84, and wherein the composition preferably comprises at least one cleaning component. One embodiment relates to a cleaning composition comprising a DNase, a protease and at least one cleaning component, wherein the DNase comprises or consists of a polypeptide selected from the group of polypeptides comprising the amino acid sequence shown in; SEQ ID NO 1, SEQ ID NO 2, SEQ ID NO 3, SEQ ID NO 4, SEQ ID NO 5, SEQ ID NO 6, SEQ ID NO 7, SEQ ID NO 8, SEQ ID NO 9, SEQ ID NO 10, SEQ ID NO 11, SEQ ID NO 12, SEQ ID NO 13, SEQ ID NO 14, SEQ ID NO 15, SEQ ID NO 16, SEQ ID NO 17, SEQ ID NO 18, SEQ ID NO 19, SEQ ID NO 20, SEQ ID NO 21, SEQ ID NO 22, SEQ ID NO 23, SEQ ID NO 24 and SEQ ID NO 25 and wherein the protease comprises or consists of the polypeptide comprising the amino acid sequence shown in SEQ ID NO 84.

One embodiment of the invention relates to a composition, preferably a cleaning composition comprising a protease, a polypeptide having DNase activity, optionally wherein the polypeptide comprise one or both of the motifs [D/M/L][S/T]GYSR[D/N] (SEQ ID NO: 73), ASXNRSKG (SEQ ID NO: 74), wherein the polypeptide is selected from the group of polypeptides:
a) a polypeptide having at least 60%, at least 65%, at least 70%, at least 75% at least 80%, at least 85%, at least 90%, at least 95%, at least 98% or 100% sequence identity to the polypeptide shown in SEQ ID NO: 1,
b) a polypeptide having at least 60%, at least 65%, at least 70%, at least 75% at least 80%, at least 85%, at least 90%, at least 95%, at least 98% or 100% sequence identity to the polypeptide shown in SEQ ID NO: 2,
c) a polypeptide having at least 60%, at least 65%, at least 70%, at least 75% at least 80%, at least 85%, at least 90%, at least 95%, at least 98% or 100% sequence identity to the polypeptide shown in SEQ ID NO: 3,
d) a polypeptide having at least 60%, at least 65%, at least 70%, at least 75% at least 80%, at least 85%, at least 90%, at least 95%, at least 98% or 100% sequence identity to the polypeptide shown in SEQ ID NO: 4,
e) a polypeptide having at least 60%, at least 65%, at least 70%, at least 75% at least 80%, at least 85%, at least 90%, at least 95%, at least 98% or 100% sequence identity to the polypeptide shown in SEQ ID NO: 5,
f) a polypeptide having at least 60%, at least 65%, at least 70%, at least 75% at least 80%, at least 85%, at least 90%, at least 95%, at least 98% or 100% sequence identity to the polypeptide shown in SEQ ID NO: 6,
g) a polypeptide having at least 60%, at least 65%, at least 70%, at least 75% at least 80%, at least 85%, at least 90%, at least 95%, at least 98% or 100% sequence identity to the polypeptide shown in SEQ ID NO: 7,
h) a polypeptide having at least 60%, at least 65%, at least 70%, at least 75% at least 80%, at least 85%, at least 90%, at least 95%, at least 98% or 100% sequence identity to the polypeptide shown in SEQ ID NO: 8,
i) a polypeptide having at least 60%, at least 65%, at least 70%, at least 75% at least 80%, at least 85%, at least 90%, at least 95%, at least 98% or 100% sequence identity to the polypeptide shown in SEQ ID NO: 9,
j) a polypeptide having at least 60%, at least 65%, at least 70%, at least 75% at least 80%, at least 85%, at least 90%, at least 95%, at least 98% or 100% sequence identity to the polypeptide shown in SEQ ID NO: 10,
k) a polypeptide having at least 60%, at least 65%, at least 70%, at least 75% at least 80%, at least 85%, at least 90%, at least 95%, at least 98% or 100% sequence identity to the polypeptide shown in SEQ ID NO: 11,
l) a polypeptide having at least 60%, at least 65%, at least 70%, at least 75% at least 80%, at least 85%, at least 90%, at least 95%, at least 98% or 100% sequence identity to the polypeptide shown in SEQ ID NO: 12,
m) a polypeptide having at least 60%, at least 65%, at least 70%, at least 75% at least 80%, at least 85%, at least 90%, at least 95%, at least 98% or 100% sequence identity to the polypeptide shown in SEQ ID NO: 13,
n) a polypeptide having at least 60%, at least 65%, at least 70%, at least 75% at least 80%, at least 85%, at least 90%, at least 95%, at least 98% or 100% sequence identity to the polypeptide shown in SEQ ID NO: 14,
o) a polypeptide having at least 60%, at least 65%, at least 70%, at least 75% at least 80%, at least 85%, at least 90%, at least 95%, at least 98% or 100% sequence identity to the polypeptide shown in SEQ ID NO: 15,
p) a polypeptide having at least 60%, at least 65%, at least 70%, at least 75% at least 80%, at least 85%, at least 90%, at least 95%, at least 98% or 100% sequence identity to the polypeptide shown in SEQ ID NO: 16,
q) a polypeptide having at least 60%, at least 65%, at least 70%, at least 75% at least 80%, at least 85%, at least 90%, at least 95%, at least 98% or 100% sequence identity to the polypeptide shown in SEQ ID NO: 17,
r) a polypeptide having at least 60%, at least 65%, at least 70%, at least 75% at least 80%, at least 85%, at least 90%, at least 95%, at least 98% or 100% sequence identity to the polypeptide shown in SEQ ID NO: 18,
s) a polypeptide having at least 60%, at least 65%, at least 70%, at least 75% at least 80%, at least 85%, at least 90%, at least 95%, at least 98% or 100% sequence identity to the polypeptide shown in SEQ ID NO: 19,
t) a polypeptide having at least 60%, at least 65%, at least 70%, at least 75% at least 80%, at least 85%, at least 90%, at least 95%, at least 98% or 100% sequence identity to the polypeptide shown in SEQ ID NO: 20,
u) a polypeptide having at least 60%, at least 65%, at least 70%, at least 75% at least 80%, at least 85%, at least 90%, at least 95%, at least 98% or 100% sequence identity to the polypeptide shown in SEQ ID NO: 21,
v) a polypeptide having at least 60%, at least 65%, at least 70%, at least 75% at least 80%, at least 85%, at least 90%, at least 95%, at least 98% or 100% sequence identity to the polypeptide shown in SEQ ID NO: 22,
w) a polypeptide having at least 60%, at least 65%, at least 70%, at least 75% at least 80%, at least 85%, at least 90%, at least 95%, at least 98% or 100% sequence identity to the polypeptide shown in SEQ ID NO: 23,
x) a polypeptide having at least 60%, at least 65%, at least 70%, at least 75% at least 80%, at least 85%, at least 90%, at least 95%, at least 98% or 100% sequence identity to the polypeptide shown in SEQ ID NO: 24, and
y) a polypeptide having at least 60%, at least 65%, at least 70%, at least 75% at least 80%, at least 85%, at least 90%, at least 95%, at least 98% or 100% sequence identity to the polypeptide shown in SEQ ID NO: 25, and wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 85, and wherein the composition preferably comprises at least one cleaning component. One embodiment relates to a cleaning composition comprising a DNase, a protease and at least one cleaning component, wherein the DNase comprises or consists of a polypeptide selected from the group of polypeptides comprising the amino acid sequence shown in; SEQ ID NO 1, SEQ ID NO 2, SEQ ID NO 3, SEQ ID NO 4, SEQ ID NO 5, SEQ ID NO 6, SEQ ID NO 7, SEQ ID NO 8, SEQ ID NO 9, SEQ ID NO 10, SEQ ID NO 11, SEQ ID NO 12, SEQ ID NO 13, SEQ ID NO 14, SEQ ID NO 15, SEQ ID NO 16, SEQ ID NO 17, SEQ ID NO 18, SEQ ID NO 19, SEQ ID NO 20, SEQ ID NO 21, SEQ ID NO 22, SEQ ID NO 23, SEQ ID NO 24 and SEQ ID NO 25 and wherein the protease comprises or consists of the polypeptide comprising the amino acid sequence shown in SEQ ID NO 85.

One embodiment of the invention relates to a composition, preferably a cleaning composition, comprising a protease, a polypeptide having DNase activity, optionally wherein the polypeptide comprise one or both of the motifs [D/M/L][S/T]GYSR[D/N] (SEQ ID NO: 73), ASXNRSKG (SEQ ID NO: 74), wherein the polypeptide is selected from the group of polypeptides:
a) a polypeptide having at least 60%, at least 65%, at least 70%, at least 75% at least 80%, at least 85%, at least 90%, at least 95%, at least 98% or 100% sequence identity to the polypeptide shown in SEQ ID NO: 1,
b) a polypeptide having at least 60%, at least 65%, at least 70%, at least 75% at least 80%, at least 85%, at least 90%, at least 95%, at least 98% or 100% sequence identity to the polypeptide shown in SEQ ID NO: 2,
c) a polypeptide having at least 60%, at least 65%, at least 70%, at least 75% at least 80%, at least 85%, at least 90%, at least 95%, at least 98% or 100% sequence identity to the polypeptide shown in SEQ ID NO: 3,
d) a polypeptide having at least 60%, at least 65%, at least 70%, at least 75% at least 80%, at least 85%, at least 90%, at least 95%, at least 98% or 100% sequence identity to the polypeptide shown in SEQ ID NO: 4,
e) a polypeptide having at least 60%, at least 65%, at least 70%, at least 75% at least 80%, at least 85%, at least 90%, at least 95%, at least 98% or 100% sequence identity to the polypeptide shown in SEQ ID NO: 5,
f) a polypeptide having at least 60%, at least 65%, at least 70%, at least 75% at least 80%, at least 85%, at least 90%, at least 95%, at least 98% or 100% sequence identity to the polypeptide shown in SEQ ID NO: 6,
g) a polypeptide having at least 60%, at least 65%, at least 70%, at least 75% at least 80%, at least 85%, at least 90%, at least 95%, at least 98% or 100% sequence identity to the polypeptide shown in SEQ ID NO: 7,
h) a polypeptide having at least 60%, at least 65%, at least 70%, at least 75% at least 80%, at least 85%, at least 90%, at least 95%, at least 98% or 100% sequence identity to the polypeptide shown in SEQ ID NO: 8,
i) a polypeptide having at least 60%, at least 65%, at least 70%, at least 75% at least 80%, at least 85%, at least 90%, at least 95%, at least 98% or 100% sequence identity to the polypeptide shown in SEQ ID NO: 9,
j) a polypeptide having at least 60%, at least 65%, at least 70%, at least 75% at least 80%, at least 85%, at least 90%, at least 95%, at least 98% or 100% sequence identity to the polypeptide shown in SEQ ID NO: 10,
k) a polypeptide having at least 60%, at least 65%, at least 70%, at least 75% at least 80%, at least 85%, at least 90%, at least 95%, at least 98% or 100% sequence identity to the polypeptide shown in SEQ ID NO: 11,
l) a polypeptide having at least 60%, at least 65%, at least 70%, at least 75% at least 80%, at least 85%, at least 90%, at least 95%, at least 98% or 100% sequence identity to the polypeptide shown in SEQ ID NO: 12,
m) a polypeptide having at least 60%, at least 65%, at least 70%, at least 75% at least 80%, at least 85%, at least 90%, at least 95%, at least 98% or 100% sequence identity to the polypeptide shown in SEQ ID NO: 13,
n) a polypeptide having at least 60%, at least 65%, at least 70%, at least 75% at least 80%, at least 85%, at least 90%, at least 95%, at least 98% or 100% sequence identity to the polypeptide shown in SEQ ID NO: 14,
o) a polypeptide having at least 60%, at least 65%, at least 70%, at least 75% at least 80%, at least 85%, at least 90%, at least 95%, at least 98% or 100% sequence identity to the polypeptide shown in SEQ ID NO: 15,
p) a polypeptide having at least 60%, at least 65%, at least 70%, at least 75% at least 80%, at least 85%, at least 90%, at least 95%, at least 98% or 100% sequence identity to the polypeptide shown in SEQ ID NO: 16,
q) a polypeptide having at least 60%, at least 65%, at least 70%, at least 75% at least 80%, at least 85%, at least 90%, at least 95%, at least 98% or 100% sequence identity to the polypeptide shown in SEQ ID NO: 17,
r) a polypeptide having at least 60%, at least 65%, at least 70%, at least 75% at least 80%, at least 85%, at least 90%, at least 95%, at least 98% or 100% sequence identity to the polypeptide shown in SEQ ID NO: 18,
s) a polypeptide having at least 60%, at least 65%, at least 70%, at least 75% at least 80%, at least 85%, at least 90%, at least 95%, at least 98% or 100% sequence identity to the polypeptide shown in SEQ ID NO: 19, t) a polypeptide having at least 60%, at least 65%, at least 70%, at least 75% at least 80%, at least 85%, at least 90%, at least 95%, at least 98% or 100% sequence identity to the polypeptide shown in SEQ ID NO: 20, u) a polypeptide having at least 60%, at least 65%, at least 70%, at least 75% at least 80%, at least 85%, at least 90%, at least 95%, at least 98% or 100% sequence identity to the polypeptide shown in SEQ ID NO: 21, v) a polypeptide having at least 60%, at least 65%, at least 70%, at least 75% at least 80%, at least 85%, at least 90%, at least 95%, at least 98% or 100% sequence identity to the polypeptide shown in SEQ ID NO: 22, w) a polypeptide having at least 60%, at least 65%, at least 70%, at least 75% at least 80%, at least 85%, at least 90%, at least 95%, at least 98% or 100% sequence identity to the polypeptide shown in SEQ ID NO: 23, x) a polypeptide having at least 60%, at least 65%, at least 70%, at least 75% at least 80%, at least 85%, at least 90%, at least 95%, at least 98% or 100% sequence identity to the polypeptide shown in SEQ ID NO: 24, and y) a polypeptide having at least 60%, at least 65%, at least 70%, at least 75% at least 80%, at least 85%, at least 90%, at least 95%, at least 98% or 100% sequence identity to the polypeptide shown in SEQ ID NO: 25, and wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 86, and wherein the composition preferably comprises at least one cleaning component. One embodiment relates to a cleaning composition comprising a DNase, a protease and at least one cleaning component, wherein the DNase comprises or consists of a polypeptide selected from the group of polypeptides comprising the amino acid sequence shown in; SEQ ID NO 1, SEQ ID NO 2, SEQ ID NO 3, SEQ ID NO 4, SEQ ID NO 5, SEQ ID NO 6, SEQ ID NO 7, SEQ ID NO 8, SEQ ID NO 9, SEQ ID NO 10, SEQ ID NO 11, SEQ ID NO 12, SEQ ID NO 13, SEQ ID NO 14, SEQ ID NO 15, SEQ ID NO 16, SEQ ID NO 17, SEQ ID NO 18, SEQ ID NO 19, SEQ ID NO 20, SEQ ID NO 21, SEQ ID NO 22, SEQ ID NO 23, SEQ ID NO 24 and SEQ ID NO 25 and wherein the protease comprises or consists of the polypeptide comprising the amino acid sequence shown in SEQ ID NO 86.

One embodiment of the invention relates to a composition, preferably a cleaning composition, comprising a protease, a polypeptide having DNase activity, optionally wherein the polypeptide comprise one or both of the motifs [V/I]PL[S/A]NAWK (SEQ ID NO: 75) or NPQL (SEQ ID NO: 76), wherein the polypeptide is selected from the group of polypeptides:

a) a polypeptide having at least 60%, at least 65%, at least 70%, at least 75% at least 80%, at least 85%, at least 90%, at least 95%, at least 98% or 100% sequence identity to the polypeptide shown in SEQ ID NO: 26, b) a polypeptide having at least 60%, at least 65%, at least 70%, at least 75% at least 80%, at least 85%, at least 90%, at least 95%, at least 98% or 100% sequence identity to the polypeptide shown in SEQ ID NO: 27, c) a polypeptide having at least 60%, at least 65%, at least 70%, at least 75% at least 80%, at least 85%, at least 90%, at least 95%, at least 98% or 100% sequence identity to the polypeptide shown in SEQ ID NO: 28, d) a polypeptide having at least 60%, at least 65%, at least 70%, at least 75% at least 80%, at least 85%, at least 90%, at least 95%, at least 98% or 100% sequence identity to the polypeptide shown in SEQ ID NO: 29, e) a polypeptide having at least 60%, at least 65%, at least 70%, at least 75% at least 80%, at least 85%, at least 90%, at least 95%, at least 98% or 100% sequence identity to the polypeptide shown in SEQ ID NO: 30, f) a polypeptide having at least 60%, at least 65%, at least 70%, at least 75% at least 80%, at least 85%, at least 90%, at least 95%, at least 98% or 100% sequence identity to the polypeptide shown in SEQ ID NO: 31, g) a polypeptide having at least 60%, at least 65%, at least 70%, at least 75% at least 80%, at least 85%, at least 90%, at least 95%, at least 98% or 100% sequence identity to the polypeptide shown in SEQ ID NO: 32, h) a polypeptide having at least 60%, at least 65%, at least 70%, at least 75% at least 80%, at least 85%, at least 90%, at least 95%, at least 98% or 100% sequence identity to the polypeptide shown in SEQ ID NO: 33, i) a polypeptide having at least 60%, at least 65%, at least 70%, at least 75% at least 80%, at least 85%, at least 90%, at least 95%, at least 98% or 100% sequence identity to the polypeptide shown in SEQ ID NO: 34, j) a polypeptide having at least 60%, at least 65%, at least 70%, at least 75% at least 80%, at least 85%, at least 90%, at least 95%, at least 98% or 100% sequence identity to the polypeptide shown in SEQ ID NO: 35, k) a polypeptide having at least 60%, at least 65%, at least 70%, at least 75% at least 80%, at least 85%, at least 90%, at least 95%, at least 98% or 100% sequence identity to the polypeptide shown in SEQ ID NO: 36, l) a polypeptide having at least 60%, at least 65%, at least 70%, at least 75% at least 80%, at least 85%, at least 90%, at least 95%, at least 98% or 100% sequence identity to the polypeptide shown in SEQ ID NO: 37, and m) a polypeptide having at least 60%, at least 65%, at least 70%, at least 75% at least 80%, at least 85%, at least 90%, at least 95%, at least 98% or 100% sequence identity to the polypeptide shown in SEQ ID NO: 38, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 79, and wherein the composition preferably comprises at least one cleaning component. One embodiment relates to a cleaning composition comprising a DNase, a protease and at least one cleaning component, wherein the DNase comprises or consists of a polypeptide selected from the group of polypeptides comprising the amino acid sequence shown in; SEQ ID NO 26, SEQ ID NO 27, SEQ ID NO 28, SEQ ID NO 29, SEQ ID NO 30, SEQ ID NO 31, SEQ ID NO 32, SEQ ID NO 33, SEQ ID NO 34, SEQ ID NO 35, SEQ ID NO 36, SEQ ID NO 37 and SEQ ID NO 38 and wherein the protease comprises or consists of the polypeptide comprising the amino acid sequence shown in SEQ ID NO 79.

One embodiment of the invention relates to a composition, preferably a cleaning composition, comprising a protease, a polypeptide having DNase activity, optionally wherein the polypeptide comprise one or both of the motifs [V/I]PL[S/A]NAWK (SEQ ID NO: 75) or NPQL (SEQ ID NO: 76), wherein the polypeptide is selected from the group of polypeptides:

a) a polypeptide having at least 60%, at least 65%, at least 70%, at least 75% at least 80%, at least 85%, at least 90%, at least 95%, at least 98% or 100% sequence identity to the polypeptide shown in SEQ ID NO: 26,
b) a polypeptide having at least 60%, at least 65%, at least 70%, at least 75% at least 80%, at least 85%, at least 90%, at least 95%, at least 98% or 100% sequence identity to the polypeptide shown in SEQ ID NO: 27,
c) a polypeptide having at least 60%, at least 65%, at least 70%, at least 75% at least 80%, at least 85%, at least 90%, at least 95%, at least 98% or 100% sequence identity to the polypeptide shown in SEQ ID NO: 28,
d) a polypeptide having at least 60%, at least 65%, at least 70%, at least 75% at least 80%, at least 85%, at least 90%, at least 95%, at least 98% or 100% sequence identity to the polypeptide shown in SEQ ID NO: 29,
e) a polypeptide having at least 60%, at least 65%, at least 70%, at least 75% at least 80%, at least 85%, at least 90%, at least 95%, at least 98% or 100% sequence identity to the polypeptide shown in SEQ ID NO: 30,
f) a polypeptide having at least 60%, at least 65%, at least 70%, at least 75% at least 80%, at least 85%, at least 90%, at least 95%, at least 98% or 100% sequence identity to the polypeptide shown in SEQ ID NO: 31,
g) a polypeptide having at least 60%, at least 65%, at least 70%, at least 75% at least 80%, at least 85%, at least 90%, at least 95%, at least 98% or 100% sequence identity to the polypeptide shown in SEQ ID NO: 32,
h) a polypeptide having at least 60%, at least 65%, at least 70%, at least 75% at least 80%, at least 85%, at least 90%, at least 95%, at least 98% or 100% sequence identity to the polypeptide shown in SEQ ID NO: 33,
i) a polypeptide having at least 60%, at least 65%, at least 70%, at least 75% at least 80%, at least 85%, at least 90%, at least 95%, at least 98% or 100% sequence identity to the polypeptide shown in SEQ ID NO: 34,
j) a polypeptide having at least 60%, at least 65%, at least 70%, at least 75% at least 80%, at least 85%, at least 90%, at least 95%, at least 98% or 100% sequence identity to the polypeptide shown in SEQ ID NO: 35,
k) a polypeptide having at least 60%, at least 65%, at least 70%, at least 75% at least 80%, at least 85%, at least 90%, at least 95%, at least 98% or 100% sequence identity to the polypeptide shown in SEQ ID NO: 36,
l) a polypeptide having at least 60%, at least 65%, at least 70%, at least 75% at least 80%, at least 85%, at least 90%, at least 95%, at least 98% or 100% sequence identity to the polypeptide shown in SEQ ID NO: 37, and
m) a polypeptide having at least 60%, at least 65%, at least 70%, at least 75% at least 80%, at least 85%, at least 90%, at least 95%, at least 98% or 100% sequence identity to the polypeptide shown in SEQ ID NO: 38,
wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 80, and wherein the composition preferably comprises at least one cleaning component. One embodiment relates to a cleaning composition comprising a DNase, a protease and at least one cleaning component, wherein the DNase comprises or consists of a polypeptide selected from the group of polypeptides comprising the amino acid sequence shown in; SEQ ID NO 26, SEQ ID NO 27, SEQ ID NO 28, SEQ ID NO 29, SEQ ID NO 30, SEQ ID NO 31, SEQ ID NO 32, SEQ ID NO 33, SEQ ID NO 34, SEQ ID NO 35, SEQ ID NO 36, SEQ ID NO 37 and SEQ ID NO 38 and wherein the protease comprises or consists of the polypeptide comprising the amino acid sequence shown in SEQ ID NO 80.

One embodiment of the invention relates to a composition, preferably a cleaning composition, comprising a protease, a polypeptide having DNase activity, optionally wherein the polypeptide comprise one or both of the motifs [V/I]PL[S/A]NAWK (SEQ ID NO: 75) or NPQL (SEQ ID NO: 76), wherein the polypeptide is selected from the group of polypeptides:
a) a polypeptide having at least 60%, at least 65%, at least 70%, at least 75% at least 80%, at least 85%, at least 90%, at least 95%, at least 98% or 100% sequence identity to the polypeptide shown in SEQ ID NO: 26,
b) a polypeptide having at least 60%, at least 65%, at least 70%, at least 75% at least 80%, at least 85%, at least 90%, at least 95%, at least 98% or 100% sequence identity to the polypeptide shown in SEQ ID NO: 27,
c) a polypeptide having at least 60%, at least 65%, at least 70%, at least 75% at least 80%, at least 85%, at least 90%, at least 95%, at least 98% or 100% sequence identity to the polypeptide shown in SEQ ID NO: 28,
d) a polypeptide having at least 60%, at least 65%, at least 70%, at least 75% at least 80%, at least 85%, at least 90%, at least 95%, at least 98% or 100% sequence identity to the polypeptide shown in SEQ ID NO: 29,
e) a polypeptide having at least 60%, at least 65%, at least 70%, at least 75% at least 80%, at least 85%, at least 90%, at least 95%, at least 98% or 100% sequence identity to the polypeptide shown in SEQ ID NO: 30,
f) a polypeptide having at least 60%, at least 65%, at least 70%, at least 75% at least 80%, at least 85%, at least 90%, at least 95%, at least 98% or 100% sequence identity to the polypeptide shown in SEQ ID NO: 31,
g) a polypeptide having at least 60%, at least 65%, at least 70%, at least 75% at least 80%, at least 85%, at least 90%, at least 95%, at least 98% or 100% sequence identity to the polypeptide shown in SEQ ID NO: 32,
h) a polypeptide having at least 60%, at least 65%, at least 70%, at least 75% at least 80%, at least 85%, at least 90%, at least 95%, at least 98% or 100% sequence identity to the polypeptide shown in SEQ ID NO: 33,
i) a polypeptide having at least 60%, at least 65%, at least 70%, at least 75% at least 80%, at least 85%, at least 90%, at least 95%, at least 98% or 100% sequence identity to the polypeptide shown in SEQ ID NO: 34,
j) a polypeptide having at least 60%, at least 65%, at least 70%, at least 75% at least 80%, at least 85%, at least 90%, at least 95%, at least 98% or 100% sequence identity to the polypeptide shown in SEQ ID NO: 35,
k) a polypeptide having at least 60%, at least 65%, at least 70%, at least 75% at least 80%, at least 85%, at least 90%, at least 95%, at least 98% or 100% sequence identity to the polypeptide shown in SEQ ID NO: 36,
l) a polypeptide having at least 60%, at least 65%, at least 70%, at least 75% at least 80%, at least 85%, at least 90%, at least 95%, at least 98% or 100% sequence identity to the polypeptide shown in SEQ ID NO: 37, and
m) a polypeptide having at least 60%, at least 65%, at least 70%, at least 75% at least 80%, at least 85%, at least 90%, at least 95%, at least 98% or 100% sequence identity to the polypeptide shown in SEQ ID NO: 38,
wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 81, and wherein the composition preferably comprises at least one cleaning component. One embodiment relates to a cleaning composition comprising a DNase, a protease and at least one cleaning component, wherein the DNase comprises or consists of a polypeptide selected from the group of polypeptides comprising the amino acid sequence shown in; SEQ ID NO 26, SEQ ID NO 27, SEQ ID NO 28, SEQ ID NO 29, SEQ ID NO 30, SEQ ID NO 31, SEQ ID NO 32, SEQ ID NO 33, SEQ ID NO 34, SEQ ID NO 35, SEQ ID NO 36, SEQ ID NO 37 and SEQ ID NO 38 and wherein the protease comprises or consists of the polypeptide comprising the amino acid sequence shown in SEQ ID NO 81.

One embodiment of the invention relates to a composition, preferably a cleaning composition, comprising a protease, a polypeptide having DNase activity, optionally wherein the polypeptide comprise one or both of the motifs [V/I]PL[S/A]NAWK (SEQ ID NO: 75) or NPQL (SEQ ID NO: 76), wherein the polypeptide is selected from the group of polypeptides:
a) a polypeptide having at least 60%, at least 65%, at least 70%, at least 75% at least 80%, at least 85%, at least 90%, at least 95%, at least 98% or 100% sequence identity to the polypeptide shown in SEQ ID NO: 26,
b) a polypeptide having at least 60%, at least 65%, at least 70%, at least 75% at least 80%, at least 85%, at least 90%, at least 95%, at least 98% or 100% sequence identity to the polypeptide shown in SEQ ID NO: 27,
c) a polypeptide having at least 60%, at least 65%, at least 70%, at least 75% at least 80%, at least 85%, at least 90%, at least 95%, at least 98% or 100% sequence identity to the polypeptide shown in SEQ ID NO: 28,
d) a polypeptide having at least 60%, at least 65%, at least 70%, at least 75% at least 80%, at least 85%, at least 90%, at least 95%, at least 98% or 100% sequence identity to the polypeptide shown in SEQ ID NO: 29,
e) a polypeptide having at least 60%, at least 65%, at least 70%, at least 75% at least 80%, at least 85%, at least 90%, at least 95%, at least 98% or 100% sequence identity to the polypeptide shown in SEQ ID NO: 30,
f) a polypeptide having at least 60%, at least 65%, at least 70%, at least 75% at least 80%, at least 85%, at least 90%, at least 95%, at least 98% or 100% sequence identity to the polypeptide shown in SEQ ID NO: 31,
g) a polypeptide having at least 60%, at least 65%, at least 70%, at least 75% at least 80%, at least 85%, at least 90%, at least 95%, at least 98% or 100% sequence identity to the polypeptide shown in SEQ ID NO: 32,
h) a polypeptide having at least 60%, at least 65%, at least 70%, at least 75% at least 80%, at least 85%, at least 90%, at least 95%, at least 98% or 100% sequence identity to the polypeptide shown in SEQ ID NO: 33,
i) a polypeptide having at least 60%, at least 65%, at least 70%, at least 75% at least 80%, at least 85%, at least 90%, at least 95%, at least 98% or 100% sequence identity to the polypeptide shown in SEQ ID NO: 34,
j) a polypeptide having at least 60%, at least 65%, at least 70%, at least 75% at least 80%, at least 85%, at least 90%, at least 95%, at least 98% or 100% sequence identity to the polypeptide shown in SEQ ID NO: 35,
k) a polypeptide having at least 60%, at least 65%, at least 70%, at least 75% at least 80%, at least 85%, at least 90%, at least 95%, at least 98% or 100% sequence identity to the polypeptide shown in SEQ ID NO: 36,
l) a polypeptide having at least 60%, at least 65%, at least 70%, at least 75% at least 80%, at least 85%, at least 90%, at least 95%, at least 98% or 100% sequence identity to the polypeptide shown in SEQ ID NO: 37, and
m) a polypeptide having at least 60%, at least 65%, at least 70%, at least 75% at least 80%, at least 85%, at least 90%, at least 95%, at least 98% or 100% sequence identity to the polypeptide shown in SEQ ID NO: 38, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 82, and wherein the composition preferably comprises at least one cleaning component. One embodiment relates to a cleaning composition comprising a DNase, a protease and at least one cleaning component, wherein the DNase comprises or consists of a polypeptide selected from the group of polypeptides comprising the amino acid sequence shown in; SEQ ID NO 26, SEQ ID NO 27, SEQ ID NO 28, SEQ ID NO 29, SEQ ID NO 30, SEQ ID NO 31, SEQ ID NO 32, SEQ ID NO 33, SEQ ID NO 34, SEQ ID NO 35, SEQ ID NO 36, SEQ ID NO 37 and SEQ ID NO 38 and wherein the protease comprises or consists of the polypeptide comprising the amino acid sequence shown in SEQ ID NO 82.

One embodiment of the invention relates to a composition, preferably a cleaning composition, comprising a protease, a polypeptide having DNase activity, optionally wherein the polypeptide comprise one or both of the motifs [V/I]PL[S/A]NAWK (SEQ ID NO: 75) or NPQL (SEQ ID NO: 76), wherein the polypeptide is selected from the group of polypeptides:
a) a polypeptide having at least 60%, at least 65%, at least 70%, at least 75% at least 80%, at least 85%, at least 90%, at least 95%, at least 98% or 100% sequence identity to the polypeptide shown in SEQ ID NO: 26,
b) a polypeptide having at least 60%, at least 65%, at least 70%, at least 75% at least 80%, at least 85%, at least 90%, at least 95%, at least 98% or 100% sequence identity to the polypeptide shown in SEQ ID NO: 27,
c) a polypeptide having at least 60%, at least 65%, at least 70%, at least 75% at least 80%, at least 85%, at least 90%, at least 95%, at least 98% or 100% sequence identity to the polypeptide shown in SEQ ID NO: 28,
d) a polypeptide having at least 60%, at least 65%, at least 70%, at least 75% at least 80%, at least 85%, at least 90%, at least 95%, at least 98% or 100% sequence identity to the polypeptide shown in SEQ ID NO: 29,
e) a polypeptide having at least 60%, at least 65%, at least 70%, at least 75% at least 80%, at least 85%, at least 90%, at least 95%, at least 98% or 100% sequence identity to the polypeptide shown in SEQ ID NO: 30,
f) a polypeptide having at least 60%, at least 65%, at least 70%, at least 75% at least 80%, at least 85%, at least 90%, at least 95%, at least 98% or 100% sequence identity to the polypeptide shown in SEQ ID NO: 31,
g) a polypeptide having at least 60%, at least 65%, at least 70%, at least 75% at least 80%, at least 85%, at least 90%, at least 95%, at least 98% or 100% sequence identity to the polypeptide shown in SEQ ID NO: 32,
h) a polypeptide having at least 60%, at least 65%, at least 70%, at least 75% at least 80%, at least 85%, at least 90%, at least 95%, at least 98% or 100% sequence identity to the polypeptide shown in SEQ ID NO: 33,
i) a polypeptide having at least 60%, at least 65%, at least 70%, at least 75% at least 80%, at least 85%, at least 90%, at least 95%, at least 98% or 100% sequence identity to the polypeptide shown in SEQ ID NO: 34,
j) a polypeptide having at least 60%, at least 65%, at least 70%, at least 75% at least 80%, at least 85%, at least 90%, at least 95%, at least 98% or 100% sequence identity to the polypeptide shown in SEQ ID NO: 35,
k) a polypeptide having at least 60%, at least 65%, at least 70%, at least 75% at least 80%, at least 85%, at least 90%, at least 95%, at least 98% or 100% sequence identity to the polypeptide shown in SEQ ID NO: 36, l) a polypeptide having at least 60%, at least 65%, at least 70%, at least 75% at least 80%, at least 85%, at least 90%, at least 95%, at least 98% or 100% sequence identity to the polypeptide shown in SEQ ID NO: 37, and m) a polypeptide having at least 60%, at least 65%, at least 70%, at least 75% at least 80%, at least 85%, at least 90%, at least 95%, at least 98% or 100% sequence identity to the polypeptide shown in SEQ ID NO: 38, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 83, and wherein the composition preferably comprises at least one cleaning component. One embodiment relates to a cleaning composition comprising a DNase, a protease and at least one cleaning component, wherein the DNase comprises or consists of a polypeptide selected from the group of polypeptides comprising the amino acid sequence shown in; SEQ ID NO 26, SEQ ID NO 27, SEQ ID NO 28, SEQ ID NO 29, SEQ ID NO 30, SEQ ID NO 31, SEQ ID NO 32, SEQ ID NO 33, SEQ ID NO 34, SEQ ID NO 35, SEQ ID NO 36, SEQ ID NO 37 and SEQ ID NO 38 and wherein the protease comprises or consists of the polypeptide comprising the amino acid sequence shown in SEQ ID NO 83.

One embodiment of the invention relates to a composition, preferably a cleaning composition, comprising a protease, a polypeptide having DNase activity, optionally wherein the polypeptide comprise one or both of the motifs [V/I]PL[S/A]NAWK (SEQ ID NO: 75) or NPQL (SEQ ID NO: 76), wherein the polypeptide is selected from the group of polypeptides:

a) a polypeptide having at least 60%, at least 65%, at least 70%, at least 75% at least 80%, at least 85%, at least 90%, at least 95%, at least 98% or 100% sequence identity to the polypeptide shown in SEQ ID NO: 26, b) a polypeptide having at least 60%, at least 65%, at least 70%, at least 75% at least 80%, at least 85%, at least 90%, at least 95%, at least 98% or 100% sequence identity to the polypeptide shown in SEQ ID NO: 27, c) a polypeptide having at least 60%, at least 65%, at least 70%, at least 75% at least 80%, at least 85%, at least 90%, at least 95%, at least 98% or 100% sequence identity to the polypeptide shown in SEQ ID NO: 28, d) a polypeptide having at least 60%, at least 65%, at least 70%, at least 75% at least 80%, at least 85%, at least 90%, at least 95%, at least 98% or 100% sequence identity to the polypeptide shown in SEQ ID NO: 29, e) a polypeptide having at least 60%, at least 65%, at least 70%, at least 75% at least 80%, at least 85%, at least 90%, at least 95%, at least 98% or 100% sequence identity to the polypeptide shown in SEQ ID NO: 30, f) a polypeptide having at least 60%, at least 65%, at least 70%, at least 75% at least 80%, at least 85%, at least 90%, at least 95%, at least 98% or 100% sequence identity to the polypeptide shown in SEQ ID NO: 31, g) a polypeptide having at least 60%, at least 65%, at least 70%, at least 75% at least 80%, at least 85%, at least 90%, at least 95%, at least 98% or 100% sequence identity to the polypeptide shown in SEQ ID NO: 32, h) a polypeptide having at least 60%, at least 65%, at least 70%, at least 75% at least 80%, at least 85%, at least 90%, at least 95%, at least 98% or 100% sequence identity to the polypeptide shown in SEQ ID NO: 33, i) a polypeptide having at least 60%, at least 65%, at least 70%, at least 75% at least 80%, at least 85%, at least 90%, at least 95%, at least 98% or 100% sequence identity to the polypeptide shown in SEQ ID NO: 34, j) a polypeptide having at least 60%, at least 65%, at least 70%, at least 75% at least 80%, at least 85%, at least 90%, at least 95%, at least 98% or 100% sequence identity to the polypeptide shown in SEQ ID NO: 35, k) a polypeptide having at least 60%, at least 65%, at least 70%, at least 75% at least 80%, at least 85%, at least 90%, at least 95%, at least 98% or 100% sequence identity to the polypeptide shown in SEQ ID NO: 36, l) a polypeptide having at least 60%, at least 65%, at least 70%, at least 75% at least 80%, at least 85%, at least 90%, at least 95%, at least 98% or 100% sequence identity to the polypeptide shown in SEQ ID NO: 37, and m) a polypeptide having at least 60%, at least 65%, at least 70%, at least 75% at least 80%, at least 85%, at least 90%, at least 95%, at least 98% or 100% sequence identity to the polypeptide shown in SEQ ID NO: 38, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 84, and wherein the composition preferably comprises at least one cleaning component. One embodiment relates to a cleaning composition comprising a DNase, a protease and at least one cleaning component, wherein the DNase comprises or consists of a polypeptide selected from the group of polypeptides comprising the amino acid sequence shown in; SEQ ID NO 26, SEQ ID NO 27, SEQ ID NO 28, SEQ ID NO 29, SEQ ID NO 30, SEQ ID NO 31, SEQ ID NO 32, SEQ ID NO 33, SEQ ID NO 34, SEQ ID NO 35, SEQ ID NO 36, SEQ ID NO 37 and SEQ ID NO 38 and wherein the protease comprises or consists of the polypeptide comprising the amino acid sequence shown in SEQ ID NO 84.

One embodiment of the invention relates to a composition, preferably a cleaning composition, comprising a protease, a polypeptide having DNase activity, optionally wherein the polypeptide comprise one or both of the motifs [V/I]PL[S/A]NAWK (SEQ ID NO: 75) or NPQL (SEQ ID NO: 76), wherein the polypeptide is selected from the group of polypeptides:

a) a polypeptide having at least 60%, at least 65%, at least 70%, at least 75% at least 80%, at least 85%, at least 90%, at least 95%, at least 98% or 100% sequence identity to the polypeptide shown in SEQ ID NO: 26, b) a polypeptide having at least 60%, at least 65%, at least 70%, at least 75% at least 80%, at least 85%, at least 90%, at least 95%, at least 98% or 100% sequence identity to the polypeptide shown in SEQ ID NO: 27, c) a polypeptide having at least 60%, at least 65%, at least 70%, at least 75% at least 80%, at least 85%, at least 90%, at least 95%, at least 98% or 100% sequence identity to the polypeptide shown in SEQ ID NO: 28, d) a polypeptide having at least 60%, at least 65%, at least 70%, at least 75% at least 80%, at least 85%, at least 90%, at least 95%, at least 98% or 100% sequence identity to the polypeptide shown in SEQ ID NO: 29, e) a polypeptide having at least 60%, at least 65%, at least 70%, at least 75% at least 80%, at least 85%, at least 90%, at least 95%, at least 98% or 100% sequence identity to the polypeptide shown in SEQ ID NO: 30, f) a polypeptide having at least 60%, at least 65%, at least 70%, at least 75% at least 80%, at least 85%, at least 90%, at least 95%, at least 98% or 100% sequence identity to the polypeptide shown in SEQ ID NO: 31,
g) a polypeptide having at least 60%, at least 65%, at least 70%, at least 75% at least 80%, at least 85%, at least 90%, at least 95%, at least 98% or 100% sequence identity to the polypeptide shown in SEQ ID NO: 32,
h) a polypeptide having at least 60%, at least 65%, at least 70%, at least 75% at least 80%, at least 85%, at least 90%, at least 95%, at least 98% or 100% sequence identity to the polypeptide shown in SEQ ID NO: 33,
i) a polypeptide having at least 60%, at least 65%, at least 70%, at least 75% at least 80%, at least 85%, at least 90%, at least 95%, at least 98% or 100% sequence identity to the polypeptide shown in SEQ ID NO: 34,
j) a polypeptide having at least 60%, at least 65%, at least 70%, at least 75% at least 80%, at least 85%, at least 90%, at least 95%, at least 98% or 100% sequence identity to the polypeptide shown in SEQ ID NO: 35,
k) a polypeptide having at least 60%, at least 65%, at least 70%, at least 75% at least 80%, at least 85%, at least 90%, at least 95%, at least 98% or 100% sequence identity to the polypeptide shown in SEQ ID NO: 36,
l) a polypeptide having at least 60%, at least 65%, at least 70%, at least 75% at least 80%, at least 85%, at least 90%, at least 95%, at least 98% or 100% sequence identity to the polypeptide shown in SEQ ID NO: 37, and
m) a polypeptide having at least 60%, at least 65%, at least 70%, at least 75% at least 80%, at least 85%, at least 90%, at least 95%, at least 98% or 100% sequence identity to the polypeptide shown in SEQ ID NO: 38, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 85, and wherein the composition preferably comprises at least one cleaning component. One embodiment relates to a cleaning composition comprising a DNase, a protease and at least one cleaning component, wherein the DNase comprises or consists of a polypeptide selected from the group of polypeptides comprising the amino acid sequence shown in; SEQ ID NO 26, SEQ ID NO 27, SEQ ID NO 28, SEQ ID NO 29, SEQ ID NO 30, SEQ ID NO 31, SEQ ID NO 32, SEQ ID NO 33, SEQ ID NO 34, SEQ ID NO 35, SEQ ID NO 36, SEQ ID NO 37 and SEQ ID NO 38 and wherein the protease comprises or consists of the polypeptide comprising the amino acid sequence shown in SEQ ID NO 85.

One embodiment of the invention relates to a composition, preferably a cleaning composition, comprising a protease, a polypeptide having DNase activity, optionally wherein the polypeptide comprise one or both of the motifs [V/I]PL[S/A]NAWK (SEQ ID NO: 75) or NPQL (SEQ ID NO: 76), wherein the polypeptide is selected from the group of polypeptides:

a) a polypeptide having at least 60%, at least 65%, at least 70%, at least 75% at least 80%, at least 85%, at least 90%, at least 95%, at least 98% or 100% sequence identity to the polypeptide shown in SEQ ID NO: 26,
b) a polypeptide having at least 60%, at least 65%, at least 70%, at least 75% at least 80%, at least 85%, at least 90%, at least 95%, at least 98% or 100% sequence identity to the polypeptide shown in SEQ ID NO: 27,
c) a polypeptide having at least 60%, at least 65%, at least 70%, at least 75% at least 80%, at least 85%, at least 90%, at least 95%, at least 98% or 100% sequence identity to the polypeptide shown in SEQ ID NO: 28,
d) a polypeptide having at least 60%, at least 65%, at least 70%, at least 75% at least 80%, at least 85%, at least 90%, at least 95%, at least 98% or 100% sequence identity to the polypeptide shown in SEQ ID NO: 29,
e) a polypeptide having at least 60%, at least 65%, at least 70%, at least 75% at least 80%, at least 85%, at least 90%, at least 95%, at least 98% or 100% sequence identity to the polypeptide shown in SEQ ID NO: 30,
f) a polypeptide having at least 60%, at least 65%, at least 70%, at least 75% at least 80%, at least 85%, at least 90%, at least 95%, at least 98% or 100% sequence identity to the polypeptide shown in SEQ ID NO: 31,
g) a polypeptide having at least 60%, at least 65%, at least 70%, at least 75% at least 80%, at least 85%, at least 90%, at least 95%, at least 98% or 100% sequence identity to the polypeptide shown in SEQ ID NO: 32,
h) a polypeptide having at least 60%, at least 65%, at least 70%, at least 75% at least 80%, at least 85%, at least 90%, at least 95%, at least 98% or 100% sequence identity to the polypeptide shown in SEQ ID NO: 33,
i) a polypeptide having at least 60%, at least 65%, at least 70%, at least 75% at least 80%, at least 85%, at least 90%, at least 95%, at least 98% or 100% sequence identity to the polypeptide shown in SEQ ID NO: 34,
j) a polypeptide having at least 60%, at least 65%, at least 70%, at least 75% at least 80%, at least 85%, at least 90%, at least 95%, at least 98% or 100% sequence identity to the polypeptide shown in SEQ ID NO: 35,
k) a polypeptide having at least 60%, at least 65%, at least 70%, at least 75% at least 80%, at least 85%, at least 90%, at least 95%, at least 98% or 100% sequence identity to the polypeptide shown in SEQ ID NO: 36,
l) a polypeptide having at least 60%, at least 65%, at least 70%, at least 75% at least 80%, at least 85%, at least 90%, at least 95%, at least 98% or 100% sequence identity to the polypeptide shown in SEQ ID NO: 37, and
m) a polypeptide having at least 60%, at least 65%, at least 70%, at least 75% at least 80%, at least 85%, at least 90%, at least 95%, at least 98% or 100% sequence identity to the polypeptide shown in SEQ ID NO: 38, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 86, and wherein the composition preferably comprises at least one cleaning component. One embodiment relates to a cleaning composition comprising a DNase, a protease and at least one cleaning component, wherein the DNase comprises or consists of a polypeptide selected from the group of polypeptides comprising the amino acid sequence shown in; SEQ ID NO 26, SEQ ID NO 27, SEQ ID NO 28, SEQ ID NO 29, SEQ ID NO 30, SEQ ID NO 31, SEQ ID NO 32, SEQ ID NO 33, SEQ ID NO 34, SEQ ID NO 35, SEQ ID NO 36, SEQ ID NO 37 and SEQ ID NO 38 and wherein the protease comprises or consists of the polypeptide comprising the amino acid sequence shown in SEQ ID NO 86.

One embodiment of the invention relates to a composition, preferably a cleaning composition, comprising a protease, a polypeptide having DNase activity, optionally wherein the polypeptide comprise one or both of the motifs P[Q/E]L[W/Y] (SEQ ID NO: 77) or [K/H/E]NAW (SEQ ID NO: 78), wherein the polypeptide is selected from the group of polypeptides:

a) a polypeptide having at least 60%, at least 65%, at least 70%, at least 75% at least 80%, at least 85%, at least 90%, at least 95%, at least 98% or 100% sequence identity to the polypeptide shown in SEQ ID NO: 39,
b) a polypeptide having at least 60%, at least 65%, at least 70%, at least 75% at least 80%, at least 85%, at least 90%, at least 95%, at least 98% or 100% sequence identity to the polypeptide shown in SEQ ID NO: 40,
c) a polypeptide having at least 60%, at least 65%, at least 70%, at least 75% at least 80%, at least 85%, at least 90%, at least 95%, at least 98% or 100% sequence identity to the polypeptide shown in SEQ ID NO: 41,
d) a polypeptide having at least 60%, at least 65%, at least 70%, at least 75% at least 80%, at least 85%, at least 90%, at least 95%, at least 98% or 100% sequence identity to the polypeptide shown in SEQ ID NO: 42,
e) a polypeptide having at least 60%, at least 65%, at least 70%, at least 75% at least 80%, at least 85%, at least 90%, at least 95%, at least 98% or 100% sequence identity to the polypeptide shown in SEQ ID NO: 43
f) a polypeptide having at least 60%, at least 65%, at least 70%, at least 75% at least 80%, at least 85%, at least 90%, at least 95%, at least 98% or 100% sequence identity to the polypeptide shown in SEQ ID NO: 44,
g) a polypeptide having at least 60%, at least 65%, at least 70%, at least 75% at least 80%, at least 85%, at least 90%, at least 95%, at least 98% or 100% sequence identity to the polypeptide shown in SEQ ID NO: 45,
h) a polypeptide having at least 60%, at least 65%, at least 70%, at least 75% at least 80%, at least 85%, at least 90%, at least 95%, at least 98% or 100% sequence identity to the polypeptide shown in SEQ ID NO: 46,
i) a polypeptide having at least 60%, at least 65%, at least 70%, at least 75% at least 80%, at least 85%, at least 90%, at least 95%, at least 98% or 100% sequence identity to the polypeptide shown in SEQ ID NO: 47,
j) a polypeptide having at least 60%, at least 65%, at least 70%, at least 75% at least 80%, at least 85%, at least 90%, at least 95%, at least 98% or 100% sequence identity to the polypeptide shown in SEQ ID NO: 48,
k) a polypeptide having at least 60%, at least 65%, at least 70%, at least 75% at least 80%, at least 85%, at least 90%, at least 95%, at least 98% or 100% sequence identity to the polypeptide shown in SEQ ID NO: 49,
l) a polypeptide having at least 60%, at least 65%, at least 70%, at least 75% at least 80%, at least 85%, at least 90%, at least 95%, at least 98% or 100% sequence identity to the polypeptide shown in SEQ ID NO: 50,
m) a polypeptide having at least 60%, at least 65%, at least 70%, at least 75% at least 80%, at least 85%, at least 90%, at least 95%, at least 98% or 100% sequence identity to the polypeptide shown in SEQ ID NO: 51,
wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 79, and wherein the composition preferably comprises at least one cleaning component. One embodiment relates to a cleaning composition comprising a DNase, a protease and at least one cleaning component, wherein the DNase comprises or consists of a polypeptide selected from the group of polypeptides comprising the amino acid sequence shown in; SEQ ID NO 39, SEQ ID NO 40, SEQ ID NO 41, SEQ ID NO 42, SEQ ID NO 43, SEQ ID NO 44, SEQ ID NO 45, SEQ ID NO 46, SEQ ID NO 47, SEQ ID NO 48, SEQ ID NO 49, SEQ ID NO 50 and SEQ ID NO 51 and wherein the protease comprises or consists of the polypeptide comprising the amino acid sequence shown in SEQ ID NO 79.

One embodiment of the invention relates to a composition, preferably a cleaning composition, comprising a protease, a polypeptide having DNase activity, optionally wherein the polypeptide comprise one or both of the motifs P[Q/E]L[W/Y] (SEQ ID NO: 77) or [K/H/E]NAW (SEQ ID NO: 78), wherein the polypeptide is selected from the group of polypeptides:
a) a polypeptide having at least 60%, at least 65%, at least 70%, at least 75% at least 80%, at least 85%, at least 90%, at least 95%, at least 98% or 100% sequence identity to the polypeptide shown in SEQ ID NO: 39,
b) a polypeptide having at least 60%, at least 65%, at least 70%, at least 75% at least 80%, at least 85%, at least 90%, at least 95%, at least 98% or 100% sequence identity to the polypeptide shown in SEQ ID NO: 40,
c) a polypeptide having at least 60%, at least 65%, at least 70%, at least 75% at least 80%, at least 85%, at least 90%, at least 95%, at least 98% or 100% sequence identity to the polypeptide shown in SEQ ID NO: 41,
d) a polypeptide having at least 60%, at least 65%, at least 70%, at least 75% at least 80%, at least 85%, at least 90%, at least 95%, at least 98% or 100% sequence identity to the polypeptide shown in SEQ ID NO: 42,
e) a polypeptide having at least 60%, at least 65%, at least 70%, at least 75% at least 80%, at least 85%, at least 90%, at least 95%, at least 98% or 100% sequence identity to the polypeptide shown in SEQ ID NO: 43
f) a polypeptide having at least 60%, at least 65%, at least 70%, at least 75% at least 80%, at least 85%, at least 90%, at least 95%, at least 98% or 100% sequence identity to the polypeptide shown in SEQ ID NO: 44,
g) a polypeptide having at least 60%, at least 65%, at least 70%, at least 75% at least 80%, at least 85%, at least 90%, at least 95%, at least 98% or 100% sequence identity to the polypeptide shown in SEQ ID NO: 45,
h) a polypeptide having at least 60%, at least 65%, at least 70%, at least 75% at least 80%, at least 85%, at least 90%, at least 95%, at least 98% or 100% sequence identity to the polypeptide shown in SEQ ID NO: 46,
i) a polypeptide having at least 60%, at least 65%, at least 70%, at least 75% at least 80%, at least 85%, at least 90%, at least 95%, at least 98% or 100% sequence identity to the polypeptide shown in SEQ ID NO: 47,
j) a polypeptide having at least 60%, at least 65%, at least 70%, at least 75% at least 80%, at least 85%, at least 90%, at least 95%, at least 98% or 100% sequence identity to the polypeptide shown in SEQ ID NO: 48,
k) a polypeptide having at least 60%, at least 65%, at least 70%, at least 75% at least 80%, at least 85%, at least 90%, at least 95%, at least 98% or 100% sequence identity to the polypeptide shown in SEQ ID NO: 49,
l) a polypeptide having at least 60%, at least 65%, at least 70%, at least 75% at least 80%, at least 85%, at least 90%, at least 95%, at least 98% or 100% sequence identity to the polypeptide shown in SEQ ID NO: 50,
m) a polypeptide having at least 60%, at least 65%, at least 70%, at least 75% at least 80%, at least 85%, at least 90%, at least 95%, at least 98% or 100% sequence identity to the polypeptide shown in SEQ ID NO: 51,
wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 80, and wherein the composition preferably comprises at least one cleaning component. One embodiment relates to a cleaning composition comprising a DNase, a protease and at least one cleaning component, wherein the DNase comprises or consists of a polypeptide selected from the group of polypeptides comprising the amino acid sequence shown in; SEQ ID NO 39, SEQ ID NO 40, SEQ ID NO 41, SEQ ID NO 42, SEQ ID NO 43, SEQ ID NO 44, SEQ ID NO 45, SEQ ID NO 46, SEQ ID NO 47, SEQ ID NO 48, SEQ ID NO 49, SEQ ID NO 50 and SEQ ID NO 51 and wherein the protease comprises or consists of the polypeptide comprising the amino acid sequence shown in SEQ ID NO 80.

One embodiment of the invention relates to a composition, preferably a cleaning composition, comprising a protease, a polypeptide having DNase activity, optionally wherein the polypeptide comprise one or both of the motifs P[Q/E]L[W/Y] (SEQ ID NO: 77) or [K/H/E]NAW (SEQ ID NO: 78), wherein the polypeptide is selected from the group of polypeptides:
 a) a polypeptide having at least 60%, at least 65%, at least 70%, at least 75% at least 80%, at least 85%, at least 90%, at least 95%, at least 98% or 100% sequence identity to the polypeptide shown in SEQ ID NO: 39,
 b) a polypeptide having at least 60%, at least 65%, at least 70%, at least 75% at least 80%, at least 85%, at least 90%, at least 95%, at least 98% or 100% sequence identity to the polypeptide shown in SEQ ID NO: 40,
 c) a polypeptide having at least 60%, at least 65%, at least 70%, at least 75% at least 80%, at least 85%, at least 90%, at least 95%, at least 98% or 100% sequence identity to the polypeptide shown in SEQ ID NO: 41,
 d) a polypeptide having at least 60%, at least 65%, at least 70%, at least 75% at least 80%, at least 85%, at least 90%, at least 95%, at least 98% or 100% sequence identity to the polypeptide shown in SEQ ID NO: 42,
 e) a polypeptide having at least 60%, at least 65%, at least 70%, at least 75% at least 80%, at least 85%, at least 90%, at least 95%, at least 98% or 100% sequence identity to the polypeptide shown in SEQ ID NO: 43
 f) a polypeptide having at least 60%, at least 65%, at least 70%, at least 75% at least 80%, at least 85%, at least 90%, at least 95%, at least 98% or 100% sequence identity to the polypeptide shown in SEQ ID NO: 44,
 g) a polypeptide having at least 60%, at least 65%, at least 70%, at least 75% at least 80%, at least 85%, at least 90%, at least 95%, at least 98% or 100% sequence identity to the polypeptide shown in SEQ ID NO: 45,
 h) a polypeptide having at least 60%, at least 65%, at least 70%, at least 75% at least 80%, at least 85%, at least 90%, at least 95%, at least 98% or 100% sequence identity to the polypeptide shown in SEQ ID NO: 46,
 i) a polypeptide having at least 60%, at least 65%, at least 70%, at least 75% at least 80%, at least 85%, at least 90%, at least 95%, at least 98% or 100% sequence identity to the polypeptide shown in SEQ ID NO: 47,
 j) a polypeptide having at least 60%, at least 65%, at least 70%, at least 75% at least 80%, at least 85%, at least 90%, at least 95%, at least 98% or 100% sequence identity to the polypeptide shown in SEQ ID NO: 48,
 k) a polypeptide having at least 60%, at least 65%, at least 70%, at least 75% at least 80%, at least 85%, at least 90%, at least 95%, at least 98% or 100% sequence identity to the polypeptide shown in SEQ ID NO: 49,
 l) a polypeptide having at least 60%, at least 65%, at least 70%, at least 75% at least 80%, at least 85%, at least 90%, at least 95%, at least 98% or 100% sequence identity to the polypeptide shown in SEQ ID NO: 50,
 m) a polypeptide having at least 60%, at least 65%, at least 70%, at least 75% at least 80%, at least 85%, at least 90%, at least 95%, at least 98% or 100% sequence identity to the polypeptide shown in SEQ ID NO: 51, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 81, and wherein the composition preferably comprises at least one cleaning component. One embodiment relates to a cleaning composition comprising a DNase, a protease and at least one cleaning component, wherein the DNase comprises or consists of a polypeptide selected from the group of polypeptides comprising the amino acid sequence shown in; SEQ ID NO 39, SEQ ID NO 40, SEQ ID NO 41, SEQ ID NO 42, SEQ ID NO 43, SEQ ID NO 44, SEQ ID NO 45, SEQ ID NO 46, SEQ ID NO 47, SEQ ID NO 48, SEQ ID NO 49, SEQ ID NO 50 and SEQ ID NO 51 and wherein the protease comprises or consists of the polypeptide comprising the amino acid sequence shown in SEQ ID NO 81.

One embodiment of the invention relates to a composition, preferably a cleaning composition, comprising a protease, a polypeptide having DNase activity, optionally wherein the polypeptide comprise one or both of the motifs P[Q/E]L[W/Y] (SEQ ID NO: 77) or [K/H/E]NAW (SEQ ID NO: 78), wherein the polypeptide is selected from the group of polypeptides:
 a) a polypeptide having at least 60%, at least 65%, at least 70%, at least 75% at least 80%, at least 85%, at least 90%, at least 95%, at least 98% or 100% sequence identity to the polypeptide shown in SEQ ID NO: 39,
 b) a polypeptide having at least 60%, at least 65%, at least 70%, at least 75% at least 80%, at least 85%, at least 90%, at least 95%, at least 98% or 100% sequence identity to the polypeptide shown in SEQ ID NO: 40,
 c) a polypeptide having at least 60%, at least 65%, at least 70%, at least 75% at least 80%, at least 85%, at least 90%, at least 95%, at least 98% or 100% sequence identity to the polypeptide shown in SEQ ID NO: 41,
 d) a polypeptide having at least 60%, at least 65%, at least 70%, at least 75% at least 80%, at least 85%, at least 90%, at least 95%, at least 98% or 100% sequence identity to the polypeptide shown in SEQ ID NO: 42,
 e) a polypeptide having at least 60%, at least 65%, at least 70%, at least 75% at least 80%, at least 85%, at least 90%, at least 95%, at least 98% or 100% sequence identity to the polypeptide shown in SEQ ID NO: 43
 f) a polypeptide having at least 60%, at least 65%, at least 70%, at least 75% at least 80%, at least 85%, at least 90%, at least 95%, at least 98% or 100% sequence identity to the polypeptide shown in SEQ ID NO: 44,
 g) a polypeptide having at least 60%, at least 65%, at least 70%, at least 75% at least 80%, at least 85%, at least 90%, at least 95%, at least 98% or 100% sequence identity to the polypeptide shown in SEQ ID NO: 45,
 h) a polypeptide having at least 60%, at least 65%, at least 70%, at least 75% at least 80%, at least 85%, at least 90%, at least 95%, at least 98% or 100% sequence identity to the polypeptide shown in SEQ ID NO: 46,
 i) a polypeptide having at least 60%, at least 65%, at least 70%, at least 75% at least 80%, at least 85%, at least 90%, at least 95%, at least 98% or 100% sequence identity to the polypeptide shown in SEQ ID NO: 47,
 j) a polypeptide having at least 60%, at least 65%, at least 70%, at least 75% at least 80%, at least 85%, at least 90%, at least 95%, at least 98% or 100% sequence identity to the polypeptide shown in SEQ ID NO: 48,
 k) a polypeptide having at least 60%, at least 65%, at least 70%, at least 75% at least 80%, at least 85%, at least 90%, at least 95%, at least 98% or 100% sequence identity to the polypeptide shown in SEQ ID NO: 49, l) a polypeptide having at least 60%, at least 65%, at least 70%, at least 75% at least 80%, at least 85%, at least 90%, at least 95%, at least 98% or 100% sequence identity to the polypeptide shown in SEQ ID NO: 50, m) a polypeptide having at least 60%, at least 65%, at least 70%, at least 75% at least 80%, at least 85%, at least 90%, at least 95%, at least 98% or 100% sequence identity to the polypeptide shown in SEQ ID NO: 51, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 82, and wherein the composition preferably comprises at least one cleaning component. One embodiment relates to a cleaning composition comprising a DNase, a protease and at least one cleaning component, wherein the DNase comprises or consists of a polypeptide selected from the group of polypeptides comprising the amino acid sequence shown in; SEQ ID NO 39, SEQ ID NO 40, SEQ ID NO 41, SEQ ID NO 42, SEQ ID NO 43, SEQ ID NO 44, SEQ ID NO 45, SEQ ID NO 46, SEQ ID NO 47, SEQ ID NO 48, SEQ ID NO 49, SEQ ID NO 50 and SEQ ID NO 51 and wherein the protease comprises or consists of the polypeptide comprising the amino acid sequence shown in SEQ ID NO 82.

One embodiment of the invention relates to a composition, preferably a cleaning composition, comprising a protease, a polypeptide having DNase activity, optionally wherein the polypeptide comprise one or both of the motifs P[Q/E]L[W/Y] (SEQ ID NO: 77) or [K/H/E]NAW (SEQ ID NO: 78), wherein the polypeptide is selected from the group of polypeptides:

a) a polypeptide having at least 60%, at least 65%, at least 70%, at least 75% at least 80%, at least 85%, at least 90%, at least 95%, at least 98% or 100% sequence identity to the polypeptide shown in SEQ ID NO: 39, b) a polypeptide having at least 60%, at least 65%, at least 70%, at least 75% at least 80%, at least 85%, at least 90%, at least 95%, at least 98% or 100% sequence identity to the polypeptide shown in SEQ ID NO: 40, c) a polypeptide having at least 60%, at least 65%, at least 70%, at least 75% at least 80%, at least 85%, at least 90%, at least 95%, at least 98% or 100% sequence identity to the polypeptide shown in SEQ ID NO: 41, d) a polypeptide having at least 60%, at least 65%, at least 70%, at least 75% at least 80%, at least 85%, at least 90%, at least 95%, at least 98% or 100% sequence identity to the polypeptide shown in SEQ ID NO: 42, e) a polypeptide having at least 60%, at least 65%, at least 70%, at least 75% at least 80%, at least 85%, at least 90%, at least 95%, at least 98% or 100% sequence identity to the polypeptide shown in SEQ ID NO: 43 f) a polypeptide having at least 60%, at least 65%, at least 70%, at least 75% at least 80%, at least 85%, at least 90%, at least 95%, at least 98% or 100% sequence identity to the polypeptide shown in SEQ ID NO: 44, g) a polypeptide having at least 60%, at least 65%, at least 70%, at least 75% at least 80%, at least 85%, at least 90%, at least 95%, at least 98% or 100% sequence identity to the polypeptide shown in SEQ ID NO: 45, h) a polypeptide having at least 60%, at least 65%, at least 70%, at least 75% at least 80%, at least 85%, at least 90%, at least 95%, at least 98% or 100% sequence identity to the polypeptide shown in SEQ ID NO: 46, i) a polypeptide having at least 60%, at least 65%, at least 70%, at least 75% at least 80%, at least 85%, at least 90%, at least 95%, at least 98% or 100% sequence identity to the polypeptide shown in SEQ ID NO: 47, j) a polypeptide having at least 60%, at least 65%, at least 70%, at least 75% at least 80%, at least 85%, at least 90%, at least 95%, at least 98% or 100% sequence identity to the polypeptide shown in SEQ ID NO: 48, k) a polypeptide having at least 60%, at least 65%, at least 70%, at least 75% at least 80%, at least 85%, at least 90%, at least 95%, at least 98% or 100% sequence identity to the polypeptide shown in SEQ ID NO: 49, l) a polypeptide having at least 60%, at least 65%, at least 70%, at least 75% at least 80%, at least 85%, at least 90%, at least 95%, at least 98% or 100% sequence identity to the polypeptide shown in SEQ ID NO: 50, m) a polypeptide having at least 60%, at least 65%, at least 70%, at least 75% at least 80%, at least 85%, at least 90%, at least 95%, at least 98% or 100% sequence identity to the polypeptide shown in SEQ ID NO: 51, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 83, and wherein the composition preferably comprises at least one cleaning component. One embodiment relates to a cleaning composition comprising a DNase, a protease and at least one cleaning component, wherein the DNase comprises or consists of a polypeptide selected from the group of polypeptides comprising the amino acid sequence shown in; SEQ ID NO 39, SEQ ID NO 40, SEQ ID NO 41, SEQ ID NO 42, SEQ ID NO 43, SEQ ID NO 44, SEQ ID NO 45, SEQ ID NO 46, SEQ ID NO 47, SEQ ID NO 48, SEQ ID NO 49, SEQ ID NO 50 and SEQ ID NO 51 and wherein the protease comprises or consists of the polypeptide comprising the amino acid sequence shown in SEQ ID NO 83.

One embodiment of the invention relates to a composition, preferably a cleaning composition, comprising a protease, a polypeptide having DNase activity, optionally wherein the polypeptide comprise one or both of the motifs P[Q/E]L[W/Y] (SEQ ID NO: 77) or [K/H/E]NAW (SEQ ID NO: 78), wherein the polypeptide is selected from the group of polypeptides:

a) a polypeptide having at least 60%, at least 65%, at least 70%, at least 75% at least 80%, at least 85%, at least 90%, at least 95%, at least 98% or 100% sequence identity to the polypeptide shown in SEQ ID NO: 39, b) a polypeptide having at least 60%, at least 65%, at least 70%, at least 75% at least 80%, at least 85%, at least 90%, at least 95%, at least 98% or 100% sequence identity to the polypeptide shown in SEQ ID NO: 40, c) a polypeptide having at least 60%, at least 65%, at least 70%, at least 75% at least 80%, at least 85%, at least 90%, at least 95%, at least 98% or 100% sequence identity to the polypeptide shown in SEQ ID NO: 41, d) a polypeptide having at least 60%, at least 65%, at least 70%, at least 75% at least 80%, at least 85%, at least 90%, at least 95%, at least 98% or 100% sequence identity to the polypeptide shown in SEQ ID NO: 42, e) a polypeptide having at least 60%, at least 65%, at least 70%, at least 75% at least 80%, at least 85%, at least 90%, at least 95%, at least 98% or 100% sequence identity to the polypeptide shown in SEQ ID NO: 43 f) a polypeptide having at least 60%, at least 65%, at least 70%, at least 75% at least 80%, at least 85%, at least 90%, at least 95%, at least 98% or 100% sequence identity to the polypeptide shown in SEQ ID NO: 44, g) a polypeptide having at least 60%, at least 65%, at least 70%, at least 75% at least 80%, at least 85%, at least 90%, at least 95%, at least 98% or 100% sequence identity to the polypeptide shown in SEQ ID NO: 45,
h) a polypeptide having at least 60%, at least 65%, at least 70%, at least 75% at least 80%, at least 85%, at least 90%, at least 95%, at least 98% or 100% sequence identity to the polypeptide shown in SEQ ID NO: 46,
i) a polypeptide having at least 60%, at least 65%, at least 70%, at least 75% at least 80%, at least 85%, at least 90%, at least 95%, at least 98% or 100% sequence identity to the polypeptide shown in SEQ ID NO: 47,
j) a polypeptide having at least 60%, at least 65%, at least 70%, at least 75% at least 80%, at least 85%, at least 90%, at least 95%, at least 98% or 100% sequence identity to the polypeptide shown in SEQ ID NO: 48,
k) a polypeptide having at least 60%, at least 65%, at least 70%, at least 75% at least 80%, at least 85%, at least 90%, at least 95%, at least 98% or 100% sequence identity to the polypeptide shown in SEQ ID NO: 49,
l) a polypeptide having at least 60%, at least 65%, at least 70%, at least 75% at least 80%, at least 85%, at least 90%, at least 95%, at least 98% or 100% sequence identity to the polypeptide shown in SEQ ID NO: 50,
m) a polypeptide having at least 60%, at least 65%, at least 70%, at least 75% at least 80%, at least 85%, at least 90%, at least 95%, at least 98% or 100% sequence identity to the polypeptide shown in SEQ ID NO: 51,
wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 84, and wherein the composition preferably comprises at least one cleaning component. One embodiment relates to a cleaning composition comprising a DNase, a protease and at least one cleaning component, wherein the DNase comprises or consists of a polypeptide selected from the group of polypeptides comprising the amino acid sequence shown in; SEQ ID NO 39, SEQ ID NO 40, SEQ ID NO 41, SEQ ID NO 42, SEQ ID NO 43, SEQ ID NO 44, SEQ ID NO 45, SEQ ID NO 46, SEQ ID NO 47, SEQ ID NO 48, SEQ ID NO 49, SEQ ID NO 50 and SEQ ID NO 51 and wherein the protease comprises or consists of the polypeptide comprising the amino acid sequence shown in SEQ ID NO 84.

One embodiment of the invention relates to a composition, preferably a cleaning composition, comprising a protease, a polypeptide having DNase activity, optionally wherein the polypeptide comprise one or both of the motifs P[Q/E]L[W/Y] (SEQ ID NO: 77) or [K/H/E]NAW (SEQ ID NO: 78), wherein the polypeptide is selected from the group of polypeptides:
a) a polypeptide having at least 60%, at least 65%, at least 70%, at least 75% at least 80%, at least 85%, at least 90%, at least 95%, at least 98% or 100% sequence identity to the polypeptide shown in SEQ ID NO: 39,
b) a polypeptide having at least 60%, at least 65%, at least 70%, at least 75% at least 80%, at least 85%, at least 90%, at least 95%, at least 98% or 100% sequence identity to the polypeptide shown in SEQ ID NO: 40,
c) a polypeptide having at least 60%, at least 65%, at least 70%, at least 75% at least 80%, at least 85%, at least 90%, at least 95%, at least 98% or 100% sequence identity to the polypeptide shown in SEQ ID NO: 41,
d) a polypeptide having at least 60%, at least 65%, at least 70%, at least 75% at least 80%, at least 85%, at least 90%, at least 95%, at least 98% or 100% sequence identity to the polypeptide shown in SEQ ID NO: 42,
e) a polypeptide having at least 60%, at least 65%, at least 70%, at least 75% at least 80%, at least 85%, at least 90%, at least 95%, at least 98% or 100% sequence identity to the polypeptide shown in SEQ ID NO: 43
f) a polypeptide having at least 60%, at least 65%, at least 70%, at least 75% at least 80%, at least 85%, at least 90%, at least 95%, at least 98% or 100% sequence identity to the polypeptide shown in SEQ ID NO: 44,
g) a polypeptide having at least 60%, at least 65%, at least 70%, at least 75% at least 80%, at least 85%, at least 90%, at least 95%, at least 98% or 100% sequence identity to the polypeptide shown in SEQ ID NO: 45,
h) a polypeptide having at least 60%, at least 65%, at least 70%, at least 75% at least 80%, at least 85%, at least 90%, at least 95%, at least 98% or 100% sequence identity to the polypeptide shown in SEQ ID NO: 46,
i) a polypeptide having at least 60%, at least 65%, at least 70%, at least 75% at least 80%, at least 85%, at least 90%, at least 95%, at least 98% or 100% sequence identity to the polypeptide shown in SEQ ID NO: 47,
j) a polypeptide having at least 60%, at least 65%, at least 70%, at least 75% at least 80%, at least 85%, at least 90%, at least 95%, at least 98% or 100% sequence identity to the polypeptide shown in SEQ ID NO: 48,
k) a polypeptide having at least 60%, at least 65%, at least 70%, at least 75% at least 80%, at least 85%, at least 90%, at least 95%, at least 98% or 100% sequence identity to the polypeptide shown in SEQ ID NO: 49,
l) a polypeptide having at least 60%, at least 65%, at least 70%, at least 75% at least 80%, at least 85%, at least 90%, at least 95%, at least 98% or 100% sequence identity to the polypeptide shown in SEQ ID NO: 50,
m) a polypeptide having at least 60%, at least 65%, at least 70%, at least 75% at least 80%, at least 85%, at least 90%, at least 95%, at least 98% or 100% sequence identity to the polypeptide shown in SEQ ID NO: 51,
wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 85, and wherein the composition preferably comprises at least one cleaning component. One embodiment relates to a cleaning composition comprising a DNase, a protease and at least one cleaning component, wherein the DNase comprises or consists of a polypeptide selected from the group of polypeptides comprising the amino acid sequence shown in; SEQ ID NO 39, SEQ ID NO 40, SEQ ID NO 41, SEQ ID NO 42, SEQ ID NO 43, SEQ ID NO 44, SEQ ID NO 45, SEQ ID NO 46, SEQ ID NO 47, SEQ ID NO 48, SEQ ID NO 49, SEQ ID NO 50 and SEQ ID NO 51 and wherein the protease comprises or consists of the polypeptide comprising the amino acid sequence shown in SEQ ID NO 85.

One embodiment of the invention relates to a composition, preferably a cleaning composition, comprising a protease, a polypeptide having DNase activity, optionally wherein the polypeptide comprise one or both of the motifs P[Q/E]L[W/Y] (SEQ ID NO: 77) or [K/H/E]NAW (SEQ ID NO: 78), wherein the polypeptide is selected from the group of polypeptides:
a) a polypeptide having at least 60%, at least 65%, at least 70%, at least 75% at least 80%, at least 85%, at least 90%, at least 95%, at least 98% or 100% sequence identity to the polypeptide shown in SEQ ID NO: 39,
b) a polypeptide having at least 60%, at least 65%, at least 70%, at least 75% at least 80%, at least 85%, at least 90%, at least 95%, at least 98% or 100% sequence identity to the polypeptide shown in SEQ ID NO: 40,
c) a polypeptide having at least 60%, at least 65%, at least 70%, at least 75% at least 80%, at least 85%, at least 90%, at least 95%, at least 98% or 100% sequence identity to the polypeptide shown in SEQ ID NO: 41,
d) a polypeptide having at least 60%, at least 65%, at least 70%, at least 75% at least 80%, at least 85%, at least 90%, at least 95%, at least 98% or 100% sequence identity to the polypeptide shown in SEQ ID NO: 42,
e) a polypeptide having at least 60%, at least 65%, at least 70%, at least 75% at least 80%, at least 85%, at least 90%, at least 95%, at least 98% or 100% sequence identity to the polypeptide shown in SEQ ID NO: 43
f) a polypeptide having at least 60%, at least 65%, at least 70%, at least 75% at least 80%, at least 85%, at least 90%, at least 95%, at least 98% or 100% sequence identity to the polypeptide shown in SEQ ID NO: 44,
g) a polypeptide having at least 60%, at least 65%, at least 70%, at least 75% at least 80%, at least 85%, at least 90%, at least 95%, at least 98% or 100% sequence identity to the polypeptide shown in SEQ ID NO: 45,
h) a polypeptide having at least 60%, at least 65%, at least 70%, at least 75% at least 80%, at least 85%, at least 90%, at least 95%, at least 98% or 100% sequence identity to the polypeptide shown in SEQ ID NO: 46,
i) a polypeptide having at least 60%, at least 65%, at least 70%, at least 75% at least 80%, at least 85%, at least 90%, at least 95%, at least 98% or 100% sequence identity to the polypeptide shown in SEQ ID NO: 47,
j) a polypeptide having at least 60%, at least 65%, at least 70%, at least 75% at least 80%, at least 85%, at least 90%, at least 95%, at least 98% or 100% sequence identity to the polypeptide shown in SEQ ID NO: 48,
k) a polypeptide having at least 60%, at least 65%, at least 70%, at least 75% at least 80%, at least 85%, at least 90%, at least 95%, at least 98% or 100% sequence identity to the polypeptide shown in SEQ ID NO: 49,
l) a polypeptide having at least 60%, at least 65%, at least 70%, at least 75% at least 80%, at least 85%, at least 90%, at least 95%, at least 98% or 100% sequence identity to the polypeptide shown in SEQ ID NO: 50,
m) a polypeptide having at least 60%, at least 65%, at least 70%, at least 75% at least 80%, at least 85%, at least 90%, at least 95%, at least 98% or 100% sequence identity to the polypeptide shown in SEQ ID NO: 51,
wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 86, and wherein the composition preferably comprises at least one cleaning component. One embodiment relates to a cleaning composition comprising a DNase, a protease and at least one cleaning component, wherein the DNase comprises or consists of a polypeptide selected from the group of polypeptides comprising the amino acid sequence shown in; SEQ ID NO 39, SEQ ID NO 40, SEQ ID NO 41, SEQ ID NO 42, SEQ ID NO 43, SEQ ID NO 44, SEQ ID NO 45, SEQ ID NO 46, SEQ ID NO 47, SEQ ID NO 48, SEQ ID NO 49, SEQ ID NO 50 and SEQ ID NO 51 and wherein the protease comprises or consists of the polypeptide comprising the amino acid sequence shown in SEQ ID NO 86.

One embodiment of the invention relates to a composition, preferably a cleaning composition, comprising a protease, a polypeptide having DNase activity, wherein the polypeptide is selected from the group of polypeptides:
a) a polypeptide having at least 60%, at least 65%, at least 70%, at least 75% at least 80%, at least 85%, at least 90%, at least 95%, at least 98% or 100% sequence identity to the polypeptide shown in SEQ ID NO: 52,
b) a polypeptide having at least 60%, at least 65%, at least 70%, at least 75% at least 80%, at least 85%, at least 90%, at least 95%, at least 98% or 100% sequence identity to the polypeptide shown in SEQ ID NO: 53,
c) a polypeptide having at least 60%, at least 65%, at least 70%, at least 75% at least 80%, at least 85%, at least 90%, at least 95%, at least 98% or 100% sequence identity to the polypeptide shown in SEQ ID NO: 54,
d) a polypeptide having at least 60%, at least 65%, at least 70%, at least 75% at least 80%, at least 85%, at least 90%, at least 95%, at least 98% or 100% sequence identity to the polypeptide shown in SEQ ID NO: 55,
e) a polypeptide having at least 60%, at least 65%, at least 70%, at least 75% at least 80%, at least 85%, at least 90%, at least 95%, at least 98% or 100% sequence identity to the polypeptide shown in SEQ ID NO: 56,
f) a polypeptide having at least 60%, at least 65%, at least 70%, at least 75% at least 80%, at least 85%, at least 90%, at least 95%, at least 98% or 100% sequence identity to the polypeptide shown in SEQ ID NO: 57,
g) a polypeptide having at least 60%, at least 65%, at least 70%, at least 75% at least 80%, at least 85%, at least 90%, at least 95%, at least 98% or 100% sequence identity to the polypeptide shown in SEQ ID NO: 58,
h) a polypeptide having at least 60%, at least 65%, at least 70%, at least 75% at least 80%, at least 85%, at least 90%, at least 95%, at least 98% or 100% sequence identity to the polypeptide shown in SEQ ID NO: 59,
i) a polypeptide having at least 60%, at least 65%, at least 70%, at least 75% at least 80%, at least 85%, at least 90%, at least 95%, at least 98% or 100% sequence identity to the polypeptide shown in SEQ ID NO: 60,
j) a polypeptide having at least 60%, at least 65%, at least 70%, at least 75% at least 80%, at least 85%, at least 90%, at least 95%, at least 98% or 100% sequence identity to the polypeptide shown in SEQ ID NO: 61,
k) a polypeptide having at least 60%, at least 65%, at least 70%, at least 75% at least 80%, at least 85%, at least 90%, at least 95%, at least 98% or 100% sequence identity to the polypeptide shown in SEQ ID NO: 62,
l) a polypeptide having at least 60%, at least 65%, at least 70%, at least 75% at least 80%, at least 85%, at least 90%, at least 95%, at least 98% or 100% sequence identity to the polypeptide shown in SEQ ID NO: 63,
m) a polypeptide having at least 60%, at least 65%, at least 70%, at least 75% at least 80%, at least 85%, at least 90%, at least 95%, at least 98% or 100% sequence identity to the polypeptide shown in SEQ ID NO: 64,
n) a polypeptide having at least 60%, at least 65%, at least 70%, at least 75% at least 80%, at least 85%, at least 90%, at least 95%, at least 98% or 100% sequence identity to the polypeptide shown in SEQ ID NO: 65,
o) a polypeptide having at least 60%, at least 65%, at least 70%, at least 75% at least 80%, at least 85%, at least 90%, at least 95%, at least 98% or 100% sequence identity to the polypeptide shown in SEQ ID NO: 66,
p) a polypeptide having at least 60%, at least 65%, at least 70%, at least 75% at least 80%, at least 85%, at least 90%, at least 95%, at least 98% or 100% sequence identity to the polypeptide shown in SEQ ID NO: 67,
q) a polypeptide having at least 60%, at least 65%, at least 70%, at least 75% at least 80%, at least 85%, at least 90%, at least 95%, at least 98% or 100% sequence identity to the polypeptide shown in SEQ ID NO: 68,
wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 79, and wherein the composition preferably comprises at least one cleaning component. One embodiment relates to a cleaning composition comprising a DNase, a protease and at least one cleaning component, wherein the DNase comprises or consists of a polypeptide selected from the group of polypeptides comprising the amino acid sequence shown in; SEQ ID NO 52, SEQ ID NO 53, SEQ ID NO 54, SEQ ID NO 55, SEQ ID NO 56, SEQ ID NO 57, SEQ ID NO 58, SEQ ID NO 59, SEQ ID NO 60, SEQ ID NO 61, SEQ ID NO 62, SEQ ID NO 63, SEQ ID NO 64, SEQ ID NO 65, SEQ ID NO 66, SEQ ID NO 67 and SEQ ID NO 68 and wherein the protease comprises or consists of the polypeptide comprising the amino acid sequence shown in SEQ ID NO 79.

One embodiment of the invention relates to a composition, preferably a cleaning composition, comprising a protease, a polypeptide having DNase activity, wherein the polypeptide is selected from the group of polypeptides:

a) a polypeptide having at least 60%, at least 65%, at least 70%, at least 75% at least 80%, at least 85%, at least 90%, at least 95%, at least 98% or 100% sequence identity to the polypeptide shown in SEQ ID NO: 52,
b) a polypeptide having at least 60%, at least 65%, at least 70%, at least 75% at least 80%, at least 85%, at least 90%, at least 95%, at least 98% or 100% sequence identity to the polypeptide shown in SEQ ID NO: 53,
c) a polypeptide having at least 60%, at least 65%, at least 70%, at least 75% at least 80%, at least 85%, at least 90%, at least 95%, at least 98% or 100% sequence identity to the polypeptide shown in SEQ ID NO: 54,
d) a polypeptide having at least 60%, at least 65%, at least 70%, at least 75% at least 80%, at least 85%, at least 90%, at least 95%, at least 98% or 100% sequence identity to the polypeptide shown in SEQ ID NO: 55,
e) a polypeptide having at least 60%, at least 65%, at least 70%, at least 75% at least 80%, at least 85%, at least 90%, at least 95%, at least 98% or 100% sequence identity to the polypeptide shown in SEQ ID NO: 56,
f) a polypeptide having at least 60%, at least 65%, at least 70%, at least 75% at least 80%, at least 85%, at least 90%, at least 95%, at least 98% or 100% sequence identity to the polypeptide shown in SEQ ID NO: 57,
g) a polypeptide having at least 60%, at least 65%, at least 70%, at least 75% at least 80%, at least 85%, at least 90%, at least 95%, at least 98% or 100% sequence identity to the polypeptide shown in SEQ ID NO: 58,
h) a polypeptide having at least 60%, at least 65%, at least 70%, at least 75% at least 80%, at least 85%, at least 90%, at least 95%, at least 98% or 100% sequence identity to the polypeptide shown in SEQ ID NO: 59,
i) a polypeptide having at least 60%, at least 65%, at least 70%, at least 75% at least 80%, at least 85%, at least 90%, at least 95%, at least 98% or 100% sequence identity to the polypeptide shown in SEQ ID NO: 60,
j) a polypeptide having at least 60%, at least 65%, at least 70%, at least 75% at least 80%, at least 85%, at least 90%, at least 95%, at least 98% or 100% sequence identity to the polypeptide shown in SEQ ID NO: 61,
k) a polypeptide having at least 60%, at least 65%, at least 70%, at least 75% at least 80%, at least 85%, at least 90%, at least 95%, at least 98% or 100% sequence identity to the polypeptide shown in SEQ ID NO: 62,
l) a polypeptide having at least 60%, at least 65%, at least 70%, at least 75% at least 80%, at least 85%, at least 90%, at least 95%, at least 98% or 100% sequence identity to the polypeptide shown in SEQ ID NO: 63,
m) a polypeptide having at least 60%, at least 65%, at least 70%, at least 75% at least 80%, at least 85%, at least 90%, at least 95%, at least 98% or 100% sequence identity to the polypeptide shown in SEQ ID NO: 64,
n) a polypeptide having at least 60%, at least 65%, at least 70%, at least 75% at least 80%, at least 85%, at least 90%, at least 95%, at least 98% or 100% sequence identity to the polypeptide shown in SEQ ID NO: 65,
o) a polypeptide having at least 60%, at least 65%, at least 70%, at least 75% at least 80%, at least 85%, at least 90%, at least 95%, at least 98% or 100% sequence identity to the polypeptide shown in SEQ ID NO: 66,
p) a polypeptide having at least 60%, at least 65%, at least 70%, at least 75% at least 80%, at least 85%, at least 90%, at least 95%, at least 98% or 100% sequence identity to the polypeptide shown in SEQ ID NO: 67,
q) a polypeptide having at least 60%, at least 65%, at least 70%, at least 75% at least 80%, at least 85%, at least 90%, at least 95%, at least 98% or 100% sequence identity to the polypeptide shown in SEQ ID NO: 68,
wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 80, and wherein the composition preferably comprises at least one cleaning component. One embodiment relates to a cleaning composition comprising a DNase, a protease and at least one cleaning component, wherein the DNase comprises or consists of a polypeptide selected from the group of polypeptides comprising the amino acid sequence shown in; SEQ ID NO 52, SEQ ID NO 53, SEQ ID NO 54, SEQ ID NO 55, SEQ ID NO 56, SEQ ID NO 57, SEQ ID NO 58, SEQ ID NO 59, SEQ ID NO 60, SEQ ID NO 61, SEQ ID NO 62, SEQ ID NO 63, SEQ ID NO 64, SEQ ID NO 65, SEQ ID NO 66, SEQ ID NO 67 and SEQ ID NO 68 and wherein the protease comprises or consists of the polypeptide comprising the amino acid sequence shown in SEQ ID NO 80.

One embodiment of the invention relates to a composition, preferably a cleaning composition, comprising a protease, a polypeptide having DNase activity, wherein the polypeptide is selected from the group of polypeptides:

a) a polypeptide having at least 60%, at least 65%, at least 70%, at least 75% at least 80%, at least 85%, at least 90%, at least 95%, at least 98% or 100% sequence identity to the polypeptide shown in SEQ ID NO: 52,
b) a polypeptide having at least 60%, at least 65%, at least 70%, at least 75% at least 80%, at least 85%, at least 90%, at least 95%, at least 98% or 100% sequence identity to the polypeptide shown in SEQ ID NO: 53,
c) a polypeptide having at least 60%, at least 65%, at least 70%, at least 75% at least 80%, at least 85%, at least 90%, at least 95%, at least 98% or 100% sequence identity to the polypeptide shown in SEQ ID NO: 54,
d) a polypeptide having at least 60%, at least 65%, at least 70%, at least 75% at least 80%, at least 85%, at least 90%, at least 95%, at least 98% or 100% sequence identity to the polypeptide shown in SEQ ID NO: 55,
e) a polypeptide having at least 60%, at least 65%, at least 70%, at least 75% at least 80%, at least 85%, at least 90%, at least 95%, at least 98% or 100% sequence identity to the polypeptide shown in SEQ ID NO: 56,
f) a polypeptide having at least 60%, at least 65%, at least 70%, at least 75% at least 80%, at least 85%, at least 90%, at least 95%, at least 98% or 100% sequence identity to the polypeptide shown in SEQ ID NO: 57, g) a polypeptide having at least 60%, at least 65%, at least 70%, at least 75% at least 80%, at least 85%, at least 90%, at least 95%, at least 98% or 100% sequence identity to the polypeptide shown in SEQ ID NO: 58,
h) a polypeptide having at least 60%, at least 65%, at least 70%, at least 75% at least 80%, at least 85%, at least 90%, at least 95%, at least 98% or 100% sequence identity to the polypeptide shown in SEQ ID NO: 59,
i) a polypeptide having at least 60%, at least 65%, at least 70%, at least 75% at least 80%, at least 85%, at least 90%, at least 95%, at least 98% or 100% sequence identity to the polypeptide shown in SEQ ID NO: 60,
j) a polypeptide having at least 60%, at least 65%, at least 70%, at least 75% at least 80%, at least 85%, at least 90%, at least 95%, at least 98% or 100% sequence identity to the polypeptide shown in SEQ ID NO: 61,
k) a polypeptide having at least 60%, at least 65%, at least 70%, at least 75% at least 80%, at least 85%, at least 90%, at least 95%, at least 98% or 100% sequence identity to the polypeptide shown in SEQ ID NO: 62,
l) a polypeptide having at least 60%, at least 65%, at least 70%, at least 75% at least 80%, at least 85%, at least 90%, at least 95%, at least 98% or 100% sequence identity to the polypeptide shown in SEQ ID NO: 63,
m) a polypeptide having at least 60%, at least 65%, at least 70%, at least 75% at least 80%, at least 85%, at least 90%, at least 95%, at least 98% or 100% sequence identity to the polypeptide shown in SEQ ID NO: 64,
n) a polypeptide having at least 60%, at least 65%, at least 70%, at least 75% at least 80%, at least 85%, at least 90%, at least 95%, at least 98% or 100% sequence identity to the polypeptide shown in SEQ ID NO: 65,
o) a polypeptide having at least 60%, at least 65%, at least 70%, at least 75% at least 80%, at least 85%, at least 90%, at least 95%, at least 98% or 100% sequence identity to the polypeptide shown in SEQ ID NO: 66,
p) a polypeptide having at least 60%, at least 65%, at least 70%, at least 75% at least 80%, at least 85%, at least 90%, at least 95%, at least 98% or 100% sequence identity to the polypeptide shown in SEQ ID NO: 67,
q) a polypeptide having at least 60%, at least 65%, at least 70%, at least 75% at least 80%, at least 85%, at least 90%, at least 95%, at least 98% or 100% sequence identity to the polypeptide shown in SEQ ID NO: 68,
wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 81, and wherein the composition preferably comprises at least one cleaning component. One embodiment relates to a cleaning composition comprising a DNase, a protease and at least one cleaning component, wherein the DNase comprises or consists of a polypeptide selected from the group of polypeptides comprising the amino acid sequence shown in; SEQ ID NO 52, SEQ ID NO 53, SEQ ID NO 54, SEQ ID NO 55, SEQ ID NO 56, SEQ ID NO 57, SEQ ID NO 58, SEQ ID NO 59, SEQ ID NO 60, SEQ ID NO 61, SEQ ID NO 62, SEQ ID NO 63, SEQ ID NO 64, SEQ ID NO 65, SEQ ID NO 66, SEQ ID NO 67 and SEQ ID NO 68 and wherein the protease comprises or consists of the polypeptide comprising the amino acid sequence shown in SEQ ID NO 81.

One embodiment of the invention relates to a composition, preferably a cleaning composition, comprising a protease, a polypeptide having DNase activity, wherein the polypeptide is selected from the group of polypeptides:
a) a polypeptide having at least 60%, at least 65%, at least 70%, at least 75% at least 80%, at least 85%, at least 90%, at least 95%, at least 98% or 100% sequence identity to the polypeptide shown in SEQ ID NO: 52,
b) a polypeptide having at least 60%, at least 65%, at least 70%, at least 75% at least 80%, at least 85%, at least 90%, at least 95%, at least 98% or 100% sequence identity to the polypeptide shown in SEQ ID NO: 53,
c) a polypeptide having at least 60%, at least 65%, at least 70%, at least 75% at least 80%, at least 85%, at least 90%, at least 95%, at least 98% or 100% sequence identity to the polypeptide shown in SEQ ID NO: 54,
d) a polypeptide having at least 60%, at least 65%, at least 70%, at least 75% at least 80%, at least 85%, at least 90%, at least 95%, at least 98% or 100% sequence identity to the polypeptide shown in SEQ ID NO: 55,
e) a polypeptide having at least 60%, at least 65%, at least 70%, at least 75% at least 80%, at least 85%, at least 90%, at least 95%, at least 98% or 100% sequence identity to the polypeptide shown in SEQ ID NO: 56,
f) a polypeptide having at least 60%, at least 65%, at least 70%, at least 75% at least 80%, at least 85%, at least 90%, at least 95%, at least 98% or 100% sequence identity to the polypeptide shown in SEQ ID NO: 57,
g) a polypeptide having at least 60%, at least 65%, at least 70%, at least 75% at least 80%, at least 85%, at least 90%, at least 95%, at least 98% or 100% sequence identity to the polypeptide shown in SEQ ID NO: 58,
h) a polypeptide having at least 60%, at least 65%, at least 70%, at least 75% at least 80%, at least 85%, at least 90%, at least 95%, at least 98% or 100% sequence identity to the polypeptide shown in SEQ ID NO: 59,
i) a polypeptide having at least 60%, at least 65%, at least 70%, at least 75% at least 80%, at least 85%, at least 90%, at least 95%, at least 98% or 100% sequence identity to the polypeptide shown in SEQ ID NO: 60,
j) a polypeptide having at least 60%, at least 65%, at least 70%, at least 75% at least 80%, at least 85%, at least 90%, at least 95%, at least 98% or 100% sequence identity to the polypeptide shown in SEQ ID NO: 61,
k) a polypeptide having at least 60%, at least 65%, at least 70%, at least 75% at least 80%, at least 85%, at least 90%, at least 95%, at least 98% or 100% sequence identity to the polypeptide shown in SEQ ID NO: 62,
l) a polypeptide having at least 60%, at least 65%, at least 70%, at least 75% at least 80%, at least 85%, at least 90%, at least 95%, at least 98% or 100% sequence identity to the polypeptide shown in SEQ ID NO: 63,
m) a polypeptide having at least 60%, at least 65%, at least 70%, at least 75% at least 80%, at least 85%, at least 90%, at least 95%, at least 98% or 100% sequence identity to the polypeptide shown in SEQ ID NO: 64,
n) a polypeptide having at least 60%, at least 65%, at least 70%, at least 75% at least 80%, at least 85%, at least 90%, at least 95%, at least 98% or 100% sequence identity to the polypeptide shown in SEQ ID NO: 65,
o) a polypeptide having at least 60%, at least 65%, at least 70%, at least 75% at least 80%, at least 85%, at least 90%, at least 95%, at least 98% or 100% sequence identity to the polypeptide shown in SEQ ID NO: 66,
p) a polypeptide having at least 60%, at least 65%, at least 70%, at least 75% at least 80%, at least 85%, at least 90%, at least 95%, at least 98% or 100% sequence identity to the polypeptide shown in SEQ ID NO: 67,
q) a polypeptide having at least 60%, at least 65%, at least 70%, at least 75% at least 80%, at least 85%, at least 90%, at least 95%, at least 98% or 100% sequence identity to the polypeptide shown in SEQ ID NO: 68, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 82, and wherein the composition preferably comprises at least one cleaning component. One embodiment relates to a cleaning composition comprising a DNase, a protease and at least one cleaning component, wherein the DNase comprises or consists of a polypeptide selected from the group of polypeptides comprising the amino acid sequence shown in; SEQ ID NO 52, SEQ ID NO 53, SEQ ID NO 54, SEQ ID NO 55, SEQ ID NO 56, SEQ ID NO 57, SEQ ID NO 58, SEQ ID NO 59, SEQ ID NO 60, SEQ ID NO 61, SEQ ID NO 62, SEQ ID NO 63, SEQ ID NO 64, SEQ ID NO 65, SEQ ID NO 66, SEQ ID NO 67 and SEQ ID NO 68 and wherein the protease comprises or consists of the polypeptide comprising the amino acid sequence shown in SEQ ID NO 82.

One embodiment of the invention relates to a composition, preferably a cleaning composition, comprising a protease, a polypeptide having DNase activity, wherein the polypeptide is selected from the group of polypeptides:
- a) a polypeptide having at least 60%, at least 65%, at least 70%, at least 75% at least 80%, at least 85%, at least 90%, at least 95%, at least 98% or 100% sequence identity to the polypeptide shown in SEQ ID NO: 52,
- b) a polypeptide having at least 60%, at least 65%, at least 70%, at least 75% at least 80%, at least 85%, at least 90%, at least 95%, at least 98% or 100% sequence identity to the polypeptide shown in SEQ ID NO: 53,
- c) a polypeptide having at least 60%, at least 65%, at least 70%, at least 75% at least 80%, at least 85%, at least 90%, at least 95%, at least 98% or 100% sequence identity to the polypeptide shown in SEQ ID NO: 54,
- d) a polypeptide having at least 60%, at least 65%, at least 70%, at least 75% at least 80%, at least 85%, at least 90%, at least 95%, at least 98% or 100% sequence identity to the polypeptide shown in SEQ ID NO: 55,
- e) a polypeptide having at least 60%, at least 65%, at least 70%, at least 75% at least 80%, at least 85%, at least 90%, at least 95%, at least 98% or 100% sequence identity to the polypeptide shown in SEQ ID NO: 56,
- f) a polypeptide having at least 60%, at least 65%, at least 70%, at least 75% at least 80%, at least 85%, at least 90%, at least 95%, at least 98% or 100% sequence identity to the polypeptide shown in SEQ ID NO: 57,
- g) a polypeptide having at least 60%, at least 65%, at least 70%, at least 75% at least 80%, at least 85%, at least 90%, at least 95%, at least 98% or 100% sequence identity to the polypeptide shown in SEQ ID NO: 58,
- h) a polypeptide having at least 60%, at least 65%, at least 70%, at least 75% at least 80%, at least 85%, at least 90%, at least 95%, at least 98% or 100% sequence identity to the polypeptide shown in SEQ ID NO: 59,
- i) a polypeptide having at least 60%, at least 65%, at least 70%, at least 75% at least 80%, at least 85%, at least 90%, at least 95%, at least 98% or 100% sequence identity to the polypeptide shown in SEQ ID NO: 60,
- j) a polypeptide having at least 60%, at least 65%, at least 70%, at least 75% at least 80%, at least 85%, at least 90%, at least 95%, at least 98% or 100% sequence identity to the polypeptide shown in SEQ ID NO: 61,
- k) a polypeptide having at least 60%, at least 65%, at least 70%, at least 75% at least 80%, at least 85%, at least 90%, at least 95%, at least 98% or 100% sequence identity to the polypeptide shown in SEQ ID NO: 62,
- l) a polypeptide having at least 60%, at least 65%, at least 70%, at least 75% at least 80%, at least 85%, at least 90%, at least 95%, at least 98% or 100% sequence identity to the polypeptide shown in SEQ ID NO: 63,
- m) a polypeptide having at least 60%, at least 65%, at least 70%, at least 75%, at least 80%, at least 85%, at least 90%, at least 95%, at least 98% or 100% sequence identity to the polypeptide shown in SEQ ID NO: 64,
- n) a polypeptide having at least 60%, at least 65%, at least 70%, at least 75% at least 80%, at least 85%, at least 90%, at least 95%, at least 98% or 100% sequence identity to the polypeptide shown in SEQ ID NO: 65,
- o) a polypeptide having at least 60%, at least 65%, at least 70%, at least 75% at least 80%, at least 85%, at least 90%, at least 95%, at least 98% or 100% sequence identity to the polypeptide shown in SEQ ID NO: 66,
- p) a polypeptide having at least 60%, at least 65%, at least 70%, at least 75%, at least 80%, at least 85%, at least 90%, at least 95%, at least 98% or 100% sequence identity to the polypeptide shown in SEQ ID NO: 67,
- q) a polypeptide having at least 60%, at least 65%, at least 70%, at least 75%, at least 80%, at least 85%, at least 90%, at least 95%, at least 98% or 100% sequence identity to the polypeptide shown in SEQ ID NO: 68, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 83, and wherein the composition preferably comprises at least one cleaning component. One embodiment relates to a cleaning composition comprising a DNase, a protease and at least one cleaning component, wherein the DNase comprises or consists of a polypeptide selected from the group of polypeptides comprising the amino acid sequence shown in; SEQ ID NO 52, SEQ ID NO 53, SEQ ID NO 54, SEQ ID NO 55, SEQ ID NO 56, SEQ ID NO 57, SEQ ID NO 58, SEQ ID NO 59, SEQ ID NO 60, SEQ ID NO 61, SEQ ID NO 62, SEQ ID NO 63, SEQ ID NO 64, SEQ ID NO 65, SEQ ID NO 66, SEQ ID NO 67 and SEQ ID NO 68 and wherein the protease comprises or consists of the polypeptide comprising the amino acid sequence shown in SEQ ID NO 83.

One embodiment of the invention relates to a composition, preferably a cleaning composition, comprising a protease, a polypeptide having DNase activity, wherein the polypeptide is selected from the group of polypeptides:
- a) a polypeptide having at least 60%, at least 65%, at least 70%, at least 75% at least 80%, at least 85%, at least 90%, at least 95%, at least 98% or 100% sequence identity to the polypeptide shown in SEQ ID NO: 52,
- b) a polypeptide having at least 60%, at least 65%, at least 70%, at least 75% at least 80%, at least 85%, at least 90%, at least 95%, at least 98% or 100% sequence identity to the polypeptide shown in SEQ ID NO: 53,
- c) a polypeptide having at least 60%, at least 65%, at least 70%, at least 75% at least 80%, at least 85%, at least 90%, at least 95%, at least 98% or 100% sequence identity to the polypeptide shown in SEQ ID NO: 54,
- d) a polypeptide having at least 60%, at least 65%, at least 70%, at least 75%, at least 80%, at least 85%, at least 90%, at least 95%, at least 98% or 100% sequence identity to the polypeptide shown in SEQ ID NO: 55,
- e) a polypeptide having at least 60%, at least 65%, at least 70%, at least 75%, at least 80%, at least 85%, at least 90%, at least 95%, at least 98% or 100% sequence identity to the polypeptide shown in SEQ ID NO: 56,
- f) a polypeptide having at least 60%, at least 65%, at least 70%, at least 75% at least 80%, at least 85%, at least 90%, at least 95%, at least 98% or 100% sequence identity to the polypeptide shown in SEQ ID NO: 57, g) a polypeptide having at least 60%, at least 65%, at least 70%, at least 75% at least 80%, at least 85%, at least 90%, at least 95%, at least 98% or 100% sequence identity to the polypeptide shown in SEQ ID NO: 58, h) a polypeptide having at least 60%, at least 65%, at least 70%, at least 75% at least 80%, at least 85%, at least 90%, at least 95%, at least 98% or 100% sequence identity to the polypeptide shown in SEQ ID NO: 59, i) a polypeptide having at least 60%, at least 65%, at least 70%, at least 75% at least 80%, at least 85%, at least 90%, at least 95%, at least 98% or 100% sequence identity to the polypeptide shown in SEQ ID NO: 60, j) a polypeptide having at least 60%, at least 65%, at least 70%, at least 75% at least 80%, at least 85%, at least 90%, at least 95%, at least 98% or 100% sequence identity to the polypeptide shown in SEQ ID NO: 61, k) a polypeptide having at least 60%, at least 65%, at least 70%, at least 75% at least 80%, at least 85%, at least 90%, at least 95%, at least 98% or 100% sequence identity to the polypeptide shown in SEQ ID NO: 62, l) a polypeptide having at least 60%, at least 65%, at least 70%, at least 75% at least 80%, at least 85%, at least 90%, at least 95%, at least 98% or 100% sequence identity to the polypeptide shown in SEQ ID NO: 63, m) a polypeptide having at least 60%, at least 65%, at least 70%, at least 75% at least 80%, at least 85%, at least 90%, at least 95%, at least 98% or 100% sequence identity to the polypeptide shown in SEQ ID NO: 64, n) a polypeptide having at least 60%, at least 65%, at least 70%, at least 75% at least 80%, at least 85%, at least 90%, at least 95%, at least 98% or 100% sequence identity to the polypeptide shown in SEQ ID NO: 65, o) a polypeptide having at least 60%, at least 65%, at least 70%, at least 75% at least 80%, at least 85%, at least 90%, at least 95%, at least 98% or 100% sequence identity to the polypeptide shown in SEQ ID NO: 66, p) a polypeptide having at least 60%, at least 65%, at least 70%, at least 75% at least 80%, at least 85%, at least 90%, at least 95%, at least 98% or 100% sequence identity to the polypeptide shown in SEQ ID NO: 67, q) a polypeptide having at least 60%, at least 65%, at least 70%, at least 75% at least 80%, at least 85%, at least 90%, at least 95%, at least 98% or 100% sequence identity to the polypeptide shown in SEQ ID NO: 68, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 84, and wherein the composition preferably comprises at least one cleaning component. One embodiment relates to a cleaning composition comprising a DNase, a protease and at least one cleaning component, wherein the DNase comprises or consists of a polypeptide selected from the group of polypeptides comprising the amino acid sequence shown in; SEQ ID NO 52, SEQ ID NO 53, SEQ ID NO 54, SEQ ID NO 55, SEQ ID NO 56, SEQ ID NO 57, SEQ ID NO 58, SEQ ID NO 59, SEQ ID NO 60, SEQ ID NO 61, SEQ ID NO 62, SEQ ID NO 63, SEQ ID NO 64, SEQ ID NO 65, SEQ ID NO 66, SEQ ID NO 67 and SEQ ID NO 68 and wherein the protease comprises or consists of the polypeptide comprising the amino acid sequence shown in SEQ ID NO 84.

One embodiment of the invention relates to a composition, preferably a cleaning composition, comprising a protease, a polypeptide having DNase activity, wherein the polypeptide is selected from the group of polypeptides:

a) a polypeptide having at least 60%, at least 65%, at least 70%, at least 75% at least 80%, at least 85%, at least 90%, at least 95%, at least 98% or 100% sequence identity to the polypeptide shown in SEQ ID NO: 52, b) a polypeptide having at least 60%, at least 65%, at least 70%, at least 75% at least 80%, at least 85%, at least 90%, at least 95%, at least 98% or 100% sequence identity to the polypeptide shown in SEQ ID NO: 53, c) a polypeptide having at least 60%, at least 65%, at least 70%, at least 75% at least 80%, at least 85%, at least 90%, at least 95%, at least 98% or 100% sequence identity to the polypeptide shown in SEQ ID NO: 54, d) a polypeptide having at least 60%, at least 65%, at least 70%, at least 75% at least 80%, at least 85%, at least 90%, at least 95%, at least 98% or 100% sequence identity to the polypeptide shown in SEQ ID NO: 55, e) a polypeptide having at least 60%, at least 65%, at least 70%, at least 75% at least 80%, at least 85%, at least 90%, at least 95%, at least 98% or 100% sequence identity to the polypeptide shown in SEQ ID NO: 56, f) a polypeptide having at least 60%, at least 65%, at least 70%, at least 75% at least 80%, at least 85%, at least 90%, at least 95%, at least 98% or 100% sequence identity to the polypeptide shown in SEQ ID NO: 57, g) a polypeptide having at least 60%, at least 65%, at least 70%, at least 75% at least 80%, at least 85%, at least 90%, at least 95%, at least 98% or 100% sequence identity to the polypeptide shown in SEQ ID NO: 58, h) a polypeptide having at least 60%, at least 65%, at least 70%, at least 75% at least 80%, at least 85%, at least 90%, at least 95%, at least 98% or 100% sequence identity to the polypeptide shown in SEQ ID NO: 59, i) a polypeptide having at least 60%, at least 65%, at least 70%, at least 75% at least 80%, at least 85%, at least 90%, at least 95%, at least 98% or 100% sequence identity to the polypeptide shown in SEQ ID NO: 60, j) a polypeptide having at least 60%, at least 65%, at least 70%, at least 75% at least 80%, at least 85%, at least 90%, at least 95%, at least 98% or 100% sequence identity to the polypeptide shown in SEQ ID NO: 61, k) a polypeptide having at least 60%, at least 65%, at least 70%, at least 75% at least 80%, at least 85%, at least 90%, at least 95%, at least 98% or 100% sequence identity to the polypeptide shown in SEQ ID NO: 62, l) a polypeptide having at least 60%, at least 65%, at least 70%, at least 75% at least 80%, at least 85%, at least 90%, at least 95%, at least 98% or 100% sequence identity to the polypeptide shown in SEQ ID NO: 63, m) a polypeptide having at least 60%, at least 65%, at least 70%, at least 75% at least 80%, at least 85%, at least 90%, at least 95%, at least 98% or 100% sequence identity to the polypeptide shown in SEQ ID NO: 64, n) a polypeptide having at least 60%, at least 65%, at least 70%, at least 75% at least 80%, at least 85%, at least 90%, at least 95%, at least 98% or 100% sequence identity to the polypeptide shown in SEQ ID NO: 65, o) a polypeptide having at least 60%, at least 65%, at least 70%, at least 75% at least 80%, at least 85%, at least 90%, at least 95%, at least 98% or 100% sequence identity to the polypeptide shown in SEQ ID NO: 66, p) a polypeptide having at least 60%, at least 65%, at least 70%, at least 75% at least 80%, at least 85%, at least 90%, at least 95%, at least 98% or 100% sequence identity to the polypeptide shown in SEQ ID NO: 67, q) a polypeptide having at least 60%, at least 65%, at least 70%, at least 75% at least 80%, at least 85%, at least 90%, at least 95%, at least 98% or 100% sequence identity to the polypeptide shown in SEQ ID NO: 68, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 85, and wherein the composition preferably comprises at least one cleaning component. One embodiment relates to a cleaning composition comprising a DNase, a protease and at least one cleaning component, wherein the DNase comprises or consists of a polypeptide selected from the group of polypeptides comprising the amino acid sequence shown in; SEQ ID NO 52, SEQ ID NO 53, SEQ ID NO 54, SEQ ID NO 55, SEQ ID NO 56, SEQ ID NO 57, SEQ ID NO 58, SEQ ID NO 59, SEQ ID NO 60, SEQ ID NO 61, SEQ ID NO 62, SEQ ID NO 63, SEQ ID NO 64, SEQ ID NO 65, SEQ ID NO 66, SEQ ID NO 67 and SEQ ID NO 68 and wherein the protease comprises or consists of the polypeptide comprising the amino acid sequence shown in SEQ ID NO 85.

One embodiment of the invention relates to a composition, preferably a cleaning composition, comprising a protease, a polypeptide having DNase activity, wherein the polypeptide is selected from the group of polypeptides:
 a) a polypeptide having at least 60%, at least 65%, at least 70%, at least 75% at least 80%, at least 85%, at least 90%, at least 95%, at least 98% or 100% sequence identity to the polypeptide shown in SEQ ID NO: 52,
 b) a polypeptide having at least 60%, at least 65%, at least 70%, at least 75%, at least 80%, at least 85%, at least 90%, at least 95%, at least 98% or 100% sequence identity to the polypeptide shown in SEQ ID NO: 53,
 c) a polypeptide having at least 60%, at least 65%, at least 70%, at least 75%, at least 80%, at least 85%, at least 90%, at least 95%, at least 98% or 100% sequence identity to the polypeptide shown in SEQ ID NO: 54,
 d) a polypeptide having at least 60%, at least 65%, at least 70%, at least 75%, at least 80%, at least 85%, at least 90%, at least 95%, at least 98% or 100% sequence identity to the polypeptide shown in SEQ ID NO: 55,
 e) a polypeptide having at least 60%, at least 65%, at least 70%, at least 75%, at least 80%, at least 85%, at least 90%, at least 95%, at least 98% or 100% sequence identity to the polypeptide shown in SEQ ID NO: 56,
 f) a polypeptide having at least 60%, at least 65%, at least 70%, at least 75%, at least 80%, at least 85%, at least 90%, at least 95%, at least 98% or 100% sequence identity to the polypeptide shown in SEQ ID NO: 57,
 g) a polypeptide having at least 60%, at least 65%, at least 70%, at least 75%, at least 80%, at least 85%, at least 90%, at least 95%, at least 98% or 100% sequence identity to the polypeptide shown in SEQ ID NO: 58,
 h) a polypeptide having at least 60%, at least 65%, at least 70%, at least 75%, at least 80%, at least 85%, at least 90%, at least 95%, at least 98% or 100% sequence identity to the polypeptide shown in SEQ ID NO: 59,
 i) a polypeptide having at least 60%, at least 65%, at least 70%, at least 75%, at least 80%, at least 85%, at least 90%, at least 95%, at least 98% or 100% sequence identity to the polypeptide shown in SEQ ID NO: 60,
 j) a polypeptide having at least 60%, at least 65%, at least 70%, at least 75%, at least 80%, at least 85%, at least 90%, at least 95%, at least 98% or 100% sequence identity to the polypeptide shown in SEQ ID NO: 61,
 k) a polypeptide having at least 60%, at least 65%, at least 70%, at least 75%, at least 80%, at least 85%, at least 90%, at least 95%, at least 98% or 100% sequence identity to the polypeptide shown in SEQ ID NO: 62,
 l) a polypeptide having at least 60%, at least 65%, at least 70%, at least 75%, at least 80%, at least 85%, at least 90%, at least 95%, at least 98% or 100% sequence identity to the polypeptide shown in SEQ ID NO: 63,
 m) a polypeptide having at least 60%, at least 65%, at least 70%, at least 75%, at least 80%, at least 85%, at least 90%, at least 95%, at least 98% or 100% sequence identity to the polypeptide shown in SEQ ID NO: 64,
 n) a polypeptide having at least 60%, at least 65%, at least 70%, at least 75% at least 80%, at least 85%, at least 90%, at least 95%, at least 98% or 100% sequence identity to the polypeptide shown in SEQ ID NO: 65,
 o) a polypeptide having at least 60%, at least 65%, at least 70%, at least 75%, at least 80%, at least 85%, at least 90%, at least 95%, at least 98% or 100% sequence identity to the polypeptide shown in SEQ ID NO: 66,
 p) a polypeptide having at least 60%, at least 65%, at least 70%, at least 75%, at least 80%, at least 85%, at least 90%, at least 95%, at least 98% or 100% sequence identity to the polypeptide shown in SEQ ID NO: 67,
 q) a polypeptide having at least 60%, at least 65%, at least 70%, at least 75%, at least 80%, at least 85%, at least 90%, at least 95%, at least 98% or 100% sequence identity to the polypeptide shown in SEQ ID NO: 68,
wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 86, and wherein the composition preferably comprises at least one cleaning component. One embodiment relates to a cleaning composition comprising a DNase, a protease and at least one cleaning component, wherein the DNase comprises or consists of a polypeptide selected from the group of polypeptides comprising the amino acid sequence shown in; SEQ ID NO 52, SEQ ID NO 53, SEQ ID NO 54, SEQ ID NO 55, SEQ ID NO 56, SEQ ID NO 57, SEQ ID NO 58, SEQ ID NO 59, SEQ ID NO 60, SEQ ID NO 61, SEQ ID NO 62, SEQ ID NO 63, SEQ ID NO 64, SEQ ID NO 65, SEQ ID NO 66, SEQ ID NO 67 and SEQ ID NO 68 and wherein the protease comprises or consists of the polypeptide comprising the amino acid sequence shown in SEQ ID NO 86.

One embodiment relates to a composition comprising
 a) at least 0.001 ppm of at least one polypeptide having DNase activity, wherein the DNase is selected for the group consisting of:
  i. a DNase comprising one or more of the motifs [T/D/S][G/N]PQL (SEQ ID NO 69), [F/LN/I][A[N/R]D[L/I/P/V] (SEQ ID NO: 70), or C[D/N]T[A/R] (SEQ ID NO: 71);
  ii. a DNase comprising the motif [D/Q][IN]DH (SEQ ID NO 72);
  iii. a DNase comprising one or both of the motifs [D/M/L][S/T]GYSR[D/N] (SEQ ID NO: 73) or ASXNRSKG (SEQ ID NO: 74);
  iv. a DNase comprising one or both of the motifs [V/I]PL[S/A]NAWK (SEQ ID NO: 75) or NPQL (SEQ ID NO: 76);
  v. a DNase comprising one or both of the motifs P[Q/E]L[W/Y] (SEQ ID NO: 77) or [K/H/E]NAW (SEQ ID NO:78);
  vi. a polypeptide having DNase activity selected from: a polypeptide having at least 80% sequence identity to the polypeptide shown in SEQ ID NO: 1, a polypeptide having at least 80% sequence identity to the polypeptide shown in SEQ ID NO: 2, a polypeptide having at least 80% sequence identity to the polypeptide shown in SEQ ID NO: 3, a polypeptide having at least 80% sequence identity to the polypeptide shown in SEQ ID NO: 4, a polypeptide having at least 80% sequence identity to the polypeptide shown in SEQ ID NO: 5, a polypeptide having at least 80% sequence identity to the polypeptide shown in SEQ ID NO: 6, a polypeptide having at least 80% sequence identity to the polypeptide shown in SEQ ID NO: 7, a polypeptide having at least 80% sequence identity to the polypeptide shown in SEQ ID NO: 8, a polypeptide having at least 80% sequence identity to the polypeptide shown in SEQ ID NO: 9, a polypeptide having at least 80% sequence identity to the polypeptide shown in SEQ ID NO: 10, a polypeptide having at least 80% sequence identity to the polypeptide shown in SEQ ID NO: 11, a polypeptide having at least 80% sequence identity to the polypeptide shown in SEQ ID NO: 12, a polypeptide having at least 80% sequence identity to the polypeptide shown in SEQ ID NO: 13, a polypeptide having at least 80% sequence identity to the polypeptide shown in SEQ ID NO: 92, a polypeptide having at least 80% sequence identity to the polypeptide shown in SEQ ID NO: 15, a polypeptide having at least 80% sequence identity to the polypeptide shown in SEQ ID NO: 16, a polypeptide having at least 80% sequence identity to the polypeptide shown in SEQ ID NO: 17, a polypeptide having at least 80% sequence identity to the polypeptide shown in SEQ ID NO: 18, a polypeptide having at least 80% sequence identity to the polypeptide shown in SEQ ID NO: 19, a polypeptide having at least 80% sequence identity to the polypeptide shown in SEQ ID NO: 20, a polypeptide having at least 80% sequence identity to the polypeptide shown in SEQ ID NO: 21, a polypeptide having at least 80% sequence identity to the polypeptide shown in SEQ ID NO: 22, a polypeptide having at least 80% sequence identity to the polypeptide shown in SEQ ID NO: 23, a polypeptide having at least 80% sequence identity to the polypeptide shown in SEQ ID NO: 24, a polypeptide having at least 80% sequence identity to the polypeptide shown in SEQ ID NO: 25, a polypeptide having at least 80% sequence identity to the polypeptide shown in SEQ ID NO: 26, a polypeptide having at least 80% sequence identity to the polypeptide shown in SEQ ID NO: 27, a polypeptide having at least 80% sequence identity to the polypeptide shown in SEQ ID NO: 28, a polypeptide having at least 80% sequence identity to the polypeptide shown in SEQ ID NO: 29, a polypeptide having at least 80% sequence identity to the polypeptide shown in SEQ ID NO: 30, a polypeptide having at least 80% sequence identity to the polypeptide shown in SEQ ID NO: 31, a polypeptide having at least 80% sequence identity to the polypeptide shown in SEQ ID NO: 32, a polypeptide having at least 80% sequence identity to the polypeptide shown in SEQ ID NO: 33, a polypeptide having at least 80% sequence identity to the polypeptide shown in SEQ ID NO: 34, a polypeptide having at least 80% sequence identity to the polypeptide shown in SEQ ID NO: 35, a polypeptide having at least 80% sequence identity to the polypeptide shown in SEQ ID NO: 36, a polypeptide having at least 80% sequence identity to the polypeptide shown in SEQ ID NO: 37, a polypeptide having at least 80% sequence identity to the polypeptide shown in SEQ ID NO: 38, a polypeptide having at least 80% sequence identity to the polypeptide shown in SEQ ID NO: 39, a polypeptide having at least 80% sequence identity to the polypeptide shown in SEQ ID NO: 40, a polypeptide having at least 80% sequence identity to the polypeptide shown in SEQ ID NO: 41, a polypeptide having at least 80% sequence identity to the polypeptide shown in SEQ ID NO: 42, a polypeptide having at least 80% sequence identity to the polypeptide shown in SEQ ID NO: 43, a polypeptide having at least 80% sequence identity to the polypeptide shown in SEQ ID NO: 44, a polypeptide having at least 80% sequence identity to the polypeptide shown in SEQ ID NO: 45, a polypeptide having at least 80% sequence identity to the polypeptide shown in SEQ ID NO: 46, a polypeptide having at least 80% sequence identity to the polypeptide shown in SEQ ID NO: 47, a polypeptide having at least 80% sequence identity to the polypeptide shown in SEQ ID NO: 48, a polypeptide having at least 80% sequence identity to the polypeptide shown in SEQ ID NO: 49, a polypeptide having at least 80% sequence identity to the polypeptide shown in SEQ ID NO: 50, a polypeptide having at least 80% sequence identity to the polypeptide shown in SEQ ID NO: 51, a polypeptide having at least 80% sequence identity to the polypeptide shown in SEQ ID NO: 52, a polypeptide having at least 80% sequence identity to the polypeptide shown in SEQ ID NO: 53, a polypeptide having at least 80% sequence identity to the polypeptide shown in SEQ ID NO: 54, a polypeptide having at least 80% sequence identity to the polypeptide shown in SEQ ID NO: 55, a polypeptide having at least 80% sequence identity to the polypeptide shown in SEQ ID NO: 56, a polypeptide having at least 80% sequence identity to the polypeptide shown in SEQ ID NO: 57, a polypeptide having at least 80% sequence identity to the polypeptide shown in SEQ ID NO: 58, a polypeptide having at least 80% sequence identity to the polypeptide shown in SEQ ID NO: 59, a polypeptide having at least 80% sequence identity to the polypeptide shown in SEQ ID NO: 60, a polypeptide having at least 80% sequence identity to the polypeptide shown in SEQ ID NO: 61, a polypeptide having at least 80% sequence identity to the polypeptide shown in SEQ ID NO: 62, a polypeptide having at least 80% sequence identity to the polypeptide shown in SEQ ID NO: 63, a polypeptide having at least 80% sequence identity to the polypeptide shown in SEQ ID NO: 64, a polypeptide having at least 80% sequence identity to the polypeptide shown in SEQ ID NO: 65, a polypeptide having at least 80% sequence identity to the polypeptide shown in SEQ ID NO: 66, a polypeptide having at least 80% sequence identity to the polypeptide shown in SEQ ID NO: 67, and a polypeptide having at least 80% sequence identity to the polypeptide shown in SEQ ID NO: 68, and b) at least 0.01 ppm of one or more protease, wherein the protease is selected from,
  i) a protease variant of a protease parent, wherein the protease variant comprises one or more alteration(s) compared to a protease shown in SEQ ID NO 79 or SEQ ID NO 80 in one or more of the following positions: 3, 4, 9, 15, 24, 27, 42, 55, 59, 60, 66, 74, 85, 96, 97, 98, 99, 100, 101, 102, 104, 116, 118, 121, 126, 127, 128, 154, 156, 157, 158, 161, 164, 176, 179, 182, 185, 188, 189, 193, 198, 199, 200, 203, 206, 211, 212, 216, 218, 226, 229, 230, 239, 246, 255, 256, 268 and 269, wherein the positions correspond to the positions of the protease shown in SEQ ID NO 79 and wherein the protease variant has at least 60%, at least 65%, at least 70%, at least 75% at least 80%, at least 85%, at least 90%, at least 95%, at least 98% but less than 100% sequence identity to SEQ ID NO 79 or SEQ ID NO 80;

ii) a protease variant of a protease parent, wherein the protease variant comprises one or more mutation selected from the group consisting of X3T, X4I, X9R, X9E, X15T, X24G, X24R, X27R, X42R, X55P, X59E, X59D, X60D, X60E, X66A, X74D, X85R, X96S, X97G, X97D, X97A, X97XD, X99E, X99D, X99G, X99M, X99N, X99R, X99H, X101A, X102I, X102Y, X102N, X104A, X116V, X116R, X118D, X118N, X120S, X126L, X127Q, X128A, X154D, X156E, X157D, X157P, X158E, X161A, X164S, X176E, X179E, X182E, X185N, X188P, X189E, X193M, X198D, X199I, X203W, X206G, X211Q, X211D, X212D, X212S, X216S, X226V, X229L, X230H, X239R, X246K, X255W, X255D, X255E, X256E, X256D X268A and X269H, wherein the positions correspond to the positions of the protease shown in SEQ ID NO 79, wherein the protease variant has at least 60%, at least 65%, at least 70%, at least 75% at least 80%, at least 85%, at least 90%, at least 95%, at least 98% but less than 100% sequence identity to SEQ ID NO 79 or SEQ ID NO 80;

iii) a protease comprising a substitution at one or more positions corresponding to positions 171, 173, 175, 179, or 180 of SEQ ID NO: 81, compared to the protease shown in SEQ ID NO 81, wherein the protease variant has a sequence identity of at least 60%, at least 65%, at least 70%, at least 75% at least 80%, at least 85%, at least 90%, at least 95%, at least 98% but less than 100% identity to amino acid sequence 1 to 311 of SEQ ID NO 81, iv) a protease comprising the amino acid sequence shown in SEQ ID NO 79, 80, 81 or a protease having at least 60%, at least 65%, at least 70%, at least 75% at least 80%, at least 85%, at least 90%, at least 95%, at least 98% or 100% sequence identity to; the polypeptide comprising amino acids 1-269 of SEQ ID NO 79, the polypeptide comprising amino acids 1-311 of SEQ ID NO 81, the polypeptide comprising amino acids 1-275 of SEQ ID NO 80;

v) a protease comprising the amino acid sequence shown in SEQ ID NO 82, SEQ ID NO 83, SEQ ID NO 84, SEQ ID NO 85, SEQ ID NO 86 or a protease having at least 60%, at least 65%, at least 70%, at least 75% at least 80%, at least 85%, at least 90%, at least 95%, at least 98%, preferably 100% sequence identity hereto; and vi) one or more of the following protease variants selected from the group:
SEQ ID NO 79+T22R+S99G+S101A+V102I+A226V+Q239R;
SEQ ID NO 80+S24G+S53G+S78N+S101N+G128A+Y217Q;
SEQ ID NO 80+S24G+S53G+S78N+S101N+G128S+Y217Q;
SEQ ID NO 79+S9E+N42R+N74D+V199I+Q200L+Y203W+S253D+N255W+L256E;
SEQ ID NO 79+S9E+N42R+N74D+H118V+Q176E+A188P+V199I+Q200L+Y203W+S250D+S253D+N255W+L256E;
SEQ ID NO 79+S9E+N42R+N74D+Q176E+A188P+V199I+Q200L+Y203W S250D+S253D+N255W+L256E;
SEQ ID NO 79+S3V+N74D+H118V+Q176E+N179E+S182E+V199I+Q200L Y203W+5210V+5250D+5253D+N255W+L256E;
SEQ ID NO 79+T22A+N60D+S99G+S101A+V102I+N114L+G157D+S182D+T207A+A226V+Q239R+N242D+E265F;
SEQ ID NO 79+S9E+N42R+N74D+H118V+Q176E+A188P+V199I+Q200L+Y203W+S250D+S253D+N255W+L256E,
SEQ ID NO 79+S9E+N42R+N74D+Q176E+A188P+V199I+Q200L+Y203W+S250D+S253D+N255W+L256E,
SEQ ID NO 79+S9E+N42R+N74D+H118V+Q176E+A188P+V199I+Q200L+Y203W+S250D+N255W+L256E+*269aH+*269bH,
SEQ ID NO 79+S3V+N74D+H118V+Q176E+N179E+S182E+V199I+Q200L+Y203W+S210V+S250D+N255W+L256E,
SEQ ID NO 79+S9E+N74D+G113W+G157P+Q176E+V199I+Q200L+Y203W+S250D+T254E+N255W+L256E,
SEQ ID NO 79+S3V+S9R+N74D+H118V+Q176E+N179E+S182E+V199I+Q200L+Y203W+S212V+S250D+N255W+L256E,
SEQ ID NO 79+S99E,
SEQ ID NO 80+L217D and c) at least one additional component e.g. cleaning component, preferably selected from surfactants, builders, bleach components, polymers, dispersing agents and additional enzymes.

The protease and DNase may be included in the cleaning composition of the present invention at a level of from 0.01 to 1000 ppm, from 1 ppm to 1000 ppm, from 10 ppm to 1000 ppm, from 50 ppm to 1000 ppm, from 100 ppm to 1000 ppm, from 150 ppm to 1000 ppm, from 200 ppm to 1000 ppm, from 250 ppm to 1000 ppm, from 250 ppm to 750 ppm, from 250 ppm to 500 ppm.

The DNases above may be combined with proteases to form a blend to be added to the wash liquor solution according to the invention. The concentration of the DNase in the wash liquor solution is typically in the range of wash liquor from 0.00001 ppm to 10 ppm, from 0.00002 ppm to 10 ppm, from 0.0001 ppm to 10 ppm, from 0.0002 ppm to 10 ppm, from 0.001 ppm to 10 ppm, from 0.002 ppm to 10 ppm, from 0.01 ppm to 10 ppm, from 0.02 ppm to 10 ppm, 0.1 ppm to 10 ppm, from 0.2 ppm to 10 ppm, from 0.5 ppm to 5 ppm. The concentration of the protease in the wash liquor solution is typically in the range of wash liquor from 0.00001 ppm to 10 ppm, from 0.00002 ppm to 10 ppm, from 0.0001 ppm to 10 ppm, from 0.0002 ppm to 10 ppm, from 0.001 ppm to 10 ppm, from 0.002 ppm to 10 ppm, from 0.01 ppm to 10 ppm, from 0.02 ppm to 10 ppm, 0.1 ppm to 10 ppm, from 0.2 ppm to 10 ppm, from 0.5 ppm to 5 ppm.

The DNases may be combined with any of the proteases below to form a blend to be added to a composition according to the invention.

One embodiment relates to a cleaning composition comprising a DNase, a protease and at least one cleaning component, wherein the amount of DNase in the composition is from 0.01 to 1000 ppm and the amount of protease is from 0.01 to 1000 ppm.

In addition to the protease and DNase the cleaning composition further comprises one or more cleaning component. One embodiment relates to a cleaning composition comprising a DNase, a protease and at least one cleaning component, wherein the cleaning component is selected from surfactants, preferably anionic and/or nonionic, builders and bleach components.

The choice of cleaning components may include, for textile care, the consideration of the type of textile to be cleaned, the type and/or degree of soiling, the temperature at which cleaning is to take place, and the formulation of the detergent product. Although components mentioned below are categorized by general header according to a particular functionality, this is not to be construed as a limitation, as a component may comprise additional functionalities as will be appreciated by the skilled artisan.

Surfactants

The cleaning composition may comprise one or more surfactants, which may be anionic and/or cationic and/or non-ionic and/or semi-polar and/or zwitterionic, or a mixture thereof. In a particular embodiment, the detergent composition includes a mixture of one or more nonionic surfactants and one or more anionic surfactants. The surfactant(s) is typically present at a level of from about 0.1% to 60% by weight, such as about 1% to about 40%, or about 3% to about 20%, or about 0.1% to about 15% or about 3% to about 10%. The surfactant(s) is chosen based on the desired cleaning application, and may include any conventional surfactant(s) known in the art.

When included therein the detergent will usually contain from about 1% to about 40% by weight of an anionic surfactant, such as from about 5% to about 30%, including from about 5% to about 15%, or from about 15% to about 20%, or from about 20% to about 25% of an anionic surfactant. Non-limiting examples of anionic surfactants include sulfates and sulfonates, in particular, linear alkylbenzenesulfonates (LAS), isomers of LAS, branched alkylbenzenesulfonates (BABS), phenylalkanesulfonates, alpha-olefinsulfonates (AOS), olefin sulfonates, alkene sulfonates, alkane-2,3-diylbis(sulfates), hydroxyalkanesulfonates and disulfonates, alkyl sulfates (AS) such as sodium dodecyl sulfate (SDS), fatty alcohol sulfates (FAS), primary alcohol sulfates (PAS), alcohol ethersulfates (AES or AEOS or FES, also known as alcohol ethoxysulfates or fatty alcohol ether sulfates), secondary alkanesulfonates (SAS), paraffin sulfonates (PS), ester sulfonates, sulfonated fatty acid glycerol esters, alpha-sulfo fatty acid methyl esters (alpha-SFMe or SES) including methyl ester sulfonate (MES), alkyl- or alkenylsuccinic acid, dodecenyl/tetradecenyl succinic acid (DTSA), fatty acid derivatives of amino acids, diesters and monoesters of sulfo-succinic acid or salt of fatty acids (soap), and combinations thereof.

When included therein the detergent will usually contain from about 1% to about 40% by weigh of a cationic surfactant, for example from about 0.5% to about 30%, in particular from about 1% to about 20%, from about 3% to about 10%, such as from about 3% to about 5%, from about 8% to about 12% or from about 10% to about 12%. Non-limiting examples of cationic surfactants include alkyldimethylethanolamine quat (ADMEAQ), cetyltrimethylammonium bromide (CTAB), dimethyldistearylammonium chloride (DSDMAC), and alkylbenzyldimethylammonium, alkyl quaternary ammonium compounds, alkoxylated quaternary ammonium (AQA) compounds, ester quats, and combinations thereof.

When included therein the detergent will usually contain from about 0.2% to about 40% by weight of a nonionic surfactant, for example from about 0.5% to about 30%, in particular from about 1% to about 20%, from about 3% to about 10%, such as from about 3% to about 5%, from about 8% to about 12%, or from about 10% to about 12%. Non-limiting examples of nonionic surfactants include alcohol ethoxylates (AE or AEO), alcohol propoxylates, propoxylated fatty alcohols (PFA), alkoxylated fatty acid alkyl esters, such as ethoxylated and/or propoxylated fatty acid alkyl esters, alkylphenol ethoxylates (APE), nonylphenol ethoxylates (NPE), alkylpolyglycosides (APG), alkoxylated amines, fatty acid monoethanolamides (FAM), fatty acid diethanolamides (FADA), ethoxylated fatty acid monoethanolamides (EFAM), propoxylated fatty acid monoethanolamides (PFAM), polyhydroxyalkyl fatty acid amides, or N-acyl N-alkyl derivatives of glucosamine (glucamides, GA, or fatty acid glucamides, FAGA), as well as products available under the trade names SPAN and TWEEN, and combinations thereof.

When included therein the detergent will usually contain from about 0.01 to about 10% by weight of a semipolar surfactant. Non-limiting examples of semipolar surfactants include amine oxides (AO) such as alkyldimethylamineoxide, N-(coco alkyl)-N,N-dimethylamine oxide and N-(tallow-alkyl)-N,N-bis(2-hydroxyethyl)amine oxide, and combinations thereof.

When included therein the detergent will usually contain from about 0.01% to about 10% by weight of a zwitterionic surfactant. Non-limiting examples of zwitterionic surfactants include betaines such as alkyldimethylbetaines, sulfobetaines, and combinations thereof.

Builders and Co-Builders

The cleaning composition may contain about 0-65% by weight, such as about 5% to about 50%, such as about 0.5% to about 20% of a detergent builder or co-builder, or a mixture thereof. In a dish wash detergent, the level of builder is typically 40-65%, particularly 50-65%. The builder and/or co-builder may particularly be a chelating agent that forms water-soluble complexes with Ca and Mg. Any builder and/or co-builder known in the art for use in cleaning detergents may be utilized. Non-limiting examples of builders include zeolites, diphosphates (pyrophosphates), triphosphates such as sodium triphosphate (STP or STPP), carbonates such as sodium carbonate, soluble silicates such as sodium metasilicate, layered silicates (e.g., SKS-6 from Hoechst), ethanolamines such as 2-aminoethan-1-ol (MEA), diethanolamine (DEA, also known as 2,2'-iminodiethan-1-ol), triethanolamine (TEA, also known as 2,2',2"-nitrilotriethan-1-ol), and (carboxymethyl)inulin (CMI), and combinations thereof.

The detergent composition may also contain 0-50% by weight, such as about 5% to about 30%, of a detergent co-builder. The detergent composition may include a co-builder alone, or in combination with a builder, for example a zeolite builder. Non-limiting examples of co-builders include homopolymers of polyacrylates or copolymers thereof, such as poly(acrylic acid) (PAA) or copoly(acrylic acid/maleic acid) (PAA/PMA). Further non-limiting examples include citrate, chelators such as aminocarboxylates, aminopolycarboxylates and phosphonates, and alkyl- or alkenylsuccinic acid. Additional specific examples include 2,2',2"-nitrilotriacetic acid (NTA), ethylenediaminetetraacetic acid (EDTA), diethylenetriaminepentaacetic acid (DTPA), iminodisuccinic acid (IDS), ethylenediamine-N,N'-disuccinic acid (EDDS), methylglycinediacetic acid (MGDA), glutamic acid-N,N-diacetic acid (GLDA), 1-hydroxyethane-1,1-diphosphonic acid (HEDP), ethylenediaminetetra(methylenephosphonic acid) (EDTMPA), diethylenetriaminepentakis(methylenephosphonic acid) (DTMPA or DTPMPA), N-(2-hydroxyethyl)iminodiacetic acid (EDG), aspartic acid-N-monoacetic acid (ASMA), aspartic acid-N,N-diacetic acid (ASDA), aspartic acid-N-monopropionic acid (ASMP), iminodisuccinic acid (IDA), N-(2-sulfomethyl)-aspartic acid (SMAS), N-(2-sulfoethyl)-aspartic acid (SEAS), N-(2-sulfomethyl)-glutamic acid (SMGL), N-(2-sulfoethyl)-glutamic acid (SEGL), N-methyliminodiacetic acid (MIDA), α-alanine-N,N-diacetic acid (α-ALDA), serine-N,N-diacetic acid (SEDA), isoserine-N,N-diacetic acid (ISDA), phenylalanine-N,N-diacetic acid (PHDA), anthranilic acid-N,N-diacetic acid (ANDA), sulfanilic acid-N,N-diacetic acid (SLDA), taurine-N,N-diacetic acid (TUDA) and sulfomethyl-N,N-diacetic acid (SMDA), N-(2-hydroxyethyl)ethylenediamine-N,N',N"-triacetic acid (HEDTA), diethanolglycine (DEG), diethylenetriamine penta(methylenephosphonic acid) (DTPMP), aminotris(methylenephosphonic acid) (ATMP), and combinations and salts thereof. Further exemplary builders and/or co-builders are described in, e.g., WO 09/102854, U.S. Pat. No. 5,977,053

Bleaching Systems

The cleaning composition may contain 0-30% by weight, such as about 1% to about 20%, such as about 0.01% to about 10% of a bleaching system. Any bleaching system comprising components known in the art for use in cleaning detergents may be utilized. Suitable bleaching system components include sources of hydrogen peroxide; sources of peracids; and bleach catalysts or boosters.

Sources of Hydrogen Peroxide:

Suitable sources of hydrogen peroxide are inorganic persalts, including alkali metal salts such as sodium percarbonate and sodium perborates (usually mono- or tetrahydrate), and hydrogen peroxide-urea (1/1).

Sources of Peracids:

Peracids may be (a) incorporated directly as preformed peracids or (b) formed in situ in the wash liquor from hydrogen peroxide and a bleach activator (perhydrolysis) or (c) formed in situ in the wash liquor from hydrogen peroxide and a perhydrolase and a suitable substrate for the latter, e.g., an ester.

a) Suitable preformed peracids include, but are not limited to, peroxycarboxylic acids such as peroxybenzoic acid and its ring-substituted derivatives, peroxy-α-naphthoic acid, peroxyphthalic acid, peroxylauric acid, peroxystearic acid, ε-phthalimidoperoxycaproic acid [phthalimidoperoxyhexanoic acid (PAP)], and o-carboxybenzamidoperoxycaproic acid; aliphatic and aromatic diperoxydicarboxylic acids such as diperoxydodecanedioic acid, diperoxyazelaic acid, diperoxysebacic acid, diperoxybrassylic acid, 2-decyldiperoxybutanedioic acid, and diperoxyphthalic, -isophthalic and -terephthalic acids; perimidic acids; peroxymonosulfuric acid; peroxydisulfuric acid; peroxyphosphoric acid; peroxysilicic acid; and mixtures of said compounds. It is understood that the peracids mentioned may in some cases be best added as suitable salts, such as alkali metal salts (e.g., Oxone®) or alkaline earth-metal salts.

b) Suitable bleach activators include those belonging to the class of esters, amides, imides, nitriles or anhydrides and, where applicable, salts thereof. Suitable examples are tetraacetylethylenediamine (TAED), sodium 4-[(3,5,5-trimethylhexanoyl)oxy]benzene-1-sulfonate (ISONOBS), sodium 4-(dodecanoyloxy)benzene-1-sulfonate (LOBS), sodium 4-(decanoyloxy)benzene-1-sulfonate, 4-(decanoyloxy)benzoic acid (DOBA), sodium 4-(nonanoyloxy)benzene-1-sulfonate (NOBS), and/or those disclosed in WO98/17767. A particular family of bleach activators of interest was disclosed in EP624154 and particularly preferred in that family is acetyl triethyl citrate (ATC). ATC or a short chain triglyceride like triacetin has the advantage that they are environmentally friendly. Furthermore, acetyl triethyl citrate and triacetin have good hydrolytical stability in the product upon storage and are efficient bleach activators. Finally, ATC is multifunctional, as the citrate released in the perhydrolysis reaction may function as a builder.

Bleach Catalysts and Boosters

The bleaching system may also include a bleach catalyst or booster.

Some non-limiting examples of bleach catalysts that may be used in the compositions of the present invention include manganese oxalate, manganese acetate, manganese-collagen, cobalt-amine catalysts and manganese triazacyclononane (MnTACN) catalysts; particularly preferred are complexes of manganese with 1,4,7-trimethyl-1,4,7-triazacyclononane (Me3-TACN) or 1,2,4,7-tetramethyl-1,4,7-triazacyclononane (Me4-TACN), in particular Me3-TACN, such as the dinuclear manganese complex [(Me3-TACN)Mn(O)3Mn(Me3-TACN)](PF6)2, and [2,2',2"-nitrilotris(ethane-1,2-diylazanylylidene-κN-methanylylidene)triphenolato-κ3O]manganese(III). The bleach catalysts may also be other metal compounds; such as iron or cobalt complexes.

In some embodiments, where a source of a peracid is included, an organic bleach catalyst or bleach booster may be used having one of the following formulae:

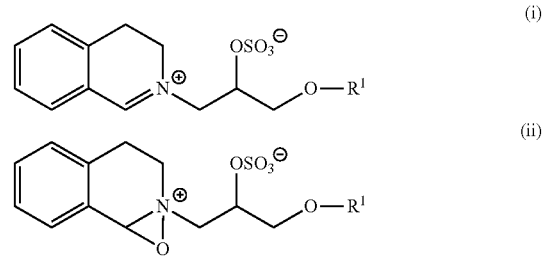

(iii) and mixtures thereof; wherein each R1 is independently a branched alkyl group containing from 9 to 24 carbons or linear alkyl group containing from 11 to 24 carbons, preferably each R1 is independently a branched alkyl group containing from 9 to 18 carbons or linear alkyl group containing from 11 to 18 carbons, more preferably each R1 is independently selected from the group consisting of 2-propylheptyl, 2-butyloctyl, 2-pentylnonyl, 2-hexyldecyl, dodecyl, tetradecyl, hexadecyl, octadecyl, isononyl, isodecyl, isotridecyl and isopentadecyl.

Other exemplary bleaching systems are described, e.g. in WO2007/087258, WO2007/087244, WO2007/087259, EP1867708 (Vitamin K) and WO2007/087242. Suitable photobleaches may for example be sulfonated zinc or aluminium phthalocyanines.

Metal Care Agents

Metal care agents may prevent or reduce the tarnishing, corrosion or oxidation of metals, including aluminium, stainless steel and non-ferrous metals, such as silver and copper. Suitable examples include one or more of the following:

(a) benzatriazoles, including benzotriazole or bis-benzotriazole and substituted derivatives thereof. Benzotriazole derivatives are those compounds in which the available substitution sites on the aromatic ring are partially or completely substituted. Suitable substituents include linear or branch-chain Ci-C20-alkyl groups (e.g., C1-C20-alkyl groups) and hydroxyl, thio, phenyl or halogen such as fluorine, chlorine, bromine and iodine.

(b) metal salts and complexes chosen from the group consisting of zinc, manganese, titanium, zirconium, hafnium, vanadium, cobalt, gallium and cerium salts and/or complexes, the metals being in one of the oxidation states II, III, IV, V or VI. In one aspect, suitable metal salts and/or metal complexes may be chosen from the group consisting of Mn(II) sulphate, Mn(II) citrate, Mn(II) stearate, Mn(II) acetylacetonate, K^TiF6 (e.g., K2TiF6), K^ZrF6 (e.g., K2ZrF6), CoSO4, Co(NOs)2 and Ce(NOs)3, zinc salts, for example zinc sulphate, hydrozincite or zinc acetate;

(c) silicates, including sodium or potassium silicate, sodium disilicate, sodium metasilicate, crystalline phyllosilicate and mixtures thereof.

Further suitable organic and inorganic redox-active substances that act as silver/copper corrosion inhibitors are disclosed in WO 94/26860 and WO 94/26859. Preferably the composition of the invention comprises from 0.1 to 5% by weight of the composition of a metal care agent, preferably the metal care agent is a zinc salt.

Hydrotropes

The cleaning composition may contain 0-10% by weight, for example 0-5% by weight, such as about 0.5 to about 5%, or about 3% to about 5%, of a hydrotrope. Any hydrotrope known in the art for use in detergents may be utilized. Non-limiting examples of hydrotropes include sodium benzenesulfonate, sodium p-toluene sulfonate (STS), sodium xylene sulfonate (SXS), sodium cumene sulfonate (SCS), sodium cymene sulfonate, amine oxides, alcohols and polyglycolethers, sodium hydroxynaphthoate, sodium hydroxynaphthalene sulfonate, sodium ethylhexyl sulfate, and combinations thereof.

Polymers

The cleaning composition may contain 0-10% by weight, such as 0.5-5%, 2-5%, 0.5-2% or 0.2-1% of a polymer. Any polymer known in the art for use in detergents may be utilized. The polymer may function as a co-builder as mentioned above, or may provide antiredeposition, fiber protection, soil release, dye transfer inhibition, grease cleaning and/or anti-foaming properties. Some polymers may have more than one of the above-mentioned properties and/or more than one of the below-mentioned motifs. Exemplary polymers include (carboxymethyl)cellulose (CMC), poly(vinyl alcohol) (PVA), poly(vinylpyrrolidone) (PVP), poly(ethyleneglycol) or poly(ethylene oxide) (PEG), ethoxylated poly(ethyleneimine), carboxymethyl inulin (CMI), and polycarboxylates such as PAA, PAA/PMA, poly-aspartic acid, and lauryl methacrylate/acrylic acid copolymers, hydrophobically modified CMC (HM-CMC) and silicones, copolymers of terephthalic acid and oligomeric glycols, copolymers of poly(ethylene terephthalate) and poly(oxyethene terephthalate) (PET-POET), PVP, poly (vinylimidazole) (PVI), poly(vinylpyridine-N-oxide) (PVPO or PVPNO) and polyvinylpyrrolidone-vinylimidazole (PVPVI). Suitable examples include PVP-K15, PVP-K30, ChromeBond S-400, ChromeBond S-403E and Chromabond S-100 from Ashland Aqualon, and Sokalan® HP 165, Sokalan® HP 50 (Dispersing agent), Sokalan® HP 53 (Dispersing agent), Sokalan® HP 59 (Dispersing agent), Sokalan® HP 56 (dye transfer inhibitor), Sokalan® HP 66 K (dye transfer inhibitor) from BASF. Further exemplary polymers include sulfonated polycarboxylates, polyethylene oxide and polypropylene oxide (PEO-PPO) and diquaternium ethoxy sulfate. Other exemplary polymers are disclosed in, e.g., WO 2006/130575. Salts of the above-mentioned polymers are also contemplated. Particularly preferred polymer is ethoxylated homopolymer Sokalan® HP 20 from BASF, which helps to prevent redeposition of soil in the wash liquor.

Fabric Hueing Agents

The cleaning compositions of the present invention may also include fabric hueing agents such as dyes or pigments, which when formulated in detergent compositions can deposit onto a fabric when said fabric is contacted with a wash liquor comprising said detergent compositions and thus altering the tint of said fabric through absorption/reflection of visible light. Fluorescent whitening agents emit at least some visible light. In contrast, fabric hueing agents alter the tint of a surface as they absorb at least a portion of the visible light spectrum. Suitable fabric hueing agents include dyes and dye-clay conjugates, and may also include pigments. Suitable dyes include small molecule dyes and polymeric dyes. Suitable small molecule dyes include small molecule dyes selected from the group consisting of dyes falling into the Colour Index (C.I.) classifications of Direct Blue, Direct Red, Direct Violet, Acid Blue, Acid Red, Acid Violet, Basic Blue, Basic Violet and Basic Red, or mixtures thereof, for example as described in WO2005/03274, WO2005/03275, WO2005/03276 and EP1876226 (hereby incorporated by reference). The detergent composition preferably comprises from about 0.00003 wt % to about 0.2 wt %, from about 0.00008 wt % to about 0.05 wt %, or even from about 0.0001 wt % to about 0.04 wt % fabric hueing agent. The composition may comprise from 0.0001 wt % to 0.2 wt % fabric hueing agent, this may be especially preferred when the composition is in the form of a unit dose pouch. Suitable hueing agents are also disclosed in, e.g. WO 2007/087257 and WO2007/087243.

Enzymes

The cleaning composition may comprise one or more additional enzymes such as one or more lipase, cutinase, an amylase, carbohydrase, cellulase, pectinase, mannanase, arabinase, galactanase, xylanase, oxidase, e.g., a laccase, and/or peroxidase. In general, the properties of the selected enzyme(s) should be compatible with the selected detergent, (i.e., pH-optimum, compatibility with other enzymatic and non-enzymatic ingredients, etc.), and the enzyme(s) should be present in effective amounts.

Cellulases

Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum* disclosed in U.S. Pat. Nos. 4,435,307, 5,648,263, 5,691,178, 5,776,757 and WO 89/09259. Especially suitable cellulases are the alkaline or neutral cellulases having colour care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. Nos. 5,457,046, 5,686, 593, 5,763,254, WO 95/24471, WO 98/12307 and WO99/001544. Other cellulases are endo-beta-1,4-glucanase enzyme having a sequence of at least 97% identity to the amino acid sequence of position 1 to position 773 of SEQ ID NO:2 of WO 2002/099091 or a family 44 xyloglucanase, which a xyloglucanase enzyme having a sequence of at least 60% identity to positions 40-559 of SEQ ID NO: 2 of WO 2001/062903.

Commercially available cellulases include Celluzyme™, and Carezyme™ (Novozymes NS) Carezyme Premium™ (Novozymes NS), Celluclean™ (Novozymes NS), Celluclean Classic™ (Novozymes NS), Cellusoft™ (Novozymes NS), Whitezyme™ (Novozymes NS), Clazinase™, and Puradax HA™ (Genencor International Inc.), and KAC-500(B)™ (Kao Corporation).

Mannanases Suitable mannanases include those of bacterial or fungal origin. Chemically or genetically modified mutants are included. The mannanase may be an alkaline mannanase of Family 5 or 26. It may be a wild-type from Bacillus or Humicola, particularly B. agaradhaerens, B. licheniformis, B. halodurans, B. clausii, or H. insolens. Suitable mannanases are described in WO 1999/064619. A commercially available mannanase is Mannaway (Novozymes NS).

Peroxidases/Oxidases

Suitable peroxidases/oxidases include those of plant, bacterial or fungal origin. Chemically modified or protein engineered mutants are included. Examples of useful peroxidases include peroxidases from Coprinus, e.g., from C. cinereus, and variants thereof as those described in WO 93/24618, WO 95/10602, and WO 98/15257. Commercially available peroxidases include Guardzyme™ (Novozymes NS).

Lipases and Cutinases

Suitable lipases and cutinases include those of bacterial or fungal origin. Chemically modified or protein engineered mutant enzymes are included. Examples include lipase from Thermomyces, e.g. from T. lanuginosus (previously named Humicola lanuginosa) as described in EP258068 and EP305216, cutinase from Humicola, e.g. H. insolens (WO96/13580), lipase from strains of Pseudomonas (some of these now renamed to Burkholderia), e.g. P. alcaligenes or P. pseudoalcaligenes (EP218272), P. cepacia (EP331376), P. sp. strain SD705 (WO95/06720 & WO96/27002), P. wisconsinensis (WO96/12012), GDSL-type Streptomyces lipases (WO10/065455), cutinase from Magnaporthe grisea (WO10/107560), cutinase from Pseudomonas mendocina (U.S. Pat. No. 5,389,536), lipase from Thermobifida fusca (WO11/084412), Geobacillus stearothermophilus lipase (WO11/084417), lipase from Bacillus subtilis (WO11/084599), and lipase from Streptomyces griseus (WO11/150157) and S. pristinaespiralis (WO12/137147). Other examples are lipase variants such as those described in EP407225, WO92/05249, WO94/01541, WO94/25578, WO95/14783, WO95/30744, WO95/35381, WO95/22615, WO96/00292, WO97/04079, WO97/07202, WO00/34450, WO00/60063, WO01/92502, WO07/87508 and WO09/109500.

Preferred commercial lipase products include Lipolase™, Lipex™; Lipolex™ and Lipoclean™ (Novozymes NS), Lumafast (originally from Genencor) and Lipomax (originally from Gist-Brocades). Still other examples are lipases sometimes referred to as acyltransferases or perhydrolases, e.g. acyltransferases with homology to Candida antarctica lipase A (WO10/111143), acyltransferase from Mycobacterium smegmatis (WO05/56782), perhydrolases from the CE 7 family (WO09/67279), and variants of the M. smegmatis perhydrolase in particular the S54V variant used in the commercial product Gentle Power Bleach from Huntsman Textile Effects Pte Ltd (WO10/100028).

Amylases

Suitable amylases include alpha-amylases and/or a glucoamylases and may be of bacterial or fungal origin. Chemically modified or protein engineered mutants are included. Amylases include, for example, alpha-amylases obtained from Bacillus, e.g., a special strain of Bacillus licheniformis, described in more detail in GB 1,296,839.

Suitable amylases include amylases having SEQ ID NO: 2 in WO 95/10603 or variants having 90% sequence identity to SEQ ID NO: 3 thereof. Preferred variants are described in WO 94/02597, WO 94/18314, WO 97/43424 and SEQ ID NO: 4 of WO 99/019467, such as variants with substitutions in one or more of the following positions: 15, 23, 105, 106, 124, 128, 133, 154, 156, 178, 179, 181, 188, 190, 197, 201, 202, 207, 208, 209, 211, 243, 264, 304, 305, 391, 408, and 444. Different suitable amylases include amylases having SEQ ID NO: 6 in WO 02/010355 or variants thereof having 90% sequence identity to SEQ ID NO: 6. Preferred variants of SEQ ID NO: 6 are those having a deletion in positions 181 and 182 and a substitution in position 193.

Other amylases which are suitable are hybrid alpha-amylase comprising residues 1-33 of the alpha-amylase derived from B. amyloliquefaciens shown in SEQ ID NO: 6 of WO 2006/066594 and residues 36-483 of the B. licheniformis alpha-amylase shown in SEQ ID NO: 4 of WO 2006/066594 or variants having 90% sequence identity thereof. Preferred variants of this hybrid alpha-amylase are those having a substitution, a deletion or an insertion in one of more of the following positions: G48, T49, G107, H156, A181, N190, M197, 1201, A209 and Q264. Most preferred variants of the hybrid alpha-amylase comprising residues 1-33 of the alpha-amylase derived from B. amyloliquefaciens shown in SEQ ID NO: 6 of WO 2006/066594 and residues 36-483 of SEQ ID NO: 4 are those having the substitutions:

M197T;

H156Y+A181T+N190F+A209V+Q264S; or

G48A+T49I+G107A+H156Y+A181T+N190F+1201F+A209V+Q264S.

Further amylases which are suitable are amylases having SEQ ID NO: 6 in WO 99/019467 or variants thereof having 90% sequence identity to SEQ ID NO: 6. Preferred variants of SEQ ID NO: 6 are those having a substitution, a deletion or an insertion in one or more of the following positions: R181, G182, H183, G184, N195, 1206, E212, E216 and K269. Particularly preferred amylases are those having deletion in positions R181 and G182, or positions H183 and G184. Additional amylases which can be used are those having SEQ ID NO: 1, SEQ ID NO: 3, SEQ ID NO: 2 or SEQ ID NO: 7 of WO 96/023873 or variants thereof having 90% sequence identity to SEQ ID NO: 1, SEQ ID NO: 2, SEQ ID NO: 3 or SEQ ID NO: 7. Preferred variants of SEQ ID NO: 1, SEQ ID NO: 2, SEQ ID NO: 3 or SEQ ID NO: 7 are those having a substitution, a deletion or an insertion in one or more of the following positions: 140, 181, 182, 183, 184, 195, 206, 212, 243, 260, 269, 304 and 476, using SEQ ID 2 of WO 96/023873 for numbering. More preferred variants are those having a deletion in two positions selected from 181, 182, 183 and 184, such as 181 and 182, 182 and 183, or positions 183 and 184. Most preferred amylase variants of SEQ ID NO: 1, SEQ ID NO: 2 or SEQ ID NO: 7 are those having a deletion in positions 183 and 184 and a substitution in one or more of positions 140, 195, 206, 243, 260, 304 and 476.

Other amylases which can be used are amylases having SEQ ID NO: 2 of WO 08/153815, SEQ ID NO: 10 in WO 01/66712 or variants thereof having 90% sequence identity to SEQ ID NO: 2 of WO 08/153815 or 90% sequence identity to SEQ ID NO: 10 in WO 01/66712. Preferred variants of SEQ ID NO: 10 in WO 01/66712 are those having a substitution, a deletion or an insertion in one of more of the following positions: 176, 177, 178, 179, 190, 201, 207, 211 and 264. Further suitable amylases are amylases having SEQ ID NO: 2 of WO 09/061380 or variants having 90% sequence identity to SEQ ID NO: 2 thereof. Preferred variants of SEQ ID NO: 2 are those having a truncation of the C-terminus and/or a substitution, a deletion or an insertion in one of more of the following positions: Q87, Q98, S125, N128, T131, T165, K178, R180, S181, T182, G183, M201, F202, N225, S243, N272, N282, Y305, R309, D319, Q320, Q359, K444 and G475. More preferred variants of SEQ ID NO: 2 are those having the substitution in one of more of the following positions: Q87E,R, Q98R, S125A, N128C, T131I, T165I, K178L, T182G, M201L, F202Y, N225E,R, N272E,R, S243Q,A,E,D, Y305R, R309A, Q320R, Q359E, K444E and G475K and/or deletion in position R180 and/or S181 or of T182 and/or G183. Most preferred amylase variants of SEQ ID NO: 2 are those having the substitutions:

N128C+K178L+T182G+Y305R+G475K;
N128C+K178L+T182G+F202Y+Y305R+D319T+ G475K;
S125A+N128C+K178L+T182G+Y305R+G475K; or
S125A+N128C+T131I+T165I+K178L+T182G+ Y305R+G475K wherein the variants are C-terminally truncated and optionally further comprises a substitution at position 243 and/or a deletion at position 180 and/or position 181.

Further suitable amylases are amylases having SEQ ID NO: 1 of WO13184577 or variants having 90% sequence identity to SEQ ID NO: 1 thereof. Preferred variants of SEQ ID NO: 1 are those having a substitution, a deletion or an insertion in one of more of the following positions: K176, R178, G179, T180, G181, E187, N192, M199, I203, S241, R458, T459, D460, G476 and G477. More preferred variants of SEQ ID NO: 1 are those having the substitution in one of more of the following positions: K176L, E187P, N192FYH, M199L, I203YF, S241QADN, R458N, T459S, D460T, G476K and G477K and/or deletion in position R178 and/or S179 or of T180 and/or G181. Most preferred amylase variants of SEQ ID NO: 1 are those having the substitutions:

E187P+I203Y+G476K
E187P+I203Y+R458N+T459S+D460T+G476K wherein the variants optionally further comprise a substitution at position 241 and/or a deletion at position 178 and/or position 179.

Further suitable amylases are amylases having SEQ ID NO: 1 of WO10104675 or variants having 90% sequence identity to SEQ ID NO: 1 thereof. Preferred variants of SEQ ID NO: 1 are those having a substitution, a deletion or an insertion in one of more of the following positions: N21, D97, V128 K177, R179, S180, I181, G182, M200, L204, E242, G477 and G478. More preferred variants of SEQ ID NO: 1 are those having the substitution in one of more of the following positions: N21D, D97N, V128I K177L, M200L, L204YF, E242QA, G477K and G478K and/or deletion in position R179 and/or S180 or of I181 and/or G182. Most preferred amylase variants of SEQ ID NO: 1 are those having the substitutions:

N21D+D97N+V128I wherein the variants optionally further comprise a substitution at position 200 and/or a deletion at position 180 and/or position 181.

Other suitable amylases are the alpha-amylase having SEQ ID NO: 12 in WO01/66712 or a variant having at least 90% sequence identity to SEQ ID NO: 12. Preferred amylase variants are those having a substitution, a deletion or an insertion in one of more of the following positions of SEQ ID NO: 12 in WO01/66712: R28, R118, N174; R181, G182, D183, G184, G186, W189, N195, M202, Y298, N299, K302, S303, N306, R310, N314; R320, H324, E345, Y396, R400, W439, R444, N445, K446, Q449, R458, N471, N484. Particular preferred amylases include variants having a deletion of D183 and G184 and having the substitutions R118K, N195F, R320K and R458K, and a variant additionally having substitutions in one or more position selected from the group: M9, G149, G182, G186, M202, T257, Y295, N299, M323, E345 and A339, most preferred a variant that additionally has substitutions in all these positions.

Other examples are amylase variants such as those described in WO2011/098531, WO2013/001078 and WO2013/001087.

Commercially available amylases are Duramyl™, Termamyl™, Fungamyl™, Stainzyme™, Stainzyme Plus™, Natalase™, Liquozyme X and BAN™ (from Novozymes NS), and Rapidase™, Purastar™/Effectenz™, Powerase, Preferenz S1000, Preferenz S100 and Preferenz S110 (from Genencor International Inc./DuPont).

Peroxidases/Oxidases

A peroxidase according to the invention is a peroxidase enzyme comprised by the enzyme classification EC 1.11.1.7, as set out by the Nomenclature Committee of the International Union of Biochemistry and Molecular Biology (IUBMB), or any fragment derived therefrom, exhibiting peroxidase activity.

Suitable peroxidases include those of plant, bacterial or fungal origin. Chemically modified or protein engineered mutants are included. Examples of useful peroxidases include peroxidases from *Coprinopsis*, e.g., from *C. cinerea* (EP 179,486), and variants thereof as those described in WO 93/24618, WO 95/10602, and WO 98/15257.

A suitable peroxidase includes a haloperoxidase enzyme, such as chloroperoxidase, bromoperoxidase and compounds exhibiting chloroperoxidase or bromoperoxidase activity. Haloperoxidases are classified according to their specificity for halide ions. Chloroperoxidases (E.C. 1.11.1.10) catalyze formation of hypochlorite from chloride ions. Preferably, the haloperoxidase is a vanadium haloperoxidase, i.e., a vanadate-containing haloperoxidase. Haloperoxidases have been isolated from many different fungi, in particular from the fungus group dematiaceous hyphomycetes, such as Caldariomyces, e.g., *C. fumago*, *Alternaria*, *Curvularia*, e.g., *C. verruculosa* and *C. inaequalis*, *Drechslera*, *Ulocladium* and *Botrytis*. Haloperoxidases have also been isolated from bacteria such as *Pseudomonas*, e.g., *P. pyrrocinia* and *Streptomyces*, e.g., *S. aureofaciens*.

A suitable oxidase includes in particular, any laccase enzyme comprised by the enzyme classification EC 1.10.3.2, or any fragment derived therefrom exhibiting laccase activity, or a compound exhibiting a similar activity, such as a catechol oxidase (EC 1.10.3.1), an o-aminophenol oxidase (EC 1.10.3.4), or a bilirubin oxidase (EC 1.3.3.5). Preferred laccase enzymes are enzymes of microbial origin. The enzymes may be derived from plants, bacteria or fungi (including filamentous fungi and yeasts). Suitable examples from fungi include a laccase derivable from a strain of *Aspergillus*, *Neurospora*, e.g., *N. crassa*, *Podospora*, *Botrytis*, *Collybia*, *Fomes*, *Lentinus*, *Pleurotus*, *Trametes*, e.g., *T. villosa* and *T. versicolor*, *Rhizoctonia*, e.g., *R. solani*,

*Coprinopsis*, e.g., *C. cinerea, C. comatus, C. friesii,* and *C. plicatilis, Psathyrella,* e.g., *P. condelleana, Panaeolus,* e.g., *P. papilionaceus, Myceliophthora,* e.g., *M. thermophila, Schytalidium,* e.g., *S. thermophilum, Polyporus,* e.g., *P. pinsitus, Phlebia,* e.g., *P. radiata* (WO 92/01046), or *Coriolus,* e.g., *C. hirsutus* (JP 2238885). Suitable examples from bacteria include a laccase derivable from a strain of *Bacillus*. A laccase derived from *Coprinopsis* or *Myceliophthora* is preferred; in particular, a laccase derived from *Coprinopsis cinerea,* as disclosed in WO 97/08325; or from *Myceliophthora thermophila,* as disclosed in WO 95/33836.

Dispersants

The cleaning compositions of the present invention can also contain dispersants. In particular, powdered detergents may comprise dispersants. Suitable water-soluble organic materials include the homo- or co-polymeric acids or their salts, in which the polycarboxylic acid comprises at least two carboxyl radicals separated from each other by not more than two carbon atoms. Suitable dispersants are for example described in Powdered Detergents, Surfactant science series volume 71, Marcel Dekker, Inc.

Dye Transfer Inhibiting Agents

The cleaning compositions of the present invention may also include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. When present in a subject composition, the dye transfer inhibiting agents may be present at levels from about 0.0001% to about 10%, from about 0.01% to about 5% or even from about 0.1% to about 3% by weight of the composition.

Fluorescent Whitening Agent

The cleaning compositions of the present invention will preferably also contain additional components that may tint articles being cleaned, such as fluorescent whitening agent or optical brighteners. Where present the brightener is preferably at a level of about 0.01% to about 0.5%. Any fluorescent whitening agent suitable for use in a laundry detergent composition may be used in the composition of the present invention. The most commonly used fluorescent whitening agents are those belonging to the classes of diaminostilbene-sulfonic acid derivatives, diarylpyrazoline derivatives and bisphenyl-distyryl derivatives. Examples of the diaminostilbene-sulfonic acid derivative type of fluorescent whitening agents include the sodium salts of: 4,4'-bis-(2-diethanolamino-4-anilino-s-triazin-6-ylamino) stilbene-2,2'-disulfonate, 4,4'-bis-(2,4-dianilino-s-triazin-6-ylamino) stilbene-2.2'-disulfonate, 4,4'-bis-(2-anilino-4-(N-methyl-N-2-hydroxy-ethylamino)-s-triazin-6-ylamino) stilbene-2,2'-disulfonate, 4,4'-bis-(4-phenyl-1,2,3-triazol-2-yl)stilbene-2,2'-disulfonate and sodium 5-(2H-naphtho[1,2-d][1,2,3] triazol-2-yl)-2-[(E)-2-phenylvinyl]benzenesulfonate.

Preferred fluorescent whitening agents are Tinopal DMS and Tinopal CBS available from Ciba-Geigy AG, Basel, Switzerland. Tinopal DMS is the disodium salt of 4,4'-bis-(2-morpholino-4-anilino-s-triazin-6-ylamino) stilbene-2,2'-disulfonate. Tinopal CBS is the disodium salt of 2,2'-bis-(phenyl-styryl)-disulfonate. Also preferred are fluorescent whitening agents is the commercially available Parawhite KX, supplied by Paramount Minerals and Chemicals, Mumbai, India. Other fluorescers suitable for use in the invention include the 1-3-diary) pyrazolines and the 7-alkylaminocoumarins. Suitable fluorescent brightener levels include lower levels of from about 0.01, from 0.05, from about 0.1 or even from about 0.2 wt % to upper levels of 0.5 or even 0.75 wt %.

Soil Release Polymers

The cleaning compositions of the present invention may also include one or more soil release polymers which aid the removal of soils from fabrics such as cotton and polyester based fabrics, in particular the removal of hydrophobic soils from polyester based fabrics. The soil release polymers may for example be nonionic or anionic terephthalte based polymers, polyvinyl caprolactam and related copolymers, vinyl graft copolymers, polyester polyamides see for example Chapter 7 in Powdered Detergents, Surfactant science series volume 71, Marcel Dekker, Inc. Another type of soil release polymers is amphiphilic alkoxylated grease cleaning polymers comprising a core structure and a plurality of alkoxylate groups attached to that core structure. The core structure may comprise a polyalkylenimine structure or a polyalkanolamine structure as described in detail in WO 2009/087523 (hereby incorporated by reference). Furthermore, random graft co-polymers are suitable soil release polymers. Suitable graft co-polymers are described in more detail in WO 2007/138054, WO 2006/108856 and WO 2006/113314 (hereby incorporated by reference). Suitable polyethylene glycol polymers include random graft co-polymers comprising: (i) hydrophilic backbone comprising polyethylene glycol; and (ii) side chain(s) selected from the group consisting of: C4-C25 alkyl group, polypropylene, polybutylene, vinyl ester of a saturated C1-C6 mono-carboxylic acid, CI-C 6 alkyl ester of acrylic or methacrylic acid, and mixtures thereof. Suitable polyethylene glycol polymers have a polyethylene glycol backbone with random grafted polyvinyl acetate side chains. The average molecular weight of the polyethylene glycol backbone can be in the range of from 2,000 Da to 20,000 Da, or from 4,000 Da to 8,000 Da. The molecular weight ratio of the polyethylene glycol backbone to the polyvinyl acetate side chains can be in the range of from 1:1 to 1:5, or from 1:1.2 to 1:2. The average number of graft sites per ethylene oxide units can be less than 1, or less than 0.8, the average number of graft sites per ethylene oxide units can be in the range of from 0.5 to 0.9, or the average number of graft sites per ethylene oxide units can be in the range of from 0.1 to 0.5, or from 0.2 to 0.4. A suitable polyethylene glycol polymer is Sokalan HP22. Other soil release polymers are substituted polysaccharide structures especially substituted cellulosic structures such as modified cellulose deriviatives such as those described in EP 1867808 or WO 2003/040279 (both are hereby incorporated by reference). Suitable cellulosic polymers include cellulose, cellulose ethers, cellulose esters, cellulose amides and mixtures thereof. Suitable cellulosic polymers include anionically modified cellulose, nonionically modified cellulose, cationically modified cellulose, zwitterionically modified cellulose, and mixtures thereof. Suitable cellulosic polymers include methyl cellulose, carboxy methyl cellulose, ethyl cellulose, hydroxyl ethyl cellulose, hydroxyl propyl methyl cellulose, ester carboxy methyl cellulose, and mixtures thereof.

Anti-Redeposition Agents

The cleaning compositions of the present invention may also include one or more anti-redeposition agents such as carboxymethylcellulose (CMC), polyvinyl alcohol (PVA), polyvinylpyrrolidone (PVP), polyoxyethylene and/or polyethyleneglycol (PEG), homopolymers of acrylic acid, copolymers of acrylic acid and maleic acid, and ethoxylated polyethyleneimines. The cellulose based polymers described under soil release polymers above may also function as anti-redeposition agents.

Rheology Modifiers

The cleaning compositions of the present invention may also include one or more rheology modifiers, structurants or thickeners, as distinct from viscosity reducing agents. The rheology modifiers are selected from the group consisting of non-polymeric crystalline, hydroxy-functional materials, polymeric rheology modifiers which impart shear thinning characteristics to the aqueous liquid matrix of a liquid detergent composition. The rheology and viscosity of the detergent can be modified and adjusted by methods known in the art, for example as shown in EP 2169040.

Other suitable cleaning composition components include, but are not limited to, anti-shrink agents, anti-wrinkling agents, bactericides, binders, carriers, dyes, enzyme stabilizers, fabric softeners, fillers, foam regulators, hydrotropes, perfumes, pigments, sod suppressors, solvents, and structurants for liquid detergents and/or structure elasticizing agents.

Formulation of Detergent Products

The cleaning composition of the present invention may be formulated, for example, as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dishwashing operations. In a specific aspect, the present invention provides a detergent additive comprising one or more enzymes as described herein. The cleaning composition of the invention may be in any convenient form, e.g., a bar, a homogenous tablet, a tablet having two or more layers, a pouch having one or more compartments, a regular or compact powder, a granule, a paste, a gel, or a regular, compact or concentrated liquid.

Pouches can be configured as single or multicompartments. It can be of any form, shape and material which is suitable for hold the composition, e.g. without allowing the release of the composition to release of the composition from the pouch prior to water contact. The pouch is made from water soluble film which encloses an inner volume. Said inner volume can be divided into compartments of the pouch. Preferred films are polymeric materials preferably polymers which are formed into a film or sheet. Preferred polymers, copolymers or derivates thereof are selected polyacrylates, and water soluble acrylate copolymers, methyl cellulose, carboxy methyl cellulose, sodium dextrin, ethyl cellulose, hydroxyethyl cellulose, hydroxypropyl methyl cellulose, malto dextrin, poly methacrylates, most preferably polyvinyl alcohol copolymers and, hydroxypropyl methyl cellulose (HPMC). Preferably the level of polymer in the film for example PVA is at least about 60%. Preferred average molecular weight will typically be about 20,000 to about 150,000. Films can also be of blended compositions comprising hydrolytically degradable and water soluble polymer blends such as polylactide and polyvinyl alcohol (known under the Trade reference M8630 as sold by MonoSol LLC, Indiana, USA) plus plasticisers like glycerol, ethylene glycerol, propylene glycol, sorbitol and mixtures thereof. The pouches can comprise a solid laundry cleaning composition or part components and/or a liquid cleaning composition or part components separated by the water soluble film. The compartment for liquid components can be different in composition than compartments containing solids: US2009/0011970 A1.

Detergent ingredients can be separated physically from each other by compartments in water dissolvable pouches or in different layers of tablets. Thereby negative storage interaction between components can be avoided. Different dissolution profiles of each of the compartments can also give rise to delayed dissolution of selected components in the wash solution.

A liquid or gel detergent, which is not unit dosed, may be aqueous, typically containing at least 20% by weight and up to 95% water, such as up to about 70% water, up to about 65% water, up to about 55% water, up to about 45% water, up to about 35% water. Other types of liquids, including without limitation, alkanols, amines, diols, ethers and polyols may be included in an aqueous liquid or gel. An aqueous liquid or gel detergent may contain from 0-30% organic solvent. A liquid or gel detergent may be non-aqueous.

Granular Cleaning Formulations

Non-dusting granulates may be produced, e.g. as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

The DNase may be formulated as a granule for example as a co-granule that combines one or more enzymes. Each enzyme will then be present in more granules securing a more uniform distribution of enzymes in the detergent. This also reduces the physical segregation of different enzymes due to different particle sizes. Methods for producing multi-enzyme co-granulate for the detergent industry is disclosed in the IP.com disclosure IPCOM000200739D.

Another example of formulation of enzymes by the use of co-granulates are disclosed in WO 2013/188331, which relates to a detergent composition comprising (a) a multi-enzyme co-granule; (b) less than 10 wt zeolite (anhydrous basis); and (c) less than 10 wt phosphate salt (anhydrous basis), wherein said enzyme co-granule comprises from 10 to 98 wt % moisture sink component and the composition additionally comprises from 20 to 80 wt % detergent moisture sink component. The multi-enzyme co-granule may comprise an enzyme of the invention and one or more enzymes selected from the group consisting of proteases, lipases, cellulases, xyloglucanases, perhydrolases, peroxidases, lipoxygenases, laccases, hemicellulases, proteases, cellulases, cellobiose dehydrogenases, xylanases, phospho lipases, esterases, cutinases, pectinases, mannanases, pectate lyases, keratinases, reductases, oxidases, phenoloxidases, ligninases, pullulanases, tannases, pentosanases, lichenases glucanases, arabinosidases, hyaluronidase, chondroitinase, amylases, and mixtures thereof. WO 2013/188331 also relates to a method of treating and/or cleaning a surface, preferably a fabric surface comprising the steps of (i) contacting said surface with the detergent composition as claimed and described herein in aqueous wash liquor, (ii) rinsing and/or drying the surface.

An embodiment of the invention relates to an enzyme granule/particle comprising the DNase and protease. The granule is composed of a core, and optionally one or more coatings (outer layers) surrounding the core. Typically, the granule/particle size, measured as equivalent spherical diameter (volume based average particle size), of the granule is 20-2000 µm, particularly 50-1500 µm, 100-1500 µm or 250-1200 µm. The core may include additional materials such as fillers, fibre materials (cellulose or synthetic fibres), stabilizing agents, solubilising agents, suspension agents, viscosity regulating agents, light spheres, plasticizers, salts, lubricants and fragrances. The core may include binders, such as synthetic polymer, wax, fat, or carbohydrate. The core may comprise a salt of a multivalent cation, a reducing agent, an antioxidant, a peroxide decomposing catalyst and/or an acidic buffer component, typically as a homogenous blend. The core may consist of an inert particle with the enzyme absorbed into it, or applied onto the surface, e.g., by fluid bed coating. The core may have a diameter of 20-2000 µm, particularly 50-1500 µm, 100-1500 µm or 250-1200 µm. The core can be prepared by granulating a blend of the ingredients, e.g., by a method comprising granulation techniques such as crystallization, precipitation, pan-coating, fluid bed coating, fluid bed agglomeration, rotary atomization, extrusion, prilling, spheronization, size reduction methods, drum granulation, and/or high shear granulation.

Methods for preparing the core can be found in Handbook of Powder Technology; Particle size enlargement by C. E. Capes; Volume 1; 1980; Elsevier.

The core of the enzyme granule/particle may be surrounded by at least one coating, e.g., to improve the storage stability, to reduce dust formation during handling, or for coloring the granule. The optional coating(s) may include a salt coating, or other suitable coating materials, such as polyethylene glycol (PEG), methyl hydroxy-propyl cellulose (MHPC) and polyvinyl alcohol (PVA). Examples of enzyme granules with multiple coatings are shown in WO 93/07263 and WO 97/23606. The coating may be applied in an amount of at least 0.1% by weight of the core, e.g., at least 0.5%, 1% or 5%. The amount may be at most 100%, 70%, 50%, 40% or 30%. The coating is preferably at least 0.1 µm thick, particularly at least 0.5 µm, at least 1 µm or at least 5 µm. In a one embodiment, the thickness of the coating is below 100 µm. In another embodiment, the thickness of the coating is below 60 µm. In an even more particular embodiment the total thickness of the coating is below 40 µm. The coating should encapsulate the core unit by forming a substantially continuous layer. A substantially continuous layer is to be understood as a coating having few or no holes, so that the core unit it is encapsulating/enclosing has few or none uncoated areas. The layer or coating should be homogeneous in thickness. The coating can further contain other materials as known in the art, e.g., fillers, antisticking agents, pigments, dyes, plasticizers and/or binders, such as titanium dioxide, kaolin, calcium carbonate or talc. A salt coating may comprise at least 60% by weight w/w of a salt, e.g., at least 65%, at least 70%, at least 75%, at least 80%, at least 85%, at least 90%, at least 95% or at least 99% by weight w/w. The salt may be added from a salt solution where the salt is completely dissolved or from a salt suspension wherein the fine particles is less than 50 µm, such as less than 10 µm or less than 5 µm. The salt coating may comprise a single salt or a mixture of two or more salts. The salt may be water soluble, and may have a solubility at least 0.1 grams in 100 g of water at 20° C., preferably at least 0.5 g per 100 g water, e.g., at least 1 g per 100 g water, e.g., at least 5 g per 100 g water. The salt may be an inorganic salt, e.g., salts of sulfate, sulfite, phosphate, phosphonate, nitrate, chloride or carbonate or salts of simple organic acids (less than 10 carbon atoms, e.g., 6 or less carbon atoms) such as citrate, malonate or acetate. Examples of cations in these salts are alkali or earth alkali metal ions, the ammonium ion or metal ions of the first transition series, such as sodium, potassium, magnesium, calcium, zinc or aluminium. Examples of anions include chloride, bromide, iodide, sulfate, sulfite, bisulfite, thiosulfate, phosphate, monobasic phosphate, dibasic phosphate, hypophosphite, dihydrogen pyrophosphate, tetraborate, borate, carbonate, bicarbonate, metasilicate, citrate, malate, maleate, malonate, succinate, lactate, formate, acetate, butyrate, propionate, benzoate, tartrate, ascorbate or gluconate. In particular alkali- or earth alkali metal salts of sulfate, sulfite, phosphate, phosphonate, nitrate, chloride or carbonate or salts of simple organic acids such as citrate, malonate or acetate may be used. The salt in the coating may have a constant humidity at 20° C. above 60%, particularly above 70%, above 80% or above 85%, or it may be another hydrate form of such a salt (e.g., anhydrate). The salt coating may be as described in WO 00/01793 or WO 2006/034710. Specific examples of suitable salts are NaCl ($CH_{20°\ C.}$=76%), $Na_2CO_3$ ($CH_{20°\ C.}$=92%), $NaNO_3$ ($CH_{20°\ C.}$=73%), $Na_2HPO_4$ ($CH_{20°\ C.}$=95%), $Na_3PO_4$ ($CH_{20°\ C.}$=92%), $NH_4Cl$ ($CH_{25°\ C.}$=79.5%), $(NH_4)_2HPO_4$ ($CH_{20°\ C.}$=93.0%), $NH_4H_2PO_4$ ($CH_{20°\ C.}$=93.1%), $(NH_4)_2SO_4$ ($CH_{20°\ C.}$=81.1%), KCl ($CH_{20°\ C.}$=85%), $K2HPO_4$ ($CH_{20°\ C.}$=92%), $KH_2PO_4$ ($CH_{20°\ C.}$=96.5%), $KNO_3$ ($CH_{20°\ C.}$=93.5%), $Na_2SO_4$ ($CH_{20°\ C.}$=93%), $K_2SO_4$ ($CH_{20°\ C.}$=98%), $KHSO_4$ ($CH_{20°\ C.}$=86%), $MgSO_4$ ($CH_{20°\ C.}$=90%), $ZnSO_4$ ($CH_{20°\ C.}$=90%) and sodium citrate ($CH_{25°\ C.}$=86%). Other examples include $NaH_2PO_4$, $(NH_4)H2PO_4$, $CuSO_4$, $Mg(NO_3)_2$ and magnesium acetate. The salt may be in anhydrous form, or it may be a hydrated salt, i.e. a crystalline salt hydrate with bound water(s) of crystallization, such as described in WO 99/32595. Specific examples include anhydrous sodium sulfate ($Na_2SO_4$), anhydrous magnesium sulfate ($MgSO_4$), magnesium sulfate heptahydrate ($MgSO_4.H_2O$), zinc sulfate heptahydrate ($ZnSO_4.7H_2O$), sodium phosphate dibasic heptahydrate ($Na_2HPO_47H_2O$), magnesium nitrate hexahydrate ($Mg(NO_3)_2(6H_2O)$), sodium citrate dihydrate and magnesium acetate tetrahydrate. Preferably the salt is applied as a solution of the salt, e.g., using a fluid bed.

One embodiment of the present invention provides a granule, which comprises:
 (a) a core comprising a DNase and a protease according to the invention, and
 (b) optionally a coating consisting of one or more layer(s) surrounding the core.

One embodiment of the invention relates to a granule, which comprises:
 (a) a core comprising a DNase and a protease wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 79, SEQ ID NO 80, SEQ ID NO 81, SEQ ID NO 82, SEQ ID NO 83, SEQ ID NO 84, SEQ ID NO 85 or SEQ ID NO 86 and wherein the is DNase has at least 60%, at least 65%, at least 70%, at least 75%, at least 80%, at least 85%, at least 90%, at least 95%, at least 98% or 100% sequence identity to the amino acid sequence shown in SEQ ID NO 13, and
 (b) optionally a coating consisting of one or more layer(s) surrounding the core.

One embodiment of the invention relates to a granule, which comprises:
 (a) a core comprising a DNase and a protease wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 79, SEQ ID NO 80, SEQ ID NO 81, SEQ ID NO 82, SEQ ID NO 83, SEQ ID NO 84, SEQ ID NO 85 or SEQ ID NO 86 and wherein the is DNase has at least 60%, at least 65%, at least 70%, at least 75%, at least 80%, at least 85%, at least 90%, at least 95%, at least 98% or 100% sequence identity to the amino acid sequence shown in SEQ ID NO 65, and
 (b) optionally a coating consisting of one or more layer(s) surrounding the core.

One embodiment of the invention relates to a granule, which comprises:
 (a) a core comprising a DNase and a protease wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 79, SEQ ID NO 80, SEQ ID NO 81, SEQ ID NO 82, SEQ ID NO 83, SEQ ID NO 84, SEQ ID NO 85 or SEQ ID NO 86 and wherein the is DNase has at least 60%, at least 65%, at least 70%, at least 75%, at least 80%, at least 85%, at least 90%, at least 95%, at least 98% or 100% sequence identity to the amino acid sequence shown in SEQ ID NO 66, and
 (b) optionally a coating consisting of one or more layer(s) surrounding the core.

One embodiment of the invention relates to a granule, which comprises:
 (a) a core comprising a DNase and a protease wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 79, SEQ ID NO 80, SEQ ID NO 81, SEQ ID NO 82, SEQ ID NO 83, SEQ ID NO 84, SEQ ID NO 85 or SEQ ID NO 86 and wherein the is DNase has at least 60%, at least 65%, at least 70%, at least 75%, at least 80%, at least 85%, at least 90%, at least 95%, at least 98% or 100% sequence identity to the amino acid sequence shown in SEQ ID NO 66, and
 (b) optionally a coating consisting of one or more layer(s) surrounding the core.

One embodiment of the invention relates to a granule, which comprises:
 (a) a core comprising a DNase and a protease wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 79, SEQ ID NO 80, SEQ ID NO 81, SEQ ID NO 82, SEQ ID NO 83, SEQ ID NO 84, SEQ ID NO 85 or SEQ ID NO 86 and wherein the is DNase has at least 60%, at least 65%, at least 70%, at least 75%, at least 80%, at least 85%, at least 90%, at least 95%, at least 98% or 100% sequence identity to the amino acid sequence shown in SEQ ID NO 67, and
 (b) optionally a coating consisting of one or more layer(s) surrounding the core.

One embodiment of the invention relates to a granule, which comprises:
 (a) a core comprising a DNase and a protease wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 79, SEQ ID NO 80, SEQ ID NO 81, SEQ ID NO 82, SEQ ID NO 83, SEQ ID NO 84, SEQ ID NO 85 or SEQ ID NO 86 and wherein the is DNase has at least 60%, at least 65%, at least 70%, at least 75%, at least 80%, at least 85%, at least 90%, at least 95%, at least 98% or 100% sequence identity to the amino acid sequence shown in SEQ ID NO 68, and
 (b) optionally a coating consisting of one or more layer(s) surrounding the core.

Uses

The present invention is also directed to methods for using the compositions thereof. Laundry/textile/fabric (House hold laundry washing, Industrial laundry washing). Hard surface cleaning (ADW, car wash, Industrial surface). The cleaning e.g. detergent composition of the present invention may be formulated, for example, as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dishwashing operations. In a specific aspect, the present invention provides a detergent additive comprising one or more enzymes as described herein.

The compositions of the invention comprise a blend of DNase and protease and effectively reduce or remove organic components, such as protein and DNA from surfaces such as textiles and hard surfaces e.g. dishes.

One embodiment of the invention relates to the use of a composition comprising a DNase and protease for reduction of redeposition. One embodiment of the invention relates to the use of a cleaning composition comprising a DNase and protease for reduction of redeposition One embodiment of the invention relates to the use of a cleaning composition comprising a DNase and protease for reduction of redeposition when the cleaning composition is applied in e.g. laundry process. One embodiment of the invention relates to the use of a cleaning composition comprising a DNase and protease for reduction of redeposition on an item e.g. textile. In one embodiment, the composition is an anti-redeposition composition.

One embodiment of the invention relates to the use of a cleaning composition comprising a DNase and protease for reduction of redeposition, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 79, SEQ ID NO 80, SEQ ID NO 81, SEQ ID NO 82, SEQ ID NO 83, SEQ ID NO 84, SEQ ID NO 85 or SEQ ID NO 86.

One embodiment of the invention relates to the use of a cleaning composition comprising a DNase and protease for reduction of redeposition, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 79, SEQ ID NO 80, SEQ ID NO 81, SEQ ID NO 82, SEQ ID NO 83, SEQ ID NO 84, SEQ ID NO 85 or SEQ ID NO 86 and wherein the DNase is obtained from *Bacillus*, preferably *Bacillus cibi, Bacillus horikoshii, Bacillus licheniformis, Bacillus subtilis, Bacillus horneckiae,*

*Bacillus idriensis, Bacillus algicola, Bacillus vietnamensis, Bacillus hwajinpoensis, Bacillus indicus, Bacillus marisflavi* or *Bacillus luciferensis*.

One embodiment of the invention relates to the use of a cleaning composition comprising a DNase and protease for reduction of redeposition, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 79, SEQ ID NO 80, SEQ ID NO 81, SEQ ID NO 82, SEQ ID NO 83, SEQ ID NO 84, SEQ ID NO 85 or SEQ ID NO 86 and wherein the DNase is obtained from *Bacillus* and comprises one or both of the motif(s) [D/M/L][S/T]GYSR[D/N] (SEQ ID NO: 73) or ASXNRSKG (SEQ ID NO: 74).

One embodiment of the invention relates to the use of a cleaning composition comprising a DNase and protease for reduction of redeposition, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 79, SEQ ID NO 80, SEQ ID NO 81, SEQ ID NO 82, SEQ ID NO 83, SEQ ID NO 84, SEQ ID NO 85 or SEQ ID NO 86 and wherein the is DNase has at least 60%, at least 65%, at least 70%, at least 75%, at least 80%, at least 85%, at least 90%, at least 95%, at least 98% or 100% sequence identity to the amino acid sequence shown in SEQ ID NO 13.

One embodiment of the invention relates to the use of a cleaning composition comprising a DNase and protease for reduction of redeposition, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 79, SEQ ID NO 80, SEQ ID NO 81, SEQ ID NO 82, SEQ ID NO 83, SEQ ID NO 84, SEQ ID NO 85 or SEQ ID NO 86 and wherein the is DNase has at least 60%, at least 65%, at least 70%, at least 75%, at least 80%, at least 85%, at least 90%, at least 95%, at least 98% or 100% sequence identity to the amino acid sequence shown in SEQ ID NO 65.

One embodiment of the invention relates to the use of a cleaning composition comprising a DNase and protease for reduction of redeposition, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 79, SEQ ID NO 80, SEQ ID NO 81, SEQ ID NO 82, SEQ ID NO 83, SEQ ID NO 84, SEQ ID NO 85 or SEQ ID NO 86 and wherein the is DNase has at least 60%, at least 65%, at least 70%, at least 75%, at least 80%, at least 85%, at least 90%, at least 95%, at least 98% or 100% sequence identity to the amino acid sequence shown in SEQ ID NO 66.

One embodiment of the invention relates to the use of a cleaning composition comprising a DNase and protease for reduction of redeposition, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 79, SEQ ID NO 80, SEQ ID NO 81, SEQ ID NO 82, SEQ ID NO 83, SEQ ID NO 84, SEQ ID NO 85 or SEQ ID NO 86 and wherein the is DNase has at least 60%, at least 65%, at least 70%, at least 75%, at least 80%, at least 85%, at least 90%, at least 95%, at least 98% or 100% sequence identity to the amino acid sequence shown in SEQ ID NO 67.

One embodiment of the invention relates to the use of a cleaning composition comprising a DNase and protease for reduction of redeposition, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 79, SEQ ID NO 80, SEQ ID NO 81, SEQ ID NO 82, SEQ ID NO 83, SEQ ID NO 84, SEQ ID NO 85 or SEQ ID NO 86 and wherein the is DNase has at least 60%, at least 65%, at least 70%, at least 75%, at least 80%, at least 85%, at least 90%, at least 95%, at least 98% or 100% sequence identity to the amino acid sequence shown in SEQ ID NO 68.

The compositions of the invention comprise a blend of DNase and protease and effectively reduce or limit malodor of e.g. textiles or hard surfaces such as dishes.

One embodiment of the invention relates to the use of a composition comprising a DNase and protease for reduction of malodor. One embodiment of the invention relates to the use of a cleaning composition comprising a DNase and protease for reduction of malodor.

One embodiment of the invention relates to the use of a cleaning composition comprising a DNase and protease for reduction of malodor when the cleaning composition is applied in e.g. laundry process. One embodiment of the invention relates to the use of a cleaning composition comprising a DNase and protease for reduction of malodor on an item e.g. textile.

One embodiment of the invention relates to the use of a cleaning composition comprising a DNase and protease for reduction of malodor, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 79, SEQ ID NO 80, SEQ ID NO 81, SEQ ID NO 82, SEQ ID NO 83, SEQ ID NO 84, SEQ ID NO 85 or SEQ ID NO 86.

One embodiment of the invention relates to the use of a cleaning composition comprising a DNase and protease for reduction of malodor, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 79, SEQ ID NO 80, SEQ ID NO 81, SEQ ID NO 82, SEQ ID NO 83, SEQ ID NO 84, SEQ ID NO 85 or SEQ ID NO 86 and wherein the DNase is obtained from *Bacillus*, preferably *Bacillus cibi, Bacillus horikoshii, Bacillus licheniformis, Bacillus subtilis, Bacillus horneckiae, Bacillus idriensis, Bacillus algicola, Bacillus vietnamensis, Bacillus hwajinpoensis, Bacillus indicus, Bacillus marisflavi* or *Bacillus luciferensis*.

One embodiment of the invention relates to the use of a cleaning composition comprising a DNase and protease for reduction of malodor, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 79, SEQ ID NO 80, SEQ ID NO 81, SEQ ID NO 82, SEQ ID NO 83, SEQ ID NO 84, SEQ ID NO 85 or SEQ ID NO 86 and wherein the DNase is obtained from *Bacillus* and comprises one or both of the motif(s) [D/M/L][S/T]GYSR[D/N] (SEQ ID NO: 73) or ASXNRSKG (SEQ ID NO: 74).

One embodiment of the invention relates to the use of a cleaning composition comprising a DNase and protease for reduction of malodor, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 79, SEQ ID NO 80, SEQ ID NO 81, SEQ ID NO 82, SEQ ID NO 83, SEQ ID NO 84, SEQ ID NO 85 or SEQ ID NO 86 and wherein the is DNase has at least 60%, at least 65%, at least 70%, at least 75%, at least 80%, at least 85%, at least 90%, at least 95%, at least 98% or 100% sequence identity to the amino acid sequence shown in SEQ ID NO 13.

One embodiment of the invention relates to the use of a cleaning composition comprising a DNase and protease for reduction of malodor, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 79, SEQ ID NO 80, SEQ ID NO 81, SEQ ID NO 82, SEQ ID NO 83, SEQ ID NO 84, SEQ ID NO 85 or SEQ ID NO 86 and wherein the is DNase has at least 60%, at least 65%, at least 70%, at least 75%, at least 80%, at least 85%, at least 90%, at least 95%, at least 98% or 100% sequence identity to the amino acid sequence shown in SEQ ID NO 65.

One embodiment of the invention relates to the use of a cleaning composition comprising a DNase and protease for reduction of malodor, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 79, SEQ ID NO 80, SEQ ID NO 81, SEQ ID NO 82, SEQ ID NO 83, SEQ ID NO 84, SEQ ID NO 85 or SEQ ID NO 86 and wherein the is DNase has at least 60%, at least 65%, at least 70%, at least 75%, at least 80%, at least 85%, at least 90%, at least 95%, at least 98% or 100% sequence identity to the amino acid sequence shown in SEQ ID NO 66.

One embodiment of the invention relates to the use of a cleaning composition comprising a DNase and protease for reduction of malodor, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 79, SEQ ID NO 80, SEQ ID NO 81, SEQ ID NO 82, SEQ ID NO 83, SEQ ID NO 84, SEQ ID NO 85 or SEQ ID NO 86 and wherein the is DNase has at least 60%, at least 65%, at least 70%, at least 75%, at least 80%, at least 85%, at least 90%, at least 95%, at least 98% or 100% sequence identity to the amino acid sequence shown in SEQ ID NO 67.

One embodiment of the invention relates to the use of a cleaning composition comprising a DNase and protease for reduction of malodor, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 79, SEQ ID NO 80, SEQ ID NO 81, SEQ ID NO 82, SEQ ID NO 83, SEQ ID NO 84, SEQ ID NO 85 or SEQ ID NO 86 and wherein the is DNase has at least 60%, at least 65%, at least 70%, at least 75%, at least 80%, at least 85%, at least 90%, at least 95%, at least 98% or 100% sequence identity to the amino acid sequence shown in SEQ ID NO 68.

The compositions of the invention comprise a blend of DNase and protease and improve whiteness of textile. One embodiment of the invention relates to the use of a composition comprising a DNase and protease for improve whiteness of an item e.g. a textile. One embodiment of the invention relates to the use of a cleaning composition comprising a DNase and protease for improve whiteness.

One embodiment of the invention relates to the use of a cleaning composition comprising a DNase and protease improve whiteness when the cleaning composition is applied in e.g. laundry process. One embodiment of the invention relates to the use of a cleaning composition comprising a DNase and protease improve whiteness on an item e.g. textile.

One embodiment of the invention relates to the use of a cleaning composition comprising a DNase and protease for improve whiteness, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 79, SEQ ID NO 80, SEQ ID NO 81, SEQ ID NO 82, SEQ ID NO 83, SEQ ID NO 84, SEQ ID NO 85 or SEQ ID NO 86.

One embodiment of the invention relates to the use of a cleaning composition comprising a DNase and protease for improve whiteness, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 79, SEQ ID NO 80, SEQ ID NO 81, SEQ ID NO 82, SEQ ID NO 83, SEQ ID NO 84, SEQ ID NO 85 or SEQ ID NO 86 and wherein the DNase is obtained from *Bacillus*, preferably *Bacillus cibi, Bacillus horikoshii, Bacillus licheniformis, Bacillus subtilis, Bacillus horneckiae, Bacillus idriensis, Bacillus algicola, Bacillus vietnamensis, Bacillus hwajinpoensis, Bacillus indicus, Bacillus marisflavi* or *Bacillus luciferensis*.

One embodiment of the invention relates to the use of a cleaning composition comprising a DNase and protease for improve whiteness, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 79, SEQ ID NO 80, SEQ ID NO 81, SEQ ID NO 82, SEQ ID NO 83, SEQ ID NO 84, SEQ ID NO 85 or SEQ ID NO 86 and wherein the DNase is obtained from *Bacillus* and comprises one or both of the motif(s) [D/M/L][S/T]GYSR[D/N] (SEQ ID NO: 73) or ASXNRSKG (SEQ ID NO: 74).

One embodiment of the invention relates to the use of a cleaning composition comprising a DNase and protease for improve whiteness, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 79, SEQ ID NO 80, SEQ ID NO 81, SEQ ID NO 82, SEQ ID NO 83, SEQ ID NO 84, SEQ ID NO 85 or SEQ ID NO 86 and wherein the is DNase has at least 60%, at least 65%, at least 70%, at least 75%, at least 80%, at least 85%, at least 90%, at least 95%, at least 98% or 100% sequence identity to the amino acid sequence shown in SEQ ID NO 13.

One embodiment of the invention relates to the use of a cleaning composition comprising a DNase and protease for improve whiteness, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 79, SEQ ID NO 80, SEQ ID NO 81, SEQ ID NO 82, SEQ ID NO 83, SEQ ID NO 84, SEQ ID NO 85 or SEQ ID NO 86 and wherein the is DNase has at least 60%, at least 65%, at least 70%, at least 75%, at least 80%, at least 85%, at least 90%, at least 95%, at least 98% or 100% sequence identity to the amino acid sequence shown in SEQ ID NO 65.

One embodiment of the invention relates to the use of a cleaning composition comprising a DNase and protease for improve whiteness, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 79, SEQ ID NO 80, SEQ ID NO 81, SEQ ID NO 82, SEQ ID NO 83, SEQ ID NO 84, SEQ ID NO 85 or SEQ ID NO 86 and wherein the is DNase has at least 60%, at least 65%, at least 70%, at least 75%, at least 80%, at least 85%, at least 90%, at least 95%, at least 98% or 100% sequence identity to the amino acid sequence shown in SEQ ID NO 66.

One embodiment of the invention relates to the use of a cleaning composition comprising a DNase and protease for improve whiteness, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 79, SEQ ID NO 80, SEQ ID NO 81, SEQ ID NO 82, SEQ ID NO 83, SEQ ID NO 84, SEQ ID NO 85 or SEQ ID NO 86 and wherein the is DNase has at least 60%, at least 65%, at least 70%, at least 75%, at least 80%, at least 85%, at least 90%, at least 95%, at least 98% or 100% sequence identity to the amino acid sequence shown in SEQ ID NO 67.

One embodiment of the invention relates to the use of a cleaning composition comprising a DNase and protease for improve whiteness, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 79, SEQ ID NO 80, SEQ ID NO 81, SEQ ID NO 82, SEQ ID NO 83, SEQ ID NO 84, SEQ ID NO 85 or SEQ ID NO 86 and wherein the is DNase has at least 60%, at least 65%, at least 70%, at least 75%, at least 80%, at least 85%, at least 90%, at least 95%, at least 98% or 100% sequence identity to the amino acid sequence shown in SEQ ID NO 68.

The compositions of the invention comprise a blend of DNase and protease and effectively reduce or remove organic components, such as protein and DNA from surfaces such as textiles and hard surfaces e.g. dishes. One embodiment of the invention relates to the use of a cleaning composition comprising a DNase, a protease and at least one cleaning component for reduction or removal of biofilm and components of biofilm, such as DNA and protease, of an item, wherein the item is a textile or a hard surface.

One embodiment of the invention relates to the use of a cleaning composition comprising a DNase, a protease and at least one cleaning component for deep cleaning of an item, wherein the item is a textile or a surface.

One embodiment of the invention relates to the use of a composition comprising a DNase and protease for reduction or removal of biofilm compounds such as DNA and protease of an item. One embodiment of the invention relates to the use of a cleaning composition comprising a DNase and protease for reduction or removal of biofilm compounds such as DNA and protease of an item such as textile. One embodiment of the invention relates to the use of a cleaning composition comprising a DNase and protease for deep cleaning e.g. reduction or removal of biofilm compounds such as DNA and protease when the cleaning composition is applied in e.g. laundry process.

One embodiment of the invention relates to the use of a cleaning composition comprising a DNase and protease for deep clean of an item, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 79, SEQ ID NO 80, SEQ ID NO 81, SEQ ID NO 82, SEQ ID NO 83, SEQ ID NO 84, SEQ ID NO 85 or SEQ ID NO 86.

One embodiment of the invention relates to the use of a cleaning composition comprising a DNase and protease for deep clean of an item, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 79, SEQ ID NO 80, SEQ ID NO 81, SEQ ID NO 82, SEQ ID NO 83, SEQ ID NO 84, SEQ ID NO 85 or SEQ ID NO 86 and wherein the DNase is obtained from *Bacillus*, preferably *Bacillus cibi, Bacillus horikoshii, Bacillus licheniformis, Bacillus subtilis, Bacillus horneckiae, Bacillus idriensis, Bacillus algicola, Bacillus vietnamensis, Bacillus hwajinpoensis, Bacillus indicus, Bacillus marisflavi* or *Bacillus luciferensis*.

One embodiment of the invention relates to the use of a cleaning composition comprising a DNase and protease for deep clean of an item, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 79, SEQ ID NO 80, SEQ ID NO 81, SEQ ID NO 82, SEQ ID NO 83, SEQ ID NO 84, SEQ ID NO 85 or SEQ ID NO 86 and wherein the DNase is obtained from *Bacillus* and comprises one or both of the motif(s) [D/M/L][S/T]GYSR[D/N] (SEQ ID NO: 73) or ASXNRSKG (SEQ ID NO: 74).

One embodiment of the invention relates to the use of a cleaning composition comprising a DNase and protease for deep clean of an item, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 79, SEQ ID NO 80, SEQ ID NO 81, SEQ ID NO 82, SEQ ID NO 83, SEQ ID NO 84, SEQ ID NO 85 or SEQ ID NO 86 and wherein the is DNase has at least 60%, at least 65%, at least 70%, at least 75%, at least 80%, at least 85%, at least 90%, at least 95%, at least 98% or 100% sequence identity to the amino acid sequence shown in SEQ ID NO 13.

One embodiment of the invention relates to the use of a cleaning composition comprising a DNase and protease for deep clean of an item, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 79, SEQ ID NO 80, SEQ ID NO 81, SEQ ID NO 82, SEQ ID NO 83, SEQ ID NO 84, SEQ ID NO 85 or SEQ ID NO 86 and wherein the is DNase has at least 60%, at least 65%, at least 70%, at least 75%, at least 80%, at least 85%, at least 90%, at least 95%, at least 98% or 100% sequence identity to the amino acid sequence shown in SEQ ID NO 65.

One embodiment of the invention relates to the use of a cleaning composition comprising a DNase and protease for deep clean of an item, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 79, SEQ ID NO 80, SEQ ID NO 81, SEQ ID NO 82, SEQ ID NO 83, SEQ ID NO 84, SEQ ID NO 85 or SEQ ID NO 86 and wherein the is DNase has at least 60%, at least 65%, at least 70%, at least 75%, at least 80%, at least 85%, at least 90%, at least 95%, at least 98% or 100% sequence identity to the amino acid sequence shown in SEQ ID NO 66.

One embodiment of the invention relates to the use of a cleaning composition comprising a DNase and protease for deep clean of an item, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 79, SEQ ID NO 80, SEQ ID NO 81, SEQ ID NO 82, SEQ ID NO 83, SEQ ID NO 84, SEQ ID NO 85 or SEQ ID NO 86 and wherein the is DNase has at least 60%, at least 65%, at least 70%, at least 75%, at least 80%, at least 85%, at least 90%, at least 95%, at least 98% or 100% sequence identity to the amino acid sequence shown in SEQ ID NO 67.

One embodiment of the invention relates to the use of a cleaning composition comprising a DNase and protease for deep clean of an item, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO 79, SEQ ID NO 80, SEQ ID NO 81, SEQ ID NO 82, SEQ ID NO 83, SEQ ID NO 84, SEQ ID NO 85 or SEQ ID NO 86 and wherein the is DNase has at least 60%, at least 65%, at least 70%, at least 75%, at least 80%, at least 85%, at least 90%, at least 95%, at least 98% or 100% sequence identity to the amino acid sequence shown in SEQ ID NO 68.

The invention further relates to a method of deep cleaning of an item, wherein the item may be textile or hard surface preferably is a textile, One embodiment of the invention relates to a method of deep cleaning on an item, comprising the steps of:
 a) contacting the item with a cleaning composition according to the invention; and
 b) and optionally rinsing the item, wherein the item is preferably a textile.

One embodiment of the invention relates to a method of deep cleaning on an item, comprising the steps of:
 a) contacting the item with a solution comprising an enzyme mixture comprising a DNase and a protease; and a cleaning component, wherein the cleaning component is selected from 0.1 to 15 wt % of at least one a surfactant; 0.5 to 20 wt % of at least one builder; and 0.01 to 10 wt % of at least one bleach component; and
 b) and optionally rinsing the item, wherein the item is preferably a textile.

One embodiment of the invention relates to a method of deep cleaning on an item, comprising the steps of:
 a) contacting the item with a solution comprising an enzyme mixture comprising a DNase and a protease; and a cleaning component, wherein the cleaning component is selected from 0.1 to 50 wt % of at least one a surfactant; 0.5 to 30 wt % of at least one builder; and 0.01 to 20 wt % of at least one bleach component; and
 b) and optionally rinsing the item, wherein the item is preferably a textile, wherein the protease has at least 60%, at least 65%, at least 70%, at least 75%, at least 80%, at least 85%, at least 90%, at least 95% or at least 98% sequence identity to the amino acid sequence shown in SEQ ID NO 79, SEQ ID NO 80, SEQ ID NO 81, SEQ ID NO 82, SEQ ID NO 83, SEQ ID NO 84, SEQ ID NO 85 or SEQ ID NO 86.

One embodiment of the invention relates to a method of deep cleaning on an item, comprising the steps of:
 a) contacting the item with a solution comprising an enzyme mixture comprising a DNase and a protease; and a cleaning component, wherein the cleaning component is selected from 0.1 to 50 wt % of at least one a surfactant; 0.5 to 30 wt % of at least one builder; and 0.01 to 20 wt % of at least one bleach component; and
 b) and optionally rinsing the item, wherein the item is preferably a textile,
wherein the protease has at least 60%, at least 65%, at least 70%, at least 75%, at least 80%, at least 85%, at least 90%, at least 95% or at least 98% sequence identity to the amino acid sequence shown in SEQ ID NO 79, SEQ ID NO 80, SEQ ID NO 81, SEQ ID NO 82, SEQ ID NO 83, SEQ ID NO 84, SEQ ID NO 85 or SEQ ID NO 86 and wherein the is DNase has at least 60%, at least 65%, at least 70%, at least 75%, at least 80%, at least 85%, at least 90%, at least 95%, at least 98% or 100% sequence identity to the amino acid sequence shown in SEQ ID NO 13.

One embodiment of the invention relates to a method of deep cleaning on an item, comprising the steps of:
 a) contacting the item with a solution comprising an enzyme mixture comprising a DNase and a protease; and a cleaning component, wherein the cleaning component is selected from 0.1 to 50 wt % of at least one a surfactant; 0.5 to 30 wt % of at least one builder; and 0.01 to 20 wt % of at least one bleach component; and
 b) and optionally rinsing the item, wherein the item is preferably a textile,
wherein the protease has at least 60%, at least 65%, at least 70%, at least 75%, at least 80%, at least 85%, at least 90%, at least 95% or at least 98% sequence identity to the amino acid sequence shown in SEQ ID NO 79, SEQ ID NO 80, SEQ ID NO 81, SEQ ID NO 82, SEQ ID NO 83, SEQ ID NO 84, SEQ ID NO 85 or SEQ ID NO 86 and wherein the is DNase has at least 60%, at least 65%, at least 70%, at least 75%, at least 80%, at least 85%, at least 90%, at least 95%, at least 98% or 100% sequence identity to the amino acid sequence shown in SEQ ID NO 65.

One embodiment of the invention relates to a method of deep cleaning on an item, comprising the steps of:
 a) contacting the item with a solution comprising an enzyme mixture comprising a DNase and a protease; and a cleaning component, wherein the cleaning component is selected from 0.1 to 50 wt % of at least one a surfactant; 0.5 to 30 wt % of at least one builder; and 0.01 to 20 wt % of at least one bleach component; and
 b) and optionally rinsing the item, wherein the item is preferably a textile,
wherein the protease has at least 60%, at least 65%, at least 70%, at least 75%, at least 80%, at least 85%, at least 90%, at least 95% or at least 98% sequence identity to the amino acid sequence shown in SEQ ID NO 79, SEQ ID NO 80, SEQ ID NO 81, SEQ ID NO 82, SEQ ID NO 83, SEQ ID NO 84, SEQ ID NO 85 or SEQ ID NO 86 and wherein the is DNase has at least 60%, at least 65%, at least 70%, at least 75%, at least 80%, at least 85%, at least 90%, at least 95%, at least 98% or 100% sequence identity to the amino acid sequence shown in SEQ ID NO 66.

One embodiment of the invention relates to a method of deep cleaning on an item, comprising the steps of:
 a) contacting the item with a solution comprising an enzyme mixture comprising a DNase and a protease; and a cleaning component, wherein the cleaning component is selected from 0.1 to 50 wt % of at least one a surfactant; 0.5 to 30 wt % of at least one builder; and 0.01 to 20 wt % of at least one bleach component; and b) and optionally rinsing the item, wherein the item is preferably a textile,
wherein the protease has at least 60%, at least 65%, at least 70%, at least 75%, at least 80%, at least 85%, at least 90%, at least 95% or at least 98% sequence identity to the amino acid sequence shown in SEQ ID NO 79, SEQ ID NO 80, SEQ ID NO 81, SEQ ID NO 82, SEQ ID NO 83, SEQ ID NO 84, SEQ ID NO 85 or SEQ ID NO 86 and wherein the is DNase has at least 60%, at least 65%, at least 70%, at least 75%, at least 80%, at least 85%, at least 90%, at least 95%, at least 98% or 100% sequence identity to the amino acid sequence shown in SEQ ID NO 67.

One embodiment of the invention relates to a method of deep cleaning on an item, comprising the steps of:
a) contacting the item with a solution comprising an enzyme mixture comprising a DNase and a protease; and a cleaning component, wherein the cleaning component is selected from 0.1 to 50 wt % of at least one a surfactant; 0.5 to 30 wt % of at least one builder; and 0.01 to 20 wt % of at least one bleach component; and
b) and optionally rinsing the item, wherein the item is preferably a textile, wherein the protease has at least 60%, at least 65%, at least 70%, at least 75%, at least 80%, at least 85%, at least 90%, at least 95% or at least 98% sequence identity to the amino acid sequence shown in SEQ ID NO 79, SEQ ID NO 80, SEQ ID NO 81, SEQ ID NO 82, SEQ ID NO 83, SEQ ID NO 84, SEQ ID NO 85 or SEQ ID NO 86 and wherein the is DNase has at least 60%, at least 65%, at least 70%, at least 75%, at least 80%, at least 85%, at least 90%, at least 95%, at least 98% or 100% sequence identity to the amino acid sequence shown in SEQ ID NO 68.

Definitions

Biofilm is produced by any group of microorganisms in which cells stick to each other or stick to a surface, such as a textile, dishware or hard surface or another kind of surface. These adherent cells are frequently embedded within a self-produced matrix of extracellular polymeric substance (EPS). Biofilm EPS is a polymeric conglomeration generally composed of extracellular DNA, proteins, and polysaccharides. Biofilms may form on living or non-living surfaces. The microbial cells growing in a biofilm are physiologically distinct from planktonic cells of the same organism, which, by contrast, are single-cells that may float or swim in a liquid medium.

Bacteria living in a biofilm usually have significantly different properties from planktonic bacteria of the same species, as the dense and protected environment of the film allows them to cooperate and interact in various ways. One benefit of this environment for the microorganisms is increased resistance to detergents and antibiotics, as the dense extracellular matrix and the outer layer of cells protect the interior of the community.

On laundry biofilm producing bacteria can be found among the following species: *Acinetobacter* sp., *Aeromicrobium* sp., *Brevundimonas* sp., *Microbacterium* sp., *Micrococcus luteus*, *Pseudomonas* sp., *Staphylococcus epidermidis*, and *Stenotrophomonas* sp. On hard surfaces biofilm producing bacteria can be found among the following species: *Acinetobacter* sp., *Aeromicrobium* sp., *Brevundimonas* sp., *Microbacterium* sp., *Micrococcus luteus*, *Pseudomonas* sp., *Staphylococcus epidermidis*, *Staphylococcus aureus* and *Stenotrophomonas* sp. In one aspect, the biofilm producing strain is *Brevundimonas* sp. In one aspect, the biofilm producing strain is *Pseudomonas alcaliphila* or *Pseudomonas fluorescens*. In one aspect, the biofilm producing strain is *Staphylococcus aureus*.

By the term "deep cleaning" is meant reduction, disruption or removal of components which may be comprised in organic matter, e.g. biofilm, such as polysaccharides, proteins, DNA, soil or other components present in the organic matter.

Cleaning component: The cleaning component e.g. the detergent adjunct ingredient is different to the DNase and protease enzymes. The precise nature of these additional cleaning components e.g. adjunct components, and levels of incorporation thereof, will depend on the physical form of the composition and the nature of the operation for which it is to be used. Suitable cleaning components e.g. adjunct materials include, but are not limited to the components described below such as surfactants, builders, flocculating aid, chelating agents, dye transfer inhibitors, enzymes, enzyme stabilizers, enzyme inhibitors, catalytic materials, bleach activators, hydrogen peroxide, sources of hydrogen peroxide, preformed peracids, polymeric agents, clay soil removal/anti-redeposition agents, brighteners, suds suppressors, dyes, perfumes, structure elasticizing agents, fabric softeners, carriers, hydrotropes, builders and co-builders, fabric huing agents, anti-foaming agents, dispersants, processing aids, and/or pigments.

Cleaning composition: The term "cleaning composition" refers to compositions that find use in the removal of undesired compounds from items to be cleaned, such as textiles. The cleaning composition may be used to e.g. clean textiles for both household cleaning and industrial cleaning. The terms encompass any materials/compounds selected for the particular type of cleaning composition desired and the form of the product (e.g., liquid, gel, powder, granulate, paste, or spray compositions) and includes, but is not limited to, detergent compositions (e.g., liquid and/or solid laundry detergents and fine fabric detergents; fabric fresheners; fabric softeners; and textile and laundry pre-spotters/pre-treatment). In addition to containing the enzymes, the cleaning composition may contain one or more additional enzymes (such as amylases, lipases, cutinases, cellulases, endoglucanases, xyloglucanases, pectinases, pectin lyases, xanthanases, peroxidases, haloperoxygenases, catalases and mannanases, or any mixture thereof), and/or cleaning components e.g. detergent adjunct ingredients such as surfactants, builders, chelators or chelating agents, bleach system or bleach components, polymers, fabric conditioners, foam boosters, suds suppressors, dyes, perfume, tannish inhibitors, optical brighteners, bactericides, fungicides, soil suspending agents, anti-corrosion agents, enzyme inhibitors or stabilizers, enzyme activators, transferase(s), hydrolytic enzymes, oxido reductases, bluing agents and fluorescent dyes, antioxidants, and solubilizers.

The term "enzyme detergency benefit" is defined herein as the advantageous effect an enzyme may add to a detergent compared to the same detergent without the enzyme. Important detergency benefits which can be provided by enzymes are stain removal with no or very little visible soils after washing and/or cleaning, prevention or reduction of redeposition of soils released in the washing process (an effect that also is termed anti-redeposition), restoring fully or partly the whiteness of textiles which originally were white but after repeated use and wash have obtained a greyish or yellowish appearance (an effect that also is termed whitening). Textile care benefits, which are not directly related to catalytic stain removal or prevention of redeposition of soils, are also important for enzyme detergency benefits.

Examples of such textile care benefits are prevention or reduction of dye transfer from one fabric to another fabric or another part of the same fabric (an effect that is also termed dye transfer inhibition or anti-backstaining), removal of protruding or broken fibers from a fabric surface to decrease pilling tendencies or remove already existing pills or fuzz (an effect that also is termed anti-pilling), improvement of the fabric-softness, colour clarification of the fabric and removal of particulate soils which are trapped in the fibers of the fabric or garment. Enzymatic bleaching is a further enzyme detergency benefit where the catalytic activity generally is used to catalyze the formation of bleaching components such as hydrogen peroxide or other peroxides. Textile care benefits, which are not directly related to catalytic stain removal or prevention of redeposition of soils, are also important for enzyme detergency benefits. Examples of such textile care benefits are prevention or reduction of dye transfer from one textile to another textile or another part of the same textile (an effect that is also termed dye transfer inhibition or anti-backstaining), removal of protruding or broken fibers from a textile surface to decrease pilling tendencies or remove already existing pills or fuzz (an effect that also is termed anti-pilling), improvement of the textile-softness, colour clarification of the textile and removal of particulate soils which are trapped in the fibers of the textile. Enzymatic bleaching is a further enzyme detergency benefit where the catalytic activity generally is used to catalyze the formation of bleaching component such as hydrogen peroxide or other peroxides or other bleaching species."

The term "hard surface cleaning" is defined herein as cleaning of hard surfaces wherein hard surfaces may include floors, tables, walls, roofs etc. as well as surfaces of hard objects such as cars (car wash) and dishes (dish wash). Dish washing includes but are not limited to cleaning of plates, cups, glasses, bowls, cutlery such as spoons, knives, forks, serving utensils, ceramics, plastics, metals, china, glass and acrylics.

The term "wash performance" is used as an enzyme's ability to remove stains present on the object to be cleaned during e.g. wash or hard surface cleaning.

The term "whiteness" is defined herein as a greying, yellowing of a textile. Loss of whiteness may be due to removal of optical brighteners/hueing agents. Greying and yellowing can be due to soil redeposition, body soils, colouring from e.g. iron and copper ions or dye transfer. Whiteness might include one or several issues from the list below: colourant or dye effects; incomplete stain removal (e.g. body soils, sebum etc.); redeposition (greying, yellowing or other discolourations of the object) (removed soils reassociate with other parts of textile, soiled or unsoiled); chemical changes in textile during application; and clarification or brightening of colours.

The term "laundering" relates to both household laundering and industrial laundering and means the process of treating textiles with a solution containing a cleaning or detergent composition of the present invention. The laundering process can for example be carried out using e.g. a household or an industrial washing machine or can be carried out by hand.

By the term "malodor" is meant an odor which is not desired on clean items. The cleaned item should smell fresh and clean without malodors adhered to the item. One example of malodor is compounds with an unpleasant smell, which may be produced by microorganisms. Another example is unpleasant smells can be sweat or body odor adhered to an item which has been in contact with human or animal. Another example of malodor can be the odor from spices, which sticks to items for example curry or other exotic spices which smells strongly.

The term "mature polypeptide" means a polypeptide in its final form following translation and any post-translational modifications, such as N-terminal processing, C-terminal truncation, glycosylation, phosphorylation, etc.

The term "textile" means any textile material including yarns, yarn intermediates, fibers, non-woven materials, natural materials, synthetic materials, and any other textile material, fabrics made of these materials and products made from fabrics (e.g., garments and other articles). The textile or fabric may be in the form of knits, wovens, denims, non-wovens, felts, yarns, and towelling. The textile may be cellulose based such as natural cellulosics, including cotton, flax/linen, jute, ramie, sisal or coir or manmade cellulosics (e.g. originating from wood pulp) including viscose/rayon, cellulose acetate fibers (tricell), lyocell or blends thereof. The textile or fabric may also be non-cellulose based such as natural polyamides including wool, camel, cashmere, mohair, rabbit and silk or synthetic polymers such as nylon, aramid, polyester, acrylic, polypropylene and spandex/elastane, or blends thereof as well as blends of cellulose based and non-cellulose based fibers. Examples of blends are blends of cotton and/or rayon/viscose with one or more companion material such as wool, synthetic fiber (e.g. polyamide fiber, acrylic fiber, polyester fiber, polyvinyl chloride fiber, polyurethane fiber, polyurea fiber, aramid fiber), and/or cellulose-containing fiber (e.g. rayon/viscose, ramie, flax/linen, jute, cellulose acetate fiber, lyocell). Fabric may be conventional washable laundry, for example stained household laundry. When the term fabric or garment is used, it is intended to include the broader term textiles as well.

The term "variant" means a polypeptide having the activity of the parent or precursor polypeptide and comprising an alteration, i.e., a substitution, insertion, and/or deletion, at one or more (e.g., several) positions compared to the precursor or parent polypeptide. A substitution means replacement of the amino acid occupying a position with a different amino acid; a deletion means removal of the amino acid occupying a position; and an insertion means adding an amino acid adjacent to and immediately following the amino acid occupying a position.

Sequence identity: The relatedness between two amino acid sequences or between two nucleotide sequences is described by the parameter "sequence identity". For purposes of the present invention, the sequence identity between two amino acid sequences is determined using the Needleman-Wunsch algorithm (Needleman and Wunsch, 1970, J. Mol. Biol. 48: 443-453) as implemented in the Needle program of the EMBOSS package (EMBOSS: The European Molecular Biology Open Software Suite, Rice et al., 2000, Trends Genet. 16: 276-277), preferably version 6.6.0 or later. The parameters used are a gap open penalty of 10, a gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

$$(\text{Identical Residues} \times 100)/(\text{Length of Alignment} - \text{Total Number of Gaps in Alignment})$$

The invention may further relate to any of the following embodiments;

Paragraph 1. A cleaning composition comprising at least 0.001 ppm DNase, at least 0.001 ppm protease and a cleaning component, wherein the cleaning component is selected from
- a. 0.1 to 15 wt % of at least one a surfactant;
- b. 0.5 to 20 wt % of at least one builder; and
- c. 0.01 to 10 wt % of at least one bleach component.

Paragraph 2. The cleaning composition according to paragraph 1, wherein the DNase comprises one or both of the motif(s) [D/M/L][S/T]GYSR[D/N] (SEQ ID NO: 73) or ASXNRSKG (SEQ ID NO: 74).

Paragraph 3. The cleaning composition according to paragraphs 1 or 2, wherein the DNase is selected from the group of polypeptides:
- a) a polypeptide having at least 80% sequence identity to the polypeptide shown in SEQ ID NO: 1,
- b) a polypeptide having at least 80% sequence identity to the polypeptide shown in SEQ ID NO: 2,
- c) a polypeptide having at least 80% sequence identity to the polypeptide shown in SEQ ID NO: 3,
- d) a polypeptide having at least 80% sequence identity to the polypeptide shown in SEQ ID NO: 4,
- e) a polypeptide having at least 80% sequence identity to the polypeptide shown in SEQ ID NO: 5,
- f) a polypeptide having at least 80% sequence identity to the polypeptide shown in SEQ ID NO: 6,
- g) a polypeptide having at least 80% sequence identity to the polypeptide shown in SEQ ID NO: 7,
- h) a polypeptide having at least 80% sequence identity to the polypeptide shown in SEQ ID NO: 8,
- i) a polypeptide having at least 80% sequence identity to the polypeptide shown in SEQ ID NO: 9,
- j) a polypeptide having at least 80% sequence identity to the polypeptide shown in SEQ ID NO: 10,
- k) a polypeptide having at least 80% sequence identity to the polypeptide shown in SEQ ID NO: 11,
- l) a polypeptide having at least 80% sequence identity to the polypeptide shown in SEQ ID NO: 12,
- m) a polypeptide having at least 80% sequence identity to the polypeptide shown in SEQ ID NO: 13,
- n) a polypeptide having at least 80% sequence identity to the polypeptide shown in SEQ ID NO: 14,
- o) a polypeptide having at least 80% sequence identity to the polypeptide shown in SEQ ID NO: 15,
- p) a polypeptide having at least 80% sequence identity to the polypeptide shown in SEQ ID NO: 16,
- q) a polypeptide having at least 80% sequence identity to the polypeptide shown in SEQ ID NO: 17,
- r) a polypeptide having at least 80% sequence identity to the polypeptide shown in SEQ ID NO: 18,
- s) a polypeptide having at least 80% sequence identity to the polypeptide shown in SEQ ID NO: 19,
- t) a polypeptide having at least 80% sequence identity to the polypeptide shown in SEQ ID NO: 20,
- u) a polypeptide having at least 80% sequence identity to the polypeptide shown in SEQ ID NO: 21,
- v) a polypeptide having at least 80% sequence identity to the polypeptide shown in SEQ ID NO: 22,
- w) a polypeptide having at least 80% sequence identity to the polypeptide shown in SEQ ID NO: 23,
- x) a polypeptide having at least 80% sequence identity to the polypeptide shown in SEQ ID NO: 24, and
- y) a polypeptide having at least 80% sequence identity to the polypeptide shown in SEQ ID NO: 25.

Paragraph 4. The cleaning composition according to paragraph 1, wherein the DNase comprises one or both of the motif(s) [V/I]PL[S/A]NAWK (SEQ ID NO: 75) or NPQL (SEQ ID NO: 76).

Paragraph 5. The cleaning composition according to paragraph 1 or 4, wherein the DNase is selected from the group of polypeptides:
- a) a polypeptide having at least 80% sequence identity to the polypeptide shown in SEQ ID NO: 26,
- b) a polypeptide having at least 80% sequence identity to the polypeptide shown in SEQ ID NO: 27,
- c) a polypeptide having at least 80% sequence identity to the polypeptide shown in SEQ ID NO: 28,
- d) a polypeptide having at least 80% sequence identity to the polypeptide shown in SEQ ID NO: 29,
- e) a polypeptide having at least 80% sequence identity to the polypeptide shown in SEQ ID NO: 30,
- f) a polypeptide having at least 80% sequence identity to the polypeptide shown in SEQ ID NO: 31,
- g) a polypeptide having at least 80% sequence identity to the polypeptide shown in SEQ ID NO: 32,
- h) a polypeptide having at least 80% sequence identity to the polypeptide shown in SEQ ID NO: 33,
- i) a polypeptide having at least 80% sequence identity to the polypeptide shown in SEQ ID NO: 34,
- j) a polypeptide having at least 80% sequence identity to the polypeptide shown in SEQ ID NO: 35,
- k) a polypeptide having at least 80% sequence identity to the polypeptide shown in SEQ ID NO: 36,
- l) a polypeptide having at least 80% sequence identity to the polypeptide shown in SEQ ID NO: 37, and
- m) a polypeptide having at least 80% sequence identity to the polypeptide shown in SEQ ID NO: 38.

Paragraph 6. The cleaning composition according to paragraph 1 wherein the DNase comprises one or both of the motif(s) P[Q/E]L[W/Y] (SEQ ID NO: 77) or [K/H/E]NAW (SEQ ID NO: 78).

Paragraph 7. The cleaning composition according to paragraphs 1 or 6, wherein the DNase is selected from the group of polypeptides:
- a) a polypeptide having at least 80% sequence identity to the polypeptide shown in SEQ ID NO: 39,
- b) a polypeptide having at least 80% sequence identity to the polypeptide shown in SEQ ID NO: 40,
- c) a polypeptide having at least 80% sequence identity to the polypeptide shown in SEQ ID NO: 41,
- d) a polypeptide having at least 80% sequence identity to the polypeptide shown in SEQ ID NO: 42,
- e) a polypeptide having at least 80% sequence identity to the polypeptide shown in SEQ ID NO: 43
- f) a polypeptide having at least 80% sequence identity to the polypeptide shown in SEQ ID NO: 44,
- g) a polypeptide having at least 80% sequence identity to the polypeptide shown in SEQ ID NO: 45,
- h) a polypeptide having at least 80% sequence identity to the polypeptide shown in SEQ ID NO: 46,
- i) a polypeptide having at least 80% sequence identity to the polypeptide shown in SEQ ID NO: 47,
- j) a polypeptide having at least 80% sequence identity to the polypeptide shown in SEQ ID NO: 48,
- k) a polypeptide having at least 80% sequence identity to the polypeptide shown in SEQ ID NO: 49,
- l) a polypeptide having at least 80% sequence identity to the polypeptide shown in SEQ ID NO: 50, and
- m) a polypeptide having at least 80% sequence identity to the polypeptide shown in SEQ ID NO: 51.

Paragraph 8. The cleaning composition according to paragraph 1, wherein the DNase is selected from the group consisting of:
a) a polypeptide obtainable from *Bacillus licheniformis* having a sequence identity to the polypeptide shown in SEQ ID NO: 65 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity,
b) a polypeptide obtainable from *Bacillus subtilis* having a sequence identity to the polypeptide shown in SEQ ID NO: 66 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity,
c) a polypeptide obtainable from *Aspergillus oryzae* having a sequence identity to the polypeptide shown in SEQ ID NO: 67 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity,
d) a polypeptide obtainable from *Trichoderma harzianum* having a sequence identity to the polypeptide shown in SEQ ID NO: 68 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity,
and combinations thereof.

Paragraph 9. The cleaning component of any of paragraphs 1 to 8 wherein the protease is selected from,
i) a protease variant of a protease parent, wherein the protease variant comprises one or more alteration(s) compared to a protease shown in SEQ ID NO 79 or SEQ ID NO 80 in one or more of the following positions: 3, 4, 9, 15, 24, 27, 42, 55, 59, 60, 66, 74, 85, 96, 97, 98, 99, 100, 101, 102, 104, 116, 118, 121, 126, 127, 128, 154, 156, 157, 158, 161, 164, 176, 179, 182, 185, 188, 189, 193, 198, 199, 200, 203, 206, 211, 212, 216, 218, 226, 229, 230, 239, 246, 255, 256, 268 and 269, wherein the positions correspond to the positions of the protease shown in SEQ ID NO 79 and wherein the protease variant has at least 80% sequence identity to SEQ ID NO 79, SEQ ID NO 80 or SEQ ID NO 81;
ii) a protease variant of a protease parent, wherein the protease variant comprises one or more mutation selected from the group consisting of S3T, V4I, S9R, S9E, A15T, S24G, S24R, K27R, N42R, S55P, G59E, G59D, N60D, N60E, V66A, N74D, N85S, N85R, G96S, G96A, S97G, S97D, S97A, S97SD, S99E, S99D, S99G, S99M, S99N, S99R, S99H, S101A, V102I, V102Y, V102N, S104A, G116V, G116R, H118D, H118N, N120S, S126L, P127Q, S128A, S154D, A156E, G157D, G157P, S158E, Y161A, R164S, Q176E, N179E, S182E, Q185N, A188P, G189E, V193M, N198D, V199I, Y203W, 5206G, L211Q, L211D, N212D, N212S, M216S, A226V, K229L, Q230H, Q239R, N246K, N255W, N255D, N255E, L256E, L256D T268A and R269H, wherein the positions correspond to the positions of the protease shown in SEQ ID NO 79, wherein the protease variant has at least 80% sequence identity to SEQ ID NO 79, SEQ ID NO 80 or SEQ ID NO 81;
iii) a protease comprising a substitution at one or more positions corresponding to positions 171, 173, 175, 179, or 180 of SEQ ID NO: 81, compared to the protease shown in SEQ ID NO 81, wherein the protease variant has a sequence identity of at least 75% but less than 100% to amino acid 1 to 311 of SEQ ID NO 81,
iv) a protease comprising the amino acid sequence shown in SEQ ID NO 79, 80, 81, 82 or a protease having at least 80% sequence identity to; the polypeptide comprising amino acids 1-269 of SEQ ID NO 79, the polypeptide comprising amino acids 1-311 of SEQ ID NO 81 the polypeptide comprising amino acids 1-275 of SEQ ID NO 80 or the polypeptide comprising amino acids 1-269 of SEQ ID NO 82;
v) one or more of the following protease variants selected from the group:
SEQ ID NO 79+T22R+S99G+S101A+V102I+A226V+Q239R;
SEQ ID NO 80+S24G+S53G+S78N+S101N+G128A+Y217Q;
SEQ ID NO 80+S24G+S53G+S78N+S101N+G128S+Y217Q;
SEQ ID NO 79+S9E+N42R+N74D+V199I+Q200L+Y203W+S253D+N255W+L256E;
SEQ ID NO 79+S9E+N42R+N74D+H118V+Q176E+A188P+V199I+Q200L+Y203W+S250D+S253D+N255W+L256E;
SEQ ID NO 79+S9E+N42R+N74D+Q176E+A188P+V199I+Q200L+Y203W 5250D+5253D+N255W+L256E;
SEQ ID NO 79+S3V+N74D+H118V+Q176E+N179E+S182E+V199I+Q200L Y203W+5210V+5250D+5253D+N255W+L256E;
SEQ ID NO 79+T22A+N60D+S99G+S101A+V102I+N114L+G157D+S182D+T207A+A226V+Q239R+N242D+E265F;
SEQ ID NO 79+S9E+N42R+N74D+H118V+Q176E+A188P+V199I+Q200L+Y203W+S250D+S253D+N255W+L256E,
SEQ ID NO 79+S9E+N42R+N74D+Q176E+A188P+V199I+Q200L+Y203W+S250D+S253D+N255W+L256E,
SEQ ID NO 79+S9E+N42R+N74D+H118V+Q176E+A188P+V199I+Q200L+Y203W+S250D+N255W+L256E+*269aH+*269bH,
SEQ ID NO 79+S3V+N74D+H118V+Q176E+N179E+S182E+V199I+Q200L+Y203W+S210V+S250D+N255W+L256E,
SEQ ID NO 79+S9E+N74D+G113W+G157P+Q176E+V199I+Q200L+Y203W+S250D+T254E+N255W+L256E,
SEQ ID NO 79+S3V+S9R+N74D+H118V+Q176E+N179E+S182E+V199I+Q200L+Y203W+S212V+S250D+N255W+L256E,
SEQ ID NO 79+S99E, and
SEQ ID NO 80+L217D.

Paragraph 10. The use of a composition according to any of the previous paragraphs for deep cleaning of an item, wherein the item is a textile or a surface.

Paragraph 11. A method of formulating a cleaning composition comprising adding a DNase, a protease and at least one cleaning component.

Paragraph 12. A kit intended for deep cleaning, wherein the kit comprises a solution of an enzyme mixture comprising a DNase and a protease.

Paragraph 13. A method of deep cleaning on an item, comprising the steps of:
a) contacting the item with a solution comprising an enzyme mixture comprising a DNase and a protease; and a cleaning component, wherein the cleaning component is selected from 0.1 to 15 wt % of at least one a surfactant; 0.5 to 20 wt % of at least one builder; and 0.01 to 10 wt % of at least one bleach component; and
b) and optionally rinsing the item, wherein the item is preferably a textile.

EXAMPLES

Assays
Assay I: Testing of DNase Activity

DNase activity was determined on DNase Test Agar with Methyl Green (BD, Franklin Lakes, N.J., USA), which was prepared according to the manual from supplier. Briefly, 21 g of agar was dissolved in 500 ml water and then autoclaved for 15 min at 121° C. Autoclaved agar was temperated to 48° C. in water bath, and 20 ml of agar was poured into petridishes with and allowed to solidify by incubation o/n at room temperature. On solidified agar plates, 5 µl of enzyme solutions are added and DNase activity is observed as colorless zones around the spotted enzyme solutions Assay II: Testing of Protease Activity Proteolytic activity can be determined by a method employing Suc-AAPF-PNA as the substrate. Suc-AAPF-PNA is an abbreviation for N-Succinyl-Alanine-Alanine-Proline-Phenylalanine-p-Nitroanilide, and is a blocked peptide which can be cleaved by endo-proteases. Following cleavage a free PNA molecule is liberated, which has a yellow color and thus can be measured by visible spectrophotometry at wavelength 405 nm. The Suc-AAPF-PNA substrate is manufactured by Bachem (cat. no. L1400, dissolved in DMSO). The protease sample to be analyzed is diluted in residual activity buffer (100 mM Tris pH 8.6). The assay is performed by transferring 3, 0 µl of diluted enzyme samples to 96 well microtiter plate and adding 70 µl substrate working solution (0.72 mg/ml in 100 mM Tris pH8.6). The solution was mixed at room temperature and absorption is measured every 20 seconds over 5 minutes at OD 405 nm. The slope (absorbance per minute) of the time dependent absorption-curve is directly proportional to the activity of the protease in question under the given set of conditions. The protease sample is diluted to a level where the slope is linear.

Assay III: Testing of DNase Activity

DNase activity was determined by using the DNaseAlert™ Kit (11-02-01-04, IDT Intergrated DNA Technologies) according to the supplier's manual. Briefly, 95 µl DNase sample was mixed with 5 µl substrate in a microtiter plate, and fluorescence was immediately measured using a Clariostar microtiter reader from BMG Labtech (536 nm excitation, 556 nm emission).

Example 1

Preparation of Swatches with Biofilm

Swatches with biofilm of *Brevundimonas* sp. was included in the present study. Bacteria was pre-grown on Tryptone Soya Agar (TSA) (pH 7.3) (CM0131; Oxoid Ltd, Basingstoke, UK) for 2-5 days at 30° C. From a single colony, a loop-full was transferred to 10 mL of TSB and incubated for 1 day at 30° C. with shaking (240 rpm). After propagation, cells were pelleted by centrifugation (Sigma Laboratory Centrifuge 6K15) (3000 g at 21° C. in 7 min) and resuspended in 10 mL of TSB diluted twice with water. Optical density (OD) at 600 nm was measured using a spectophometer (POLARstar Omega (BMG Labtech, Ortenberg, Germany). Fresh TSB diluted twice with water was inoculated to an OD600 nm of 0.03, and 50 mL was added into a petridish (diameter 125 mm), in which a swatch (80 mm×120 mm) of sterile cotton (WFK10A). After incubation (48 h at 15° C. with shaking (100 rpm), swatches were rinsed twice with 0.9% (w/v) NaCl and dried in LAF bench for 60 min. Swatches were stored at 4° C. prior to wash.

Wash Experiment

Wash experiment was performed using the Automatic Mechanical Stress Assay (AMSA). With AMSA, the wash performance of many small volume enzyme-detergent solutions can be examined at the same time. The AMSA plate has many slots for test solutions, and a lid that firmly squeezes the textile to be washed against the slot openings. During the wash, the plate, test solutions, textile and lid are vigorously shaken to bring the test solution in contact with the textile and apply mechanical stress in a regular, periodic, oscillating manner.

The wash experiment was conducted under the experimental conditions specified below:

| | |
|---|---|
| Detergent dosage | 3.3 g/L (liquid detergent) |
| Test solution volume | 160 micro L |
| pH | pH 8 |
| Wash time | 20 minutes |
| Temperature | 30° C. |
| Water hardness | 15° dH |
| Soil | Wfk09V 0.7 g/L |

Model detergents and test materials were as follows:

| | |
|---|---|
| Laundry liquid model detergent | Model detergent A |
| Test material | *Brevundimonas* sp. 2-day biofilm grown on WFK10 (cotton) or WFK30A (polyester) |

For wash experiments, Model detergent A (containing 12% LAS, 11% AEO Biosoft N25-7 (NI), 7% AEOS (SLES), 6% MPG, 3% ethanol, 3% TEA, 2.75% cocoa soap, 2.75% soya soap, 2% glycerol, 2% sodium hydroxide, 2% sodium citrate, 1% sodium formiate, 0.2% DTMPA and 0.2% PCA (all percentages are w/w)) (3.3 g/L) dissolved in water hardness 15° dH (Ca:Mg:NaHCO$_3$-=4:1:1.5) was used. Soil was subsequently added to reach a concentration of 0.7 g soil/L (WFKO9V pigment soil) to reveal biofilm. After washing, textiles were flushed in tap water and dried over night before scanning. Wash experiments were done twice.

Wash performance was measured as the brightness of the WFKO9V pigment soiled, washed textile. Brightness can also be expressed as the intensity of the light reflected from the sample when illuminated with white light. When the sample is soiled, the intensity of the reflected light is lower, than that of a clean sample. Therefore, the intensity of the reflected light can be used to measure wash performance. Intensity measurements were made with a professional flatbed scanner (Kodak iQsmart, Kodak, Midtager 29, DK-2605 Brøndby, Denmark), which was used to capture an image of the washed and dried textile. To extract a value for the light intensity from the scanned images, 24-bit pixel values from the image were converted into values for red, green and blue (RGB). The intensity value (Int) was calculated by adding the RGB values together as vectors and then taking the length of the resulting vector:

Example 2

Wash Synergy Between DNase and Protease

To asses wash synergy between DNase (SEQ ID NO 13) and protease (SEQ ID NO 82 and SEQ ID NO 79), biofilm-harboring textile was AMSA washed a) in the absence of enzyme (blank), b) in the presence of DNase alone, c) in the presence of protease alone and d) with a mixture of DNase and protease. The resulting textile intensities and corresponding wash performances (WPs) are listed in Table 1-4. Wash performances (deep cleaning performance) attributable to DNase ($WP_{DNase}$), protease ($WP_{Prot}$) and the mixture of the two ($WP_{DNase+Prot}$) were quantified as the difference in intensity between textile washed with and without enzyme: $WP_{DNase}=I_{DNase}-I_{Blank}$, $WP_{Prot}=I_{Prot}-I_{Blank}$, $WP_{DNase+Prot}=I_{DNase+Prot}-I_{Blank}$. The synergistic component of wash performance $WP_{syn}$ was quantified as the extent to which wash performance of mixed DNase and protease ($WP_{DNase+Prot}$) exceeded the sum of the individual wash performances of DNase alone and protease alone:

$$WP_{syn}=WP_{DNase+Prot}-(WP_{DNase}+WP_{Prot}).$$

TABLE 1

Synergistic effect of DNase (SEQ ID NO 13) and protease with SEQ ID NO 82

| | | I | WP | $WP_{syn}$ |
|---|---|---|---|---|
| Blank | No enzyme | 285.460 | — | — |
| DNase | 0.00002 ppm DNase | 298.681 | 13.22 | — |
| | 6 nM protease | 282.347 | -3.11 | — |
| Protease | 60 nM protease | 286.253 | 0.79 | — |
| | 600 nM protease | 284.427 | -1.03 | — |
| | 0.00002 ppm DNase + 6 nM protease | 300.267 | 14.807 | 4.70 |
| DNase + Protease | 0.00002 ppm DNase + 60 nM protease | 304.673 | 19.213 | 5.20 |
| | 0.00002 ppm DNase + 600 nM protease | 305.648 | 20.188 | 8.00 |

TABLE 2

Synergistic effect of DNase (SEQ ID NO 13) and protease with SEQ ID NO 82.

| | | I | WP | $WP_{syn}$ |
|---|---|---|---|---|
| Blank | No enzyme | 286.616 | — | — |
| DNase | 0.00002 ppm DNase | 322.453 | 35.84 | — |
| protease | 6 nM protease | 286.651 | 0.04 | — |
| | 60 nM protease | 285.708 | -0.91 | — |
| | 600 nM protease | 288.408 | 1.79 | — |
| DNase + protease | 0.00002 ppm DNase + 6 nM protease | 330.331 | 43.716 | 7.84 |
| | 0.00002 ppm DNase + 60 nM protease | 334.346 | 47.731 | 12.80 |
| | 0.00002 ppm DNase + 600 nM protease | 337.477 | 50.862 | 13.23 |

TABLE 3

Synergistic effect of DNase (SEQ ID NO 13) and protease with SEQ ID NO 79

| | | I | WP | $WP_{syn}$ |
|---|---|---|---|---|
| Blank | No enzyme | 285.460 | — | — |
| DNase | 0.00002 ppm DNase | 298.681 | 13.22 | — |
| protease | 6 nM protease | 283.830 | -1.63 | — |
| | 60 nM protease | 288.018 | 2.56 | — |
| | 600 nM protease | 286.411 | 0.95 | — |
| DNase + protease | 0.00002 ppm DNase + 6 nM protease | 302.809 | 17.349 | 5.76 |
| | 0.00002 ppm DNase + 60 nM protease | 309.238 | 23.778 | 8.00 |
| | 0.00002 ppm DNase + 600 nM protease | 310.335 | 24.875 | 10.70 |

TABLE 4

Synergistic effect of DNase (SEQ ID NO 13) and protease with SEQ ID NO 79

| | | I | WP | $WP_{syn}$ |
|---|---|---|---|---|
| Blank | No enzyme | 286.616 | — | — |
| DNase | 0.00002 ppm DNase | 322.453 | 35.84 | — |
| protease | 6 nM protease | 288.982 | 2.37 | — |
| | 60 nM protease | 290.442 | 3.83 | — |
| | 600 nM protease | 289.461 | 2.85 | — |
| DNase + protease | 0.00002 ppm DNase + 6 nM protease | 333.971 | 47.356 | 9.15 |
| | 0.00002 ppm DNase + 60 nM protease | 335.698 | 49.082 | 9.42 |
| | 0.00002 ppm DNase + 600 nM protease | 336.602 | 49.986 | 11.30 |

Example 3

Isolating Laundry Specific Bacterial Strains

One strain of *Brevundimonas* sp. isolated from laundry was used in the present example. The *Brevundimonas* sp. was isolated during a study, where the bacterial diversity in laundry after washing at 15, 40 and 60° C., respectively, was investigated. The study was conducted on laundry collected from Danish households. For each wash, 20 g of laundry items (tea towel, towel, dish cloth, bib, T-shirt armpit, T-shirt collar, socks) in the range 4:3:2:2:1:1:1 was used. Washing was performed in a Laundr-O-Meter (LOM) at 15, 40 or 60° C. For washing at 15 and 40° C., Ariel Sensitive White & Color was used, whereas WFK IEC-A* model detergent was used for washing at 60° C. Ariel Sensitive White & Color was prepared by weighing out 5.1 g and adding tap water up to 1000 ml followed by stirring for 5 minutes. WFK IEC-A model detergent (which is available from WFK Testgewebe GmbH) was prepared by weighing out 5 g and adding tap water up to 1300 ml followed by stirring for 15 min. Washing was performed for 1 hour at 15, 40 and 60° C., respectively, followed by 2 times rinsing with tap water for 20 min at 15° C. Laundry was sampled immediately after washing at 15, 40 and 60° C., respectively. Twenty grams of laundry was added 0.9% (w/v) NaCl (1.06404; Merck, Darmstadt, Germany) with 0.5% (w/w) tween 80 to yield a 1:10 dilution in stomacher bag. The mixture was homogenized using a Stomacher for 2 minutes at medium speed. After homogenization, ten-fold dilutions were prepared in 0.9% (w/v) NaCl. Bacteria were enumerated on Tryptone Soya Agar (TSA) (CM0129, Oxoid, Basingstoke, Hampshire, UK) incubated aerobically at 30° C. for 5-7 days. To suppress growth of yeast and moulds, 0.2% sorbic acid (359769, Sigma) and 0.1% cycloheximide (18079; Sigma) were added. Bacterial colonies were selected from countable plates and purified by restreaking twice on TSA. For long time storage, purified isolates were stored at −80° C. in TSB containing 20% (w/v) glycerol (49779; Sigma).

Preparation of Swatches with Biofilm

Swatches with biofilm of *Brevundimonas* sp. was included in the present study. Bacteria was pre-grown on Tryptone Soya Agar (TSA) (pH 7.3) (CM0131; Oxoid Ltd, Basingstoke, UK) for 2-5 days at 30° C. From a single colony, a loop-full was transferred to 10 mL of TSB and incubated for 1 day at 30° C. with shaking (240 rpm). After propagation, cells were pelleted by centrifugation (Sigma Laboratory Centrifuge 6K15) (3000 g at 21° C. in 7 min) and resuspended in 10 mL of TSB diluted twice with water. Optical density (OD) at 600 nm was measured using a spectophometer (POLARstar Omega (BMG Labtech, Ortenberg, Germany). Fresh TSB diluted twice with water was inoculated to an $OD_{600nm}$ of 0.03, and 50 mL was added into a petridish (diameter 125 mm), in which a swatch (80 mm×120 mm) of sterile cotton (WFK10A) was placed. After incubation (72 h at 15° C. with shaking (100 rpm), swatches were rinsed twice with 0.9% (w/v) NaCl and dried in LAF bench for 60 min. Swatches were stored at 4° C. prior to wash.

Wash Experiment

Wash experiment was performed using the Automatic Mechanical Stress Assay (AMSA) as described above.

Model detergents and test materials were as follows:

| | |
|---|---|
| Laundry liquid model detergent | Model detergent A |
| Test material | *Brevundimonas* sp. 3-day biofilm grown on WFK10 (cotton) |

For wash experiments, Model detergent A (containing 12% LAS, 11% AEO Biosoft N25-7 (NI), 7% AEOS (SLES), 6% MPG, 3% ethanol, 3% TEA, 2.75% cocoa soap, 2.75% soya soap, 2% glycerol, 2% sodium hydroxide, 2% sodium citrate, 1% sodium formiate, 0.2% DTMPA and 0.2% PCA (all percentages are w/w)) (3.3 g/L) dissolved in water hardness 15° dH (Ca:Mg:NaHCO$_3$=4:1:1.5) was used. Soil was subsequently added to reach a concentration of 0.7 g soil/L (WFKO9V pigment soil) to reveal biofilm. After washing, textiles were flushed in tap water and dried over night before scanning. Wash experiments were done twice.

Wash performance was measured as the brightness of the WFKO9V pigment soiled, washed textile. Brightness can also be expressed as the intensity of the light reflected from the sample when illuminated with white light. When the sample is soiled, the intensity of the reflected light is lower, than that of a clean sample. Therefore, the intensity of the reflected light can be used to measure wash performance. Intensity measurements were made with a professional flatbed scanner (Kodak iQsmart, Kodak, Midtager 29, DK-2605 Brøndby, Denmark), which was used to capture an image of the washed and dried textile. To extract a value for the light intensity from the scanned images, 24-bit pixel values from the image were converted into values for red, green and blue (RGB). The intensity value (Int) was calculated by adding the RGB values together as vectors and then taking the length of the resulting vector:

$$Int = \sqrt{r^2 + g^2 + b^2}.$$

Wash Synergy Between DNase and Proteases

To asses wash synergy between DNase and protease (Protease A (SEQ ID NO 79), protease B (SEQ ID NO 81), protease C (SEQ ID NO 82), protease D (SEQ ID NO 83), protease E (SEQ ID NO 84), protease F (SEQ ID NO 85), protease G (SEQ ID NO 86), biofilm-harboring textile was AMSA washed a) in the absence of enzyme (blank), b) in the presence of DNase alone, c) in the presence of protease alone and d) with a mixture of DNase and protease. The resulting textile intensities and corresponding wash performances (WPs) are listed in Table 4 (Protease a), Table 5 (Protease B), Table 6 (Protease C), Table 7 (Protease D), Table 8 (Protease E), Table 9 (Protease F) and Table 10 (Protease G). Wash performances attributable to DNase ($WP_{DNase}$), protease ($WP_{Prot}$) and the mixture of the two ($WP_{DNase+Prot}$) were quantified as the difference in intensity between textile washed with and without enzyme: $WP_{DNase}=I_{DNase}-I_{Blank}$, $WP_{Prot}=I_{Prot}-I_{Blank}$, $WP_{DNase+Prot}=I_{DNase+Prot}-I_{Blank}$. The synergistic component of wash performance $WP_{syn}$ was quantified as the extent to which wash performance of mixed DNase and Protease ($WP_{DNase+Prot}$) exceeded the sum of the individual wash performances of DNases alone and Protease alone:

$$WP_{syn} = WP_{DNase+Prot} - (WP_{DNase} + WP_{Prot}).$$

TABLE 4

Synergistic effect of DNase and Protease A.

| | | I | WP | WPsyn |
|---|---|---|---|---|
| Blank | No enzyme | 285.8 | — | — |
| DNase | 0.00002 ppm DNase | 292.7 | 6.9 | — |
| Protease A | 60 nM Protease A | 287.8 | 2.0 | — |
| DNase + Protease A | 0.00002 ppm DNase + 60 nM Protease A | 312.9 | 27.1 | 18.2 |

TABLE 5

Synergistic effect of DNase and Protease B.

| | | I | WP | WPsyn |
|---|---|---|---|---|
| Blank | No enzyme | 285.8 | — | — |
| DNase | 0.00002 ppm DNase | 292.7 | 6.9 | — |
| Protease B | 60 nM Protease B | 281.5 | −4.4 | — |
| DNase + Protease B | 0.00002 ppm DNase + 60 nM Protease B | 303.4 | 17.6 | 15.1 |

TABLE 6

Synergistic effect of DNase and Protease C.

| | | I | WP | WPsyn |
|---|---|---|---|---|
| Blank | No enzyme | 285.8 | — | — |
| DNase | 0.00002 ppm DNase | 292.7 | 6.9 | — |
| Protease C | 60 nM Protease C | 285.2 | −0.7 | — |
| DNase + Protease C | 0.00002 ppm DNase + 60 nM Protease C | 310.3 | 24.5 | 18.3 |

TABLE 7

Synergistic effect of DNase and Protease D.

| | | I | WP | WPsyn |
|---|---|---|---|---|
| Blank | No enzyme | 285.8 | — | — |
| DNase | 0.00002 ppm DNase | 292.7 | 6.9 | — |
| Protease D | 60 nM Protease D | 294.8 | 9.0 | — |
| DNase + Protease D | 0.00002 ppm DNase + 60 nM Protease D | 309.7 | 23.9 | 8.0 |

TABLE 8

Synergistic effect of DNase and Protease E.

|  |  | I | WP | WPsyn |
|---|---|---|---|---|
| Blank | No enzyme | 285.8 | — | — |
| DNase | 0.00002 ppm DNase | 292.7 | 6.9 | — |
| Protease E | 60 nM Protease E | 285.6 | −0.3 | — |
| DNase + Protease E | 0.00002 ppm DNase + 60 nM Protease E | 315.7 | 29.9 | 23.3 |

TABLE 9

Synergistic effect of DNase and Protease F.

|  |  | I | WP | WPsyn |
|---|---|---|---|---|
| Blank | No enzyme | 285.8 | — | — |
| DNase | 0.00002 ppm DNase | 292.7 | 6.9 | — |
| Protease F | 60 nM Protease F | 291.9 | 6.0 | — |
| DNase + Protease F | 0.00002 ppm DNase + 60 nM Protease F | 310.0 | 24.2 | 11.3 |

TABLE 10

Synergistic effect of DNase and Protease G.

|  |  | I | WP | WPsyn |
|---|---|---|---|---|
| Blank | No enzyme | 285.8 | — | — |
| DNase | 0.00002 ppm DNase | 292.7 | 6.9 | — |
| Protease G | 60 nM Protease G | 279.0 | −6.8 | — |
| DNase + Protease G | 0.00002 ppm DNase + 60 nM Protease G | 304.1 | 18.3 | 18.2 |

---

What is claimed is:

1. A cleaning composition comprising a DNase, a subtilisin protease and at least one cleaning component, wherein the DNase comprises one or both of the motif(s) [D/M/L][S/T]GYSR[D/N] (SEQ ID NO: 73) or ASXNRSKG (SEQ ID NO: 74) and has at least 90% sequence identity to the amino acid sequence shown in SEQ ID NO: 13, and the subtilisin protease has at least 90% sequence identity to the amino acid sequence shown in SEQ ID NO: 86.

2. A cleaning composition according to claim 1, wherein the subtilisin protease has at least 92% sequence identity to the amino acid sequence shown in SEQ ID NO 86.

3. A cleaning composition according to claim 1, wherein the subtilisin protease has at least 95% sequence identity to the amino acid sequence shown in SEQ ID NO 86.

4. A cleaning composition according to claim 1, wherein the DNase has at least 92% sequence identity to the amino acid sequence shown in SEQ ID NO: 13.

5. A cleaning composition according to claim 1, wherein the DNase has at least 95% sequence identity to the amino acid sequence shown in SEQ ID NO: 13.

6. A cleaning composition according to claim 1 wherein the amount of DNase in the composition is from 0.01 to 1000 ppm and the amount of protease is from 0.01 to 1000 ppm.

7. A cleaning composition according to claim 1, wherein the cleaning component is selected from surfactants, preferably anionic and/or nonionic, builders and bleach components.

8. A method of formulating a cleaning composition according to claim 1 comprising adding a DNase, a subtilisin protease and at least one cleaning component, wherein the DNase comprises one or both of the motif(s) [D/M/L][S/T]GYSR[D/N] (SEQ ID NO: 73) or ASXNRSKG (SEQ ID NO: 74) and has at least 90% sequence identity to the amino acid sequence shown in SEQ ID NO: 13, and the subtilisin protease has at least 90% sequence identity to the amino acid sequence shown in SEQ ID NO: 86.

9. A kit intended for deep cleaning, wherein the kit comprises a cleaning composition according to claim 1.

10. A method of deep cleaning of an item, comprising the steps of:
   a) contacting the item with a cleaning composition according to claim 1; and
   b) rinsing the item.

* * * * *

SEQUENCE LISTING

<160> NUMBER OF SEQ ID NOS: 86

<210> SEQ ID NO 1
<211> LENGTH: 182
<212> TYPE: PRT
<213> ORGANISM: Bacillus sp-62451

<400> SEQUENCE: 1

Leu Pro Pro Asp Leu Pro Ser Lys Ser Thr Thr Gln Ala Gln Leu Asn
1               5                   10                  15

Ser Leu Asn Val Lys Asn Glu Glu Ser Met Ser Gly Tyr Ser Arg Glu
            20                  25                  30

Lys Phe Pro His Trp Ile Ser Gln Gly Asp Gly Cys Asp Thr Arg Gln
        35                  40                  45

Val Ile Leu Lys Arg Asp Ala Asp Asn Tyr Ser Gly Asn Cys Pro Val
    50                  55                  60

Thr Ser Gly Lys Trp Tyr Ser Tyr Tyr Asp Gly Ile Thr Phe Asn Asp
65                  70                  75                  80

Pro Ser Gln Leu Asp Ile Asp His Val Val Pro Leu Ala Glu Ala Trp
                85                  90                  95

Arg Ser Gly Ala Ser Ser Trp Ser Thr Ala Lys Arg Glu Asp Phe Ala
            100                 105                 110

Asn Asp Leu Asn Gly Pro Gln Leu Ile Ala Val Ser Ala Ser Ser Asn
        115                 120                 125

Arg Ser Lys Gly Asp Gln Asp Pro Ser Thr Trp Gln Pro Pro Arg Ala
    130                 135                 140

Gly Ala Asn Cys Ala Tyr Ala Lys Met Trp Ile Asn Thr Lys Tyr Asn
145                 150                 155                 160

Trp Gly Leu His Leu Gln Ser Ser Glu Lys Thr Ala Leu Gln Gly Met
                165                 170                 175

Leu Asn Ser Cys Ser Tyr
            180

<210> SEQ ID NO 2
<211> LENGTH: 182
<212> TYPE: PRT
<213> ORGANISM: Bacillus horikoshii

<400> SEQUENCE: 2

```
Leu Pro Pro Gly Thr Pro Thr Lys Ser Glu Ala Gln Asn Gln Leu Asn
1               5                   10                  15

Ser Leu Thr Val Lys Ser Glu Gly Ser Met Thr Gly Tyr Ser Arg Asp
            20                  25                  30

Leu Phe Pro His Trp Ser Gly Gln Gly Asn Gly Cys Asp Thr Arg Gln
        35                  40                  45

Ile Val Leu Gln Arg Asp Ala Asp Tyr Tyr Thr Gly Thr Cys Pro Thr
    50                  55                  60

Thr Ser Gly Lys Trp Tyr Ser Tyr Phe Asp Gly Val Ile Val Tyr Ser
65                  70                  75                  80

Pro Ser Glu Ile Asp Ile Asp His Ile Val Pro Leu Ala Glu Ala Trp
                85                  90                  95

Arg Ser Gly Ala Ser Ser Trp Thr Thr Glu Gln Arg Arg Ala Phe Ala
            100                 105                 110

Asn Asp Leu Asn Gly Pro Gln Leu Ile Ala Val Thr Ala Ser Val Asn
        115                 120                 125

Arg Ser Lys Gly Asp Gln Asp Pro Ser Thr Trp Gln Pro Pro Arg Ala
    130                 135                 140

Gly Ala Arg Cys Ala Tyr Ala Lys Trp Trp Ile Asn Thr Lys His Arg
145                 150                 155                 160

Trp Asn Leu His Leu Gln Ser Ser Glu Lys Ser Ser Leu Gln Thr Met
                165                 170                 175

Leu Asn Gly Cys Ala Tyr
                180

<210> SEQ ID NO 3
<211> LENGTH: 182
<212> TYPE: PRT
<213> ORGANISM: Bacillus sp-62520

<400> SEQUENCE: 3

Leu Pro Pro Gly Thr Pro Ser Lys Ser Glu Ala Gln Ser Gln Leu Asn
1               5                   10                  15

Ala Leu Thr Val Lys Pro Glu Asp Pro Met Thr Gly Tyr Ser Arg Asp
            20                  25                  30

His Phe Pro His Trp Ile Ser Gln Gly Asn Gly Cys Asn Thr Arg Gln
        35                  40                  45

Ile Val Leu Gln Arg Asp Ala Asp Tyr Tyr Ser Gly Ala Cys Pro Val
    50                  55                  60

Thr Thr Gly Lys Trp Tyr Ser Tyr Phe Asp Gly Val Ile Val Tyr Ser
65                  70                  75                  80

Pro Ser Glu Ile Asp Ile Asp His Ile Val Pro Leu Ala Glu Ala Trp
                85                  90                  95

Arg Ser Gly Ala Ser Ser Trp Thr Thr Glu Lys Arg Arg Ser Phe Ala
            100                 105                 110

Asn Asp Leu Asn Gly Pro Gln Leu Ile Ala Val Thr Ala Ser Val Asn
        115                 120                 125

Arg Ser Lys Gly Asp Gln Asp Pro Ser Thr Trp Gln Pro Pro Arg Ala
    130                 135                 140

Gly Ala Arg Cys Ala Tyr Ala Lys Trp Trp Ile Asn Thr Lys His Arg
145                 150                 155                 160

Trp Gly Leu His Leu Gln Ser Ser Glu Lys Ser Ser Leu Gln Ser Met
                165                 170                 175

Leu Asn Gly Cys Ala Tyr
```

180

<210> SEQ ID NO 4
<211> LENGTH: 182
<212> TYPE: PRT
<213> ORGANISM: Bacillus sp-62520

<400> SEQUENCE: 4

```
Leu Pro Pro Gly Thr Pro Ser Lys Ser Glu Ala Gln Ser Gln Leu Asn
1               5                   10                  15

Ala Leu Thr Val Lys Pro Glu Asp Pro Met Thr Gly Tyr Ser Arg Asp
            20                  25                  30

His Phe Pro His Trp Ile Ser Gln Gly Asn Gly Cys Asn Thr Arg Gln
        35                  40                  45

Ile Val Leu Gln Arg Asp Ala Asp Tyr Tyr Ser Gly Ala Cys Pro Val
    50                  55                  60

Thr Thr Gly Lys Trp Tyr Ser Tyr Phe Asp Gly Val Ile Val Tyr Ser
65                  70                  75                  80

Pro Ser Glu Ile Asp Ile Asp His Ile Val Pro Leu Ala Glu Ala Trp
                85                  90                  95

Arg Ser Gly Ala Ser Ser Trp Thr Thr Glu Gln Arg Arg Ser Phe Ala
            100                 105                 110

Asn Asp Leu Asn Gly Pro Gln Leu Ile Ala Val Thr Ala Ser Val Asn
        115                 120                 125

Arg Ser Lys Gly Asp Gln Asp Pro Ser Thr Trp Gln Pro Pro Arg Ala
    130                 135                 140

Gly Ala Arg Cys Ala Tyr Ala Lys Trp Trp Ile Asn Thr Lys His Arg
145                 150                 155                 160

Trp Gly Leu His Leu Gln Ser Ser Glu Lys Ser Ser Leu Gln Ser Met
                165                 170                 175

Leu Asn Gly Cys Ala Tyr
            180
```

<210> SEQ ID NO 5
<211> LENGTH: 182
<212> TYPE: PRT
<213> ORGANISM: Bacillus horikoshii

<400> SEQUENCE: 5

```
Leu Pro Pro Gly Thr Pro Ser Lys Ser Glu Ala Gln Ser Gln Leu Asn
1               5                   10                  15

Ser Leu Thr Val Lys Ser Glu Asp Pro Met Thr Gly Tyr Ser Arg Asp
            20                  25                  30

His Phe Pro His Trp Ser Gly Gln Gly Asn Gly Cys Asp Thr Arg Gln
        35                  40                  45

Ile Val Leu Gln Arg Asp Ala Asp Tyr Tyr Ser Gly Asn Cys Pro Val
    50                  55                  60

Thr Ser Gly Lys Trp Tyr Ser Tyr Phe Asp Gly Val Ile Val Tyr Ser
65                  70                  75                  80

Pro Ser Glu Ile Asp Ile Asp His Val Val Pro Leu Ala Glu Ala Trp
                85                  90                  95

Arg Ser Gly Ala Ser Ser Trp Thr Thr Glu Gln Arg Arg Ser Phe Ala
            100                 105                 110

Asn Asp Leu Asn Gly Pro Gln Leu Ile Ala Val Thr Ala Ser Val Asn
        115                 120                 125

Arg Ser Lys Gly Asp Gln Asp Pro Ser Thr Trp Gln Pro Pro Arg Ala
```

```
            130                 135                 140
Gly Ala Arg Cys Ala Tyr Ala Lys Trp Trp Ile Asn Thr Lys His Arg
145                 150                 155                 160

Trp Asn Leu His Leu Gln Ser Ser Glu Lys Ser Ala Leu Gln Thr Met
                165                 170                 175

Leu Asn Gly Cys Val Tyr
            180

<210> SEQ ID NO 6
<211> LENGTH: 182
<212> TYPE: PRT
<213> ORGANISM: Bacillus horikoshii

<400> SEQUENCE: 6

Leu Pro Pro Gly Thr Pro Ser Lys Ser Glu Ala Gln Ser Gln Leu Asn
1               5                   10                  15

Ser Leu Thr Val Lys Thr Glu Asp Pro Met Thr Gly Tyr Ser Arg Asp
            20                  25                  30

Leu Phe Pro His Trp Ser Gly Gln Gly Ser Gly Cys Asp Thr Arg Gln
        35                  40                  45

Ile Val Leu Gln Arg Asp Ala Asp Tyr Phe Thr Gly Thr Cys Pro Thr
    50                  55                  60

Thr Ser Gly Lys Trp Tyr Ser Tyr Phe Asp Gly Val Ile Val Tyr Ser
65                  70                  75                  80

Pro Ser Glu Ile Asp Val Asp His Ile Val Pro Leu Ala Glu Ala Trp
                85                  90                  95

Arg Ser Gly Ala Ser Ser Trp Thr Thr Glu Gln Arg Arg Ala Phe Ala
            100                 105                 110

Asn Asp Leu Thr Gly Pro Gln Leu Ile Ala Val Thr Ala Ser Val Asn
        115                 120                 125

Arg Ser Lys Gly Asp Gln Asp Pro Ser Thr Trp Gln Pro Pro Arg Ala
    130                 135                 140

Gly Ala Arg Cys Ala Tyr Ala Lys Trp Trp Ile Asn Thr Lys His Arg
145                 150                 155                 160

Trp Asn Leu His Leu Gln Ser Ser Glu Lys Ser Ser Leu Gln Thr Met
                165                 170                 175

Leu Asn Gly Cys Ala Tyr
            180

<210> SEQ ID NO 7
<211> LENGTH: 182
<212> TYPE: PRT
<213> ORGANISM: Bacillus sp-16840

<400> SEQUENCE: 7

Leu Pro Pro Gly Thr Pro Ser Lys Ser Glu Ala Gln Ser Gln Leu Asn
1               5                   10                  15

Ala Leu Thr Val Lys Ala Glu Asp Pro Met Thr Gly Tyr Ser Arg Asn
            20                  25                  30

Leu Phe Pro His Trp Asn Ser Gln Gly Asn Gly Cys Asn Thr Arg Gln
        35                  40                  45

Leu Val Leu Gln Arg Asp Ala Asp Tyr Tyr Ser Gly Asn Cys Pro Val
    50                  55                  60

Thr Ser Gly Arg Trp Tyr Ser Tyr Phe Asp Gly Val Val Val Thr Ser
65                  70                  75                  80

Pro Ser Glu Ile Asp Ile Asp His Ile Val Pro Leu Ala Glu Ala Trp
```

```
                    85                  90                  95
Arg Ser Gly Ala Ser Ser Trp Thr Thr Glu Lys Arg Lys Glu Phe Ala
                100                 105                 110

Asn Asp Leu Asn Gly Pro Gln Leu Ile Ala Val Thr Ala Ser Val Asn
            115                 120                 125

Arg Ser Lys Gly Asp Gln Asp Pro Ser Thr Trp Gln Pro Pro Arg Ala
        130                 135                 140

Ala Ala Arg Cys Gly Tyr Ala Lys Trp Trp Ile Asn Thr Lys Tyr Arg
145                 150                 155                 160

Trp Asp Leu Ser Leu Gln Ser Ser Glu Lys Ser Ser Leu Gln Thr Met
                165                 170                 175

Leu Asn Thr Cys Ser Tyr
            180

<210> SEQ ID NO 8
<211> LENGTH: 182
<212> TYPE: PRT
<213> ORGANISM: Bacillus sp-16840

<400> SEQUENCE: 8

Leu Pro Pro Gly Thr Pro Ser Lys Ser Gln Ala Gln Ser Gln Leu Asn
1               5                   10                  15

Ala Leu Thr Val Lys Ala Glu Asp Pro Met Thr Gly Tyr Ser Arg Asn
            20                  25                  30

Leu Phe Pro His Trp Ser Ser Gln Gly Asn Gly Cys Asn Thr Arg Gln
        35                  40                  45

Leu Val Leu Gln Arg Asp Ala Asp Tyr Tyr Ser Gly Asn Cys Pro Val
    50                  55                  60

Thr Ser Gly Arg Trp Tyr Ser Tyr Phe Asp Gly Val Val Val Thr Ser
65                  70                  75                  80

Pro Ser Glu Ile Asp Ile Asp His Ile Val Pro Leu Ala Glu Ala Trp
                85                  90                  95

Arg Ser Gly Ala Ser Ser Trp Thr Thr Glu Lys Arg Arg Glu Phe Ala
                100                 105                 110

Asn Asp Leu Asn Gly Pro Gln Leu Ile Ala Val Thr Ala Ser Val Asn
            115                 120                 125

Arg Ser Lys Gly Asp Gln Asp Pro Ser Thr Trp Gln Pro Pro Arg Val
        130                 135                 140

Ala Ala Arg Cys Gly Tyr Ala Lys Trp Trp Ile Asn Thr Lys Tyr Arg
145                 150                 155                 160

Trp Asp Leu Ser Leu Gln Ser Ser Glu Lys Ser Ser Leu Gln Thr Met
                165                 170                 175

Leu Asn Thr Cys Ser Tyr
            180

<210> SEQ ID NO 9
<211> LENGTH: 182
<212> TYPE: PRT
<213> ORGANISM: Bacillus sp-62668

<400> SEQUENCE: 9

Leu Pro Pro Gly Thr Pro Ser Lys Ser Glu Ala Gln Ser Gln Leu Thr
1               5                   10                  15

Ser Leu Thr Val Lys Pro Glu Asp Pro Met Thr Gly Tyr Ser Arg Asp
            20                  25                  30

His Phe Pro His Trp Ile Ser Gln Gly Asn Gly Cys Asn Thr Arg Gln
```

```
              35                  40                  45
Ile Val Leu Gln Arg Asp Ala Asp Tyr Tyr Ser Gly Asn Cys Pro Val
 50                  55                  60

Thr Thr Gly Lys Trp Tyr Ser Tyr Phe Asp Gly Val Ile Val Tyr Ser
 65                  70                  75                  80

Pro Ser Glu Ile Asp Ile Asp His Ile Val Pro Leu Ala Glu Ala Trp
                 85                  90                  95

Arg Ser Gly Ala Ser Ser Trp Thr Ala Glu Gln Arg Arg Asn Phe Ala
                100                 105                 110

Asn Asp Leu Asn Gly Pro Gln Leu Ile Ala Val Thr Ala Ser Val Asn
            115                 120                 125

Arg Ser Lys Gly Asp Gln Asp Pro Ser Thr Trp Gln Pro Pro Arg Thr
130                 135                 140

Gly Ala Arg Cys Ala Tyr Ala Lys Trp Trp Ile Asn Thr Lys Tyr Arg
145                 150                 155                 160

Trp Gly Leu His Leu Gln Ser Ser Glu Lys Ser Ser Leu Gln Ser Met
                165                 170                 175

Leu Asn Gly Cys Ala Tyr
            180

<210> SEQ ID NO 10
<211> LENGTH: 183
<212> TYPE: PRT
<213> ORGANISM: Bacillus sp-13395

<400> SEQUENCE: 10

Ala Phe Pro Pro Gly Thr Pro Ser Lys Ser Thr Ala Gln Ser Gln Leu
 1                   5                  10                  15

Asn Ser Leu Thr Val Lys Ser Glu Gly Ser Met Thr Gly Tyr Ser Arg
                 20                  25                  30

Asp Lys Phe Pro His Trp Ile Ser Gln Gly Asp Gly Cys Asp Thr Arg
             35                  40                  45

Gln Leu Val Leu Lys Arg Asp Gly Asp Tyr Tyr Ser Gly Asn Cys Pro
 50                  55                  60

Val Thr Ser Gly Lys Trp Tyr Ser Tyr Tyr Asp Gly Ile Ala Val Tyr
 65                  70                  75                  80

Ser Pro Ser Glu Ile Asp Ile Asp His Ile Val Pro Leu Ala Glu Ala
                 85                  90                  95

Trp Arg Ser Gly Ala Ser Gly Trp Thr Thr Glu Lys Arg Gln Asn Phe
                100                 105                 110

Ala Asn Asp Leu Asn Gly Pro Gln Leu Ile Ala Val Thr Ala Ser Val
            115                 120                 125

Asn Arg Ser Lys Gly Asp Gln Asp Pro Ser Thr Trp Gln Pro Pro Arg
130                 135                 140

Ser Gly Ser His Cys Ala Tyr Ala Lys Met Trp Val Asn Thr Lys Tyr
145                 150                 155                 160

Arg Trp Gly Leu His Leu Gln Ser Ala Glu Lys Ser Ala Leu Gln Ser
                165                 170                 175

Met Leu Asn Ala Cys Ser Tyr
            180

<210> SEQ ID NO 11
<211> LENGTH: 185
<212> TYPE: PRT
<213> ORGANISM: Bacillus horneckiae
```

<400> SEQUENCE: 11

```
Ala Ser Ala Phe Pro Pro Gly Thr Pro Ser Lys Ser Thr Ala Gln Ser
1               5                   10                  15
Gln Leu Asn Ser Leu Thr Val Lys Ser Glu Gly Ser Met Thr Gly Tyr
            20                  25                  30
Ser Arg Asp Lys Phe Pro His Trp Ile Ser Gln Gly Asp Gly Cys Asp
        35                  40                  45
Thr Arg Gln Leu Val Leu Lys Arg Asp Gly Asp Tyr Tyr Ser Gly Asn
    50                  55                  60
Cys Pro Val Thr Ser Gly Lys Trp Tyr Ser Tyr Asp Gly Ile Thr
65                  70                  75                  80
Val Tyr Ser Pro Ser Glu Ile Asp Ile Asp His Ile Val Pro Leu Ala
                85                  90                  95
Glu Ala Trp Arg Ser Gly Ala Ser Gly Trp Thr Thr Glu Lys Arg Gln
            100                 105                 110
Ser Phe Ala Asn Asp Leu Asn Gly Pro Gln Leu Ile Ala Val Thr Ala
        115                 120                 125
Ser Val Asn Arg Ser Lys Gly Asp Gln Asp Pro Ser Thr Trp Gln Pro
    130                 135                 140
Pro Arg Ser Gly Ser His Cys Ala Tyr Ala Lys Met Trp Val Asn Thr
145                 150                 155                 160
Lys Tyr Arg Trp Gly Leu His Val Gln Ser Ala Glu Lys Ser Ala Leu
                165                 170                 175
Gln Ser Met Leu Asn Ala Cys Ser Tyr
            180                 185
```

<210> SEQ ID NO 12
<211> LENGTH: 182
<212> TYPE: PRT
<213> ORGANISM: Bacillus sp-11238

<400> SEQUENCE: 12

```
Phe Pro Pro Glu Ile Pro Ser Lys Ser Thr Ala Gln Ser Gln Leu Asn
1               5                   10                  15
Ser Leu Thr Val Lys Ser Glu Asp Ala Met Thr Gly Tyr Ser Arg Asp
            20                  25                  30
Lys Phe Pro His Trp Ile Ser Gln Gly Asp Gly Cys Asp Thr Arg Gln
        35                  40                  45
Met Val Leu Lys Arg Asp Ala Asp Tyr Tyr Ser Gly Ser Cys Pro Val
    50                  55                  60
Thr Ser Gly Lys Trp Tyr Ser Tyr Asp Gly Ile Thr Val Tyr Ser
65                  70                  75                  80
Pro Ser Glu Ile Asp Ile Asp His Ile Val Pro Leu Ala Glu Ala Trp
                85                  90                  95
Arg Ser Gly Ala Ser Ser Trp Thr Thr Glu Lys Arg Arg Asn Phe Ala
            100                 105                 110
Asn Asp Leu Asn Gly Pro Gln Leu Ile Ala Val Thr Ala Ser Val Asn
        115                 120                 125
Arg Ser Lys Gly Asp Gln Asp Pro Ser Thr Trp Gln Pro Pro Arg Ser
    130                 135                 140
Gly Ala Arg Cys Ala Tyr Ala Lys Met Trp Val Asn Thr Lys Tyr Arg
145                 150                 155                 160
Trp Gly Leu His Leu Gln Ser Ala Glu Lys Ser Gly Leu Glu Ser Met
                165                 170                 175
```

```
Leu Asn Thr Cys Ser Tyr
            180

<210> SEQ ID NO 13
<211> LENGTH: 182
<212> TYPE: PRT
<213> ORGANISM: Bacillus cibi

<400> SEQUENCE: 13

Thr Pro Pro Gly Thr Pro Ser Lys Ser Ala Gln Ser Gln Leu Asn
1               5                   10                  15

Ala Leu Thr Val Lys Thr Glu Gly Ser Met Ser Gly Tyr Ser Arg Asp
            20                  25                  30

Leu Phe Pro His Trp Ile Ser Gln Gly Ser Gly Cys Asp Thr Arg Gln
        35                  40                  45

Val Val Leu Lys Arg Asp Ala Asp Ser Tyr Ser Gly Asn Cys Pro Val
    50                  55                  60

Thr Ser Gly Ser Trp Tyr Ser Tyr Tyr Asp Gly Val Thr Phe Thr Asn
65                  70                  75                  80

Pro Ser Asp Leu Asp Ile Asp His Ile Val Pro Leu Ala Glu Ala Trp
                85                  90                  95

Arg Ser Gly Ala Ser Ser Trp Thr Thr Ser Lys Arg Gln Asp Phe Ala
            100                 105                 110

Asn Asp Leu Ser Gly Pro Gln Leu Ile Ala Val Ser Ala Ser Thr Asn
        115                 120                 125

Arg Ser Lys Gly Asp Gln Asp Pro Ser Thr Trp Gln Pro Pro Arg Ser
    130                 135                 140

Gly Ala Ala Cys Gly Tyr Ser Lys Trp Trp Ile Ser Thr Lys Tyr Lys
145                 150                 155                 160

Trp Gly Leu Ser Leu Gln Ser Ser Glu Lys Thr Ala Leu Gln Gly Met
                165                 170                 175

Leu Asn Ser Cys Ser Tyr
            180

<210> SEQ ID NO 14
<211> LENGTH: 182
<212> TYPE: PRT
<213> ORGANISM: Bacillus sp-18318

<400> SEQUENCE: 14

Phe Pro Pro Gly Thr Pro Ser Lys Ser Thr Ala Gln Ser Gln Leu Asn
1               5                   10                  15

Ser Leu Thr Val Lys Ser Glu Gly Ser Met Thr Gly Tyr Ser Arg Asp
            20                  25                  30

Lys Phe Pro His Trp Ile Gly Gln Gly Ser Gly Cys Asp Thr Arg Gln
        35                  40                  45

Leu Val Leu Gln Arg Asp Ala Asp Tyr Tyr Ser Gly Ser Cys Pro Val
    50                  55                  60

Thr Ser Gly Lys Trp Tyr Ser Tyr Tyr Asp Gly Val Thr Phe Tyr Asp
65                  70                  75                  80

Pro Ser Asp Leu Asp Ile Asp His Val Val Pro Leu Ala Glu Ala Trp
                85                  90                  95

Arg Ser Gly Ala Ser Ser Trp Ser Thr Gln Lys Arg Lys Asp Phe Ala
            100                 105                 110

Asn Asp Leu Ser Gly Pro Gln Leu Ile Ala Val Ser Ala Ser Ser Asn
        115                 120                 125
```

```
Arg Ser Lys Gly Asp Gln Asp Pro Ser Thr Trp Gln Pro Thr Arg Ser
130                 135                 140

Gly Ala Ala Cys Gly Tyr Ser Lys Trp Trp Ile Ser Thr Lys His Lys
145             150                 155                 160

Trp Gly Leu Ser Leu Gln Ser Ser Glu Lys Asn Ala Leu Gln Gly Met
                165                 170                 175

Leu Asn Ser Cys Val Tyr
            180

<210> SEQ ID NO 15
<211> LENGTH: 182
<212> TYPE: PRT
<213> ORGANISM: Bacillus idriensis

<400> SEQUENCE: 15

Leu Pro Pro Gly Thr Pro Ser Lys Ser Thr Ala Gln Ser Gln Leu Asn
1               5                   10                  15

Ala Leu Thr Val Gln Thr Glu Gly Ser Met Thr Gly Tyr Ser Arg Asp
                20                  25                  30

Lys Phe Pro His Trp Ile Ser Gln Gly Asn Gly Cys Asp Thr Arg Gln
            35                  40                  45

Val Val Leu Gln Arg Asp Ala Asp Tyr Tyr Ser Gly Thr Cys Pro Val
    50                  55                  60

Thr Ser Gly Lys Trp Tyr Ser Tyr Tyr Asp Gly Val Thr Leu Tyr Asn
65                  70                  75                  80

Pro Ser Asp Leu Asp Ile Asp His Val Val Ala Leu Ala Glu Ala Trp
                85                  90                  95

Arg Ser Gly Ala Ser Ser Trp Thr Thr Asp Lys Arg Glu Asp Phe Ala
                100                 105                 110

Asn Asp Leu Ser Gly Thr Gln Leu Ile Ala Val Ser Ala Ser Thr Asn
            115                 120                 125

Arg Ser Lys Gly Asp Gln Asp Pro Ser Thr Trp Gln Pro Pro Arg Ser
130                 135                 140

Gly Ala Ala Cys Gly Tyr Ala Lys Trp Trp Ile Ser Thr Lys Tyr Lys
145             150                 155                 160

Trp Asn Leu Asn Leu Gln Ser Ser Glu Lys Thr Ala Leu Gln Ser Met
                165                 170                 175

Leu Asn Ser Cys Ser Tyr
            180

<210> SEQ ID NO 16
<211> LENGTH: 182
<212> TYPE: PRT
<213> ORGANISM: Bacillus algicola

<400> SEQUENCE: 16

Phe Pro Pro Gly Thr Pro Ser Lys Ser Glu Ala Gln Ser Gln Leu Asn
1               5                   10                  15

Ser Leu Thr Val Gln Ser Glu Gly Ser Met Ser Gly Tyr Ser Arg Asp
                20                  25                  30

Lys Phe Pro His Trp Ile Gly Gln Gly Asn Gly Cys Asp Thr Arg Gln
            35                  40                  45

Leu Val Leu Gln Arg Asp Ala Asp Tyr Tyr Ser Gly Asp Cys Pro Val
    50                  55                  60

Thr Ser Gly Lys Trp Tyr Ser Tyr Phe Asp Gly Val Thr Val Tyr Asp
65                  70                  75                  80
```

```
Pro Ser Asp Leu Asp Ile Asp His Met Val Pro Met Ala Glu Ala Trp
                85                  90                  95

Arg Ser Gly Ala Ser Ser Trp Ser Thr Gln Lys Arg Glu Asp Phe Ala
            100                 105                 110

Asn Asp Leu Ser Gly Pro His Leu Ile Ala Val Thr Ala Ser Ser Asn
        115                 120                 125

Arg Ser Lys Gly Asp Gln Asp Pro Ser Thr Trp Lys Pro Thr Arg Tyr
    130                 135                 140

Gly Ala His Cys Gly Tyr Ala Lys Trp Trp Ile Asn Thr Lys Tyr Val
145                 150                 155                 160

Tyr Asp Leu Thr Leu Gln Ser Ser Glu Lys Thr Glu Leu Gln Ser Met
                165                 170                 175

Leu Asn Thr Cys Ser Tyr
            180

<210> SEQ ID NO 17
<211> LENGTH: 182
<212> TYPE: PRT
<213> ORGANISM: Enviromental sample J

<400> SEQUENCE: 17

Leu Pro Pro Asn Ile Pro Ser Lys Ala Asp Ala Leu Thr Lys Leu Asn
1               5                   10                  15

Ala Leu Thr Val Gln Thr Glu Gly Pro Met Thr Gly Tyr Ser Arg Asp
            20                  25                  30

Leu Phe Pro His Trp Ser Ser Gln Gly Asn Gly Cys Asn Thr Arg His
        35                  40                  45

Val Val Leu Lys Arg Asp Ala Asp Ser Val Val Asp Thr Cys Pro Val
    50                  55                  60

Thr Thr Gly Arg Trp Tyr Ser Tyr Tyr Asp Gly Leu Val Phe Thr Ser
65                  70                  75                  80

Ala Ser Asp Ile Asp Ile Asp His Val Val Pro Leu Ala Glu Ala Trp
                85                  90                  95

Arg Ser Gly Ala Ser Ser Trp Thr Ser Thr Lys Arg Gln Ser Phe Ala
            100                 105                 110

Asn Asp Leu Asn Gly Pro Gln Leu Ile Ala Val Ser Ala Thr Ser Asn
        115                 120                 125

Arg Ser Lys Gly Asp Gln Asp Pro Ser Thr Trp Gln Pro Pro Arg Ala
    130                 135                 140

Gly Ala Arg Cys Ala Tyr Ala Lys Met Trp Val Glu Thr Lys Ser Arg
145                 150                 155                 160

Trp Gly Leu Thr Leu Gln Ser Ser Glu Lys Ala Ala Leu Gln Thr Ala
                165                 170                 175

Ile Asn Ala Cys Ser Tyr
            180

<210> SEQ ID NO 18
<211> LENGTH: 182
<212> TYPE: PRT
<213> ORGANISM: Bacillus vietnamensis

<400> SEQUENCE: 18

Phe Pro Pro Gly Thr Pro Ser Lys Ser Thr Ala Gln Ser Gln Leu Asn
1               5                   10                  15

Ala Leu Thr Val Lys Ser Glu Ser Ser Met Thr Gly Tyr Ser Arg Asp
            20                  25                  30
```

```
Lys Phe Pro His Trp Ile Gly Gln Arg Asn Gly Cys Asp Thr Arg Gln
             35                  40                  45

Leu Val Leu Gln Arg Asp Ala Asp Ser Tyr Ser Gly Ser Cys Pro Val
 50                  55                  60

Thr Ser Gly Ser Trp Tyr Ser Tyr Tyr Asp Gly Val Thr Phe Thr Asp
 65                  70                  75                  80

Pro Ser Asp Leu Asp Ile Asp His Val Val Pro Leu Ala Glu Ala Trp
                 85                  90                  95

Arg Ser Gly Ala Ser Ser Trp Thr Thr Ala Lys Arg Glu Asp Phe Ala
                100                 105                 110

Asn Asp Leu Ser Gly Pro Gln Leu Ile Ala Val Ser Ala Ser Ser Asn
                115                 120                 125

Arg Ser Lys Gly Asp Gln Asp Pro Ser Thr Trp Gln Pro Pro Arg Ser
            130                 135                 140

Gly Ala Ala Cys Gly Tyr Ser Lys Trp Trp Ile Ser Thr Lys Tyr Lys
145                 150                 155                 160

Trp Gly Leu Ser Leu Gln Ser Ser Glu Lys Thr Ala Leu Gln Gly Met
                165                 170                 175

Leu Asn Ser Cys Ile Tyr
            180

<210> SEQ ID NO 19
<211> LENGTH: 182
<212> TYPE: PRT
<213> ORGANISM: Bacillus hwajinpoensis

<400> SEQUENCE: 19

Ile Pro Pro Gly Thr Pro Ser Lys Ser Ala Ala Gln Ser Gln Leu Asp
 1               5                  10                  15

Ser Leu Ala Val Gln Ser Glu Gly Ser Met Ser Gly Tyr Ser Arg Asp
                 20                  25                  30

Lys Phe Pro His Trp Ile Gly Gln Gly Asn Gly Cys Asp Thr Arg Gln
             35                  40                  45

Leu Val Leu Gln Arg Asp Ala Asp Tyr Tyr Ser Gly Asp Cys Pro Val
 50                  55                  60

Thr Ser Gly Lys Trp Tyr Ser Tyr Phe Asp Gly Val Gln Val Tyr Asp
 65                  70                  75                  80

Pro Ser Tyr Leu Asp Ile Asp His Met Val Pro Leu Ala Glu Ala Trp
                 85                  90                  95

Arg Ser Gly Ala Ser Ser Trp Ser Thr Gln Lys Arg Glu Asp Phe Ala
                100                 105                 110

Asn Asp Leu Asp Gly Pro His Leu Ile Ala Val Thr Ala Ser Ser Asn
                115                 120                 125

Arg Ser Lys Gly Asp Gln Asp Pro Ser Thr Trp Lys Pro Thr Arg Tyr
            130                 135                 140

Ser Ala His Cys Gly Tyr Ala Lys Trp Trp Ile Asn Thr Lys Tyr Val
145                 150                 155                 160

Tyr Asp Leu Asn Leu Gln Ser Ser Glu Lys Ser Ala Leu Gln Ser Met
                165                 170                 175

Leu Asn Thr Cys Ser Tyr
            180

<210> SEQ ID NO 20
<211> LENGTH: 182
<212> TYPE: PRT
<213> ORGANISM: Paenibacillus mucilaginosus
```

<400> SEQUENCE: 20

Leu Pro Pro Gly Thr Pro Ser Lys Ser Thr Ala Gln Ser Gln Leu Asn
1               5                   10                  15

Ser Leu Thr Val Lys Ser Glu Ser Thr Met Thr Gly Tyr Ser Arg Asp
            20                  25                  30

Lys Phe Pro His Trp Thr Ser Gln Gly Gly Cys Asp Thr Arg Gln
        35                  40                  45

Val Val Leu Lys Arg Asp Ala Asp Tyr Tyr Ser Gly Ser Cys Pro Val
    50                  55                  60

Thr Ser Gly Lys Trp Tyr Ser Tyr Tyr Asp Gly Ile Thr Val Tyr Ser
65                  70                  75                  80

Pro Ser Glu Ile Asp Ile Asp His Ile Val Pro Leu Ala Glu Ala Trp
                85                  90                  95

Arg Ser Gly Ala Ser Ser Trp Thr Thr Glu Lys Arg Gln Asn Phe Ala
            100                 105                 110

Asn Asp Leu Gly Gly Pro Gln Leu Ile Ala Val Thr Ala Ser Ser Asn
        115                 120                 125

Arg Ala Lys Gly Asp Gln Asp Pro Ser Thr Trp Lys Pro Thr Arg Ser
130                 135                 140

Gly Ala His Cys Ala Tyr Ala Lys Trp Trp Ile Asn Thr Lys Tyr Arg
145                 150                 155                 160

Trp Gly Leu His Leu Gln Ser Ser Glu Lys Thr Ala Leu Gln Ser Met
                165                 170                 175

Leu Asn Thr Cys Ser Tyr
            180

<210> SEQ ID NO 21
<211> LENGTH: 182
<212> TYPE: PRT
<213> ORGANISM: Bacillus indicus

<400> SEQUENCE: 21

Thr Pro Pro Gly Thr Pro Ser Lys Ser Thr Ala Gln Thr Gln Leu Asn
1               5                   10                  15

Ala Leu Thr Val Lys Thr Glu Gly Ser Met Thr Gly Tyr Ser Arg Asp
            20                  25                  30

Leu Phe Pro His Trp Ile Ser Gln Gly Ser Gly Cys Asp Thr Arg Gln
        35                  40                  45

Val Val Leu Lys Arg Asp Ala Asp Tyr Tyr Ser Gly Ser Cys Pro Val
    50                  55                  60

Thr Ser Gly Lys Trp Tyr Ser Tyr Tyr Asp Gly Val Thr Phe Tyr Asp
65                  70                  75                  80

Pro Ser Asp Leu Asp Ile Asp His Ile Val Pro Leu Ala Glu Ala Trp
                85                  90                  95

Arg Ser Gly Ala Ser Ser Trp Thr Thr Ser Lys Arg Gln Asp Phe Ala
            100                 105                 110

Asn Asp Leu Ser Gly Pro Gln Leu Ile Ala Val Ser Ala Ser Thr Asn
        115                 120                 125

Arg Ser Lys Gly Asp Gln Asp Pro Ser Thr Trp Gln Pro Pro Arg Ala
130                 135                 140

Gly Ala Ala Cys Gly Tyr Ser Lys Trp Trp Ile Ser Thr Lys Tyr Lys
145                 150                 155                 160

Trp Gly Leu Ser Leu Gln Ser Ser Glu Lys Thr Ala Leu Gln Gly Met
                165                 170                 175

```
Leu Asn Ser Cys Ser Tyr
            180

<210> SEQ ID NO 22
<211> LENGTH: 182
<212> TYPE: PRT
<213> ORGANISM: Bacillus marisflavi

<400> SEQUENCE: 22

Thr Pro Pro Val Thr Pro Ser Lys Ala Thr Ser Gln Ser Gln Leu Asn
1               5                   10                  15

Gly Leu Thr Val Lys Thr Glu Gly Ala Met Thr Gly Tyr Ser Arg Asp
            20                  25                  30

Lys Phe Pro His Trp Ser Ser Gln Gly Gly Cys Asp Thr Arg Gln
        35                  40                  45

Val Val Leu Lys Arg Asp Ala Asp Ser Tyr Ser Gly Asn Cys Pro Val
    50                  55                  60

Thr Ser Gly Ser Trp Tyr Ser Tyr Tyr Asp Gly Val Lys Phe Thr Asn
65                  70                  75                  80

Pro Ser Asp Leu Asp Ile Asp His Ile Val Pro Leu Ala Glu Ala Trp
                85                  90                  95

Arg Ser Gly Ala Ser Ser Trp Thr Thr Ala Gln Arg Glu Ala Phe Ala
            100                 105                 110

Asn Asp Leu Ser Gly Ser Gln Leu Ile Ala Val Ser Ala Ser Ser Asn
        115                 120                 125

Arg Ser Lys Gly Asp Gln Asp Pro Ser Thr Trp Gln Pro Pro Arg Ala
    130                 135                 140

Gly Ala Lys Cys Gly Tyr Ala Lys Trp Trp Ile Ser Thr Lys Ser Lys
145                 150                 155                 160

Trp Asn Leu Ser Leu Gln Ser Ser Glu Lys Thr Ala Leu Gln Gly Met
                165                 170                 175

Leu Asn Ser Cys Val Tyr
            180

<210> SEQ ID NO 23
<211> LENGTH: 184
<212> TYPE: PRT
<213> ORGANISM: Bacillus luciferensis

<400> SEQUENCE: 23

Ala Ser Leu Pro Pro Gly Ile Pro Ser Leu Ser Thr Ala Gln Ser Gln
1               5                   10                  15

Leu Asn Ser Leu Thr Val Lys Ser Glu Gly Ser Leu Thr Gly Tyr Ser
            20                  25                  30

Arg Asp Val Phe Pro His Trp Ile Ser Gln Gly Ser Gly Cys Asp Thr
        35                  40                  45

Arg Gln Val Val Leu Lys Arg Asp Ala Asp Tyr Tyr Ser Gly Asn Cys
    50                  55                  60

Pro Val Thr Ser Gly Lys Trp Tyr Ser Tyr Tyr Asp Gly Val Thr Val
65                  70                  75                  80

Tyr Ser Pro Ser Glu Ile Asp Ile Asp His Val Val Pro Leu Ala Glu
                85                  90                  95

Ala Trp Arg Ser Gly Ala Ser Ser Trp Thr Thr Glu Lys Arg Gln Asn
            100                 105                 110

Phe Ala Asn Asp Leu Asn Gly Pro Gln Leu Ile Ala Val Thr Ala Ser
        115                 120                 125
```

Ser Asn Arg Ser Lys Gly Asp Gln Asp Pro Ser Thr Trp Gln Pro Thr
130                 135                 140

Arg Thr Gly Ala Arg Cys Ala Tyr Ala Lys Met Trp Ile Asn Thr Lys
145                 150                 155                 160

Tyr Arg Trp Gly Leu His Leu Gln Ser Ser Glu Lys Ser Ala Leu Gln
                165                 170                 175

Ser Met Leu Asn Thr Cys Ser Tyr
            180

<210> SEQ ID NO 24
<211> LENGTH: 182
<212> TYPE: PRT
<213> ORGANISM: Bacillus marisflavi

<400> SEQUENCE: 24

Thr Pro Pro Val Thr Pro Ser Lys Glu Thr Ser Gln Ser Gln Leu Asn
1               5                   10                  15

Gly Leu Thr Val Lys Thr Glu Gly Ala Met Thr Gly Tyr Ser Arg Asp
                20                  25                  30

Lys Phe Pro His Trp Ser Ser Gln Gly Gly Cys Asp Thr Arg Gln
            35                  40                  45

Val Val Leu Lys Arg Asp Ala Asp Ser Tyr Ser Gly Asn Cys Pro Val
    50                  55                  60

Thr Ser Gly Ser Trp Tyr Ser Tyr Asp Gly Val Lys Phe Thr His
65                  70                  75                  80

Pro Ser Asp Leu Asp Ile Asp His Ile Val Pro Leu Ala Glu Ala Trp
                85                  90                  95

Arg Ser Gly Ala Ser Ser Trp Thr Thr Ala Gln Arg Glu Ala Phe Ala
            100                 105                 110

Asn Asp Leu Ser Gly Ser Gln Leu Ile Ala Val Ser Ala Ser Ser Asn
        115                 120                 125

Arg Ser Lys Gly Asp Gln Asp Pro Ser Thr Trp Gln Pro Pro Arg Ala
    130                 135                 140

Gly Ala Lys Cys Gly Tyr Ala Lys Trp Trp Ile Ser Thr Lys Ser Lys
145                 150                 155                 160

Trp Asn Leu Ser Leu Gln Ser Ser Glu Lys Thr Ala Leu Gln Gly Met
                165                 170                 175

Leu Asn Ser Cys Val Tyr
            180

<210> SEQ ID NO 25
<211> LENGTH: 182
<212> TYPE: PRT
<213> ORGANISM: Bacillus sp. SA2-6

<400> SEQUENCE: 25

Leu Pro Ser Gly Ile Pro Ser Lys Ser Thr Ala Gln Ser Gln Leu Asn
1               5                   10                  15

Ser Leu Thr Val Lys Ser Glu Gly Ser Met Thr Gly Tyr Ser Arg Asp
                20                  25                  30

Lys Phe Pro His Trp Ile Ser Gln Gly Gly Cys Asp Thr Arg Gln
            35                  40                  45

Val Val Leu Lys Arg Asp Ala Asp Tyr Tyr Ser Gly Asn Cys Pro Val
    50                  55                  60

Thr Ser Gly Lys Trp Tyr Ser Tyr Asp Gly Ile Ser Val Tyr Ser
65                  70                  75                  80

-continued

```
Pro Ser Glu Ile Asp Ile Asp His Val Val Pro Leu Ala Glu Ala Trp
                85                  90                  95

Arg Ser Gly Ala Ser Ser Trp Thr Thr Thr Lys Arg Gln Asn Phe Ala
            100                 105                 110

Asn Asp Leu Asn Gly Pro Gln Leu Ile Ala Val Thr Ala Ser Val Asn
        115                 120                 125

Arg Ser Lys Gly Asp Gln Asp Pro Ser Thr Trp Gln Pro Pro Arg Tyr
    130                 135                 140

Gly Ala Arg Cys Ala Tyr Ala Lys Met Trp Ile Asn Thr Lys Tyr Arg
145                 150                 155                 160

Trp Asp Leu Asn Leu Gln Ser Ser Glu Lys Ser Ser Leu Gln Ser Met
                165                 170                 175

Leu Asp Thr Cys Ser Tyr
            180

<210> SEQ ID NO 26
<211> LENGTH: 191
<212> TYPE: PRT
<213> ORGANISM: Pyrenochaetopsis sp.

<400> SEQUENCE: 26

Leu Pro Ser Pro Leu Leu Ile Ala Arg Ser Pro Pro Asn Ile Pro Ser
1               5                   10                  15

Ala Thr Thr Ala Lys Thr Gln Leu Ala Gly Leu Thr Val Ala Pro Gln
            20                  25                  30

Gly Pro Gln Thr Gly Tyr Ser Arg Asp Leu Phe Pro His Trp Ile Thr
        35                  40                  45

Gln Ser Gly Thr Cys Asn Thr Arg Glu Val Val Leu Lys Arg Asp Gly
    50                  55                  60

Thr Asn Val Val Thr Asn Ser Ala Cys Ala Ser Thr Ser Gly Ser Trp
65                  70                  75                  80

Leu Ser Pro Tyr Asp Gly Lys Thr Trp Asp Ser Ala Ser Asp Ile Gln
                85                  90                  95

Ile Asp His Leu Val Pro Leu Ser Asn Ala Trp Lys Ser Gly Ala Ala
            100                 105                 110

Ala Trp Thr Thr Ala Gln Arg Gln Ala Phe Ala Asn Asp Leu Thr His
        115                 120                 125

Pro Gln Leu Val Ala Val Thr Gly Ser Val Asn Glu Ser Lys Gly Asp
    130                 135                 140

Asp Gly Pro Glu Asp Trp Lys Pro Pro Leu Ala Ser Tyr Tyr Cys Thr
145                 150                 155                 160

Tyr Ala Ser Met Trp Thr Ala Val Lys Ser Asn Tyr Lys Leu Thr Ile
                165                 170                 175

Thr Ser Ala Glu Lys Ser Ala Leu Thr Ser Met Leu Ala Thr Cys
            180                 185                 190

<210> SEQ ID NO 27
<211> LENGTH: 190
<212> TYPE: PRT
<213> ORGANISM: Vibrissea flavovirens

<400> SEQUENCE: 27

Thr Pro Leu Pro Ile Ile Ala Arg Thr Pro Asn Ile Pro Thr Thr
1               5                   10                  15

Ala Thr Ala Lys Ser Gln Leu Ala Ala Leu Thr Val Ala Ala Ala Gly
            20                  25                  30
```

Pro Gln Thr Gly Tyr Ser Arg Asp Leu Phe Pro Thr Trp Ile Thr Ile
            35                  40                  45

Ser Gly Thr Cys Asn Thr Arg Glu Thr Val Leu Lys Arg Asp Gly Thr
 50                  55                  60

Asn Val Val Asp Ser Ala Cys Val Ala Thr Ser Gly Ser Trp Tyr
65                  70                  75                  80

Ser Pro Tyr Asp Gly Ala Thr Trp Thr Ala Ala Ser Asp Val Asp Ile
            85                  90                  95

Asp His Met Val Pro Leu Ser Asn Ala Trp Lys Ser Gly Ala Ser Ala
            100                 105                 110

Trp Thr Thr Ala Gln Arg Gln Thr Phe Ala Asn Asp Leu Thr Asn Pro
            115                 120                 125

Gln Leu Leu Ala Val Thr Asp Asn Val Asn Gln Ala Lys Gly Asp Ser
    130                 135                 140

Gly Pro Glu Asp Trp Lys Pro Ser Leu Thr Ser Tyr Trp Cys Thr Tyr
145                 150                 155                 160

Ala Lys Met Trp Val Lys Val Lys Thr Val Tyr Asp Leu Thr Ile Thr
                165                 170                 175

Ser Ala Glu Lys Thr Ala Leu Thr Thr Met Leu Asn Thr Cys
            180                 185                 190

<210> SEQ ID NO 28
<211> LENGTH: 192
<212> TYPE: PRT
<213> ORGANISM: Setosphaeria rostrata

<400> SEQUENCE: 28

Ala Pro Thr Ser Ser Pro Leu Val Ala Arg Ala Pro Asn Val Pro
1               5                   10                  15

Ser Lys Ala Glu Ala Thr Ser Gln Leu Ala Gly Leu Thr Val Ala Pro
                20                  25                  30

Gln Gly Pro Gln Thr Gly Tyr Ser Arg Asp Leu Phe Pro His Trp Ile
            35                  40                  45

Thr Gln Ser Gly Thr Cys Asn Thr Arg Glu Thr Val Leu Lys Arg Asp
 50                  55                  60

Gly Thr Asn Val Val Thr Asn Ser Ala Cys Ala Ser Thr Ser Gly Ser
65                  70                  75                  80

Trp Phe Ser Pro Tyr Asp Gly Ala Thr Trp Thr Ala Ala Ser Asp Val
            85                  90                  95

Asp Ile Asp His Met Val Pro Leu Ser Asn Ala Trp Lys Ser Gly Ala
            100                 105                 110

Ala Ser Trp Thr Thr Ala Arg Arg Gln Ala Phe Ala Asn Asp Leu Thr
            115                 120                 125

Asn Pro Gln Leu Leu Ala Val Thr Asp Asn Val Asn Gln Ala Lys Gly
    130                 135                 140

Asp Lys Gly Pro Glu Asp Trp Lys Pro Pro Leu Thr Ser Tyr Tyr Cys
145                 150                 155                 160

Thr Tyr Ser Lys Met Trp Ile Lys Val Lys Ser Val Trp Gly Leu Thr
                165                 170                 175

Ile Thr Ser Ala Glu Lys Ser Ala Leu Thr Ser Met Leu Ala Thr Cys
            180                 185                 190

<210> SEQ ID NO 29
<211> LENGTH: 192
<212> TYPE: PRT

<213> ORGANISM: Endophragmiella valdina

<400> SEQUENCE: 29

```
Ala Pro Val Pro Gly His Leu Met Pro Arg Ala Pro Asn Val Pro
1               5                   10                  15

Thr Thr Ala Ala Ala Lys Thr Ala Leu Ala Gly Leu Thr Val Gln Ala
                20                  25                  30

Gln Gly Ser Gln Thr Gly Tyr Ser Arg Asp Leu Phe Pro His Trp Ile
            35                  40                  45

Thr Gln Ser Gly Thr Cys Asn Thr Arg Glu Val Val Leu Lys Arg Asp
        50                  55                  60

Gly Thr Asn Val Val Thr Asp Ser Ala Cys Ala Ala Thr Ser Gly Thr
65                  70                  75                  80

Trp Val Ser Pro Tyr Asp Gly Ala Thr Trp Thr Ala Ala Ser Asp Val
                85                  90                  95

Asp Ile Asp His Met Val Pro Leu Ser Asn Ala Trp Lys Ser Gly Ala
            100                 105                 110

Ala Ser Trp Thr Thr Ala Gln Arg Gln Ala Phe Ala Asn Asp Leu Thr
        115                 120                 125

Asn Pro Gln Leu Leu Ala Val Thr Asp Asn Val Asn Gln Ser Lys Gly
    130                 135                 140

Asp Lys Gly Pro Glu Asp Trp Lys Pro Pro Leu Thr Ser Tyr Tyr Cys
145                 150                 155                 160

Thr Tyr Ala Lys Met Trp Val Lys Val Lys Ser Val Tyr Ser Leu Thr
                165                 170                 175

Ile Thr Ser Ala Glu Lys Thr Ala Leu Thr Ser Met Leu Asn Thr Cys
            180                 185                 190
```

<210> SEQ ID NO 30
<211> LENGTH: 190
<212> TYPE: PRT
<213> ORGANISM: Corynespora cassiicola

<400> SEQUENCE: 30

```
Leu Pro Ala Pro Leu Val Pro Arg Ala Pro Gly Ile Pro Thr Thr
1               5                   10                  15

Ser Ala Ala Arg Ser Gln Leu Ala Gly Leu Thr Val Ala Ala Gln Gly
                20                  25                  30

Pro Gln Thr Gly Tyr Ser Arg Asp Leu Phe Pro His Trp Ile Thr Gln
            35                  40                  45

Ser Gly Ser Cys Asn Thr Arg Glu Val Val Leu Ala Arg Asp Gly Thr
        50                  55                  60

Gly Val Val Gln Asp Ser Ser Cys Ala Ala Thr Ser Gly Thr Trp Arg
65                  70                  75                  80

Ser Pro Phe Asp Gly Ala Thr Trp Thr Ala Ala Ser Asp Val Asp Ile
                85                  90                  95

Asp His Met Val Pro Leu Ser Asn Ala Trp Lys Ser Gly Ala Ala Ser
            100                 105                 110

Trp Thr Thr Ser Arg Arg Gln Ala Phe Ala Asn Asp Leu Thr Asn Pro
        115                 120                 125

Gln Leu Ile Ala Val Thr Asp Asn Val Asn Gln Ser Lys Gly Asp Lys
    130                 135                 140

Gly Pro Glu Asp Trp Lys Pro Pro Leu Thr Ser Tyr Tyr Cys Thr Tyr
145                 150                 155                 160

Ala Lys Met Trp Val Arg Val Lys Ser Val Tyr Ser Leu Thr Ile Thr
```

165                 170                 175

Ser Ala Glu Lys Ser Ala Leu Thr Ser Met Leu Asp Thr Cys
            180                 185                 190

<210> SEQ ID NO 31
<211> LENGTH: 192
<212> TYPE: PRT
<213> ORGANISM: Paraphoma sp. XZ1965

<400> SEQUENCE: 31

Ala Pro Ala Pro Val His Leu Val Ala Arg Ala Pro Asn Val Pro
1               5                   10                  15

Thr Ala Ala Gln Ala Gln Thr Gln Leu Ala Gly Leu Thr Val Ala Ala
            20                  25                  30

Gln Gly Pro Gln Thr Gly Tyr Ser Arg Asp Leu Phe Pro His Trp Ile
            35                  40                  45

Thr Gln Ser Gly Ala Cys Asn Thr Arg Glu Thr Val Leu Lys Arg Asp
        50                  55                  60

Gly Thr Gly Val Val Gln Asp Ser Ala Cys Ala Ala Thr Ser Gly Thr
65                  70                  75                  80

Trp Lys Ser Pro Tyr Asp Gly Ala Thr Trp Thr Ala Ala Ser Asp Val
                85                  90                  95

Asp Ile Asp His Met Val Pro Leu Ser Asn Ala Trp Lys Ser Gly Ala
                100                 105                 110

Ala Ser Trp Thr Thr Ala Arg Arg Gln Ala Phe Ala Asn Asp Leu Thr
            115                 120                 125

Asn Pro Gln Leu Leu Ala Val Thr Asp Asn Val Asn Gln Ala Lys Gly
        130                 135                 140

Asp Lys Gly Pro Glu Asp Trp Lys Pro Pro Leu Thr Ser Tyr Tyr Cys
145                 150                 155                 160

Ile Tyr Ala Arg Met Trp Ile Lys Val Lys Ser Val Tyr Ser Leu Thr
                165                 170                 175

Ile Thr Ser Ala Glu Lys Ser Ala Leu Thr Ser Met Leu Gly Thr Cys
            180                 185                 190

<210> SEQ ID NO 32
<211> LENGTH: 186
<212> TYPE: PRT
<213> ORGANISM: Monilinia fructicola

<400> SEQUENCE: 32

Thr Pro Val Pro Ala Pro Thr Gly Ile Pro Ser Thr Ser Val Ala Asn
1               5                   10                  15

Thr Gln Leu Ala Ala Leu Thr Val Ala Ala Ala Gly Ser Gln Asp Gly
            20                  25                  30

Tyr Ser Arg Asp Leu Phe Pro His Trp Ile Thr Ile Ser Gly Ala Cys
            35                  40                  45

Asn Thr Arg Glu Thr Val Leu Lys Arg Asp Gly Thr Asn Val Val Val
        50                  55                  60

Asn Ser Ala Cys Ala Ala Thr Ser Gly Thr Trp Val Ser Pro Tyr Asp
65                  70                  75                  80

Gly Ala Thr Trp Thr Ala Ala Ser Asp Val Asp Ile Asp His Leu Val
                85                  90                  95

Pro Leu Ser Asn Ala Trp Lys Ala Gly Ala Ser Ser Trp Thr Thr Ala
            100                 105                 110

Gln Arg Gln Ala Phe Ala Asn Asp Leu Val Asn Pro Gln Leu Leu Ala

```
            115                 120                 125
Val Thr Asp Ser Val Asn Gln Gly Lys Ser Asp Ser Gly Pro Glu Ala
            130                 135                 140
Trp Lys Pro Ser Leu Lys Ser Tyr Trp Cys Thr Tyr Ala Lys Met Trp
145                 150                 155                 160
Ile Lys Val Lys Tyr Val Tyr Asp Leu Thr Ile Thr Ser Ala Glu Lys
                165                 170                 175
Ser Ala Leu Val Thr Met Met Asp Thr Cys
            180                 185

<210> SEQ ID NO 33
<211> LENGTH: 190
<212> TYPE: PRT
<213> ORGANISM: Curvularia lunata

<400> SEQUENCE: 33

Ala Pro Ala Pro Leu Ser Ala Arg Ala Pro Asn Ile Pro Ser Lys
1               5                   10                  15
Ala Asp Ala Thr Ser Gln Leu Ala Gly Leu Thr Val Ala Ala Gln Gly
                20                  25                  30
Pro Gln Thr Gly Tyr Ser Arg Asp Leu Phe Pro His Trp Ile Thr Gln
            35                  40                  45
Ser Gly Thr Cys Asn Thr Arg Glu Thr Val Leu Lys Arg Asp Gly Thr
        50                  55                  60
Asn Val Val Thr Ser Ser Cys Ala Ala Thr Ser Gly Thr Trp Phe
65                  70                  75                  80
Ser Pro Tyr Asp Gly Ala Thr Trp Thr Ala Ala Ser Asp Val Asp Ile
                85                  90                  95
Asp His Val Val Pro Leu Ser Asn Ala Trp Lys Ser Gly Ala Ala Ser
                100                 105                 110
Trp Thr Thr Ala Arg Arg Gln Ala Phe Ala Asn Asp Leu Thr Asn Pro
            115                 120                 125
Gln Leu Ile Ala Val Thr Asp Ser Val Asn Gln Ala Lys Gly Asp Lys
        130                 135                 140
Gly Pro Glu Asp Trp Lys Pro Pro Leu Ser Ser Tyr Tyr Cys Thr Tyr
145                 150                 155                 160
Ser Lys Met Trp Ile Lys Val Lys Ser Val Tyr Gly Leu Thr Val Thr
                165                 170                 175
Ser Ala Glu Lys Ser Ala Leu Ser Ser Met Leu Ala Thr Cys
                180                 185                 190

<210> SEQ ID NO 34
<211> LENGTH: 191
<212> TYPE: PRT
<213> ORGANISM: Penicillium reticulisporum

<400> SEQUENCE: 34

Leu Pro Ala Pro Glu Ala Leu Pro Ala Pro Gly Val Pro Ser Ala
1               5                   10                  15
Ser Thr Ala Gln Ser Glu Leu Ala Ala Leu Thr Val Ala Ala Gln Gly
                20                  25                  30
Ser Gln Asp Gly Tyr Ser Arg Ser Lys Phe Pro His Trp Ile Thr Gln
            35                  40                  45
Ser Gly Ser Cys Asp Thr Arg Asp Val Val Leu Lys Arg Asp Gly Thr
        50                  55                  60
Asn Val Val Gln Ser Ala Ser Gly Cys Thr Ile Thr Ser Gly Lys Trp
```

```
                65                  70                  75                  80
Val Ser Pro Tyr Asp Gly Ala Thr Trp Thr Ala Ser Ser Asp Val Asp
                    85                  90                  95

Ile Asp His Leu Val Pro Leu Ser Asn Ala Trp Lys Ser Gly Ala Ser
                100                 105                 110

Gly Trp Thr Thr Ala Ala Arg Gln Ala Phe Ala Asn Asp Leu Thr Asn
                115                 120                 125

Pro Gln Leu Leu Val Val Thr Asp Asn Val Asn Glu Ser Lys Gly Asp
                130                 135                 140

Lys Gly Pro Glu Glu Trp Lys Pro Pro Leu Thr Ser Tyr Tyr Cys Thr
145                 150                 155                 160

Tyr Ala Glu Met Trp Val Lys Val Lys Ser Val Tyr Lys Leu Thr Ile
                165                 170                 175

Thr Ser Ala Glu Lys Ser Ala Leu Thr Ser Met Leu Ser Thr Cys
                180                 185                 190

<210> SEQ ID NO 35
<211> LENGTH: 191
<212> TYPE: PRT
<213> ORGANISM: Penicillium quercetorum

<400> SEQUENCE: 35

Leu Pro Ala Pro Glu Pro Ala Pro Ser Pro Gly Ile Pro Ser Ala
1               5                   10                  15

Ser Thr Ala Arg Ser Glu Leu Ala Ser Leu Thr Val Ala Pro Gln Gly
                20                  25                  30

Ser Gln Asp Gly Tyr Ser Arg Ala Lys Phe Pro His Trp Ile Lys Gln
                35                  40                  45

Ser Gly Ser Cys Asp Thr Arg Asp Val Val Leu Glu Arg Asp Gly Thr
50                  55                  60

Asn Val Val Gln Ser Ser Thr Gly Cys Thr Ile Thr Gly Gly Thr Trp
65                  70                  75                  80

Val Ser Pro Tyr Asp Gly Ala Thr Trp Thr Ala Ser Ser Asp Val Asp
                85                  90                  95

Ile Asp His Leu Val Pro Leu Ser Asn Ala Trp Lys Ser Gly Ala Ser
                100                 105                 110

Ala Trp Thr Thr Ala Gln Arg Gln Ala Phe Ala Asn Asp Leu Thr Asn
                115                 120                 125

Pro Gln Leu Val Ala Val Thr Asp Asn Val Asn Glu Ala Lys Gly Asp
                130                 135                 140

Lys Gly Pro Glu Glu Trp Lys Pro Pro Leu Thr Ser Tyr Tyr Cys Thr
145                 150                 155                 160

Tyr Ala Glu Met Trp Val Lys Val Lys Ser Val Tyr Lys Leu Thr Ile
                165                 170                 175

Thr Ser Ala Glu Lys Ser Ala Leu Ser Ser Met Leu Asn Thr Cys
                180                 185                 190

<210> SEQ ID NO 36
<211> LENGTH: 192
<212> TYPE: PRT
<213> ORGANISM: Setophaeosphaeria sp.

<400> SEQUENCE: 36

Leu Pro Ala Pro Val Thr Leu Glu Ala Arg Ala Pro Pro Asn Ile Pro
1               5                   10                  15

Ser Thr Ala Ser Ala Asn Thr Leu Leu Ala Gly Leu Thr Val Ala Ala
```

```
                 20                  25                  30
Gln Gly Ser Gln Thr Gly Tyr Ser Arg Asp Leu Phe Pro His Trp Ile
             35                  40                  45

Thr Gln Ser Gly Thr Cys Asn Thr Arg Glu Thr Val Leu Lys Arg Asp
         50                  55                  60

Gly Thr Gly Val Val Thr Asp Ser Ala Cys Ala Ser Thr Ser Gly Ser
 65                  70                  75                  80

Trp Tyr Ser Val Tyr Asp Gly Ala Thr Trp Thr Ala Ala Ser Asp Val
                 85                  90                  95

Asp Ile Asp His Val Val Pro Leu Ser Asn Ala Trp Lys Ser Gly Ala
             100                 105                 110

Ala Ser Trp Thr Thr Ala Arg Arg Gln Ser Phe Ala Asn Asp Leu Thr
         115                 120                 125

Asn Pro Gln Leu Ile Ala Val Thr Asp Asn Val Asn Gln Ala Lys Gly
     130                 135                 140

Asp Lys Gly Pro Glu Asp Trp Lys Pro Pro Leu Thr Ser Tyr Tyr Cys
145                 150                 155                 160

Thr Tyr Ala Lys Met Trp Val Lys Val Lys Ser Val Tyr Ser Leu Thr
                 165                 170                 175

Ile Thr Ser Ala Glu Lys Thr Ala Leu Thr Ser Met Leu Asn Thr Cys
             180                 185                 190

<210> SEQ ID NO 37
<211> LENGTH: 192
<212> TYPE: PRT
<213> ORGANISM: Alternaria sp. XZ2545

<400> SEQUENCE: 37

Leu Pro Ala Pro Val Thr Leu Glu Ala Arg Ala Pro Pro Asn Ile Pro
  1               5                  10                  15

Thr Thr Ala Ala Ala Lys Thr Gln Leu Ala Gly Leu Thr Val Ala Ala
                 20                  25                  30

Gln Gly Pro Gln Thr Gly Tyr Ser Arg Asp Leu Phe Pro His Trp Ile
             35                  40                  45

Thr Gln Ser Gly Thr Cys Asn Thr Arg Glu Thr Val Leu Lys Arg Asp
         50                  55                  60

Gly Thr Gly Val Val Thr Asp Ser Ala Cys Ala Ser Thr Ser Gly Ser
 65                  70                  75                  80

Trp Phe Ser Val Tyr Asp Gly Ala Thr Trp Thr Ala Ala Ser Asp Val
                 85                  90                  95

Asp Ile Asp His Val Val Pro Leu Ser Asn Ala Trp Lys Ser Gly Ala
             100                 105                 110

Ala Ser Trp Thr Thr Ala Arg Arg Gln Ser Phe Ala Asn Asp Leu Thr
         115                 120                 125

Asn Pro Gln Leu Ile Ala Val Thr Asp Asn Val Asn Gln Ala Lys Gly
     130                 135                 140

Asp Lys Gly Pro Glu Asp Trp Lys Pro Pro Leu Thr Ser Tyr Tyr Cys
145                 150                 155                 160

Thr Tyr Ala Lys Met Trp Val Lys Val Lys Ser Val Tyr Ala Leu Thr
                 165                 170                 175

Ile Thr Ser Ala Glu Lys Thr Ala Leu Thr Ser Met Leu Asn Thr Cys
             180                 185                 190

<210> SEQ ID NO 38
<211> LENGTH: 192
```

<212> TYPE: PRT
<213> ORGANISM: Alternaria sp.

<400> SEQUENCE: 38

```
Leu Pro Ala Pro Val Thr Leu Glu Ala Arg Ala Pro Asn Ile Pro
1               5                   10                  15

Thr Thr Ala Ala Ala Lys Thr Gln Leu Ala Gly Leu Thr Val Ala Ala
                20                  25                  30

Gln Gly Pro Gln Thr Gly Tyr Ser Arg Asp Leu Phe Pro His Trp Ile
            35                  40                  45

Thr Gln Ser Gly Ser Cys Asn Thr Arg Glu Val Val Leu Gln Arg Asp
        50                  55                  60

Gly Thr Gly Val Val Thr Asp Ser Ala Cys Ala Ala Thr Ser Gly Ser
65                  70                  75                  80

Trp Tyr Ser Val Tyr Asp Gly Ala Thr Trp Thr Ala Ala Ser Asp Val
                85                  90                  95

Asp Ile Asp His Met Val Pro Leu Ser Asn Ala Trp Lys Ser Gly Ala
                100                 105                 110

Ala Ser Trp Thr Thr Ala Arg Arg Gln Ala Phe Ala Asn Asp Leu Thr
            115                 120                 125

Asn Pro Gln Leu Leu Ala Val Thr Asp Asn Val Asn Gln Ala Lys Gly
        130                 135                 140

Asp Lys Gly Pro Glu Asp Trp Lys Pro Pro Leu Thr Ser Tyr Tyr Cys
145                 150                 155                 160

Thr Tyr Ala Lys Met Trp Val Lys Val Lys Ser Val Tyr Ala Leu Thr
                165                 170                 175

Ile Thr Ser Ala Glu Lys Thr Ala Leu Thr Ser Met Leu Asn Thr Cys
            180                 185                 190
```

<210> SEQ ID NO 39
<211> LENGTH: 186
<212> TYPE: PRT
<213> ORGANISM: Trichoderma reesei

<400> SEQUENCE: 39

```
Ala Pro Leu Pro Ala Pro Gly Ile Pro Ser Glu Asp Thr Ala Arg
1               5                   10                  15

Thr Gln Leu Ala Gly Leu Thr Val Ala Val Gly Ser Gly Thr Gly
                20                  25                  30

Tyr Ser Arg Asp Leu Phe Pro Thr Trp Asp Ala Ile Ser Gly Asn Cys
            35                  40                  45

Asn Ala Arg Glu Tyr Val Leu Lys Arg Asp Gly Glu Gly Val Gln Val
        50                  55                  60

Asn Asn Ala Cys Glu Ala Gln Ser Gly Ser Trp Ile Ser Pro Tyr Asp
65                  70                  75                  80

Asn Ala Ser Phe Thr Asn Ala Ser Ser Leu Asp Ile Asp His Met Val
                85                  90                  95

Pro Leu Lys Asn Ala Trp Ile Ser Gly Ala Ser Thr Trp Thr Thr Ala
                100                 105                 110

Gln Arg Glu Ala Leu Ala Asn Asp Val Ser Arg Pro Gln Leu Trp Ala
            115                 120                 125

Val Ser Ala Ser Ser Asn Arg Ser Lys Gly Asp Arg Ser Pro Asp Gln
        130                 135                 140

Trp Lys Pro Pro Leu Thr Ser Phe Tyr Cys Thr Tyr Ala Lys Ser Trp
145                 150                 155                 160
```

Ile Asp Val Lys Ser Tyr Tyr Lys Leu Thr Ile Thr Ser Ala Glu Lys
165                 170                 175

Thr Ala Leu Ser Ser Met Leu Asp Thr Cys
            180                 185

<210> SEQ ID NO 40
<211> LENGTH: 188
<212> TYPE: PRT
<213> ORGANISM: Chaetomium thermophilum

<400> SEQUENCE: 40

Ala Pro Ala Pro Gln Pro Thr Pro Pro Gly Ile Pro Ser Arg Ser Thr
1               5                   10                  15

Ala Gln Ser Tyr Leu Asn Ser Leu Thr Val Ala Ala Ser Tyr Asp Asp
            20                  25                  30

Gly Asn Tyr Asn Arg Asp Leu Phe Pro His Trp Asn Thr Val Ser Gly
        35                  40                  45

Thr Cys Asn Thr Arg Glu Tyr Val Leu Lys Arg Asp Gly Ser Asn Val
50                  55                  60

Val Thr Asn Ser Ala Cys Gln Ala Thr Ser Gly Thr Trp Tyr Ser Pro
65                  70                  75                  80

Tyr Asp Gly Ala Thr Trp Thr Ala Ala Ser Asp Ile Asp Ile Asp His
                85                  90                  95

Met Val Pro Leu Lys Asn Ala Trp Ile Ser Gly Ala Asn Thr Trp Ser
            100                 105                 110

Ser Ser Lys Arg Ser Ser Phe Ala Asn Asp Ile Asn Ser Pro Gln Leu
        115                 120                 125

Trp Ala Val Thr Asp Ser Val Asn Gln Ser Lys Gly Asp Lys Ser Pro
130                 135                 140

Asp Lys Trp Lys Pro Pro Leu Thr Thr Phe Tyr Cys Thr Tyr Ala Lys
145                 150                 155                 160

Ser Trp Ile Thr Val Lys Tyr Asn Tyr Asn Leu Thr Ile Thr Ser Ala
                165                 170                 175

Glu Lys Ser Ala Leu Gln Asn Met Ile Asn Thr Cys
            180                 185

<210> SEQ ID NO 41
<211> LENGTH: 190
<212> TYPE: PRT
<213> ORGANISM: Scytalidium thermophilum

<400> SEQUENCE: 41

Leu Pro Ala Pro Ala Pro Met Pro Thr Pro Pro Gly Ile Pro Ser Lys
1               5                   10                  15

Ser Thr Ala Gln Ser Gln Leu Asn Ala Leu Thr Val Lys Ala Ser Tyr
            20                  25                  30

Asp Asp Gly Lys Tyr Lys Arg Asp Leu Phe Pro His Trp Asn Thr Val
        35                  40                  45

Ser Gly Thr Cys Asn Thr Arg Glu Tyr Val Leu Lys Arg Asp Gly Val
50                  55                  60

Asn Val Val Thr Asn Ser Ala Cys Ala Ala Thr Ser Gly Thr Trp Tyr
65                  70                  75                  80

Ser Pro Phe Asp Gly Ala Thr Trp Thr Ala Ala Ser Asp Val Asp Ile
                85                  90                  95

Asp His Met Val Pro Leu Lys Asn Ala Trp Ile Ser Gly Ala Asn Asn
            100                 105                 110

Trp Thr Ser Thr Lys Arg Thr Gln Phe Ala Asn Asp Ile Asn Leu Pro
            115                 120                 125

Gln Leu Trp Ala Val Thr Asp Val Asn Gln Ala Lys Gly Asp Lys
    130                 135                 140

Ser Pro Asp Lys Trp Lys Pro Leu Thr Ser Phe Tyr Cys Thr Tyr
145                 150                 155                 160

Ala Lys Ser Trp Ile Thr Val Lys Tyr Asn Tyr Gly Leu Ser Ile Thr
                165                 170                 175

Ser Ala Glu Lys Ser Ala Leu Thr Ser Met Ile Asn Thr Cys
            180                 185                 190

<210> SEQ ID NO 42
<211> LENGTH: 186
<212> TYPE: PRT
<213> ORGANISM: Metapochonia suchlasporia

<400> SEQUENCE: 42

Val Pro Val Pro Ala Pro Pro Gly Ile Pro Ser Thr Ser Thr Ala Lys
1               5                   10                  15

Thr Leu Leu Ala Gly Leu Lys Val Ala Val Pro Leu Ser Gly Asp Gly
            20                  25                  30

Tyr Ser Arg Glu Lys Phe Pro Leu Trp Glu Thr Ile Gln Gly Thr Cys
        35                  40                  45

Asn Ala Arg Glu Phe Val Leu Lys Arg Asp Gly Thr Asp Val Lys Thr
50                  55                  60

Asn Asn Ala Cys Val Ala Glu Ser Gly Asn Trp Val Ser Pro Tyr Asp
65                  70                  75                  80

Gly Val Lys Phe Thr Ala Ala Arg Asp Leu Asp Ile Asp His Met Val
                85                  90                  95

Pro Leu Lys Asn Ala Trp Ile Ser Gly Ala Ser Gln Trp Thr Thr Glu
            100                 105                 110

Arg Arg Lys Ala Leu Ala Asn Asp Ile Thr Arg Pro Gln Leu Trp Ala
        115                 120                 125

Val Ser Ala His Ala Asn Arg Gly Lys Ser Asp Asp Ser Pro Asp Glu
    130                 135                 140

Trp Lys Pro Pro Leu Lys Thr Phe Trp Cys Thr Tyr Ala Lys Ser Trp
145                 150                 155                 160

Val Gln Val Lys Ser Phe Tyr Glu Leu Thr Ile Thr Asp Ala Glu Lys
                165                 170                 175

Gly Ala Leu Ala Gly Met Leu Asp Ser Cys
            180                 185

<210> SEQ ID NO 43
<211> LENGTH: 198
<212> TYPE: PRT
<213> ORGANISM: Daldinia fissa

<400> SEQUENCE: 43

Ala Pro Ala Pro Ile Pro Val Ala Glu Pro Ala Pro Met Pro Met Pro
1               5                   10                  15

Thr Pro Pro Gly Ile Pro Ser Ala Ser Ser Ala Lys Ser Gln Leu Ala
            20                  25                  30

Ser Leu Thr Val Lys Ala Ala Val Asp Asp Gly Gly Tyr Gln Arg Asp
        35                  40                  45

Leu Phe Pro Thr Trp Asp Thr Ile Thr Gly Thr Cys Asn Thr Arg Glu
50                  55                  60

```
Tyr Val Leu Lys Arg Asp Gly Ala Asn Val Gln Val Gly Ser Asp Cys
 65                  70                  75                  80

Tyr Pro Thr Ser Gly Thr Trp Thr Ser Pro Tyr Asp Gly Gly Lys Trp
                 85                  90                  95

Thr Ser Pro Ser Asp Val Asp Ile Asp His Met Val Pro Leu Lys Asn
            100                 105                 110

Ala Trp Val Ser Gly Ala Asn Lys Trp Thr Thr Ala Lys Arg Glu Gln
        115                 120                 125

Phe Ala Asn Asp Val Asp Arg Pro Gln Leu Trp Ala Val Thr Asp Asn
    130                 135                 140

Val Asn Ser Ser Lys Gly Asp Lys Ser Pro Asp Thr Trp Lys Pro Pro
145                 150                 155                 160

Leu Thr Ser Phe Tyr Cys Thr Tyr Ala Ser Ala Tyr Val Ala Val Lys
                165                 170                 175

Ser Tyr Trp Gly Leu Thr Ile Thr Ser Ala Glu Lys Ser Ala Leu Ser
                180                 185                 190

Asp Met Leu Gly Thr Cys
                195

<210> SEQ ID NO 44
<211> LENGTH: 188
<212> TYPE: PRT
<213> ORGANISM: Acremonium sp. XZ2007

<400> SEQUENCE: 44

Leu Pro Leu Gln Ser Arg Asp Pro Pro Gly Ile Pro Ser Thr Ala Thr
  1               5                  10                  15

Ala Lys Ser Leu Leu Asn Gly Leu Thr Val Lys Ala Trp Ser Asn Glu
                 20                  25                  30

Gly Thr Tyr Asp Arg Asp Leu Phe Pro His Trp Gln Thr Ile Glu Gly
             35                  40                  45

Thr Cys Asn Ala Arg Glu Tyr Val Leu Lys Arg Asp Gly Gln Asn Val
         50                  55                  60

Val Val Asn Ser Ala Cys Thr Ala Gln Ser Gly Thr Trp Lys Ser Val
 65                  70                  75                  80

Tyr Asp Gly Glu Thr Thr Asn Ser Ala Ser Asp Leu Asp Ile Asp His
                 85                  90                  95

Met Ile Pro Leu Lys Asn Ala Trp Ile Ser Gly Ala Ala Thr Trp Thr
            100                 105                 110

Thr Ala Gln Arg Thr Ser Phe Ala Asn Asp Ile Ser Ser Pro Gln Leu
        115                 120                 125

Trp Ala Val Thr Ala Gly Val Asn Arg Ser Lys Ser Asp Arg Ser Pro
    130                 135                 140

Asp Thr Trp Val Pro Pro Leu Ala Ser Phe His Cys Thr Tyr Gly Lys
145                 150                 155                 160

Ala Trp Val Gln Val Lys Ser Lys Trp Ala Leu Ser Ile Thr Ser Ala
                165                 170                 175

Glu Lys Ser Ala Leu Thr Gly Leu Leu Asn Lys Cys
                180                 185

<210> SEQ ID NO 45
<211> LENGTH: 182
<212> TYPE: PRT
<213> ORGANISM: Acremonium dichromosporum

<400> SEQUENCE: 45
```

```
Ile Pro Pro Gly Ile Pro Ser Glu Ala Thr Ala Arg Ser Leu Leu Ser
1               5                   10                  15

Ser Leu Thr Val Ala Pro Thr Val Asp Asp Gly Thr Tyr Asp Arg Asp
                20                  25                  30

Leu Phe Pro His Trp Ser Ser Val Glu Gly Asn Cys Asn Ala Arg Glu
            35                  40                  45

Phe Val Leu Arg Arg Asp Gly Asp Gly Val Ser Val Gly Asn Asp Cys
        50                  55                  60

Tyr Pro Thr Ala Gly Thr Trp Thr Cys Pro Tyr Asp Gly Lys Arg His
65                  70                  75                  80

Ser Val Pro Ser Asp Val Ser Ile Asp His Met Val Pro Leu His Asn
                85                  90                  95

Ala Trp Met Thr Gly Ala Ser Glu Trp Thr Thr Ala Glu Arg Glu Ala
                100                 105                 110

Phe Ala Asn Asp Ile Asp Gly Pro Gln Leu Trp Ala Val Thr Ser Thr
            115                 120                 125

Thr Asn Ser Gln Lys Gly Ser Asp Ala Pro Asp Glu Trp Gln Pro Pro
        130                 135                 140

Gln Thr Ser Ile His Cys Lys Tyr Ala Ala Trp Ile Gln Val Lys
145                 150                 155                 160

Ser Thr Tyr Asp Leu Thr Val Ser Ser Ala Glu Gln Ala Ala Leu Glu
                165                 170                 175

Glu Met Leu Gly Arg Cys
            180
```

<210> SEQ ID NO 46
<211> LENGTH: 188
<212> TYPE: PRT
<213> ORGANISM: Sarocladium sp. XZ2014

<400> SEQUENCE: 46

```
Val Pro Ile Pro Leu Pro Asp Pro Pro Gly Ile Pro Ser Ser Ser Thr
1               5                   10                  15

Ala Asn Thr Leu Leu Ala Gly Leu Thr Val Arg Ala Ser Ser Asn Glu
                20                  25                  30

Asp Thr Tyr Asn Arg Asp Leu Phe Pro His Trp Val Ala Ile Ser Gly
            35                  40                  45

Asn Cys Asn Ala Arg Glu Tyr Val Leu Arg Arg Asp Gly Thr Asn Val
        50                  55                  60

Val Val Asn Thr Ala Cys Val Pro Gln Ser Gly Thr Trp Arg Ser Pro
65                  70                  75                  80

Tyr Asp Gly Glu Ser Thr Thr Asn Ala Ser Asp Leu Asp Ile Asp His
                85                  90                  95

Met Val Pro Leu Lys Asn Ala Trp Ile Ser Gly Ala Ala Ser Trp Thr
                100                 105                 110

Thr Ala Lys Arg Gln Asp Phe Ala Asn Asp Val Ser Gly Pro Gln Leu
            115                 120                 125

Trp Ala Val Thr Ala Gly Val Asn Arg Ser Lys Gly Asp Lys Ser Pro
        130                 135                 140

Asp Ser Trp Val Pro Leu Ala Ser Phe His Cys Thr Tyr Ala Arg
145                 150                 155                 160

Ser Trp Ile Gln Val Lys Ser Ser Trp Ala Leu Ser Val Thr Ser Ala
                165                 170                 175

Glu Lys Ala Ala Leu Thr Asp Leu Leu Ser Thr Cys
            180                 185
```

<210> SEQ ID NO 47
<211> LENGTH: 186
<212> TYPE: PRT
<213> ORGANISM: Metarhizium sp. HNA15-2

<400> SEQUENCE: 47

```
Val Pro Val Pro Ala Pro Pro Gly Ile Pro Thr Ala Ser Thr Ala Arg
1               5                   10                  15

Thr Leu Leu Ala Gly Leu Lys Val Ala Thr Pro Leu Ser Gly Asp Gly
            20                  25                  30

Tyr Ser Arg Thr Leu Phe Pro Thr Trp Glu Thr Ile Glu Gly Thr Cys
        35                  40                  45

Asn Ala Arg Glu Phe Val Leu Lys Arg Asp Gly Thr Asp Val Gln Thr
    50                  55                  60

Asn Thr Ala Cys Val Ala Gln Ser Gly Asn Trp Val Ser Pro Tyr Asp
65                  70                  75                  80

Gly Val Ala Phe Thr Ala Ala Ser Asp Leu Asp Ile Asp His Met Val
                85                  90                  95

Pro Leu Lys Asn Ala Trp Ile Ser Gly Ala Ser Gln Trp Thr Thr Asp
            100                 105                 110

Lys Arg Lys Gly Leu Ala Asn Asp Ile Thr Arg Pro Gln Leu Trp Ala
        115                 120                 125

Val Ser Ala His Ala Asn Arg Ala Lys Gly Asp Ser Ser Pro Asp Glu
    130                 135                 140

Trp Lys Pro Pro Leu Lys Thr Phe Trp Cys Thr Tyr Ala Arg Ser Trp
145                 150                 155                 160

Val Gln Val Lys Ser Tyr Tyr Ala Leu Thr Ile Thr Asp Ala Glu Lys
                165                 170                 175

Gly Ala Leu Ser Gly Met Leu Asp Ser Cys
            180                 185
```

<210> SEQ ID NO 48
<211> LENGTH: 188
<212> TYPE: PRT
<213> ORGANISM: Acremonium sp. XZ2414

<400> SEQUENCE: 48

```
Ala Pro Ile Ala Val Arg Asp Pro Pro Gly Ile Pro Ser Ala Ser Thr
1               5                   10                  15

Ala Asn Thr Leu Leu Ala Gly Leu Thr Val Arg Ala Ser Ser Asn Glu
            20                  25                  30

Asp Ser Tyr Asp Arg Asn Leu Phe Pro His Trp Ser Ala Ile Ser Gly
        35                  40                  45

Asn Cys Asn Ala Arg Glu Phe Val Leu Glu Arg Asp Gly Thr Asn Val
    50                  55                  60

Val Val Asn Asn Ala Cys Val Ala Gln Ser Gly Thr Trp Arg Ser Pro
65                  70                  75                  80

Tyr Asp Gly Glu Thr Thr Gly Asn Ala Ser Asp Leu Asp Ile Asp His
                85                  90                  95

Met Val Pro Leu Lys Asn Ala Trp Ile Ser Gly Ala Ser Ser Trp Ser
            100                 105                 110

Thr Thr Arg Arg Gln Glu Phe Ala Asn Asp Val Ser Gly Pro Gln Leu
        115                 120                 125

Trp Ala Val Thr Ala Gly Val Asn Arg Ser Lys Gly Asp Arg Ser Pro
130                 135                 140
```

-continued

Asp Ser Trp Val Pro Pro Leu Ala Ser Phe His Cys Thr Tyr Ala Lys
145                 150                 155                 160

Ser Trp Val Gln Val Lys Ser Ser Trp Ser Leu Ser Val Thr Ser Ala
            165                 170                 175

Glu Lys Ala Ala Leu Ser Asp Leu Leu Gly Thr Cys
        180                 185

<210> SEQ ID NO 49
<211> LENGTH: 186
<212> TYPE: PRT
<213> ORGANISM: Isaria tenuipes

<400> SEQUENCE: 49

Ala Pro Val Pro Glu Pro Pro Gly Ile Pro Ser Thr Ser Thr Ala Gln
1               5                   10                  15

Ser Asp Leu Asn Ser Leu Gln Val Ala Ala Ser Gly Ser Gly Asp Gly
            20                  25                  30

Tyr Ser Arg Ala Glu Phe Pro His Trp Val Ser Val Glu Gly Ser Cys
        35                  40                  45

Asp Ser Arg Glu Tyr Val Leu Lys Arg Asp Gly Gln Asp Val Gln Ala
    50                  55                  60

Asp Ser Ser Cys Lys Ile Thr Ser Gly Thr Trp Val Ser Pro Tyr Asp
65                  70                  75                  80

Ala Thr Thr Trp Thr Asn Ser Ser Lys Val Asp Ile Asp His Leu Val
                85                  90                  95

Pro Leu Lys Asn Ala Trp Ile Ser Gly Ala Ser Ser Trp Thr Lys Ala
            100                 105                 110

Gln Arg Gln Asp Phe Ala Asn Asp Ile Lys Arg Pro Gln Leu Tyr Ala
        115                 120                 125

Val Ser Glu Asn Ala Asn Arg Ser Lys Gly Asp Arg Ser Pro Asp Gly
    130                 135                 140

Trp Lys Pro Pro Leu Lys Ser Phe Tyr Cys Thr Tyr Ala Lys Ser Trp
145                 150                 155                 160

Val Ala Val Lys Ser Tyr Tyr Lys Leu Thr Ile Thr Ser Ala Glu Lys
                165                 170                 175

Ser Ala Leu Gly Asp Met Leu Asp Thr Cys
            180                 185

<210> SEQ ID NO 50
<211> LENGTH: 184
<212> TYPE: PRT
<213> ORGANISM: Scytalidium circinatum

<400> SEQUENCE: 50

Ala Pro Pro Gly Ile Pro Ser Ala Ser Thr Ala Ser Ser Leu Leu Gly
1               5                   10                  15

Glu Leu Ala Val Ala Glu Pro Val Asp Asp Gly Ser Tyr Asp Arg Asp
            20                  25                  30

Leu Phe Pro His Trp Glu Pro Ile Pro Gly Glu Thr Ala Cys Ser Ala
        35                  40                  45

Arg Glu Tyr Val Leu Arg Arg Asp Gly Thr Gly Val Glu Thr Gly Ser
    50                  55                  60

Asp Cys Tyr Pro Thr Ser Gly Thr Trp Ser Ser Pro Tyr Asp Gly Gly
65                  70                  75                  80

Ser Trp Thr Ala Pro Ser Asp Val Asp Ile Asp His Met Val Pro Leu
                85                  90                  95

```
Lys Asn Ala Trp Ile Ser Gly Ala Ser Glu Trp Thr Thr Ala Glu Arg
            100                 105                 110

Glu Ala Phe Ala Asn Asp Ile Asp Gly Pro Gln Leu Trp Ala Val Thr
        115                 120                 125

Asp Glu Val Asn Gln Ser Lys Ser Asp Gln Ser Pro Asp Glu Trp Lys
130                 135                 140

Pro Pro Leu Ser Ser Phe Tyr Cys Thr Tyr Ala Cys Ala Trp Ile Gln
145                 150                 155                 160

Val Lys Ser Thr Tyr Ser Leu Ser Ile Ser Ser Ala Glu Gln Ala Ala
                165                 170                 175

Leu Glu Asp Met Leu Gly Ser Cys
            180
```

<210> SEQ ID NO 51
<211> LENGTH: 186
<212> TYPE: PRT
<213> ORGANISM: Metarhizium lepidiotae

<400> SEQUENCE: 51

```
Val Pro Val Pro Ala Pro Pro Gly Ile Pro Thr Ala Ser Thr Ala Arg
1               5                   10                  15

Thr Leu Leu Ala Gly Leu Lys Val Ala Thr Pro Leu Ser Gly Asp Gly
            20                  25                  30

Tyr Ser Arg Thr Leu Phe Pro Thr Trp Glu Thr Ile Glu Gly Thr Cys
        35                  40                  45

Asn Ala Arg Glu Phe Val Leu Lys Arg Asp Gly Thr Asp Val Gln Thr
    50                  55                  60

Asn Thr Ala Cys Val Ala Glu Ser Gly Asn Trp Val Ser Pro Tyr Asp
65                  70                  75                  80

Gly Val Ser Phe Thr Ala Ala Ser Asp Leu Asp Ile Asp His Met Val
                85                  90                  95

Pro Leu Lys Asn Ala Trp Ile Ser Gly Ala Ser Gln Trp Thr Thr Asp
            100                 105                 110

Lys Arg Lys Asp Leu Ala Asn Asp Ile Thr Arg Pro Gln Leu Trp Ala
        115                 120                 125

Val Ser Ala His Ala Asn Arg Ser Lys Gly Asp Ser Ser Pro Asp Glu
    130                 135                 140

Trp Lys Pro Pro Leu Gln Thr Phe Trp Cys Thr Tyr Ser Lys Ser Trp
145                 150                 155                 160

Ile Gln Val Lys Ser His Tyr Ser Leu Thr Ile Thr Asp Ala Glu Lys
                165                 170                 175

Gly Ala Leu Ser Gly Met Leu Asp Ser Cys
            180                 185
```

<210> SEQ ID NO 52
<211> LENGTH: 226
<212> TYPE: PRT
<213> ORGANISM: Thermobispora bispora

<400> SEQUENCE: 52

```
Leu Asp Ile Ala Asp Gly Arg Pro Ala Gly Lys Ala Glu Ala
1               5                   10                  15

Ala Thr Gly Thr Ser Pro Leu Ala Asn Pro Asp Gly Thr Arg Pro Gly
            20                  25                  30

Leu Ala Ala Ile Thr Ser Ala Asp Glu Arg Ala Glu Ala Arg Ala Leu
        35                  40                  45
```

```
Ile Glu Arg Leu Arg Thr Lys Gly Arg Gly Pro Lys Thr Gly Tyr Glu
 50                  55                  60

Arg Glu Lys Phe Gly Tyr Ala Trp Ala Asp Ser Val Asp Gly Ile Pro
 65                  70                  75                  80

Phe Gly Arg Asn Gly Cys Asp Thr Arg Asn Asp Val Leu Lys Arg Asp
             85                  90                  95

Gly Gln Arg Leu Gln Phe Arg Ser Gly Ser Asp Cys Val Val Ile Ser
            100                 105                 110

Met Thr Leu Phe Asp Pro Tyr Thr Gly Lys Thr Ile Glu Trp Thr Lys
            115                 120                 125

Gln Asn Ala Ala Glu Val Gln Ile Asp His Val Val Pro Leu Ser Tyr
        130                 135                 140

Ser Trp Gln Met Gly Ala Ser Arg Trp Ser Asp Glu Lys Arg Arg Gln
145                 150                 155                 160

Leu Ala Asn Asp Pro Leu Asn Leu Met Pro Val Asp Gly Ala Thr Asn
                165                 170                 175

Ser Arg Lys Gly Asp Ser Gly Pro Ala Ser Trp Leu Pro Pro Arg Arg
            180                 185                 190

Glu Ile Arg Cys Ala Tyr Val Val Arg Phe Ala Gln Val Ala Leu Lys
            195                 200                 205

Tyr Asp Leu Pro Val Thr Thr Ala Asp Lys Glu Thr Met Leu Gln Gln
        210                 215                 220

Cys Ser
225

<210> SEQ ID NO 53
<211> LENGTH: 191
<212> TYPE: PRT
<213> ORGANISM: Sporormia fimetaria

<400> SEQUENCE: 53

Leu Pro Ala Pro Val Leu Glu Lys Arg Thr Pro Asn Ile Pro Ser
  1               5                  10                  15

Thr Ser Thr Ala Gln Ser Leu Leu Ser Gly Leu Thr Val Ala Pro Gln
             20                  25                  30

Gly Ser Gln Thr Gly Tyr Ser Arg Asp Leu Phe Pro His Trp Ile Thr
         35                  40                  45

Val Ser Gly Thr Cys Asn Thr Arg Glu Thr Val Leu Lys Arg Asp Gly
 50                  55                  60

Ser Asn Val Val Thr Asp Ser Ala Cys Ala Ser Val Ser Gly Ser Trp
 65                  70                  75                  80

Tyr Ser Thr Tyr Asp Gly Ala Thr Trp Thr Ala Ala Ser Asp Val Asp
                 85                  90                  95

Ile Asp His Val Val Pro Leu Ser Asn Ala Trp Lys Ser Gly Ala Ala
            100                 105                 110

Ser Trp Thr Thr Ala Arg Arg Gln Ala Phe Ala Asn Asp Leu Thr Asn
            115                 120                 125

Pro Gln Leu Ile Ala Val Thr Asp Asn Val Asn Gln Ala Lys Gly Asp
        130                 135                 140

Gln Gly Pro Glu Ser Trp Lys Pro Pro Leu Thr Ser Tyr Tyr Cys Thr
145                 150                 155                 160

Tyr Ala Lys Met Trp Val Lys Val Lys Ser Val Tyr Ser Leu Thr Val
                165                 170                 175

Thr Ser Ala Glu Lys Ser Ala Leu Ser Ser Met Leu Gly Thr Cys
```

```
                180                 185                 190

<210> SEQ ID NO 54
<211> LENGTH: 193
<212> TYPE: PRT
<213> ORGANISM: Pycnidiophora cf.dispera

<400> SEQUENCE: 54

Leu Pro Ala Pro Ala Pro Val Leu Val Ala Arg Glu Pro Pro Asn Ile
1               5                   10                  15

Pro Ser Thr Ser Ser Ala Gln Ser Met Leu Ser Gly Leu Thr Val Lys
            20                  25                  30

Ala Gln Gly Pro Gln Asp Gly Tyr Ser Arg Asp Leu Phe Pro His Trp
        35                  40                  45

Ile Thr Ile Ser Gly Thr Cys Asn Thr Arg Glu Thr Val Leu Lys Arg
50                  55                  60

Asp Gly Thr Asn Val Val Thr Asn Ser Ala Cys Ala Ser Thr Ser Gly
65                  70                  75                  80

Ser Trp Tyr Ser Pro Tyr Asp Gly Ala Thr Trp Thr Ala Ala Ser Asp
                85                  90                  95

Val Asp Ile Asp His Ile Val Pro Leu Ser Asn Ala Trp Lys Ser Gly
            100                 105                 110

Ala Ala Ser Trp Thr Thr Ser Arg Arg Gln Gln Phe Ala Asn Asp Leu
        115                 120                 125

Thr Asn Pro Gln Leu Ile Ala Val Thr Asp Ser Val Asn Gln Ala Lys
130                 135                 140

Gly Asp Lys Gly Pro Glu Asp Trp Lys Pro Ser Arg Thr Ser Tyr His
145                 150                 155                 160

Cys Thr Tyr Ala Lys Met Trp Ile Lys Val Lys Ser Val Tyr Ser Leu
                165                 170                 175

Thr Val Thr Ser Ala Glu Lys Ser Ala Leu Thr Thr Met Leu Asn Thr
            180                 185                 190

Cys

<210> SEQ ID NO 55
<211> LENGTH: 199
<212> TYPE: PRT
<213> ORGANISM: Enviromental sample D

<400> SEQUENCE: 55

Asp Thr Asp Pro Glu Pro Val Ala Gly Ser Ala Leu Glu Ala Leu Ala
1               5                   10                  15

Gly Leu Glu Val Lys Gly Pro Gly Pro Asp Thr Gly Tyr Glu Arg Ala
            20                  25                  30

Leu Phe Gly Pro Pro Trp Ala Asp Val Asp Gly Asn Gly Cys Asp Thr
        35                  40                  45

Arg Asn Asp Ile Leu Ala Arg Asp Leu Thr Asp Leu Thr Phe Ser Thr
50                  55                  60

Arg Gly Asp Val Cys Glu Val Arg Thr Gly Thr Phe Asp Asp Pro Tyr
65                  70                  75                  80

Thr Gly Glu Thr Ile Asp Phe Arg Arg Gly Asn Ala Ser Ala Ala
                85                  90                  95

Val Gln Ile Asp His Val Val Pro Leu Leu Asp Ala Trp Arg Lys Gly
            100                 105                 110

Ala Arg Ala Trp Asp Asp Glu Thr Arg Arg Gln Phe Ala Asn Asp Pro
        115                 120                 125
```

```
Leu Asn Leu Leu Ala Ser Asp Gly Pro Ala Asn Gln Ser Lys Gly Ala
    130                 135                 140

Arg Asp Ala Ser Ala Trp Leu Pro Pro Asn His Ala Phe Arg Cys Pro
145                 150                 155                 160

Tyr Val Ala Arg Gln Ile Ala Val Lys Ala Ala Tyr Glu Leu Ser Val
                165                 170                 175

Thr Pro Ser Glu Ser Glu Ala Met Ala Arg Val Leu Ala Asp Cys Pro
            180                 185                 190

Ala Glu Pro Leu Pro Ala Gly
        195

<210> SEQ ID NO 56
<211> LENGTH: 199
<212> TYPE: PRT
<213> ORGANISM: Enviromental sample O

<400> SEQUENCE: 56

Asp Asp Glu Pro Glu Pro Ala Arg Gly Ser Ala Leu Glu Ala Leu Ala
1               5                   10                  15

Arg Leu Glu Val Val Gly Pro Gly Pro Asp Thr Gly Tyr Glu Arg Glu
                20                  25                  30

Leu Phe Gly Pro Ala Trp Ala Asp Val Asp Gly Asn Gly Cys Asp Thr
            35                  40                  45

Arg Asn Asp Ile Leu Ala Arg Asp Leu Thr Asp Leu Thr Phe Ser Thr
    50                  55                  60

Arg Gly Glu Val Cys Glu Val Arg Thr Gly Thr Phe Gln Asp Pro Tyr
65                  70                  75                  80

Thr Gly Glu Thr Ile Asp Phe Arg Arg Gly Asn Ala Thr Ser Met Ala
                85                  90                  95

Val Gln Ile Asp His Val Val Pro Leu Met Asp Ala Trp Arg Lys Gly
            100                 105                 110

Ala Arg Ala Trp Asp Asp Glu Thr Arg Arg Gln Phe Ala Asn Asp Pro
        115                 120                 125

Leu Asn Leu Leu Ala Ser Asp Gly Pro Ala Asn Gln Ser Lys Gly Ala
    130                 135                 140

Arg Asp Ala Ser Ala Trp Leu Pro Pro Asn His Ala Phe Arg Cys Pro
145                 150                 155                 160

Tyr Val Ala Arg Gln Ile Ala Val Lys Thr Ala Tyr Glu Leu Ser Val
                165                 170                 175

Thr Pro Ser Glu Ser Glu Ala Met Ala Arg Val Leu Ala Asp Cys Pro
            180                 185                 190

Ala Glu Pro Val Pro Ala Gly
        195

<210> SEQ ID NO 57
<211> LENGTH: 186
<212> TYPE: PRT
<213> ORGANISM: Clavicipitaceae sp-70249

<400> SEQUENCE: 57

Val Pro Val Pro Ala Pro Pro Gly Ile Pro Ser Thr Ser Thr Ala Lys
1               5                   10                  15

Thr Leu Leu Ala Gly Leu Lys Val Ala Thr Pro Leu Ser Gly Asp Gly
                20                  25                  30

Tyr Ser Arg Asp Lys Phe Pro Thr Trp Glu Thr Ile Gln Gly Thr Cys
            35                  40                  45
```

```
Asn Ala Arg Glu Phe Val Ile Lys Arg Asp Gly Thr Asp Val Lys Thr
 50                  55                  60

Asn Ser Ala Cys Val Ala Glu Ser Gly Asn Trp Val Ser Pro Tyr Asp
 65                  70                  75                  80

Gly Val Lys Phe Thr Ala Ala Arg Asp Leu Asp Ile Asp His Met Val
                 85                  90                  95

Pro Leu Lys Asn Ala Trp Ile Ser Gly Ala Ser Gln Trp Thr Thr Glu
                100                 105                 110

Gln Arg Lys Ala Leu Ala Asn Asp Ile Thr Arg Pro Gln Leu Trp Ala
                115                 120                 125

Val Ser Ala His Ala Asn Arg Gly Lys Ser Asp Ser Pro Asp Glu
130                 135                 140

Trp Lys Pro Pro Leu Lys Thr Phe Trp Cys Thr Tyr Ala Lys Ser Trp
145                 150                 155                 160

Val Gln Val Lys Ser Phe Tyr Lys Leu Thr Ile Thr Asp Thr Glu Lys
                165                 170                 175

Gly Ala Leu Ala Gly Met Leu Asp Thr Cys
                180                 185
```

<210> SEQ ID NO 58
<211> LENGTH: 187
<212> TYPE: PRT
<213> ORGANISM: Westerdykella sp. AS85-2

<400> SEQUENCE: 58

```
Phe Pro Ala Pro Ala Ser Val Leu Glu Ala Arg Ala Pro Pro Asn Ile
 1               5                  10                  15

Pro Ser Ala Ser Thr Ala Gln Ser Leu Leu Val Gly Leu Thr Val Gln
                 20                  25                  30

Pro Gln Gly Pro Gln Asp Gly Tyr Ser Arg Asp Leu Phe Pro His Trp
                 35                  40                  45

Ile Thr Ile Ser Gly Thr Cys Asn Thr Arg Glu Thr Val Leu Lys Arg
 50                  55                  60

Asp Gly Ser Asn Val Val Thr Asn Ser Ala Cys Ala Ala Thr Ser Gly
 65                  70                  75                  80

Thr Trp Tyr Ser Pro Tyr Asp Gly Ala Thr Trp Thr Ser Ala Ser Asp
                 85                  90                  95

Val Asp Ile Asp His Leu Val Pro Leu Ser Asn Ala Trp Lys Ser Gly
                100                 105                 110

Ala Ala Ser Trp Thr Thr Ala Lys Arg Gln Gln Phe Ala Asn Asp Leu
                115                 120                 125

Thr Asn Pro Gln Leu Leu Ala Val Thr Asp Arg Val Asn Gln Ala Lys
130                 135                 140

Gly Asp Lys Gly Pro Glu Ala Trp Lys Pro Ser Leu Ala Ser Tyr His
145                 150                 155                 160

Cys Thr Tyr Ala Lys Met Trp Val Lys Val Lys Ser Lys Asp Val Arg
                165                 170                 175

Leu Thr Gly Asn Trp Thr Lys Asp Asp Gly Trp
                180                 185
```

<210> SEQ ID NO 59
<211> LENGTH: 194
<212> TYPE: PRT
<213> ORGANISM: Humicolopsis cephalosporioides

<400> SEQUENCE: 59

Ala Pro Thr Pro Ala Pro Val Glu Leu Glu Arg Arg Thr Pro Pro Asn
1               5                   10                  15

Ile Pro Thr Thr Ala Ser Ala Lys Ser Leu Leu Ala Gly Leu Thr Val
            20                  25                  30

Ala Ala Gln Gly Pro Gln Thr Gly Tyr Ser Arg Asp Leu Phe Pro His
        35                  40                  45

Trp Ile Thr Ile Ser Gly Ser Cys Asn Thr Arg Glu Thr Val Leu Lys
    50                  55                  60

Arg Asp Gly Thr Gly Val Val Thr Asp Ser Ala Cys Ala Ser Thr Ala
65                  70                  75                  80

Gly Ser Trp Tyr Ser Pro Tyr Asp Gly Ala Thr Trp Thr Ala Ala Ser
                85                  90                  95

Asp Val Asp Ile Asp His Met Val Pro Leu Ser Asn Ala Trp Lys Ser
                100                 105                 110

Gly Ala Ala Gln Trp Thr Thr Ala Arg Arg Gln Asp Phe Ala Asn Asp
            115                 120                 125

Leu Thr Asn Pro Gln Leu Phe Ala Val Thr Asp Asn Val Asn Gln Glu
    130                 135                 140

Lys Gly Asp Lys Gly Pro Glu Asp Trp Lys Pro Ser Leu Thr Ser Tyr
145                 150                 155                 160

Tyr Cys Thr Tyr Ala Lys Ala Trp Val Lys Val Lys Ser Val Trp Ala
                165                 170                 175

Leu Thr Ile Thr Ser Ala Glu Lys Ser Ala Leu Thr Thr Met Leu Asn
            180                 185                 190

Thr Cys

<210> SEQ ID NO 60
<211> LENGTH: 190
<212> TYPE: PRT
<213> ORGANISM: Neosartorya massa

<400> SEQUENCE: 60

Ile Pro Ala Pro Val Ala Leu Pro Thr Pro Pro Gly Ile Pro Ser Ala
1               5                   10                  15

Ala Thr Ala Glu Ser Glu Leu Ala Ala Leu Thr Val Ala Ala Gln Gly
            20                  25                  30

Ser Ser Ser Gly Tyr Ser Arg Asp Leu Phe Pro His Trp Ile Ser Gln
        35                  40                  45

Gly Gly Ser Cys Asn Thr Arg Glu Val Val Leu Ala Arg Asp Gly Ser
    50                  55                  60

Gly Val Val Lys Asp Ser Asn Cys Tyr Pro Thr Ser Gly Ser Trp Tyr
65                  70                  75                  80

Ser Pro Tyr Asp Gly Ala Thr Thr Gln Ala Ser Asp Val Asp Ile
                85                  90                  95

Asp His Val Val Pro Leu Ala Asn Ala Trp Arg Ser Gly Ala Ser Lys
                100                 105                 110

Trp Thr Thr Ser Gln Arg Gln Ala Phe Ala Asn Asp Leu Thr Asn Pro
            115                 120                 125

Gln Leu Met Ala Val Thr Asp Asn Val Asn Gln Ala Lys Gly Asp Asp
    130                 135                 140

Gly Pro Glu Ala Trp Lys Pro Pro Leu Thr Ser Tyr Tyr Cys Thr Tyr
145                 150                 155                 160

Ala Lys Met Trp Val Arg Val Lys Tyr Val Tyr Asp Leu Thr Ile Thr
                165                 170                 175

```
Ser Ala Glu Lys Ser Ala Leu Val Ser Met Leu Asp Thr Cys
            180                 185                 190

<210> SEQ ID NO 61
<211> LENGTH: 191
<212> TYPE: PRT
<213> ORGANISM: Roussoella intermedia

<400> SEQUENCE: 61

Ala Pro Thr Pro Ala Leu Leu Pro Arg Ala Pro Asn Ile Pro Ser
1               5                   10                  15

Thr Ala Thr Ala Lys Ser Gln Leu Ala Ala Leu Thr Val Ala Ala Gln
                20                  25                  30

Gly Pro Gln Asp Gly Tyr Ser Arg Asp Leu Phe Pro His Trp Ile Thr
            35                  40                  45

Gln Ser Gly Ser Cys Asn Thr Arg Glu Val Val Leu Lys Arg Asp Gly
        50                  55                  60

Thr Asn Val Val Gln Asp Ser Ser Cys Ala Ala Thr Ser Gly Thr Trp
65                  70                  75                  80

Val Ser Pro Phe Asp Gly Ala Thr Trp Thr Ala Ala Ser Asp Val Asp
                85                  90                  95

Ile Asp His Leu Val Pro Leu Ser Asn Ala Trp Lys Ser Gly Ala Ala
            100                 105                 110

Ser Trp Thr Thr Ala Arg Arg Gln Ser Phe Ala Asn Asp Leu Thr Asn
        115                 120                 125

Pro Gln Leu Leu Ala Val Thr Asp Glu Val Asn Gln Ala Lys Gly Asp
    130                 135                 140

Lys Gly Pro Glu Ala Trp Lys Pro Pro Leu Ala Ser Tyr His Cys Thr
145                 150                 155                 160

Tyr Ala Lys Met Trp Val Lys Val Lys Ser Thr Tyr Ser Leu Thr Ile
                165                 170                 175

Thr Ser Ala Glu Lys Ser Ala Leu Thr Thr Met Leu Asn Thr Cys
            180                 185                 190

<210> SEQ ID NO 62
<211> LENGTH: 191
<212> TYPE: PRT
<213> ORGANISM: Pleosporales

<400> SEQUENCE: 62

Leu Pro Thr Pro Ser Leu Val Lys Arg Thr Pro Asn Ile Pro Ser
1               5                   10                  15

Thr Thr Ser Ala Lys Ser Leu Leu Ala Gly Leu Thr Val Ala Ala Gln
                20                  25                  30

Gly Pro Gln Asp Gly Tyr Ser Arg Asp Leu Phe Pro His Trp Ile Thr
            35                  40                  45

Ile Ser Gly Thr Cys Asn Thr Arg Glu Thr Val Leu Lys Arg Asp Gly
        50                  55                  60

Thr Asn Val Val Thr Asp Ser Ala Cys Ala Ser Thr Ser Gly Ser Trp
65                  70                  75                  80

Tyr Ser Thr Tyr Asp Gly Ala Thr Trp Thr Ala Ala Ser Asp Val Asp
                85                  90                  95

Ile Asp His Val Val Pro Leu Ser Asn Ala Trp Lys Ser Gly Ala Ala
            100                 105                 110

Ser Trp Thr Thr Ala Arg Arg Gln Ser Phe Ala Asn Asp Leu Thr Asn
        115                 120                 125
```

```
Pro Gln Leu Ile Ala Val Thr Asp Ser Val Asn Gln Ser Lys Gly Asp
    130                 135                 140

Lys Gly Pro Glu Ser Trp Lys Pro Pro Leu Thr Ser Tyr His Cys Thr
145                 150                 155                 160

Tyr Ala Lys Met Trp Val Lys Val Lys Asp Val Tyr Ser Leu Thr Val
                165                 170                 175

Thr Ser Ala Glu Lys Ser Ala Leu Thr Thr Met Leu Asn Thr Cys
            180                 185                 190

<210> SEQ ID NO 63
<211> LENGTH: 192
<212> TYPE: PRT
<213> ORGANISM: Phaeosphaeria sp.

<400> SEQUENCE: 63

Leu Pro Ala Pro Ile His Leu Thr Ala Arg Ala Pro Asn Ile Pro
1               5                   10                  15

Ser Ala Ser Glu Ala Arg Thr Gln Leu Ala Gly Leu Thr Val Ala Ala
                20                  25                  30

Gln Gly Pro Gln Asp Gly Tyr Ser Arg Asp Leu Phe Pro His Trp Ile
            35                  40                  45

Thr Gln Ser Gly Thr Cys Asn Thr Arg Glu Thr Val Leu Lys Arg Asp
    50                  55                  60

Gly Thr Asn Val Val Thr Asn Ser Ala Cys Ala Ser Thr Ser Gly Ser
65                  70                  75                  80

Trp Phe Ser Pro Tyr Asp Gly Ala Thr Trp Thr Ala Ala Ser Asp Val
                85                  90                  95

Asp Ile Asp His Met Val Pro Leu Ser Asn Ala Trp Lys Ser Gly Ala
                100                 105                 110

Ala Ser Trp Thr Thr Ala Arg Arg Gln Ala Phe Ala Asn Asp Leu Thr
            115                 120                 125

Asn Pro Gln Leu Leu Ala Val Thr Asp Asn Val Asn Gln Ala Lys Gly
    130                 135                 140

Asp Lys Gly Pro Glu Asp Trp Lys Pro Pro Leu Thr Ser Tyr Tyr Cys
145                 150                 155                 160

Thr Tyr Ala Arg Met Trp Val Lys Val Lys Ser Val Tyr Ala Leu Thr
                165                 170                 175

Val Thr Ser Ala Glu Lys Ser Ala Leu Thr Ser Met Leu Gly Thr Cys
            180                 185                 190

<210> SEQ ID NO 64
<211> LENGTH: 189
<212> TYPE: PRT
<213> ORGANISM: Didymosphaeria futilis

<400> SEQUENCE: 64

Leu Pro Thr Pro Asn Thr Leu Glu Ala Arg Ala Pro Asn Ile Pro
1               5                   10                  15

Ser Thr Ser Ala Ala Gln Ser Gln Leu Ser Ala Leu Thr Val Ala Ala
                20                  25                  30

Gln Gly Pro Gln Thr Gly Tyr Ser Arg Asp Leu Phe Pro His Trp Ile
            35                  40                  45

Thr Gln Ser Gly Thr Cys Asn Thr Arg Glu Thr Val Leu Lys Arg Asp
    50                  55                  60

Gly Thr Asn Val Leu Thr Asp Ser Ala Cys Ala Ser Thr Ser Gly Ser
65                  70                  75                  80
```

```
Trp Lys Ser Pro Tyr Asp Gly Ala Thr Trp Thr Ala Ala Ser Asp Val
            85                  90                  95

Asp Ile Asp His Val Val Pro Leu Ser Asn Ala Trp Lys Ser Gly Ala
            100                 105                 110

Ala Ser Trp Thr Thr Ala Arg Arg Gln Ser Phe Ala Asn Asp Leu Thr
            115                 120                 125

Asn Pro Gln Leu Ile Ala Val Thr Asp Asn Val Asn Gln Ala Lys Gly
130                 135                 140

Asp Lys Gly Pro Glu Asp Trp Lys Pro Pro Leu Thr Ser Tyr Tyr Cys
145                 150                 155                 160

Thr Tyr Ala Lys Met Trp Val Lys Val Lys Ser Val Tyr Ser Leu Thr
            165                 170                 175

Ile Thr Ser Ala Glu Lys Ser Ala Leu Thr Met Leu Ala
            180                 185

<210> SEQ ID NO 65
<211> LENGTH: 109
<212> TYPE: PRT
<213> ORGANISM: Bacillus licheniformis

<400> SEQUENCE: 65

Ala Arg Tyr Asp Asp Ile Leu Tyr Phe Pro Ala Ser Arg Tyr Pro Glu
1               5                   10                  15

Thr Gly Ala His Ile Ser Asp Ala Ile Lys Ala Gly His Ser Asp Val
            20                  25                  30

Cys Thr Ile Glu Arg Ser Gly Ala Asp Lys Arg Arg Gln Glu Ser Leu
        35                  40                  45

Lys Gly Ile Pro Thr Lys Pro Gly Phe Asp Arg Asp Glu Trp Pro Met
50                  55                  60

Ala Met Cys Glu Glu Gly Lys Gly Ala Ser Val Arg Tyr Val Ser
65                  70                  75                  80

Ser Ser Asp Asn Arg Gly Ala Gly Ser Trp Val Gly Asn Arg Leu Ser
            85                  90                  95

Gly Phe Ala Asp Gly Thr Arg Ile Leu Phe Ile Val Gln
            100                 105

<210> SEQ ID NO 66
<211> LENGTH: 110
<212> TYPE: PRT
<213> ORGANISM: Bacillus subtilis

<400> SEQUENCE: 66

Ala Ser Ser Tyr Asp Lys Val Leu Tyr Phe Pro Leu Ser Arg Tyr Pro
1               5                   10                  15

Glu Thr Gly Ser His Ile Arg Asp Ala Ile Ala Glu Gly His Pro Asp
            20                  25                  30

Ile Cys Thr Ile Asp Arg Asp Gly Ala Asp Lys Arg Arg Glu Glu Ser
            35                  40                  45

Leu Lys Gly Ile Pro Thr Lys Pro Gly Tyr Asp Arg Asp Glu Trp Pro
    50                  55                  60

Met Ala Val Cys Glu Glu Gly Gly Ala Gly Ala Asp Val Arg Tyr Val
65                  70                  75                  80

Thr Pro Ser Asp Asn Arg Gly Ala Gly Ser Trp Val Gly Asn Gln Met
            85                  90                  95

Ser Ser Tyr Pro Asp Gly Thr Arg Val Leu Phe Ile Val Gln
            100                 105                 110
```

<210> SEQ ID NO 67
<211> LENGTH: 221
<212> TYPE: PRT
<213> ORGANISM: Aspergillus oryzae

<400> SEQUENCE: 67

Val Pro Val Asn Pro Glu Pro Asp Ala Thr Ser Val Glu Asn Val Ala
1               5                   10                  15

Leu Lys Thr Gly Ser Gly Asp Ser Gln Ser Asp Pro Ile Lys Ala Asp
            20                  25                  30

Leu Glu Val Lys Gly Gln Ser Ala Leu Pro Phe Asp Val Asp Cys Trp
        35                  40                  45

Ala Ile Leu Cys Lys Gly Ala Pro Asn Val Leu Gln Arg Val Asn Glu
    50                  55                  60

Lys Thr Lys Asn Ser Asn Arg Asp Arg Ser Gly Ala Asn Lys Gly Pro
65                  70                  75                  80

Phe Lys Asp Pro Gln Lys Trp Gly Ile Lys Ala Leu Pro Pro Lys Asn
                85                  90                  95

Pro Ser Trp Ser Ala Gln Asp Phe Lys Ser Pro Glu Glu Tyr Ala Phe
            100                 105                 110

Ala Ser Ser Leu Gln Gly Gly Thr Asn Ala Ile Leu Ala Pro Val Asn
        115                 120                 125

Leu Ala Ser Gln Asn Ser Gln Gly Gly Val Leu Asn Gly Phe Tyr Ser
    130                 135                 140

Ala Asn Lys Val Ala Gln Phe Asp Pro Ser Lys Pro Gln Gln Thr Lys
145                 150                 155                 160

Gly Thr Trp Phe Gln Ile Thr Lys Phe Thr Gly Ala Ala Gly Pro Tyr
                165                 170                 175

Cys Lys Ala Leu Gly Ser Asn Asp Lys Ser Val Cys Asp Lys Asn Lys
            180                 185                 190

Asn Ile Ala Gly Asp Trp Gly Phe Asp Pro Ala Lys Trp Ala Tyr Gln
        195                 200                 205

Tyr Asp Glu Lys Asn Asn Lys Phe Asn Tyr Val Gly Lys
    210                 215                 220

<210> SEQ ID NO 68
<211> LENGTH: 188
<212> TYPE: PRT
<213> ORGANISM: Trichoderma harzianum

<400> SEQUENCE: 68

Ala Pro Ala Pro Met Pro Thr Pro Pro Gly Ile Pro Thr Glu Ser Ser
1               5                   10                  15

Ala Arg Thr Gln Leu Ala Gly Leu Thr Val Ala Val Ala Gly Ser Gly
            20                  25                  30

Thr Gly Tyr Ser Arg Asp Leu Phe Pro Thr Trp Asp Ala Ile Ser Gly
        35                  40                  45

Asn Cys Asn Ala Arg Glu Tyr Val Leu Lys Arg Asp Gly Glu Gly Val
    50                  55                  60

Gln Val Asn Asn Ala Cys Glu Ser Gln Ser Gly Thr Trp Ile Ser Pro
65                  70                  75                  80

Tyr Asp Asn Ala Ser Phe Thr Asn Ala Ser Leu Asp Ile Asp His
                85                  90                  95

Met Val Pro Leu Lys Asn Ala Trp Ile Ser Gly Ala Ser Ser Trp Thr
            100                 105                 110

Thr Ala Gln Arg Glu Ala Leu Ala Asn Asp Val Ser Arg Pro Gln Leu
            115                 120                 125

Trp Ala Val Ser Ala Ser Ala Asn Arg Ser Lys Gly Asp Arg Ser Pro
        130                 135                 140

Asp Gln Trp Lys Pro Pro Leu Thr Ser Phe Tyr Cys Thr Tyr Ala Lys
145                 150                 155                 160

Ser Trp Ile Asp Val Lys Ser Phe Tyr Lys Leu Thr Ile Thr Ser Ala
                165                 170                 175

Glu Lys Thr Ala Leu Ser Ser Met Leu Asp Thr Cys
            180                 185

<210> SEQ ID NO 69
<211> LENGTH: 5
<212> TYPE: PRT
<213> ORGANISM: Artificial
<220> FEATURE:
<223> OTHER INFORMATION: Motif
<220> FEATURE:
<221> NAME/KEY: MISC_FEATURE
<222> LOCATION: (1)..(1)
<223> OTHER INFORMATION: Xaa = Thr (T) or Asp (D) or Ser (S)
<220> FEATURE:
<221> NAME/KEY: MISC_FEATURE
<222> LOCATION: (2)..(2)
<223> OTHER INFORMATION: Xaa = Gly (G) or Asn (N)

<400> SEQUENCE: 69

Xaa Xaa Pro Gln Leu
1               5

<210> SEQ ID NO 70
<211> LENGTH: 5
<212> TYPE: PRT
<213> ORGANISM: Artificial
<220> FEATURE:
<223> OTHER INFORMATION: Motif
<220> FEATURE:
<221> NAME/KEY: MISC_FEATURE
<222> LOCATION: (1)..(1)
<223> OTHER INFORMATION: Xaa = F (phe) or L (Leu) or Y (Tyr) or I (Ile)
<220> FEATURE:
<221> NAME/KEY: MISC_FEATURE
<222> LOCATION: (3)..(3)
<223> OTHER INFORMATION: Xaa = N (Asn) or R (Arg)
<220> FEATURE:
<221> NAME/KEY: MISC_FEATURE
<222> LOCATION: (5)..(5)
<223> OTHER INFORMATION: Xaa = L (Leu) or I (Ile) or P (Phe) or V (Val)

<400> SEQUENCE: 70

Xaa Ala Xaa Asp Xaa
1               5

<210> SEQ ID NO 71
<211> LENGTH: 4
<212> TYPE: PRT
<213> ORGANISM: Artificial
<220> FEATURE:
<223> OTHER INFORMATION: Motif
<220> FEATURE:
<221> NAME/KEY: MISC_FEATURE
<222> LOCATION: (2)..(2)
<223> OTHER INFORMATION: Xaa= Asp (D) or Asn (N)
<220> FEATURE:
<221> NAME/KEY: MISC_FEATURE
<222> LOCATION: (4)..(4)
<223> OTHER INFORMATION: Xaa= Ala (A) or Arg (R)

<400> SEQUENCE: 71

Cys Xaa Thr Xaa
1

<210> SEQ ID NO 72
<211> LENGTH: 4
<212> TYPE: PRT
<213> ORGANISM: Artificial
<220> FEATURE:
<223> OTHER INFORMATION: Motif
<220> FEATURE:
<221> NAME/KEY: MISC_FEATURE
<222> LOCATION: (1)..(1)
<223> OTHER INFORMATION: Xaa = Asp (D) or Gln (Q)
<220> FEATURE:
<221> NAME/KEY: MISC_FEATURE
<222> LOCATION: (2)..(2)
<223> OTHER INFORMATION: Xaa = Ile (I) or Val (V)

<400> SEQUENCE: 72

Xaa Xaa Asp His
1

<210> SEQ ID NO 73
<211> LENGTH: 7
<212> TYPE: PRT
<213> ORGANISM: Artificial
<220> FEATURE:
<223> OTHER INFORMATION: Motif
<220> FEATURE:
<221> NAME/KEY: MISC_FEATURE
<222> LOCATION: (1)..(1)
<223> OTHER INFORMATION: Xaa = Asp (D) or Met (M) or Leu (L)
<220> FEATURE:
<221> NAME/KEY: MISC_FEATURE
<222> LOCATION: (2)..(2)
<223> OTHER INFORMATION: Xaa = Ser (S) or Thr (T)
<220> FEATURE:
<221> NAME/KEY: MISC_FEATURE
<222> LOCATION: (7)..(7)
<223> OTHER INFORMATION: Xaa = Asp (D) or Asn (N)

<400> SEQUENCE: 73

Xaa Xaa Gly Tyr Ser Arg Xaa
1               5

<210> SEQ ID NO 74
<211> LENGTH: 8
<212> TYPE: PRT
<213> ORGANISM: Artificial
<220> FEATURE:
<223> OTHER INFORMATION: Motif
<220> FEATURE:
<221> NAME/KEY: MISC_FEATURE
<222> LOCATION: (3)..(3)
<223> OTHER INFORMATION: Xaa = any amino acid

<400> SEQUENCE: 74

Ala Ser Xaa Asn Arg Ser Lys Gly
1               5

<210> SEQ ID NO 75
<211> LENGTH: 8
<212> TYPE: PRT
<213> ORGANISM: Artificial
<220> FEATURE:
<223> OTHER INFORMATION: Motif
<220> FEATURE:
<221> NAME/KEY: MISC_FEATURE
<222> LOCATION: (1)..(1)
<223> OTHER INFORMATION: Xaa = Val (V) or Ile (I)
<220> FEATURE:

```
<221> NAME/KEY: MISC_FEATURE
<222> LOCATION: (4)..(4)
<223> OTHER INFORMATION: Xaa = Ser (S) or Ala (A)

<400> SEQUENCE: 75

Xaa Pro Leu Xaa Asn Ala Trp Lys
1               5

<210> SEQ ID NO 76
<211> LENGTH: 4
<212> TYPE: PRT
<213> ORGANISM: Artificial
<220> FEATURE:
<223> OTHER INFORMATION: Motif

<400> SEQUENCE: 76

Asn Pro Gln Leu
1

<210> SEQ ID NO 77
<211> LENGTH: 4
<212> TYPE: PRT
<213> ORGANISM: Artificial
<220> FEATURE:
<223> OTHER INFORMATION: Motif
<220> FEATURE:
<221> NAME/KEY: MISC_FEATURE
<222> LOCATION: (2)..(2)
<223> OTHER INFORMATION: Xaa = Gln (Q) or Glu(E)
<220> FEATURE:
<221> NAME/KEY: MISC_FEATURE
<222> LOCATION: (4)..(4)
<223> OTHER INFORMATION: Xaa = Trp (W) or Tyr (Y)

<400> SEQUENCE: 77

Pro Xaa Leu Xaa
1

<210> SEQ ID NO 78
<211> LENGTH: 4
<212> TYPE: PRT
<213> ORGANISM: Artificial
<220> FEATURE:
<223> OTHER INFORMATION: Motif
<220> FEATURE:
<221> NAME/KEY: MISC_FEATURE
<222> LOCATION: (1)..(1)
<223> OTHER INFORMATION: Xaa=Lys (K) or His (H) or Glu (E)

<400> SEQUENCE: 78

Xaa Asn Ala Trp
1

<210> SEQ ID NO 79
<211> LENGTH: 269
<212> TYPE: PRT
<213> ORGANISM: Bacillus lentus

<400> SEQUENCE: 79

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Ser Gly Ser Gly Ser Val Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265

<210> SEQ ID NO 80
<211> LENGTH: 275
<212> TYPE: PRT
<213> ORGANISM: Bacillus amyloliquefaciens

<400> SEQUENCE: 80

Ala Gln Ser Val Pro Tyr Gly Val Ser Gln Ile Lys Ala Pro Ala Leu
1               5                   10                  15

His Ser Gln Gly Tyr Thr Gly Ser Asn Val Lys Val Ala Val Ile Asp
                20                  25                  30

Ser Gly Ile Asp Ser Ser His Pro Asp Leu Lys Val Ala Gly Gly Ala
            35                  40                  45

Ser Met Val Pro Ser Glu Thr Asn Pro Phe Gln Asp Asn Asn Ser His
        50                  55                  60

Gly Thr His Val Ala Gly Thr Val Ala Ala Leu Asn Asn Ser Ile Gly
65                  70                  75                  80

Val Leu Gly Val Ala Pro Ser Ala Ser Leu Tyr Ala Val Lys Val Leu
                85                  90                  95

Gly Ala Asp Gly Ser Gly Gln Tyr Ser Trp Ile Ile Asn Gly Ile Glu
            100                 105                 110

Trp Ala Ile Ala Asn Asn Met Asp Val Ile Asn Met Ser Leu Gly Gly
        115                 120                 125

Pro Ser Gly Ser Ala Ala Leu Lys Ala Ala Val Asp Lys Ala Val Ala
    130                 135                 140

Ser Gly Val Val Val Ala Ala Ala Gly Asn Glu Gly Thr Ser Gly
145                 150                 155                 160

Ser Ser Ser Thr Val Gly Tyr Pro Gly Lys Tyr Pro Ser Val Ile Ala

```
            165                 170                 175
Val Gly Ala Val Asp Ser Ser Asn Gln Arg Ala Ser Phe Ser Ser Val
            180                 185                 190

Gly Pro Glu Leu Asp Val Met Ala Pro Gly Val Ser Ile Gln Ser Thr
            195                 200                 205

Leu Pro Gly Asn Lys Tyr Gly Ala Tyr Asn Gly Thr Ser Met Ala Ser
            210                 215                 220

Pro His Val Ala Gly Ala Ala Leu Ile Leu Ser Lys His Pro Asn
225                 230                 235                 240

Trp Thr Asn Thr Gln Val Arg Ser Ser Leu Glu Asn Thr Thr Lys
                245                 250                 255

Leu Gly Asp Ser Phe Tyr Tyr Gly Lys Gly Leu Ile Asn Val Gln Ala
                260                 265                 270

Ala Ala Gln
        275

<210> SEQ ID NO 81
<211> LENGTH: 311
<212> TYPE: PRT
<213> ORGANISM: Bacillus sp.

<400> SEQUENCE: 81

Ala Val Pro Ser Thr Gln Thr Pro Trp Gly Ile Lys Ser Ile Tyr Asn
1               5                   10                  15

Asp Gln Ser Ile Thr Lys Thr Gly Gly Ser Gly Ile Lys Val Ala
            20                  25                  30

Val Leu Asp Thr Gly Val Tyr Thr Ser His Leu Asp Leu Ala Gly Ser
            35                  40                  45

Ala Glu Gln Cys Lys Asp Phe Thr Gln Ser Asn Pro Leu Val Asp Gly
        50                  55                  60

Ser Cys Thr Asp Arg Gln Gly His Gly Thr His Val Ala Gly Thr Val
65                  70                  75                  80

Leu Ala His Gly Gly Ser Asn Gly Gln Gly Val Tyr Gly Val Ala Pro
                85                  90                  95

Gln Ala Lys Leu Trp Ala Tyr Lys Val Leu Gly Asp Asn Gly Ser Gly
            100                 105                 110

Tyr Ser Asp Asp Ile Ala Ala Ile Arg His Val Ala Asp Glu Ala
            115                 120                 125

Ser Arg Thr Gly Ser Lys Val Val Ile Asn Met Ser Leu Gly Ser Ser
130                 135                 140

Ala Lys Asp Ser Leu Ile Ala Ser Ala Val Asp Tyr Ala Tyr Gly Lys
145                 150                 155                 160

Gly Val Leu Ile Val Ala Ala Gly Asn Ser Gly Ser Gly Ser Asn
                165                 170                 175

Thr Ile Gly Phe Pro Gly Gly Leu Val Asn Ala Val Ala Val Ala Ala
            180                 185                 190

Leu Glu Asn Val Gln Gln Asn Gly Thr Tyr Arg Val Ala Asp Phe Ser
            195                 200                 205

Ser Arg Gly Asn Pro Ala Thr Ala Gly Asp Tyr Ile Ile Gln Glu Arg
        210                 215                 220

Asp Ile Glu Val Ser Ala Pro Gly Ala Ser Val Glu Ser Thr Trp Tyr
225                 230                 235                 240

Thr Gly Gly Tyr Asn Thr Ile Ser Gly Thr Ser Met Ala Thr Pro His
                245                 250                 255
```

```
Val Ala Gly Leu Ala Ala Lys Ile Trp Ser Ala Asn Thr Ser Leu Ser
            260                 265                 270

His Ser Gln Leu Arg Thr Glu Leu Gln Asn Arg Ala Lys Val Tyr Asp
        275                 280                 285

Ile Lys Gly Gly Ile Gly Ala Gly Thr Gly Asp Asp Tyr Ala Ser Gly
    290                 295                 300

Phe Gly Tyr Pro Arg Val Lys
305                 310

<210> SEQ ID NO 82
<211> LENGTH: 269
<212> TYPE: PRT
<213> ORGANISM: Bacillus lentus

<400> SEQUENCE: 82

Ala Gln Ser Val Pro Trp Gly Ile Glu Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Arg Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asp Asn Ser Ile Gly Val Leu
65                  70                  75                  80

Gly Val Ala Pro Ser Ala Glu Leu Tyr Ala Val Lys Val Leu Gly Ala
                85                  90                  95

Ser Gly Ser Gly Ser Val Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Ile Leu Ser Thr Trp Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Asp Thr Trp Glu
                245                 250                 255

Tyr Gly Ser Gly Leu Val Asn Ala Glu Ala Ala Thr Arg
            260                 265

<210> SEQ ID NO 83
<211> LENGTH: 311
<212> TYPE: PRT
<213> ORGANISM: Bacillus sp.

<400> SEQUENCE: 83
```

-continued

Ala Val Pro Ser Thr Gln Thr Pro Trp Gly Ile Lys Ser Ile Tyr Asn
1               5                   10                  15

Asp Gln Ser Ile Thr Lys Thr Gly Lys Gly Ile Lys Val Ala
            20                  25                  30

Val Leu Asp Thr Gly Val Tyr Thr Ser His Leu Asp Leu Ala Gly Ser
            35                  40                  45

Ala Glu Gln Cys Lys Asp Phe Thr Gln Ser Asn Pro Leu Val Asp Gly
    50                  55                  60

Ser Cys Thr Asp Arg Gln Gly His Gly Thr His Val Ala Gly Thr Val
65                  70                  75                  80

Leu Ala His Gly Gly Ser Asn Gly Gln Gly Val Tyr Gly Val Ala Pro
                85                  90                  95

Gln Ala Lys Leu Trp Ala Tyr Lys Val Leu Gly Asp Lys Gly Glu Gly
                100                 105                 110

Tyr Ser Asp Asp Ile Ala Ala Ile Arg His Val Ala Asp Glu Ala
                115                 120                 125

Ser Arg Thr Gly Ser Lys Val Ile Asn Met Ser Leu Gly Ser Ser
        130                 135                 140

Ala Lys Asp Ser Leu Ile Ala Ser Ala Val Asp Tyr Ala Tyr Gly Lys
145                 150                 155                 160

Gly Val Leu Ile Val Ala Ala Gly Asn Glu Gly Pro Lys Pro Asn
                165                 170                 175

Thr Ile Gly Tyr Pro Ala Gly Phe Val Asn Ala Val Ala Ala Ala
            180                 185                 190

Leu Glu Asn Val Gln Glu Lys Gly Thr Tyr Arg Val Ala Asp Phe Ser
        195                 200                 205

Ser Arg Gly Asn Pro Ala Thr Ala Gly Asp Tyr Ile Ile Gln Glu Arg
    210                 215                 220

Asp Ile Glu Val Ser Ala Pro Gly Ala Ser Val Glu Ser Thr Trp Tyr
225                 230                 235                 240

Thr Gly Gly Tyr Asn Thr Ile Ser Gly Thr Ser Met Ala Thr Pro His
                245                 250                 255

Val Ala Gly Leu Ala Ala Lys Ile Trp Ser Ala Asn Thr Ser Leu Ser
                260                 265                 270

His Ser Gln Leu Arg Thr Glu Leu Gln Asn Arg Ala Lys Val Tyr Asp
        275                 280                 285

Ile Lys Gly Gly Ile Gly Ala Gly Pro Gly Asp Asp Tyr Ala Ser Gly
        290                 295                 300

Phe Gly Tyr Pro Arg Val Lys
305                 310

<210> SEQ ID NO 84
<211> LENGTH: 269
<212> TYPE: PRT
<213> ORGANISM: Bacillus lentus

<400> SEQUENCE: 84

Ala Gln Thr Ile Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
            35                  40                  45

Phe Val Pro Gly Glu Pro Ser Thr Gln Asp Gly Asn Gly His Gly Thr
        50                  55                  60

```
His Val Ala Gly Thr Ile Ala Ala Leu Asn Asn Ser Ile Gly Val Leu
 65                  70                  75                  80

Gly Val Ala Pro Ser Ala Glu Leu Tyr Ala Val Lys Val Leu Gly Ala
                 85                  90                  95

Asp Gly Glu Gly Ala Ile Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Ile Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265

<210> SEQ ID NO 85
<211> LENGTH: 269
<212> TYPE: PRT
<213> ORGANISM: Bacillus lentus

<400> SEQUENCE: 85

Ala Gln Ser Val Pro Trp Gly Ile Ser Arg Val Gln Ala Pro Ala Ala
 1

```
                        165                 170                 175
Asn Asn Asn Arg Ala Asp Phe Ser Gln Tyr Gly Ala Gly Leu Asp Ile
                180                 185                 190

Val Ala Pro Gly Val Asn Val Gln Ser Thr Tyr Pro Gly Ser Ala Tyr
            195                 200                 205

Ala Ser Leu Asn Gly Thr Ser Met Ala Thr Pro His Val Ala Gly Ala
210                 215                 220

Ala Val Leu Val Lys Gln Lys Asn Pro Ser Trp Ser Asn Val Arg Ile
225                 230                 235                 240

Arg Asp His Leu Lys Asn Thr Ala Thr Ser Leu Gly Ser Thr Asn Leu
                245                 250                 255

Tyr Gly Ser Gly Leu Val Asn Ala Phe Ala Ala Thr Arg
            260                 265

<210> SEQ ID NO 86
<211> LENGTH: 269
<212> TYPE: PRT
<213> ORGANISM: Bacillus lentus

<400> SEQUENCE: 86

Ala Gln Ser Val Pro Trp Gly Ile Ser Arg Val Gln Ala Pro Ala Ala
1               5                   10                  15

His Asn Arg Gly Leu Arg Gly Ser Gly Val Lys Val Ala Val Leu Asp
                20                  25                  30

Thr Gly Ile Ser Thr His Pro Asp Leu Asn Ile Arg Gly Gly Ala Ser
            35                  40                  45

Phe Val Pro Gly Glu Pro Ser Thr Gln Asp Gly Asn Gly His Gly Thr
50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Ser Gly Gly Gly Ala Ile Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
                180                 185                 190

Val Ala Pro Gly Val Asn Val Gln Ser Thr Tyr Pro Gly Ser Thr Tyr
            195                 200                 205

Ala Ser Leu Asn Gly Thr Ser Met Ala Thr Pro His Val Ala Gly Ala
210                 215                 220

Ala Val Leu Val Lys Gln Lys Asn Pro Ser Trp Ser Asn Val Arg Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265
```